United States Patent
Merino et al.

(10) Patent No.: US 10,023,872 B2
(45) Date of Patent: Jul. 17, 2018

(54) METHODS FOR PRODUCING HETEROLOGOUS POLYPEPTIDES IN MUTANTS OF TRICHODERMA

(71) Applicant: Novozymes, Inc., Davis, CA (US)

(72) Inventors: Sandra Merino, Davis, CA (US); Judilee Quintos, Davis, CA (US); Debbie Yaver, Davis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 14/652,755

(22) PCT Filed: Dec. 20, 2013

(86) PCT No.: PCT/US2013/076977
§ 371 (c)(1),
(2) Date: Jun. 16, 2015

(87) PCT Pub. No.: WO2014/100612
PCT Pub. Date: Jun. 26, 2014

(65) Prior Publication Data
US 2015/0315600 A1   Nov. 5, 2015

Related U.S. Application Data

(60) Provisional application No. 61/745,165, filed on Dec. 21, 2012.

(51) Int. Cl.
*C12N 15/00* (2006.01)
*C12P 21/00* (2006.01)
(Continued)

(52) U.S. Cl.
CPC ............... *C12N 15/52* (2013.01); *C12N 9/88* (2013.01); *C12N 9/93* (2013.01); *C12P 21/00* (2013.01); *C12P 21/02* (2013.01)

(58) Field of Classification Search
CPC ... C12N 9/88; C12N 9/93; C12P 21/00; C12P 21/02
See application file for complete search history.

(56) References Cited

FOREIGN PATENT DOCUMENTS

| WO | 1996000787 A2 | 1/1996 |
|---|---|---|
| WO | 1997026330 A1 | 7/1997 |

(Continued)

OTHER PUBLICATIONS

Degenkolb et al, 2012, Chem. Biodiversity 9(3), 499-535.
(Continued)

*Primary Examiner* — Reza Ghafoorian
(74) *Attorney, Agent, or Firm* — Robert Starnes

(57) ABSTRACT

The present invention relates to mutants of a parent *Trichoderma* strain, comprising a polynucleotide encoding a polypeptide and one or more genes selected from the group consisting of a peptaibol synthetase gene, a paracelsin synthetase gene, a first terpene cyclase gene, a second terpene cyclase gene, and a third terpene cyclase gene, wherein one or more of the genes are modified rendering the mutant strain deficient in the production of one or more of the enzymes selected from the group consisting of a peptaibol synthetase, a paracelsin synthetase, a first terpene cyclase, a second terpene cyclase, and a third terpene cyclase compared to the parent *Trichoderma* strain when cultivated under identical conditions. The present invention also relates to methods of producing a polypeptide in such mutants and methods for producing such mutants.

4 Claims, 2 Drawing Sheets

(51) Int. Cl.
  *C12N 15/52* (2006.01)
  *C12P 21/02* (2006.01)
  *C12N 9/88* (2006.01)
  *C12N 9/00* (2006.01)

(56) References Cited

FOREIGN PATENT DOCUMENTS

| WO | 2005056772 A1 | 6/2005 |
| WO | 2012001169 A1 | 1/2012 |
| WO | 2012110778 A2 | 8/2012 |
| WO | 2014025605 A1 | 2/2014 |

OTHER PUBLICATIONS

Kubicek et al, 2011, Gene Biol 12, R40.
Lerman et al, 2012, Nature Comm.
Mukherjee et al, 2006, Curr Genet 50(3), 193-202.
Mukherjee et al, 2011, J Biol Chem 286 (6), 4544-4554.
Mukherjee et al, 2012, Microbiol 158, 35-45.
Neuhof et al, 2007, Microbiol 153, 3417-3437.
Nevalainen et al, 1994, J Biotechnol 37, 193-200.
Nikolouli et al, 2012, Biotechnol Lett 34, 1393-1403.
Riteeni et al, 1995, J Nat Prod 58(11), 1745-1748.
Stein et al, 1996, J Biol Chem 286, 4544-4554.
Su et al, 2012, Adv Appl Microbiol 81, 1-61.
Vizcaino et al, 2006, Folia Microbiol 51 (2), 114-120.
Ward, 2012, Biotechnol Advanc 30(5), 1119-1139.
Wei et al, 2005, Ca J Microbiol 51(5),423-429.
Whitmore et al, 2004, Nucleic Acids Res 32, D593-D594.
Wiest et al, 2002, J Biol Chem 277(23), 20862-20868.
Zocher et al, 1997, Adv Microb Physiol 38, 85-131.
Bruckner et al, 1984, Experientia 40, 1189-1197.
Bruckner et al, 1983, Experientia 39, 528-530.
Song et al, 2011, Acta Microbiol Sinica 51(4), 438-444.
Martinez et al, 2008, Nature Biotechnol 26(5)—supplementary text and figures.
Martinez et al, 2008, Nature Biotechnol 26(5), 553-560.

METHODS FOR PRODUCING HETEROLOGOUS POLYPEPTIDES IN MUTANTS OF TRICHODERMA

CROSS-REFERENCE TO RELATED APPLICATIONS

This application is a 35 U.S.C. § 371 national application of PCT/US2013/076977 filed on Dec. 20, 2013, which claims priority or the benefit under 35 U.S.C. § 119 of U.S. Provisional Application No. 61/745,165 filed on Dec. 21, 2012, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to *Trichoderma* mutant strains deficient in the production of secondary metabolites, methods of obtaining the *Trichoderma* mutant strains, and methods of producing heterologous polypeptides in the *Trichoderma* mutant strains.

Description of the Related Art

*Trichoderma* has been shown to be useful as a host cell for the recombinant production of polypeptides having biological activity (WO 96/00787 and WO 97/26330). *Trichoderma* hosts with the desirable traits of increased protein expression and secretion may not necessarily have the most desirable characteristics for successful fermentation. The fermentation may not be optimal because of the production of biological substances detrimental to the production, recovery, or application of a particular polypeptide of interest.

Peptaibols are synthesized by large multidomain enzymes known as non-ribosomal peptide synthetases that assemble compounds from a range of precursors (including nonproteinogenic amino acids and hydroxy or carboxyl acids), which can be N-methylated, acylated, reduced, or epimerized (Marahiel et al., 1997, *Chem. Rev.* 97: 2651-2674; Zocher and Keller, 1997, *Adv. Microb. Physiol.* 38: 85-131). The synthetases have a modular structure in which each module is a semiautonomous unit that recognizes, activates, and modifies a single residue of the final peptide. Each module can be further partitioned into distinct adenylation, thiolation, and condensation domains, which together represent a minimal repeating unit of such a synthetase (Stein et al., 1996, *Journal of Biological Chemistry* 271: 15428-15435).

Mukherjee et al., 2012, *Microbiology* 158: 35-45, describe secondary metabolism in *Trichoderma*. Mukherjee et al., 2011, *Journal of Biological Chemistry* 286: 4544-4554, disclose two classes of new peptaibols synthesized by a single non-ribosomal peptide synthetase of *Trichoderma virens*. Kubicek et al., 2011, *Genome Biology* 12: R40, describe a comparative genome sequence analysis underscoring mycoparasitism as the ancestral life style of *Trichoderma*. Neohof et al., 2007, *Microbiology* 153: 3417-3437, describe intact-cell MALDI-TOF mass spectrometry analysis of peptaibol formation by the genus *Trichoderma*.

Mukherjee et al., 2012, supra, also describe that several *Trichoderma* spp. strains produce terpenoids synthesized from five-carbon isopentenyl units by the action of terpene cyclases. The *T. virens* genome harbors six terpene cyclases, while *T. atroviride* and *T. reesei* have three each.

The present invention relates to improved *Trichoderma* hosts that combine the capacity for expression of commercial quantities of a polypeptide of interest while being deficient in the production of peptaibol(s) and terpene(s) that can complicate production, recovery, or application of the polypeptide.

SUMMARY OF THE INVENTION

The present invention relates to mutants of a parent *Trichoderma* strain, comprising a polynucleotide encoding a heterologous polypeptide and one or more (e.g., several) genes selected from the group consisting of a peptaibol synthetase gene, a paracelsin synthetase gene, a first terpene cyclase gene, a second terpene cyclase gene, and a third terpene cyclase gene, wherein one or more of the genes are modified rendering the mutant strain deficient in the production of one or more (e.g., several) enzymes selected from the group consisting of a peptaibol synthetase, a paracelsin synthetase, a first terpene cyclase, a second terpene cyclase, and a third terpene cyclase compared to the parent *Trichoderma* strain when cultivated under identical conditions.

The present invention also relates to methods of producing a heterologous polypeptide, comprising:

(a) cultivating a mutant of a parent *Trichoderma* strain in a medium for the production of the heterologous polypeptide, wherein the mutant strain comprises a polynucleotide encoding the heterologous polypeptide and one or more (e.g., several) genes selected from the group consisting of a peptaibol synthetase gene, a paracelsin synthetase gene, a first terpene cyclase gene, a second terpene cyclase gene, and a third terpene cyclase gene, wherein one or more of the genes are modified rendering the mutant strain deficient in the production of one or more (e.g., several) enzymes selected from the group consisting of a peptaibol synthetase, a paracelsin synthetase, a first terpene cyclase, a second terpene cyclase, and a third terpene cyclase compared to the parent *Trichoderma* strain when cultivated under identical conditions; and optionally (b) recovering the heterologous polypeptide from the cultivation medium.

The present invention further relates to methods of obtaining mutants of a parent *Trichoderma* strain, comprising:

(a) modifying one or more (e.g., several) genes selected from the group consisting of a peptaibol synthetase gene, a paracelsin synthetase gene, a first terpene cyclase gene, a second terpene cyclase gene, and a third terpene cyclase gene; and (b) identifying a mutant strain from step (a) wherein one or more of the genes are modified rendering the mutant strain deficient in the production of one or more (e.g., several) enzymes selected from the group consisting of a peptaibol synthetase, a paracelsin synthetase, a first terpene cyclase, a second terpene cyclase, and a third terpene cyclase compared to the parent *Trichoderma* strain when cultivated under identical conditions.

DEFINITIONS

Figure 1:
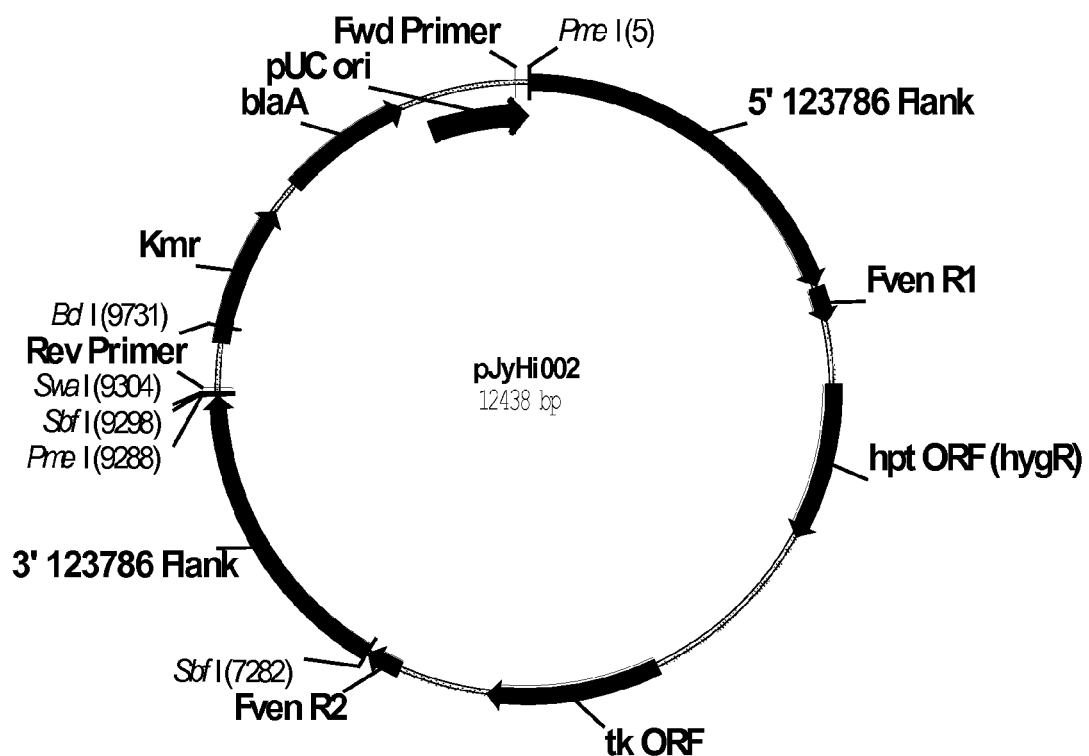
FIG. 1 shows a restriction map of pJyHi002.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Aspartic protease: The term "aspartic protease" means a protease that uses an aspartate residue(s) for catalyzing the hydrolysis of peptide bonds in peptides and proteins. Aspartic proteases are a family of protease enzymes that use an aspartate residue for catalysis of their peptide substrates. In general, they have two highly-conserved aspartates in the active site and are optimally active at acidic pH (Szecsi, 1992, *Scand. J. Clin. Lab. In vest.* Suppl. 210: 5-22). For purposes of the present invention, aspartic protease activity is determined according to the procedure described in WO 2011/075677.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a polypeptide. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Deficient: The term "deficient" means a *Trichoderma* mutant strain that produces no detectable activity of one or more (e.g., several) enzymes selected from the group consisting of a peptaibol synthetase, a paracelsin synthetase, a first terpene cyclase, and a third terpene cyclase compared to the parent *Trichoderma* strain when cultivated under identical conditions, or, in the alternative, produces preferably at least 25% less, more preferably at least 50% less, even more preferably at least 75% less, and most preferably at least 95% less of one or more (e.g., several) enzymes selected from the group consisting of a peptaibol synthetase, a paracelsin synthetase, a first terpene cyclase, a second terpene cyclase, and a third terpene cyclase than the parent *Trichoderma* strain when cultivated under identical conditions. The level of peptaibol, paracelsin, or terpenoid produced by a *Trichoderma* mutant strain of the present invention may be determined using methods described by Neuhof et al., 2007, *Microbiology* 153: 3417-3437 or Degenkolb et al., 2012, *Chemistry & Biodiversity* 9: 499-535.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Host cell: The term "host cell" means any cell type that is susceptible to transformation, transfection, transduction, or the like with a nucleic acid construct or expression vector comprising a polynucleotide. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc.

Mature polypeptide coding sequence: The term "mature polypeptide coding sequence" means a polynucleotide that encodes a mature polypeptide having enzyme activity.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Modification: The term "modification" means introduction, substitution, or removal of one or more (e.g., several) nucleotides in a gene or a control sequence required for the transcription or translation thereof, or gene disruption, gene conversion, gene deletion, or random or specific mutagenesis of a gene, e.g., a peptaibol synthetase gene, a paracelsin synthetase gene, a first terpene cyclase gene, a second terpene cyclase gene, a third terpene cyclase gene, or a combination thereof. The deletion of one or more (e.g., several) of the peptaibol synthetase gene, the paracelsin synthetase gene, the first terpene cyclase gene, the second terpene cyclase gene, and the third terpene cyclase gene may be partial or complete. The modification results in a decrease in or elimination (inactivation) of expression of the peptaibol synthetase, the paracelsin synthetase, the first terpene cyclase, the second terpene cyclase, the third terpene cyclase, or a combination thereof. In a preferred aspect, one or more (e.g., several) of the peptaibol synthetase gene, the paracelsin synthetase gene, the first terpene cyclase gene, the second terpene cyclase gene, and the third terpene cyclase gene are inactivated.

Non-ribosomal peptide synthetases: The term "non-ribosomal peptide synthetases" means enzymes involved in the biosynthesis of a class of non-ribosomally synthesized peptides known as peptaibols, containing non-proteinogenic amino acids (particularly alpha-aminoisobutyric acid).

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Paracelsin: The term "paracelsin" means a peptide antibiotic containing alpha-aminoisobutyric acid. Paracelsin is a peptaibol characterized by the presence of phenylalaninol as the C-terminal amino alcohol and by the specific amino acid content and sequence of peptaibols (Przybylski et al., 1984, *Biomed. Mass Spectrometry* 11, 569; Brückner et al., 1983, *Experientia* 39: 528-530; Brückner et al., 1984, *Experientia* 40: 1189-1197; Ritieni et al., 1995, *Journal of Natural Products* 58: 1745-1748; Pócsfalvi et al., 1997, *Rapid Commun. Mass Spectrometry* 11: 922-930).

Paracelsin synthetase: The term "paracelsin synthetase" means a peptaibol synthetase that catalyzes the formation of paracelsin.

Peptaibol: The term "peptaibol" means peptides characterized by short linear chain lengths (≤20 residues), C-terminal alcohol residues, and high levels of non-standard amino acids, principally alpha-aminoisobutyric acid, isovaline, and the imino acid hydroxyproline. Peptaibol subfamilies 1, 4, 5 and 9 have been described (Szekeres et al., 2005, *Acta. Microbiol. Immunol. Hung.* 52: 137-168). Subfamily 1 (SF1) comprises about half of the known structures and includes peptides ranging from 18 to 20 residues in length. All of these peptides have partial sequence identities or similarities. Subfamily 4 (SF4) is comprised of peptides of 11-14 residues, also sharing sequence similarities, but having no sequence relationship to SF1. Subfamilies 5 and 9 (SF5 and SF9) have only a few members and comprise peptides with 11 or 6 and 7 residues, respectively, again with no sequence similarities to the other subfamilies (Neuhof et al., 2007, *Microbiology* 153: 3417-3427; Whitmore et al., 2004, *Nucleic Acids Research* 32 D593-D594; Mukherjee et al., 2011, *J. Biol. Chem.* 286: 4544-4554).

Peptaibol synthetase: The term "peptaibol synthetase" means a non-ribosomal peptide synthetase that is involved in the synthesis of one or more peptaibol(s).

Polypeptide fragment: The term "polypeptide fragment" means a polypeptide having one or more (e.g., several) amino acids deleted from the amino and/or carboxyl terminus of a polypeptide, wherein the fragment has enzyme activity, e.g., paracelsin synthetase, peptaibol synthetase, or terpene cyclase activity. In one aspect, a fragment contains at least 85% of the amino acid residues, e.g., at least 90% of the amino acid residues or at least 95% of the amino acid residues of a peptaibol synthetase, a paracelsin synthetase, or a terpene cyclase, such as SEQ ID NO: 2, SEQ ID NO: 4, SEQ ID NO: 6, SEQ ID NO: 8, or SEQ ID NO: 10; or homologous sequences thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment–
    Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are a gap open penalty of 10, a gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
    Alignment–Total Number of Gaps in Alignment)

Subsequence: The term "subsequence" means a nucleotide sequence having one or more (e.g., several) nucleotides deleted from the 5' and/or 3' end of a polypeptide coding sequence, wherein the subsequence encodes a polypeptide fragment having enzyme activity, e.g., paracelsin synthetase, peptaibol synthetase, or terpene synthase activity. In one aspect, a subsequence contains at least 85% of the nucleotides, e.g., at least 90% of the nucleotides or at least 95% of the nucleotides of a polynucleotide encoding a peptaibol synthetase, a paracelsin synthetase, or a terpene cyclase, such as SEQ ID NO: 1, SEQ ID NO: 3, SEQ ID NO: 5, SEQ ID NO: 7, or SEQ ID NO: 9; or homologous sequences thereof.

Subtilisin-like serine protease: The term "subtilisin-like serine protease" means a protease with a substrate specificity similar to subtilisin that uses a serine residue for catalyzing the hydrolysis of peptide bonds in peptides and proteins. Subtilisin-like proteases (subtilases) are serine proteases characterized by a catalytic triad of the three amino acids aspartate, histidine, and serine. The arrangement of these catalytic residues is shared with the prototypical subtilisin from *Bacillus licheniformis* (Siezen and Leunissen, 1997, *Protein Science* 6: 501-523). For purposes of the present invention, subtilisin-like serine protease activity is determined according to the procedure described in WO 2011/075677.

Terpene cyclase: The term "terpene cyclase" means an enzyme that catalyzes the formation of cyclic terpenes through the cyclization of linear terpenes (e.g., isopentenyl-pyrophosphate, geranyl-pyrophosphate, farnesyl-pyrophosphate, and geranylgeranyl-pyrophosphate) containing varying numbers of isoprene units. The *T. virens* genome harbors six terpene cyclases, while *T. atroviride* and *T. reesei* have three each.

Terpene: The term "terpene" means a group of natural products composed of several isoprene units, which are synthesized from isopentenyl pyrophosphate. A terpene is also known as a terpenoid or an isoprenoid.

Trypsin-like serine protease: The term "trypsin-like serine protease" means a protease with a substrate specificity similar to trypsin that uses a serine residue for catalyzing the hydrolysis of peptide bonds in peptides and proteins. For purposes of the present invention, trypsin-like serine protease activity is determined according to the procedure described by WO 2011/075677.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

DETAILED DESCRIPTION OF THE INVENTION

The present invention relates to mutants of a parent *Trichoderma* strain, comprising a polynucleotide encoding a heterologous polypeptide and one or more (e.g., several) genes selected from the group consisting of a peptaibol synthetase gene, a paracelsin synthetase gene, a first terpene cyclase gene, a second terpene cyclase gene, and a third terpene cyclase gene, wherein one or more of the genes are modified rendering the mutant strain deficient in the production of one or more (e.g., several) enzymes selected from the group consisting of a peptaibol synthetase, a paracelsin synthetase, a first terpene cyclase, a second terpene cyclase, and a third terpene cyclase compared to the parent *Trichoderma* strain when cultivated under identical conditions.

The present invention also relates to methods of producing a heterologous polypeptide, comprising: (a) cultivating a mutant of a parent *Trichoderma* strain in a medium for the production of the heterologous polypeptide, wherein the mutant strain comprises a polynucleotide encoding the heterologous polypeptide and one or more (e.g., several) genes selected from the group consisting of a peptaibol synthetase gene, a paracelsin synthetase gene, a first terpene cyclase gene, a second terpene cyclase gene, and a third terpene cyclase gene, wherein one or more of the genes are modified rendering the mutant strain deficient in the production of one or more (e.g., several) enzymes selected from the group consisting of a peptaibol synthetase, a paracelsin synthetase, a first terpene cyclase, a second terpene cyclase, and a third terpene cyclase compared to the parent *Trichoderma* strain when cultivated under identical conditions; and optionally (b) recovering the heterologous polypeptide from the cultivation medium.

The present invention further relates to methods of obtaining mutants of a parent *Trichoderma* strain, comprising: (a) modifying one or more (e.g., several) genes selected from the group consisting of a peptaibol synthetase gene, a paracelsin synthetase gene, a first terpene cyclase gene, a second terpene cyclase gene, and a third terpene cyclase gene; and (b) identifying a mutant strain from step (a) wherein one or more of the genes are modified rendering the mutant strain deficient in the production of one or more (e.g., several) enzymes selected from the group consisting of a peptaibol synthetase, a paracelsin synthetase, a first terpene cyclase, a second terpene cyclase, and a third terpene cyclase compared to the parent *Trichoderma* strain when cultivated under identical conditions.

The terms "a peptaibol synthetase gene" and "a paracelsin synthetase gene" can also be referred to herein as "a first peptaibol synthetase gene" and "a second peptaibol synthetase gene", respectively. The terms "a peptaibol synthetase" and "a paracelsin synthetase" can also be referred to herein as "a first peptaibol synthetase" and "a second peptaibol synthetase", respectively.

An advantage of the present invention is elimination or reduction of one or more (e.g., several) enzyme activities, which may be detrimental to the production, recovery, and/or application of a particular polypeptide of interest.

In the methods of the present invention, the parent *Trichoderma* strain may be any *Trichoderma* strain such as a wild-type *Trichoderma* strain or a mutant thereof. The parent *Trichoderma* strain may be *Trichoderma harzianum*, *Trichoderma koningii*, *Trichoderma longibrachiatum*, *Trichoderma reesei*, or *Trichoderma viride*; or the alternative sexual form thereof, i.e., *Hypocrea*.

In another aspect, the parent *Trichoderma* strain is *Trichoderma harzianum*. In another aspect, the parent *Trichoderma* strain is *Trichoderma koningii*. In another aspect, the parent *Trichoderma* strain is *Trichoderma longibrachiatum*. In another aspect, the parent *Trichoderma* strain is *Trichoderma reesei*. In another aspect, the parent *Trichoderma* strain is *Trichoderma viride*.

In another aspect, the parent *Trichoderma reesei* strain is *Trichoderma reesei* RutC30. In another aspect, the parent *Trichoderma reesei* strain is a mutant of *Trichoderma reesei*. In another aspect, the parent *Trichoderma reesei* strain is a mutant of *Trichoderma reesei* RutC30. In another aspect, the parent *Trichoderma reesei* strain is a morphological mutant of *Trichoderma reesei* (WO 97/26330).

A *Trichoderma* mutant strain of the present invention may be constructed by reducing or eliminating expression of one or more (e.g., several) genes selected from the group consisting of a peptaibol synthetase gene, a paracelsin synthetase gene, a first terpene cyclase gene, a second terpene cyclase gene, and a third terpene cyclase gene using methods well known in the art, such as insertions, disruptions, replacements, or deletions. A portion of the gene can be modified such as the coding region or a control sequence required for expression of the coding region. Such a control sequence of the gene may be a promoter sequence or a functional part thereof, i.e., a part that is sufficient for affecting expression of the gene. For example, a promoter sequence may be inactivated resulting in no expression or a weaker promoter may be substituted for the native promoter sequence to reduce expression of the coding sequence. Other control sequences for possible modification include, but are not limited to, a leader, propeptide sequence, signal sequence, transcription terminator, and transcriptional activator.

The *Trichoderma* mutant strains may be constructed by gene deletion techniques to eliminate or reduce expression of the genes. Gene deletion techniques enable the partial or complete removal of the gene thereby eliminating their expression. In such methods, deletion of the gene is accomplished by homologous recombination using a plasmid that has been constructed to contiguously contain the 5' and 3' regions flanking the gene.

The *Trichoderma* mutant strains may also be constructed by introducing, substituting, and/or removing one or more (e.g., several) nucleotides in the gene or a control sequence thereof required for the transcription or translation thereof. For example, nucleotides may be inserted or removed, e.g., for the introduction of a stop codon, the removal of the start codon, or a frame-shift of the open reading frame. Such a modification may be accomplished by site-directed mutagenesis or PCR generated mutagenesis in accordance with methods known in the art. See, for example, Botstein and Shortle, 1985, *Science* 229: 4719; Lo et al., 1985, *Proceedings of the National Academy of Sciences USA* 81: 2285; Higuchi et al., 1988, *Nucleic Acids Research* 16: 7351; Shimada, 1996, *Meth. Mol. Biol.* 57: 157; Ho et al., 1989, *Gene* 77: 61; Horton et al., 1989, *Gene* 77: 61; and Sarkar and Sommer, 1990, *Bio Techniques* 8: 404.

The *Trichoderma* mutant strains may also be constructed by gene disruption techniques by inserting into the gene a disruptive nucleic acid construct comprising a nucleic acid fragment homologous to the gene that will create a duplication of the region of homology and incorporate construct DNA between the duplicated regions. Such a gene disruption can eliminate gene expression if the inserted construct separates the promoter of the gene from the coding region or interrupts the coding sequence such that a non-functional gene product results. A disrupting construct may be simply a selectable marker gene accompanied by 5' and 3' regions homologous to the gene. The selectable marker enables identification of transformants containing the disrupted gene.

The *Trichoderma* mutant strains may also be constructed by the process of gene conversion (see, for example, Iglesias and Trautner, 1983, *Molecular General Genetics* 189: 73-76). For example, in the gene conversion method, a nucleotide sequence corresponding to the gene is mutagenized in vitro to produce a defective nucleotide sequence, which is then transformed into the parent *Trichoderma* strain to produce a defective gene. By homologous recombination, the defective nucleotide sequence replaces the endogenous gene. It may be desirable that the defective nucleotide sequence also comprises a marker for selection of transformants containing the defective gene.

The *Trichoderma* mutant strains may also be constructed by established anti-sense techniques using a nucleotide sequence complementary to the nucleotide sequence of the gene (Parish and Stoker, 1997, *FEMS Microbiology Letters* 154: 151-157). More specifically, expression of the gene by a *Trichoderma* strain may be reduced or inactivated by introducing a nucleotide sequence complementary to the nucleotide sequence of the gene, which may be transcribed in the strain and is capable of hybridizing to the mRNA produced in the strain. Under conditions allowing the complementary anti-sense nucleotide sequence to hybridize to the mRNA, the amount of protein translated is thus reduced or eliminated.

The *Trichoderma* mutant strains may also be constructed by established RNA interference (RNAi) techniques (see, for example, WO 2005/056772 and WO 2008/080017).

The *Trichoderma* mutant strains may be further constructed by random or specific mutagenesis using methods well known in the art, including, but not limited to, chemical mutagenesis (see, for example, Hopwood, *The Isolation of Mutants in Methods in Microbiology* (J. R. Norris and D. W. Ribbons, eds.) pp. 363-433, Academic Press, New York, 1970). Modification of the gene may be performed by subjecting the parent strain to mutagenesis and screening for mutant strains in which expression of the gene has been reduced or inactivated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG) O-methyl hydroxylamine, nitrous acid, ethyl methane sulphonate (EMS), sodium bisulphite, formic acid, and nucleotide analogues. When such agents are used, the mutagenesis is typically performed by incubating the parent strain to be mutagenized in the presence of the mutagenizing agent of choice under suitable conditions, and selecting for mutants exhibiting reduced or no expression of the gene.

In one aspect, the modification results in the inactivation of one or more (e.g., several) genes selected from the group consisting of a peptaibol synthetase gene, a paracelsin synthetase gene, a first terpene cyclase gene, a second terpene cyclase gene, and a third terpene cyclase gene. In another aspect, the modification results in a decrease in expression of one or more (e.g., several) genes selected from the group consisting of a peptaibol synthetase gene, a paracelsin synthetase gene, a first terpene cyclase gene, a second terpene cyclase gene, and a third terpene cyclase gene. In another aspect, the modification results in expression of one or more (e.g., several) genes selected from the group consisting of a peptaibol synthetase gene, a paracelsin synthetase gene, a first terpene cyclase gene, a second terpene cyclase gene, and a third terpene cyclase gene being decreased, inactivated, or a combination thereof.

In another aspect, the mutant comprises a modification of a peptaibol synthetase gene. In another aspect, the mutant comprises a modification of a paracelsin synthetase gene. In another aspect, the mutant comprises a modification of a first terpene cyclase gene. In another aspect, the mutant comprises a modification of a second terpene cyclase gene. In another aspect, the mutant comprises a modification of a third terpene cyclase gene.

In another aspect, the mutant comprises a modification of a peptaibol synthetase gene and a paracelsin synthetase gene. In another aspect, the mutant comprises a modification of a peptaibol synthetase gene and a first terpene cyclase gene. In another aspect, the mutant comprises a modification of a peptaibol synthetase gene and a second terpene cyclase gene. In another aspect, the mutant comprises a modification of a peptaibol synthetase gene and a third terpene cyclase gene. In another aspect, the mutant comprises a modification of a paracelsin synthetase gene and a first terpene cyclase gene. In another aspect, the mutant comprises a modification of a paracelsin synthetase gene and a second terpene cyclase gene. In another aspect, the mutant comprises a modification of a paracelsin synthetase gene and a third terpene cyclase gene. In another aspect, the mutant comprises a modification of a first terpene cyclase gene and a second terpene cyclase gene. In another aspect, the mutant comprises a modification of a first terpene cyclase gene and a third terpene cyclase gene. In another aspect, the mutant comprises a modification of a second terpene cyclase gene and a third terpene cyclase gene.

In another aspect, the mutant comprises a modification of a peptaibol synthetase gene, a paracelsin synthetase gene, and a first terpene cyclase gene. In another aspect, the mutant comprises a modification of a paracelsin synthetase gene, a first terpene cyclase gene, and a second terpene cyclase gene. In another aspect, the mutant comprises a modification of a paracelsin synthetase gene, a second terpene cyclase gene, and a third terpene cyclase gene. In another aspect, the mutant comprises a modification of a peptaibol synthetase gene, a paracelsin synthetase gene, and a second terpene cyclase gene. In another aspect, the mutant comprises a modification of a peptaibol synthetase gene, a paracelsin synthetase gene, and a third terpene cyclase gene. In another aspect, the mutant comprises a modification of a paracelsin synthetase gene, a first terpene cyclase gene, and a third terpene cyclase gene. In another aspect, the mutant comprises a modification of a peptaibol synthetase gene, a first terpene cyclase gene, and a second terpene cyclase gene. In another aspect, the mutant comprises a modification of a peptaibol synthetase gene, a second terpene cyclase gene, and a third terpene cyclase gene. In another aspect, the mutant comprises a modification of a peptaibol synthetase gene, a first terpene cyclase gene, and a third terpene cyclase gene. In another aspect, the mutant comprises a modification of a first terpene cyclase gene, a second terpene cyclase gene, and a third terpene cyclase gene.

In another aspect, the mutant comprises a modification of a peptaibol synthetase gene, a paracelsin synthetase gene, a first terpene cyclase gene, and a second terpene cyclase gene. In another aspect, the mutant comprises a modification of a paracelsin synthetase gene, a first terpene cyclase gene, a second terpene cyclase gene, and a third terpene cyclase gene. In another aspect, the mutant comprises a modification of a peptaibol synthetase gene, a first terpene cyclase gene, a second terpene cyclase gene, and a third terpene cyclase gene. In another aspect, the mutant comprises a modification of a peptaibol synthetase gene, a paracelsin synthetase gene, a second terpene cyclase gene, and a third terpene cyclase gene. In another aspect, the mutant comprises a modification of a peptaibol synthetase gene, a paracelsin synthetase gene, a first terpene cyclase gene, and a third terpene cyclase gene.

In another aspect, the mutant comprises a modification of a peptaibol synthetase gene, a paracelsin synthetase gene, a first terpene cyclase gene, a second terpene cyclase gene, and a third terpene cyclase gene.

In one aspect, the peptaibol synthetase gene encodes a polypeptide having peptaibol synthetase activity comprising or consisting of an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 2. In another aspect, the peptaibol synthetase gene encodes a polypeptide having peptaibol synthetase activity comprising or consisting of SEQ ID NO: 2.

In another aspect, the peptaibol synthetase gene comprises a polynucleotide comprising or consisting of a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1 or the cDNA sequence thereof. In another aspect, the peptaibol synthetase gene comprises a polynucleotide comprising or consisting of SEQ ID NO: 1.

In another aspect, the peptaibol synthetase gene comprises a polynucleotide that hybridizes under very low stringency conditions, low stringency conditions, medium stringency conditions, medium-high stringency conditions, high stringency conditions, or very high stringency conditions with SEQ ID NO: 1 or the cDNA sequence thereof; or the full-length complement thereof.

In another aspect, the paracelsin synthetase gene encodes a polypeptide having paracelsin synthetase activity comprising or consisting of an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4. In another aspect, the paracelsin synthetase gene encodes a polypeptide having paracelsin synthetase activity comprising or consisting of SEQ ID NO: 4.

In another aspect, the paracelsin synthetase gene comprises a polynucleotide comprising or consisting of a nucleotide sequence having at least 60%, e.g., e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3. In another aspect, the paracelsin synthetase gene comprises a polynucleotide comprising or consisting of SEQ ID NO: 3.

In another aspect, the paracelsin synthetase gene comprises a polynucleotide that hybridizes under very low stringency conditions, low stringency conditions, medium stringency conditions, medium-high stringency conditions, high stringency conditions, or very high stringency conditions with SEQ ID NO: 3 or the cDNA sequence thereof; or the full-length complement thereof.

In another aspect, the first terpene cyclase gene encodes a polypeptide having terpene cyclase activity comprising or consisting of an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 6. In another aspect, the first terpene cyclase gene encodes a polypeptide having terpene cyclase activity comprising or consisting of SEQ ID NO: 6.

In another aspect, the first terpene cyclase gene comprises a polynucleotide comprising or consisting of a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 5 or the genomic DNA sequence thereof. In another aspect, the first terpene cyclase gene comprises a polynucleotide comprising or consisting of SEQ ID NO: 5.

In another aspect, the first terpene cyclase gene comprises a polynucleotide that hybridizes under very low stringency conditions, low stringency conditions, medium stringency conditions, medium-high stringency conditions, high stringency conditions, or very high stringency conditions with SEQ ID NO: 5 or the genomic DNA sequence thereof; or the full-length complement thereof.

In another aspect, the second terpene cyclase gene encodes a polypeptide having terpene cyclase activity comprising or consisting of an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 8. In another aspect, the second terpene cyclase gene encodes a polypeptide having terpene cyclase activity comprising or consisting of SEQ ID NO: 8.

In another aspect, the second terpene cyclase gene comprises a polynucleotide comprising or consisting of a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 7 or the genomic DNA sequence thereof. In another aspect, the second terpene cyclase gene comprises a polynucleotide comprising or consisting of SEQ ID NO: 7.

In another aspect, the second terpene cyclase gene comprises a polynucleotide that hybridizes under very low stringency conditions, low stringency conditions, medium stringency conditions, medium-high stringency conditions, high stringency conditions, or very high stringency conditions with SEQ ID NO: 7 or the genomic DNA sequence; or the full-length complement thereof.

In another aspect, the third terpene cyclase gene encodes a polypeptide having terpene cyclase activity comprising or consisting of an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10.

In another aspect, the third terpene cyclase gene encodes a polypeptide having terpene cyclase activity comprising or consisting of SEQ ID NO: 10.

In another aspect, the third terpene cyclase gene comprises a polynucleotide comprising or consisting of a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9 or the genomic DNA sequence thereof. In another aspect, the third terpene cyclase gene comprises a polynucleotide comprising or consisting of SEQ ID NO: 9.

In another aspect, the third terpene cyclase gene comprises a polynucleotide that hybridizes under very low stringency conditions, low stringency conditions, medium stringency conditions, medium-high stringency conditions, high stringency conditions, or very high stringency conditions with SEQ ID NO: 9 or the genomic DNA sequence thereof; or the full-length complement thereof.

The nucleotide sequences disclosed herein or subsequences thereof, as well as the amino acid sequences thereof or fragments thereof, may be used to design nucleic acid probes to identify and clone homologous DNA of the genes described above from strains of different genera or species according to methods well known in the art. In particular, such probes can be used for hybridization with the genomic DNA or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin).

Thus, a genomic DNA or cDNA library prepared from such other organisms may be screened for DNA that hybridizes with the probes described above. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with the nucleotide sequences disclosed herein or subsequences thereof, the carrier material is used in a Southern blot. For purposes of the present invention, hybridization indicates that the nucleic acid sequence hybridizes to a labeled nucleic acid probe corresponding to the nucleotide sequences disclosed herein, its complementary strand, or a subsequence thereof, under very low to very high stringency conditions. Molecules to which the nucleic acid probe hybridizes under these conditions are detected using X-ray film.

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

A nucleotide sequence homologous or complementary to a gene described herein may be used from other microbial sources to modify the corresponding gene in a *Trichoderma* strain of choice.

In another aspect, the modification of a gene in the *Trichoderma* mutant strain is unmarked with a selectable marker. Removal of the selectable marker gene may be accomplished by culturing the mutants on a counter-selection medium. Where the selectable marker gene contains repeats flanking its 5' and 3' ends, the repeats will facilitate the looping out of the selectable marker gene by homologous recombination when the mutant strain is submitted to counter-selection. The selectable marker gene may also be removed by homologous recombination by introducing into the mutant strain a nucleic acid fragment comprising 5' and 3' regions of the defective gene, but lacking the selectable marker gene, followed by selecting on a counter-selection medium. By homologous recombination, the defective gene containing the selectable marker gene is replaced with the nucleic acid fragment lacking the selectable marker gene. Other methods known in the art may also be used.

It will be understood that the methods of the present invention are not limited to a particular order for obtaining the *Trichoderma* mutant strain. The modification of a gene may be introduced into the parent strain at any step in the construction of the strain for the production of a polypeptide of interest. It is preferred that the *Trichoderma* mutant strain has already been made peptaibol, paracelsin, and/or terpene-deficient prior to such a construction.

In a further aspect of the present invention, the mutants of *Trichoderma* strains may contain additional modifications, e.g., deletions or disruptions, of other genes, which may encode substances detrimental to the production, recovery, or application of a polypeptide of interest.

In one aspect, the *Trichoderma* strain further comprises a modification, e.g., disruption or deletion, of one or more (e.g., several) genes encoding a proteolytic activity selected from the group consisting of an aminopeptidase, dipeptidylaminopeptidase, tripeptidylaminopeptidase, carboxypeptidase, metalloprotease, cysteine protease, and vacuolar protease.

In a preferred aspect, the *Trichoderma* strain further comprises a modification, e.g., disruption or deletion, of one or more (e.g., several) genes selected from the group consisting of a first subtilisin-like serine protease gene, a first aspartic protease gene, a trypsin-like serine protease gene, a second subtilisin-like serine protease gene, and a second aspartic protease gene, as described in WO 2011/075677, which is incorporated herein by reference in its entirety.

In another aspect, the *Trichoderma* strain further comprises a modification, e.g., disruption or deletion, of one or more (e.g., several) additional genes encoding enzymes selected from the group consisting of an oxidoreductase, a transferase, a hydrolase, a lyase, an isomerase, or a ligase.

In another aspect, the *Trichoderma* strain further comprises a modification, e.g., disruption or deletion, of one or more (e.g., several) additional genes encoding enzymes selected from the group consisting of an acetylmannan esterase, acetylxylan esterase, aminopeptidase, alpha-amylase, arabinanase, arabinofuranosidase, carbohydrase, carboxypeptidase, catalase, cellobiohydrolase, cellulase, cellulose inducing protein, chitinase, coumaric acid esterase, cyclodextrin glycosyltransferase, cutinase, cyclodextrin glycosyltransferase, deoxyribonuclease, endoglucanase, esterase, expansin, feruloyl esterase, AA9 (GH61) polypeptide, alpha-galactosidase, beta-galactosidase, glucocerebrosidase, glucose oxidase, alpha-glucosidase, beta-glucosidase, glucuronidase, glucuronoyl esterase, haloperoxidase, hemicellulase, invertase, isomerase, laccase, ligase, lipase, mannanase, mannosidase, mutanase, oxidase, pectinolytic enzyme, peroxidase, phospholipase, phytase, phenoloxidase, polyphenoloxidase, proteolytic enzyme, ribonuclease, swollenin, alpha-1,6-transglucosidase, transglutaminase, urokinase, xylanase, or beta-xylosidase.

In another aspect, the *Trichoderma* strain further comprises a modification, e.g., disruption or deletion, of one or more (e.g., several) additional genes encoding enzymes selected from the group consisting of an endoglucanase, a cellobiohydrolase, and a beta-glucosidase, In the methods of the present invention, the *Trichoderma* mutant strain preferably produces at least the same amount of a heterologous polypeptide of interest as the corresponding parent *Trichoderma* strain when cultured under identical production conditions. In another aspect, the mutant strain produces at least 5% more, e.g., at least 10% more, at least 25% more, at least 50% more, at least 75% more, and at least 100% more of the heterologous polypeptide than the corresponding parent *Trichoderma* strain when cultured under identical production conditions.

The *Trichoderma* mutant strains are cultivated in a nutrient medium for production of the heterologous polypeptide of interest using methods known in the art. For example, the strain may be cultivated by shake flask cultivation or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted polypeptide can be recovered directly from the medium. If the polypeptide is not secreted, it may be obtained from cell lysates. A whole broth comprising a heterologous polypeptide of interest can also be recovered.

The polypeptide of interest may be detected using methods known in the art that are specific for the polypeptide. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of an enzyme. Procedures for determining enzyme activity are known in the art for many enzymes (see, for example, D. Schomburg and M. Salzmann (eds.), *Enzyme Handbook*, Springer-Verlag, New York, 1990).

The resulting polypeptide may be isolated by methods known in the art. For example, a polypeptide of interest may be isolated from the cultivation medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989).

The heterologous polypeptide of interest may be any polypeptide foreign to the *Trichoderma* strain. The polypeptide may be encoded by a single gene or two or more genes. The term "polynucleotide encoding the polypeptide" will be understood to encompass one or more (e.g., several) genes involved in the production of the polypeptide. The term "heterologous polypeptide" is defined herein as a polypeptide that is not native to the host strain; a native polypeptide in which structural modifications have been made to alter the native polypeptide, e.g., the protein sequence of a native polypeptide; or a native polypeptide whose expression is quantitatively altered as a result of a manipulation of the polynucleotide or host strain by recombinant DNA techniques, e.g., a stronger promoter, multiple copies of a DNA encoding the polypeptide. Thus, the present invention also encompasses, within the scope of the term "heterologous polypeptides," such recombinant production of native polypeptides, to the extent that such expression involves the use of genetic elements not native to the *Trichoderma* strain, or use of native elements that have been manipulated to function in a manner that do not normally occur in the host strain.

The heterologous polypeptide may be any polypeptide having a biological activity of interest. The term "polypeptide" is not meant herein to refer to a specific length of the encoded product and, therefore, encompasses peptides, oligopeptides, and proteins. The term "polypeptide" also includes naturally occurring allelic and engineered variations of a polypeptide. The term "polypeptide" further encompasses hybrid and fusion polypeptides.

A hybrid polypeptide comprises a combination of partial polypeptide sequences obtained from at least two different polypeptides wherein one or more (e.g., several) may be heterologous to the *Trichoderma* strain.

A fusion polypeptide or cleavable fusion polypeptide comprises a polypeptide fused at the N-terminus or the C-terminus of another polypeptide. A fusion polypeptide is produced by fusing a polynucleotide encoding one polypeptide to a polynucleotide encoding another polypeptide. Techniques for producing fusion polypeptides are known in the art, and include ligating the coding sequences encoding the polypeptides so that they are in frame and that expression of the fusion polypeptide is under control of the same promoter (s) and terminator. Fusion polypeptides may also be constructed using intein technology in which fusion polypeptides are created post-translationally (Cooper et al., 1993, *EMBO J*. 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol*. 3: 568-576; Svetina et al., 2000, *J. Biotechnol*. 76: 245-251; Rasmussen-Wilson et al., 1997, *Appl. Environ. Microbiol*. 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

In one aspect, the polypeptide is an antibody, an antigen, an antimicrobial peptide, an enzyme, a growth factor, a hormone, an immunodilator, a neurotransmitter, a receptor, a reporter protein, a structural protein, or a transcription factor.

In another aspect, the polypeptide is an oxidoreductase, a transferase, a hydrolase, a lyase, an isomerase, or a ligase. In another aspect, the polypeptide is an acetylmannan esterase, acetylxylan esterase, aminopeptidase, alpha-amylase, arabinanase, arabinofuranosidase, carbohydrase, carboxypeptidase, catalase, cellobiohydrolase, cellulase, cellulose inducing protein, chitinase, coumaric acid esterase, cyclodextrin glycosyltransferase, cutinase, cyclodextrin glycosyltransferase, deoxyribonuclease, endoglucanase, esterase, expansin, feruloyl esterase, AA9 (GH61) polypeptide, alpha-galactosidase, beta-galactosidase, glucocerebrosidase, glucose oxidase, alpha-glucosidase, beta-glucosidase, glucuronidase, glucuronoyl esterase, haloperoxidase, hemicellulase, invertase, isomerase, laccase, ligase, lipase, mannanase, mannosidase, mutanase, oxidase, pectinolytic enzyme, peroxidase, phospholipase, phytase, phenoloxidase, polyphenoloxidase, proteolytic enzyme, ribonuclease, swollenin, alpha-1,6-transglucosidase, transglutaminase, urokinase, xylanase, or beta-xylosidase.

In another aspect, the polypeptide is an albumin, a collagen, a tropoelastin, an elastin, or a gelatin.

In another aspect, the polypeptide is an endoglucanase. In another aspect, the polypeptide is a cellobiohydrolase. In another aspect, the polypeptide is a beta-glucosidase. In another aspect, the polypeptide is an AA9 (GH61) polypeptide. In another aspect, the polypeptide is a xylanase. In another aspect, the polypeptide is a beta-xylosidase. In another aspect, the polypeptide is an acetylxylan esterase. In another aspect, the polypeptide is a feruloyl esterase. In another aspect, the polypeptide is an arabinofuranosidase. In another aspect, the polypeptide is a glucuronidase. In another aspect, the polypeptide is an acetylmannan esterase. In another aspect, the polypeptide is an arabinanase. In another aspect, the polypeptide is a coumaric acid esterase. In another aspect, the polypeptide is a galactosidase. In another aspect, the polypeptide is a glucuronoyl esterase. In another aspect, the polypeptide is a mannanase. In another aspect, the polypeptide is a mannosidase. In another aspect, the polypeptide is a cellulose inducing protein. In another aspect, the polypeptide is an expansin. In another aspect, the polypeptide is a Swollenin.

In the methods of the present invention, the mutant of the *Trichoderma* strain is a recombinant strain, comprising a polynucleotide encoding a heterologous polypeptide, which is advantageously used in the recombinant production of the polypeptide. The strain is preferably transformed with a vector comprising the polynucleotide encoding the heterologous polypeptide followed by integration of the vector into the chromosome. "Transformation" means introducing a vector comprising the polynucleotide into a host strain so that the vector is maintained as a chromosomal integrant or as a self-replicating extra-chromosomal vector. Integration is generally considered to be an advantage as the polynucleotide is more likely to be stably maintained in the strain. Integration of the vector into the chromosome can occur by homologous recombination, non-homologous recombination, or transposition.

The polynucleotide encoding a heterologous polypeptide may be obtained from any prokaryotic, eukaryotic, or other source, e.g., archaeabacteria. For purposes of the present invention, the term "obtained from" as used herein in connection with a given source shall mean that the polypeptide is produced by the source or by a strain in which a gene from the source has been inserted.

In the methods of the present invention, a mutant *Trichoderma* strain of the present invention may also be used for the recombinant production of a polypeptide that is native to the *Trichoderma* strain. The native polypeptide may be produced by recombinant means by, for example, placing a gene encoding the polypeptide under the control of a different promoter to enhance expression of the substance, expediting its export outside the strain by use of, for example, a signal sequence, or increasing the copy number of a gene encoding the polypeptide normally produced by the *Trichoderma* strain.

The techniques used to isolate or clone a polynucleotide encoding a polypeptide of interest are known in the art and include isolation from genomic DNA, preparation from cDNA, or a combination thereof. The cloning of such a polynucleotide from such genomic DNA can be effected, e.g., by using the well-known polymerase chain reaction (PCR). See, for example, Innis et al., 1990, PCR Protocols: A Guide to Methods and Application, Academic Press, New York. The cloning procedures may involve excision and isolation of a desired nucleic acid fragment comprising the polynucleotide encoding the polypeptide, insertion of the fragment into a vector molecule, and incorporation of the recombinant vector into a mutant *Trichoderma* strain of the present invention where multiple copies or clones of the polynucleotide will be replicated. The polynucleotide may be of genomic, cDNA, RNA, semisynthetic, synthetic origin, or any combinations thereof.

An isolated polynucleotide encoding a heterologous polypeptide may be manipulated in a variety of ways to provide for expression of the polypeptide in a mutant *Trichoderma* strain of the present invention. Manipulation of the polynucleotide's sequence prior to its insertion into a vector may be desirable or necessary depending on the expression vector. The techniques for modifying polynucleotide sequences utilizing recombinant DNA methods are well known in the art.

A nucleic acid construct comprising a polynucleotide encoding a polypeptide may be operably linked to one or more (e.g., several) control sequences capable of directing expression of the coding sequence in a mutant *Trichoderma* strain of the present invention under conditions compatible with the control sequences.

The control sequence may be an appropriate promoter, a nucleotide sequence that is recognized by a mutant *Trichoderma* strain of the present invention for expression of the polynucleotide encoding the polypeptide. The promoter contains transcriptional control sequences that mediate expression of the polypeptide. The promoter may be any nucleotide sequence that shows transcriptional activity in the mutant *Trichoderma* strain, including mutant, truncated, and hybrid promoters, and may be obtained from genes encoding extracellular or intracellular polypeptides either native or heterologous (foreign) to the mutant *Trichoderma* strain.

Examples of suitable promoters for directing the transcription of the nucleic acid constructs in the methods of the present invention are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, *Trichoderma reesei* glyceraldehyde-6 phosphate dehydrogenase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

The control sequence may also be a transcription terminator, which is recognized by a host cell to terminate transcription. The terminator is operably linked to the 3'-terminus of the polynucleotide encoding the polypeptide. Any terminator that is functional in a *Trichoderma* strain may be used in the present invention.

Preferred terminators are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

The control sequence may also be a leader, a nontranslated region of an mRNA that is important for translation by a mutant *Trichoderma* strain of the present invention. The leader is operably linked to the 5'-terminus of the polynucleotide encoding the polypeptide. Any leader that is functional in the mutant *Trichoderma* strain may be used in the present invention.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3' terminus of the nucleotide sequence and, when transcribed, is recognized by the mutant *Trichoderma* strain as a signal to add polyadenosine residues to transcribed mRNA. Any polyadenylation sequence that is functional in the mutant *Trichoderma* strain may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthetase, *Fusarium oxysporum* trypsin-like protease, and *Aspergillus niger* alpha-glucosidase.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of the mutant *Trichoderma* strain, i.e., secreted into a culture medium, may be used in the present invention.

Effective signal peptide coding regions for the mutant *Trichoderma* strains are the signal peptide coding regions obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding region may be obtained from genes for *Saccharomyces cerevisiae* alpha-factor, *Rhizomucor miehei* aspartic proteinase, and *Myceliophthora thermophila* laccase (WO 95/33836).

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the mutant *Trichoderma* strain. Examples of regulatory sequences are those that cause expression of the gene to be turned on or off in response to a chemical or physical stimulus, including the presence of a regulatory compound. Regulatory systems in filamentous fungi such as the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

In the methods of the present invention, a recombinant expression vector comprising a polynucleotide encoding a polypeptide of interest, a promoter, and transcriptional and translational stop signals may be used for the recombinant production of the polypeptide of interest. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on its compatibility with the mutant *Trichoderma* strain into which the vector is to be introduced. The vector may be a linear or closed circular plasmid.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, *Molecular Cloning, A Laboratory Manual*, 2d edition, Cold Spring Harbor, New York).

A vector comprising the nucleotide sequence can be introduced, e.g., by transformation, into the mutant *Trichoderma* strain so that the vector is maintained as a chromosomal integrant or as a self-replicating extra-chromosomal vector. Integration is generally considered to be an advantage as the nucleotide sequence is more likely to be stably maintained in the strain. Integration of the vector into the chromosome occurs by homologous recombination, non-homologous recombination, or transposition.

The introduction of an expression vector into the mutant *Trichoderma* strain may involve a process consisting of protoplast formation, transformation of the protoplasts, and regeneration of the strain wall in a manner known per se. Suitable procedures for transformation of *Trichoderma* strains are described in Malardier et al., 1989, *Gene* 78: 147-156, and WO 96/00787.

The present invention is further described by the following examples that should not be construed as limiting the scope of the invention.

EXAMPLES

Strains

*Trichoderma reesei* strain 981-O-8 (D4) is a mutagenized strain of *Trichoderma reesei* RutC30 (Montenecourt and Eveleigh, 1979, *Adv. Chem. Ser.* 181: 289-301. *Trichoderma reesei* strain AgJg115-104-7B1 is a ku70 disrupted strain of *Trichoderma reesei* RutC30.

Media and Solutions

Overlay PDA medium was composed of 39 g of Potato Dextrose Agar (Difco) and deionized water to 1 liter supplemented with 100 µg of hygromycin B per ml.

PDA plates were composed of 39 g of Potato Dextrose Agar (Difco) and deionized water to 1 liter.

PEG buffer was composed of 500 g of PEG 4000, 10 mM $CaCl_2$, 10 mM Tris-HCl pH 7.5, and deionized water to 1 liter; filter sterilized.

SOC medium was composed of 20 g of tryptone, 5 g of yeast extract, 0.5 g of NaCl, 10 ml of 20 mM KCl, and deionized water to 1 liter.

STC was composed of 0.8 M or 1 M sorbitol, 10 mM or 25 mM $CaCl_2$, and 10 mM or 25 mM Tris-HCl, pH 7.5 or pH 8; filter sterilized.

TAE buffer was composed of 4.82 g of Tris Base, 1.14 ml of Glacial acetic acid, 2 ml of 0.5 M EDTA pH 8.0, and deionized water to 1 liter.

TBE buffer was composed of 10.8 g of Tris base, 5.5 g of boric acid, 4 ml of 0.5 M EDTA pH 8.0, and deionized water to 1 liter.

TE buffer was composed of 10 mM Tris-0.1 mM EDTA pH 8.0.

2XYT plus ampicillin plates were composed of 16 g of tryptone, 10 g of yeast extract, 5 g of NaCl, 15 g of Bacto agar, 1 ml of 100 mg/ml ampicillin stock, and deionized water to 1 liter.

YEG medium was composed of 5 g of yeast extract, 20 g of glucose, and deionized water to 1 liter.

YP medium was composed of 10 g of yeast extract, 20 g of Bacto peptone, and deionized water to 1 liter.

Example 1: *Trichoderma reesei* Strain 981-O-8 Genomic DNA Extraction

*Trichoderma reesei* strain 981-O-8 was grown in 50 ml of YEG medium in a baffled shake flask at 28° C. for 2 days with agitation at 200 rpm. Mycelia were harvested by filtration using MIRACLOTH® (Calbiochem, La Jolla, Calif., USA), washed twice in deionized water, and frozen under liquid nitrogen. Frozen mycelia were ground, by mortar and pestle, to a fine powder, and total DNA was isolated using a DNEASY® Plant Maxi Kit (QIAGEN Inc., Valencia, Calif., USA).

Example 2: *Trichoderma reesei* Protoplast Generation and Transformation

Protoplast preparation and transformation were performed using a modification of the protocol described by Penttila et al., 1987, Gene 61: 155-164. Briefly, *Trichoderma reesei* strain AgJg115-104-7B1 was cultivated in 25 ml of YP medium supplemented with 2% (w/v) glucose at 28° C. for 17 hours with gentle agitation at 90 rpm. Mycelia were collected by filtration using a Millipore Vacuum Driven Disposable Filtration System (Millipore, Bedford, Mass., USA) and washed twice with deionized water and twice with 1.2 M sorbitol. Protoplasts were generated by suspending the washed mycelia in 30 ml of 1.2 M sorbitol containing 15 mg of GLUCANEX® 200 G (Novozymes NS, Bagsvaerd, Denmark) per ml and 0.36 units of chitinase (Sigma Chemical Co., St. Louis, Mo., USA) per ml for 15-25 minutes at 34° C. with gentle shaking at 90 rpm. Protoplasts were collected by centrifugation at 400×g for 7 minutes and washed twice with cold 1.2 M sorbitol. The protoplasts were counted using a hemacytometer and re-suspended to a final concentration of 1×10$^8$ protoplasts per ml in STC. Excess protoplasts were stored in a Cryo 1° C. Freezing Container (Nalgene, Rochester, N.Y., USA) at −80° C.

Approximately 2 µg of each of the deletion cassettes described in the following Examples were digested with Pme I. Each digestion reaction was purified by 0.8% agarose gel electrophoresis using TBE buffer where a DNA band was excised from the gel and extracted using a NUCLEOSPIN® Gel and PCR Cleanup kit (Macherey-Nagel GmbH & Co. KG, Düren, Germany). The resulting purified DNA was added to 100 µl of the protoplast solution and mixed gently. PEG buffer (250 µl) was added and mixed, and then the mixture was incubated at 34° C. for 30 minutes. STC (3 ml) was then added and mixed, and the mixture was spread onto PDA plates supplemented with 1 M sucrose. After incubation at 28° C. for 16 hours, 15 ml of overlay PDA medium supplemented with 100 µg of hygromycin B per ml were added to each plate. The plates were incubated at 28° C. for 4-6 days.

Example 3: Construction of a Peptaibol Synthetase Gene Deletion Vector

The 5' flanking sequence of the *Trichoderma reesei* strain 981-O-8 peptaibol synthetase gene (Trirre2:123786; SEQ ID NO: 1 for the genomic DNA sequence and SEQ ID NO: 2 for the deduced amino acid sequence) was amplified from genomic DNA of *T. reesei* strain 981-O-8 using the gene-specific forward and reverse primers shown below.
Forward Primer (1201181):

(SEQ ID NO: 11)
5'-*tcacatggtttaaac*ggcgcgccGACCCGAAAGAACGCAAAAGTCC

AT-3'

Reverse Primer (1201182):

(SEQ ID NO: 12)
5'-*agccttgttttgtc*GTGTCAAGAACTTGGATCTCCTAGGAG-3'

The underlined portion is an Asc I site introduced for cloning and the region in italics represents an introduced extension corresponding to a homologous region of the site of vector insertion necessary for cloning.

The amplification reaction was composed of 137 ng of *T. reesei* 981-O-8 genomic DNA, 200 µm dNTP's, 0.4 µM primers, 3% DMSO, 5× PHUSION® HF Buffer with 1.5 mM MgCl$_2$ (New England Biolabs, Inc., Ipswich, Mass., USA), and 2 units of PHUSION® Hot Start High-Fidelity DNA Polymerase (New England Biolabs, Inc., Ipswich, Mass., USA) in a final volume of 50 µl. The amplification reaction was performed in a ROBOCYCLER® (Agilent Technologies, Santa Clara, Calif., USA) programmed for 1 cycle at 98° C. for 3 minutes; 35 cycles each at 98° C. for 10 seconds, 55° C. for 30 seconds, and 72° C. for 1.5 minutes; and 1 cycle at 72° C. for 10 minutes. PCR products were separated by 0.8% agarose gel electrophoresis using TBE buffer where a 2.4 kb product was observed. The 2.4 kb PCR product was excised from the gel and purified using a MINELUTE® Gel Extraction Kit (QIAGEN Inc., Valencia, Calif., USA) according to the manufacturer's protocol.

The 2.4 kb PCR product was inserted into Asc I-digested pJfyS1579-41-11 (WO 2011/075677) using an IN-FUSION® HD ADVANTAGE® PCR Cloning Kit (Clontech, Palo Alto, Calif., USA) according to the manufacturer's protocol. The reaction was composed of 100 ng of pJfyS1579-41-11, 60 ng of the PCR product, and 2 µl of IN-FUSION® HD Enzyme Premix (Clontech, Palo Alto, Calif., USA) in a 10 µl reaction volume. The reaction was incubated for 15 minutes at 50° C. Two and a half µl were used to transform SOLOPACK® Gold Supercompetent (Agilent, Santa Clara, Calif., USA) cells. The DNA was added to the cells and incubated for 30 minutes on ice followed by a heat-shock at 42° C. for 30 seconds. Then SOC medium (250 µl) was added and incubated at 37° C. for 1 hour. The reaction was spread onto 2XYT plus ampicillin plates and incubated overnight at 37° C. Plasmid DNA was purified from several transformants using a BIOROBOT® 9600 (QIAGEN Inc., Valencia, Calif., USA) and analyzed by DNA sequencing using a 3130XL Genetic Analyzer (Life Technologies, Carlsbad, Calif., USA) to identify a plasmid containing the desired insert. One clone containing the insert was identified and designated plasmid pJyHi002A. Plasmid pJyHi002A was used to insert the 3' flank of the peptaibol synthetase gene.

The 3' peptaibol synthetase gene flanking sequence was amplified from *T. reesei* 981-O-8 genomic DNA using PHUSION® Hot Start High-Fidelity DNA Polymerase (New England Biolabs, Inc., Ipswich, Mass., USA) and the gene-specific forward and reverse primers shown below.
Forward Primer (1201183):

(SEQ ID NO: 13)
5'-*cctagttggagtatt*cctgcaggTCCTCATCTGTGGCTCATATTAG

GT-3'

Reverse Primer (1201524):

(SEQ ID NO: 14)
5'-*tggccatatttaaat*cctgcagggtttaaacCAAGG

CGGGATAGTGTCGGTTCTT-3'

The underlined portion is a Sbf I site introduced for cloning, the region in italics represents an introduced extension corresponding to a homologous region of the site of vector insertion necessary for cloning, and the bold portion is an introduced Pme I site for later removal of the bacterial propagation portion of the plasmid.

The amplification reaction was composed of 137 ng of *T. reesei* 981-O-8 genomic DNA, 200 µm dNTP's, 0.4 µM primers, 3% DMSO, 5× PHUSION® HF Buffer with 1.5 mM MgCl$_2$, and 2 units of PHUSION® Hot Start High-Fidelity DNA Polymerase in a final volume of 50 µl. The amplification reaction was performed in an ROBOCYCLER® programmed for 1 cycle at 98° C. for 3 minutes; 35 cycles each at 98° C. for 10 seconds, 55° C. for 30 seconds, and 72° C. for 1 minute; and 1 cycle at 72° C. for 10 minutes. PCR products were separated by 0.8% agarose gel electrophoresis using TBE buffer where a 2.0 kb fragment was excised from the gel and agarose was extracted using a NUCLEOSPIN® Extract II Kit (Clontech, Palo Alto, Calif., USA) according to the manufacturer's protocol.

The 2.0 kb PCR product was inserted into Sbf 1-digested pJyHi002A using an IN-FUSION® HD ADVANTAGE® PCR Cloning Kit according to the manufacturer's protocol. The reaction was composed of 100 ng of pJyHi002A, 50 ng of the 2.0 kb PCR product, and 2 µl of IN-FUSION® Enzyme (Clontech, Palo Alto, Calif., USA) in a 10 µl reaction volume. The reaction was incubated for 15 minutes at 50° C. Forty µl of TE buffer were added to the reaction and 2.5 µl were used to transform SOLOPACK® Gold Supercompetent cells according to the manufacturer's protocol. The DNA was added to the cells and incubated for 30 minutes on ice followed by a heat-shock at 42° C. for 30 seconds. Then SOC medium (250 µl) was added and incubated at 37° C. for 1 hour. The reaction was spread onto 2XYT plus ampicillin plates and incubated overnight at 37° C. Plasmid DNA was purified from several transformants using a BIOROBOT® 9600 and analyzed by DNA sequencing using a 3130XL Genetic Analyzer to identify a plasmid containing the desired insert. One clone containing the insert was identified and designated plasmid pJyHi002 (FIG. 1). Plasmid pJyHi002 was used to delete the peptaibol synthetase gene.

Example 4: Generation of Peptaibol Synthetase Gene Deleted *Trichoderma reesei* Strain

*Trichoderma reesei* strain AgJg115-104-7B1 was transformed as described in Example 2 with plasmid pJyHi002. Transformants were transferred from PDA plates supplemented with 1 M sucrose with sterile inoculation loops to new PDA plates and grown at 28° C. for 7 days.

Transformants of *Trichoderma reesei* strain AgJg115-104-7B1 containing the pJyHi002 deletion vector in the peptaibol synthetase locus, thereby deleting the peptaibol synthetase gene, were screened by fungal spore PCR using a PHIRE® Plant Direct PCR Kit (Thermo Fisher Scientific, Waltham, Mass., USA) and the primers shown below.
Forward Primer (1202690):

```
                                           (SEQ ID NO: 15)
5'-TGCCCCACGATATCTCTCCTTCTCC-3'
```

Reverse Primer (067947):

```
                                           (SEQ ID NO: 16)
5'-CTACATCGAAGCTGAAAGCACGAGA-3'
```

Spores from several transformants were collected using a 1 µl loop and transferred to 15 µl of dilution buffer provided by the Kit. The spore samples were incubated at room temperature for 3 minutes and centrifuged at 2000×g for one minute. One microliter of each spore sample was used as template. The reaction was composed of 1 µl of a spore suspension, 10 µl of 2× PHIRE® Plant PCR Buffer (Thermo Scientific, Waltham, Mass., USA), 0.5 µM primer 1202690, 0.5 µM primer 067947, 0.4 µl of PHIRE® Hot Start DNA Polymerase (Thermo Scientific, Waltham, Mass., USA), and 8.2 µl of water. The reaction was performed in an EPPENDORF® MASTERCYCLER® (Eppendorf AG, Hamburg, Germany) programmed for 1 cycle at 95° C. for 10 minutes; 35 cycles each at 95° C. for 30 seconds, 55° C. for 30 seconds, and 72° C. for 5 minutes 45 seconds; 1 cycle at 72° C. for 15 minutes; and a 4° C. hold. Since primer 1202690 is located upstream of the 5' flanking region and primer 067947 is located in the hpt marker, only transformants with the deletion cassette in the correct locus would yield a PCR product. PCR products were separated by 0.8% agarose gel electrophoresis using TBE buffer where a 3.7 kb fragment was observed indicating the deletion cassette was in the correct locus.

The transformants were then analyzed by Southern analysis according to the following procedure. Genomic DNA from each of the transformants was extracted using a MASTERPURE™ Yeast DNA Purification Kit (Epicentre, Madison, Wis., USA). Each transformant was cultivated in 25 ml of YP medium supplemented with 2% glucose in shake flasks for 72 hours with agitation at 200 rpm. The mycelia were collected from the cultures by filtration using Whatman 1 filter paper (Fisher Scientific, Pittsburgh, Pa., USA). The filter paper was inserted in a ceramic funnel placed into a sidearm flask. Under vacuum, the culture broth was filtered and rinsed with water and filtered again. The mycelia were transferred to 2 ml tubes and then dried overnight using a SPEEDVAC® concentrator (Thermo Fisher Scientific, Waltham, Mass., USA). The dried mycelia were crushed with a metal tool in each tube and approximately 50 µl of the dried mycelia were transferred to new tubes. Three hundred microliters of Yeast Cell Lysis Solution (Epicentre, Madison, Wis., USA) were added to each tube and vortexed. The samples were incubated at 65° C. for 20 minutes and then placed on ice for 5 minutes. One hundred fifty microliters of MPC Protein Precipitation Reagent (Epicentre, Madison, Wis., USA) were added to each tube and then the reactions were vortexed. The tubes were centrifuged for 10 minutes at 9300×g. The supernatants were transferred to microcentrifuge tubes followed by 0.5 ml of isopropanol, and then the tubes were centrifuged at 9300×g for 10 minutes. The supernatants were discarded and each of the pellets was washed with 0.5 ml of 70% ethanol. The ethanol was removed and discarded and the pellets were briefly dried using a SPEEDVAC® concentrator. Then the pellets were resuspended in 60 µl of TE buffer. The samples were incubated at 65° C. for about an hour to dissolve the pellet and then 0.3 µl of 100 mg/ml RNAse A (QIAGEN Inc., Valencia, Calif., USA) was added and the samples were incubated at 37° C. for an hour.

Approximately two micrograms of each genomic DNA sample were digested with 30 units of Bcl I and 10 units of Swa I for 16 hours. The digestions were subjected to 0.8% agarose gel electrophoresis using TAE buffer and blotted onto NYTRAN® SuperCharge blotting membrane (Schleicher & Schuell BioScience, Keene, N.H., USA) using a TURBOBLOTTER® (Schleicher & Schuell BioScience, Keene, N.H., USA) for approximately 12-16 hours following the manufacturer's recommendations. A PCR probe, hybridizing to the 5' flanking sequence of the peptaibol synthetase gene, was synthesized by incorporation of digoxigenin-11-dUTP by PCR using a PCR DIG Probe Synthesis Kit (Roche Molecular Biochemicals, Indianapolis, Ind., USA) according to the manufacturer's protocol and the following forward and reverse primers:
Forward Primer (1201259):

```
                                           (SEQ ID NO: 17)
5'-TAGCTAGCTGTCTTGGATGAATCGAGGTTG-3'
```

Reverse Primer (1202008):

```
                                           (SEQ ID NO: 18)
5'-TCGTCTTCATGAGCATGTTGTTGGG-3'
```

The amplification reaction (50 µl) was composed of 200 µm dNTP's, 0.5 µM primers, 3% DMSO, 5× PHUSION® HF Buffer with 1.5 mM $MgCl_2$, and 2 units of PHUSION® Hot Start High-Fidelity DNA Polymerase in a final volume of 50 µl. The amplification reaction was performed in a ROBOCYCLER® programmed for 1 cycle at 98° C. for 3 minutes; 35 cycles each at 98° C. for 10 seconds, 55° C. for 15 seconds, and 72° C. for 1.5 minutes; and 1 cycle at 72° C. for 10 minutes. PCR products were separated by 0.8% agarose gel electrophoresis using TBE buffer where a 0.5 kb fragment was excised from the gel and agarose was extracted using a MINELUTE® Gel Extraction Kit according to the manufacturer's protocol. The purified fragment was used as template for labelling with digoxygenin using a PCR DIG Probe Synthesis Kit. The reaction consisted of 5 µl of PCR buffer with $MgCl_2$ (Roche, Indianapolis, Ind., USA), 5 µl of PCR DIG probe synthesis mix which includes 200 µM dNTP (Roche Molecular Biochemicals, Indianapolis, Ind., USA), 1 µM forward primer 1201259, 1 µM reverse primer 1202008, 2.6 units of Enzyme mix, EXPAND® High Fidelity (Roche, Indianapolis, Ind., USA), and 100 µg of template DNA up to a volume of 50 µl. The amplification reaction was performed in a ROBOCYCLER® programmed for 1 cycle at 95° C. for 2 minutes; 30 cycles each at 95° C. for 30 seconds, 60° C. for 30 seconds, and 72° C. for 40 seconds; and 1 cycle at 72° C. for 10 minutes.

The incorporation of digoxygenin was confirmed by a molecular weight shift of the labelled probe which ran at approximately 0.5 kb. Hybridization was performed in DIG Easy Hyb buffer (Roche Molecular Biochemicals, Indianapolis, Ind., USA) at 42° C. for 15-17 hours. The membrane was then washed in 2×SSC plus 0.1% SDS for 5 minutes at room temperature followed by two washes in 0.5×SSC plus 0.1% SDS for 15 minutes each at 65° C. The probe-target hybrids were detected by a chemiluminescent assay (Roche Molecular Biochemicals, Indianapolis, Ind., USA) following the manufacturer's instructions Southern analysis indicated that several of the transformants harbored the deletion cassette in a single copy. One transformant containing the peptaibol synthase gene deletion was designated *Trichoderma reesei* JyHi002-26A.

Example 5: Construction of a Paracelsin Synthetase Gene Deletion Vector

The 5' flanking sequence of the *Trichoderma reesei* strain 981-O-8 paracelsin synthetase gene (Trirre2:23171; SEQ ID NO: 3 for the genomic DNA sequence and SEQ ID NO: 4 for the deduced amino acid sequence) was amplified from genomic DNA of *T. reesei* strain 981-O-8 using the gene-specific forward and reverse primers shown below.
Forward Primer (1201177):

(SEQ ID NO: 19)
5'-tcacatggtttaaacggcgcgccTACTACCTAGTAC

AGTGCTTATTTA-3'

Reverse Primer (1201178):

(SEQ ID NO: 20)
5'-agccttgttttgtcGTTTTTTCTCCAAATTTGTACAG

AATTATCT-3'

The underlined portion is an Asc I site introduced for cloning and the region in italics represents an introduced extension corresponding to a homologous region of the site of vector insertion necessary for cloning.

The amplification reaction was composed of 137 ng of *T. reesei* 981-O-8 genomic DNA, 200 µm dNTP's, 0.4 µM primers, 3% DMSO, 5× PHUSION® HF Buffer with 1.5 mM $MgCl_2$, and 2 units of PHUSION® Hot Start High-Fidelity DNA Polymerase in a final volume of 50 µl. The amplification reaction was performed in an ROBOCYCLER® programmed for 1 cycle at 98° C. for 3 minutes; 35 cycles each at 98° C. for 10 seconds, 55° C. for 30 seconds, and 72° C. for 1 minute; and 1 cycle at 72° C. for 10 minutes. PCR products were separated by 0.8% agarose gel electrophoresis using TBE buffer where a 2.0 kb PCR product was observed. The 2.0 kb PCR product was excised from the gel and purified using a MINELUTE® Gel Extraction Kit according to the manufacturer's protocol.

The 2.0 kb PCR product was inserted into Asc I-digested pJfyS1579-41-11 (WO 2011/075677) using an IN-FUSION® HD ADVANTAGE® PCR Cloning Kit according to the manufacturer's protocol. The reaction was composed of 200 ng of pJfyS1579-41-11, 100 ng of the PCR product, and 2 µl of IN-FUSION® HD Enzyme Premix in a 10 µl reaction volume. The reaction was incubated for 15 minutes at 50° C. Two and a half µl were used to transform SOLOPACK® Gold Supercompetent cells. The DNA was added to the cells and incubated for 30 minutes on ice followed by a heat-shock at 42° C. for 30 seconds. Then SOC medium (250 µl) was added and incubated at 37° C. for 1 hour. The reaction was spread onto 2XYT plus ampicillin plates and incubated overnight at 37° C. Plasmid DNA was purified from several transformants using a BIOROBOT® 9600 and analyzed by DNA sequencing using a 3130XL Genetic Analyzer to identify a plasmid containing the desired insert. One clone containing the insert was identified and designated plasmid pJyHi001A. Plasmid pJyHi001A was used to insert the 3' flank of the paracelsin synthetase gene.

The 3' paracelsin synthetase gene flanking sequence was amplified from *T. reesei* 981-O-8 genomic DNA using PHUSION® Hot Start High-Fidelity DNA Polymerase and the gene-specific forward and reverse primers shown below.
Forward Primer (1201179):

(SEQ ID NO: 21)
5'-cctagttggagtattcctgcaggAGGAATTGTGCCT

GGCTGTTGAGTT-3'

Reverse Primer (1201523):

(SEQ ID NO: 22)
5'-tggccatatttaaatcctgcagggtttaaacGCTTA

TCGATCCGGCATATCGCTCT-3'

The underlined portion is a Sbf I site introduced for cloning, the region in italics represents an introduced extension corresponding to a homologous region of the site of vector insertion necessary for cloning, and the bold portion is an introduced Pme I site for later removal of the bacterial propagation portion of the plasmid.

The amplification reaction was composed of 137 ng of *T. reesei* 981-O-8 genomic DNA, 200 µm dNTP's, 0.4 µM primers, 3% DMSO, 5× PHUSION® HF Buffer with 1.5 mM $MgCl_2$, and 2 units of PHUSION® Hot Start High-Fidelity DNA Polymerase in a final volume of 50 µl. The amplification reaction was performed in an ROBOCYCLER® programmed for 1 cycle at 98° C. for 3 minutes; 35 cycles each at 98° C. for 10 seconds, 55° C. for 30 seconds, and 72° C. for 1 minute; and 1 cycle at 72° C. for 10 minutes. PCR products were separated by 0.8% agarose gel electrophoresis using TBE buffer where a 2.0 kb fragment was excised from the gel and agarose was extracted using a NUCLEOSPIN® Extract II Kit according to the manufacturer's protocol.

Figure 2:
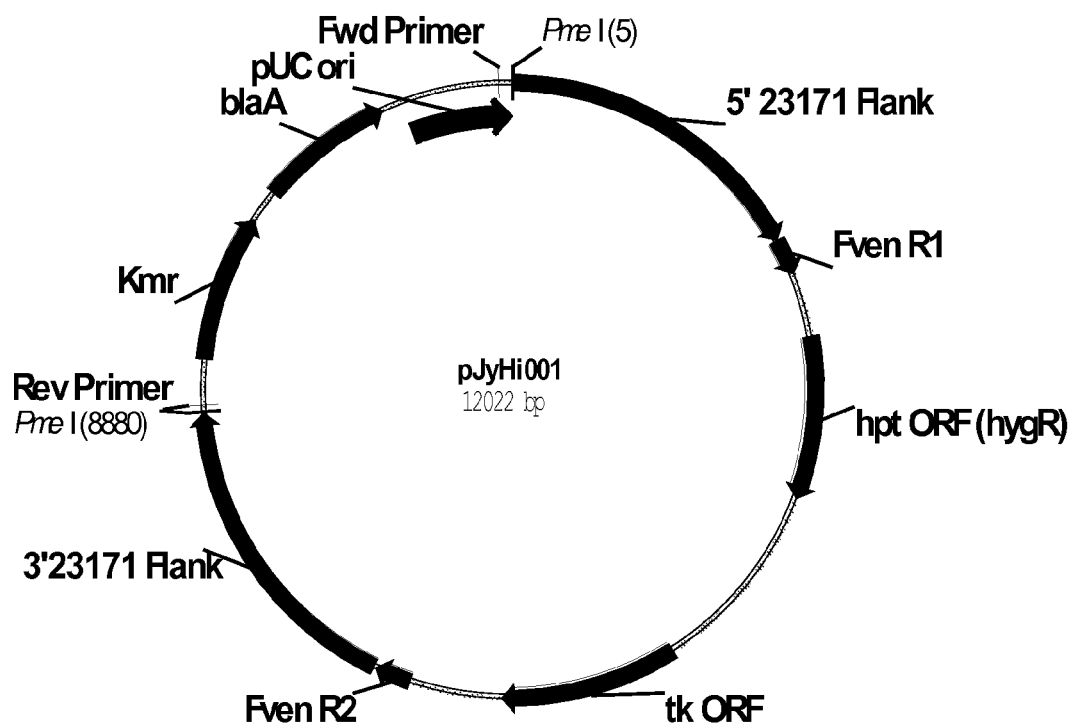
FIG. 2 shows a restriction map of pJyHi001.

The 2.0 kb PCR product was inserted into Sbf 1-digested pJyHi001A using an IN-FUSION® HD ADVANTAGE® PCR Cloning Kit according to the manufacturer's protocol. The reaction was composed of 200 ng of pJyHi001A, 50 ng of the 2.0 kb PCR product, and 2 µl of IN-FUSION® Enzyme in a 10 µl reaction volume. The reaction was incubated for 15 minutes at 50° C. Forty µl of TE buffer were added to the reaction and 2.5 µl were used to transform SOLOPACK® Gold Supercompetent cells. The DNA was added to the cells and incubated for 30 minutes on ice followed by a heat-shock at 42° C. for 30 seconds. Then SOC medium (250 µl) was added and incubated at 37° C. for 1 hour. The reaction was spread onto 2XYT plus ampicillin plates and incubated overnight at 37° C. Plasmid DNA was purified from several transformants using a BIOROBOT® 9600 and analyzed by DNA sequencing using a 3130XL Genetic Analyzer to identify a plasmid containing the desired insert. One clone containing the insert was identified and designated plasmid pJyHi001 (FIG. 2). Plasmid pJyHi001 was used to delete the paracelsin synthetase gene.

Example 6: Generation of Paracelsin Synthetase Gene Deleted *Trichoderma reesei* Strain

*Trichoderma reesei* strain AgJg115-104-7B1 was transformed as described in Example 2 with plasmid pJyHi001. Transformants were transferred from PDA plates supplemented with 1 M sucrose with sterile inoculation loops to new PDA plates and grown at 28° C. for 7 days.

Transformants of *Trichoderma reesei* strain AgJg115-104-7B1 containing the pJyHi001 deletion vector in the paracelsin synthetase locus, thereby deleting the paracelsin synthetase gene, were screened by fungal spore PCR using a PHIRE® Plant Direct PCR Kit and the primers shown below.

Forward Primer (1202687):

(SEQ ID NO: 23)
5'-TACCTTACAGGCCCTCCGCGAGCTA-3'

Reverse Primer (067947):

(SEQ ID NO: 24)
5'-CTACATCGAAGCTGAAAGCACGAGA-3'

Spores from several transformants were collected using a 1 µl loop and transferred to 15 µl of dilution buffer provided by the Kit. The spore samples were incubated at room temperature for 3 minutes and centrifuged at 2000×g for one minute. One microliter of each spore sample was used as template. The reaction was composed of 1 µl of a spore suspension, 10 µl of 2× PHIRE® Plant PCR Buffer, 0.5 µM primer 1202687, 0.5 µM primer 067947, 0.4 µl of PHIRE® Hot Start DNA Polymerase, and 8.2 µl of water. The reaction was performed in an EPPENDORF® MASTERCYCLER® programmed for 1 cycle at 98° C. for 5 minutes; 40 cycles each at 98° C. for 5 seconds and 72° C. for 1 minute 30 seconds; 1 cycle at 72° C. for 1 minute; and a 4° C. hold. Since primer 1202687 is located upstream of the 5' flanking region and primer 067947 is located in the hpt marker, only transformants with the deletion cassette in the correct locus would yield a PCR product. PCR products were separated by 0.8% agarose gel electrophoresis using TBE buffer where a 3.2 kb fragment was observed indicating the deletion cassette was in the correct locus.

The transformants were then analyzed by Southern analysis according to the following procedure. Genomic DNA from each of the transformants was extracted using a MASTERPURE™ Yeast DNA Purification Kit. Each transformant was cultivated in 25 ml of YP medium supplemented with 2% glucose in shake flasks for 72 hours with agitation at 200 rpm. The mycelia were collected from the cultures by filtration using Whatman 1 filter paper. The filter paper was inserted in a ceramic funnel placed into a sidearm flask. Under vacuum, the culture broth was filtered and rinsed with water and filtered again. The mycelia were transferred to 2 ml tubes and then dried overnight using a SPEEDVAC® concentrator. The dried mycelia were crushed with a metal tool in each tube and approximately 50 µl of the dried mycelia was transferred to new tubes. Three hundred microliters of Yeast Cell Lysis Solution were added to each tube and vortexed. The samples were incubated at 65° C. for 20 minutes and then placed on ice for 5 minutes. One hundred fifty microliters of MPC Protein Precipitation Reagent were added to each tube and then the reactions were vortexed. The tubes were centrifuged for 10 minutes at 9300×g. The supernatants were transferred to microcentrifuge tubes followed by 0.5 ml of isopropanol, and then the tubes were centrifuged at 9300×g for 10 minutes. The supernatants were discarded and each of the pellets was washed with 0.5 ml of 70% ethanol. The ethanol was removed and discarded and the pellets were briefly dried using a SPEEDVAC® concentrator. Then the pellets were resuspended in 60 µl of TE buffer. The samples were incubated at 65° C. for about an hour to dissolve the pellet and then 0.3 µl of 100 mg/ml RNAse A was added and the samples were incubated at 37° C. for an hour.

Approximately two micrograms of each genomic DNA sample were digested with 20 units of BsiW I for 6 hours. The digestions were subjected to 0.8% agarose gel electrophoresis using TAE buffer and blotted onto NYTRAN® SuperCharge blotting membrane using a TURBOBLOTTER® for approximately 12-16 hours following the manufacturer's recommendations. A PCR probe, hybridizing to the 5' flanking sequence of the paracelsin synthetase gene, was synthesized by incorporation of digoxigenin-11-dUTP by PCR using a PCR DIG Probe Synthesis Kit according to the manufacturer's protocol and the following forward and reverse primers:

Forward Primer (1201253):

(SEQ ID NO: 25)
5'-ATGTTGGAGCCTTGCCTCCAGAGTCCTCAC-3'

Reverse Primer (1202005):

(SEQ ID NO: 26)
5'-GGGTTCAGTCCAGAAGCAGAACCAGGATCA-3'

The amplification reaction (50 µl) was composed of 200 µm dNTP's, 0.5 µM primers, 3% DMSO, 5× PHUSION® HF Buffer with 1.5 mM MgCl$_2$, and 2 units of PHUSION® Hot Start High-Fidelity DNA Polymerase in a final volume of 50 µl. The amplification reaction was performed in a ROBOCYCLER® programmed for 1 cycle at 98° C. for 1 minute; 35 cycles each at 98° C. for 10 seconds, 55° C. for 30 seconds, and 72° C. for 15 seconds; and 1 cycle at 72° C. for 10 minutes. PCR products were separated by 0.8% agarose gel electrophoresis using TBE buffer where a 0.5 kb fragment was excised from the gel and agarose was extracted using a MINELUTE® Gel Extraction Kit. The purified fragment was used as template for labelling with digoxygenin using a PCR DIG Probe Synthesis Kit. The reaction consisted of 5 µl of PCR buffer with MgCl$_2$, 5 µl of PCR DIG probe synthesis mix which includes 200 µM dNTP, 1 µM forward primer 1201253, 1 µM reverse primer 1202005, 2.6 units of Enzyme mix, EXPAND® High Fidelity, and 100 µg of template DNA up to a volume of 50 µl. The amplification reaction was performed in a ROBOCYCLER® programmed for 1 cycle at 95° C. for 2 minutes; 30 cycles each at 95° C. for 30 seconds, 60° C. for 30 seconds, and 72° C. for 40 seconds; and 1 cycle at 72° C. for 10 minutes.

The incorporation of digoxygenin was confirmed by a molecular weight shift of the labelled probe which ran at approximately 0.5 kb. Hybridization was performed in DIG Easy Hyb buffer at 42° C. for 15-17 hours. The membrane was then washed in 2×SSC plus 0.1% SDS for 5 minutes at room temperature followed by two washes in 0.5×SSC plus 0.1% SDS for 15 minutes each at 65° C. The probe-target hybrids were detected by a chemiluminescent assay (Roche Molecular Biochemicals, Indianapolis, Ind., USA) following the manufacturer's instructions.

The transformants were also analyzed by PCR using PHUSION® Hot Start High-Fidelity DNA Polymerase and the primers shown below.
Forward Primer (1202689):

```
                                      (SEQ ID NO: 27)
5'-CAGATGAGCCCTACATGACGCCAGC-3'
```

Reverse Primer (1200592):

```
                                      (SEQ ID NO: 28)
5'-GGCTCCATACCGACGATATGC-3'
```

The amplification reaction was composed of 150 ng of genomic DNA, 200 µm dNTP's, 0.4 µM primers, 3% DMSO, 5× PHUSION® HF Buffer with 1.5 mM MgCl$_2$, and 2 units of PHUSION® Hot Start High-Fidelity DNA Polymerase in a final volume of 50 µl. The amplification reaction was performed in an ROBOCYCLER® programmed for 1 cycle at 98° C. for 30 seconds; 35 cycles each at 98° C. for 10 seconds, 70° C. for 30 seconds, and 72° C. for 2 minutes 18 seconds; and 1 cycle at 72° C. for 10 minutes. PCR products were separated by 0.8% agarose gel electrophoresis using TBE buffer where a 4.6 kb PCR product was expected if the paracelsin synthetase deletion cassette was integrated.

Both Southern and PCR analysis indicated that several of the transformants harbored the deletion cassette in a single copy. One transformant containing the paracelsin synthetase gene deletion was designated *Trichoderma reesei* JyHi001-4B.

The present invention is further described by the following numbered paragraphs:

[1] A mutant of a parent *Trichoderma* strain, comprising a polynucleotide encoding a heterologous polypeptide and one or more genes selected from the group consisting of a peptaibol synthetase gene, a paracelsin synthetase gene, a first terpene cyclase gene, a second terpene cyclase gene, and a third terpene cyclase gene, wherein one or more of the genes are modified rendering the mutant strain deficient in the production of one or more enzymes selected from the group consisting of a peptaibol synthetase, a paracelsin synthetase, a first terpene cyclase, a second terpene cyclase, and a third terpene cyclase compared to the parent *Trichoderma* strain when cultivated under identical conditions.

[2] The mutant of paragraph 1, which comprises a modification of the peptaibol synthetase gene.

[3] The mutant of paragraph 1 or 2, which comprises a modification of the paracelsin synthetase gene.

[4] The mutant of any of paragraphs 1-3, which comprises a modification of the first terpene cyclase gene.

[5] The mutant of any of paragraphs 1-4, which comprises a modification of the second terpene cyclase gene.

[6] The mutant of any of paragraphs 1-5, which comprises a modification of the third terpene cyclase gene.

[7] The mutant of paragraph 1-6, which comprises a modification of the peptaibol synthetase gene, the paracelsin synthetase gene, the first terpene cyclase gene, the second terpene cyclase gene, and the third terpene cyclase gene.

[8] The mutant of any of paragraphs 1-7, wherein the *Trichoderma* strain is selected from the group consisting of *Trichoderma harzianum, Trichoderma koningii, Trichoderma longibrachiatum, Trichoderma reesei*, and *Trichoderma viride*.

[9] The mutant of any of paragraphs 1-8, wherein the *Trichoderma* strain is *Trichoderma reesei*.

[10] The mutant of any of paragraphs 1-9, which produces at least 25% less of one or more of the enzymes selected from the group consisting of the peptaibol synthetase, the paracelsin synthetase, the first terpene cyclase, the second terpene cyclase, and the third terpene cyclase compared to the parent *Trichoderma* strain when cultivated under identical conditions.

[11] The mutant of any of paragraphs 1-10, which is completely deficient in one or more of the enzymes selected from the group consisting of the peptaibol synthetase, the paracelsin synthetase, the first terpene cyclase, the second terpene cyclase, and the third terpene cyclase compared to the parent *Trichoderma* strain when cultivated under identical conditions.

[12] The mutant of any of paragraphs 1-11, wherein the peptaibol synthetase gene encodes a polypeptide having peptaibol synthetase activity selected from the group consisting of: (a) a polypeptide comprising an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 2; (b) a polypeptide encoded by a polynucleotide that hybridizes under at least low stringency conditions, at least medium stringency conditions, at least medium-high stringency conditions, at least high stringency conditions, or at least very high stringency conditions with SEQ ID NO: 1 or the cDNA sequence thereof; or the full-length complement thereof; and (c) a polypeptide encoded by a polynucleotide comprising a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1 or the cDNA sequence thereof.

[13] The mutant of any of paragraphs 1-12, wherein the peptaibol synthetase gene encodes a polypeptide having peptaibol synthetase activity comprising or consisting of SEQ ID NO: 2.

[14] The mutant of any of paragraphs 1-13, wherein the paracelsin synthetase gene encodes a polypeptide having paracelsin synthetase activity selected from the group consisting of: (a) polypeptide comprising or consisting of an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4; (b) a polypeptide encoded by a polynucleotide that hybridizes under at least low stringency conditions, at least medium stringency conditions, at least medium-high stringency conditions, at least high stringency conditions, or at least very high stringency conditions with SEQ ID NO: 3 or the cDNA sequence thereof; or the full-length complement thereof; and (c) a polypeptide encoded by a polynucleotide comprising or consisting of a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3 or the cDNA sequence thereof.

[15] The mutant of any of paragraphs 1-14, wherein the paracelsin synthetase gene encodes a polypeptide having paracelsin synthetase activity comprising or consisting of SEQ ID NO: 4.

[16] The mutant of any of paragraphs 1-15, wherein the first terpene cyclase gene encodes a polypeptide having terpene cyclase activity selected from the group consisting of: (a) a polypeptide comprising an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 6; (b) a polypeptide encoded by a polynucleotide that hybridizes under at least low stringency conditions, at least medium stringency conditions, at least medium-high stringency conditions, at least high stringency conditions, or at least very high stringency conditions with SEQ ID NO: 5 or the genomic DNA sequence thereof; or the full-length complement thereof; and (c) a polypeptide encoded by a polynucleotide comprising a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 5 or the genomic DNA sequence thereof.

[17] The mutant of any of paragraphs 1-16, wherein the first terpene cyclase gene encodes a polypeptide having terpene cyclase activity comprising or consisting of SEQ ID NO: 6.

[18] The mutant of any of paragraphs 1-17, wherein the second terpene cyclase gene encodes a polypeptide having terpene cyclase activity selected from the group consisting of: (a) a polypeptide comprising or consisting of an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 8; (b) a polypeptide encoded by a polynucleotide that hybridizes under at least low stringency conditions, at least medium stringency conditions, at least medium-high stringency conditions, at least high stringency conditions, or at least very high stringency conditions with SEQ ID NO: 7 or the genomic DNA sequence thereof; or the full-length complement thereof; and (c) a polypeptide encoded by a polynucleotide comprising or consisting of a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 7 or the genomic DNA sequence thereof.

[19] The mutant of any of paragraphs 1-18, wherein the second terpene cyclase gene encodes a polypeptide having terpene cyclase activity comprising or consisting of SEQ ID NO: 8.

[20] The mutant of any of paragraphs 1-19, wherein the third terpene cyclase gene encodes a polypeptide having terpene cyclase activity selected from the group consisting of: (a) a polypeptide comprising an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10; (b) a polypeptide encoded by a polynucleotide that hybridizes under at least low stringency conditions, at least medium stringency conditions, at least medium-high stringency conditions, at least high stringency conditions, or at least very high stringency conditions with SEQ ID NO: 9 or the genomic DNA sequence thereof; or the full-length complement thereof; and (c) a polypeptide encoded by a polynucleotide comprising a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9 or the genomic DNA sequence thereof.

[21] The mutant of any of paragraphs 1-20, wherein the third terpene cyclase gene encodes a polypeptide having terpene cyclase activity comprising or consisting of SEQ ID NO: 10.

[22] A method of producing a heterologous polypeptide, comprising: cultivating a mutant of a parent *Trichoderma* strain in a medium for the production of the heterologous polypeptide, wherein the mutant strain comprises a polynucleotide encoding the heterologous polypeptide and one or more genes selected from the group consisting of a peptaibol synthetase gene, a paracelsin synthetase gene, a first terpene cyclase gene, a second terpene cyclase gene, and a third terpene cyclase gene, wherein one or more of the genes are modified rendering the mutant strain deficient in the production of one or more enzymes selected from the group consisting of a peptaibol synthetase, a paracelsin synthetase, a first terpene cyclase, a second terpene cyclase, and a third terpene cyclase compared to the parent *Trichoderma* strain when cultivated under identical conditions.

[23] The method of paragraph 22, further comprising recovering the heterologous polypeptide from the cultivation medium.

[24] The method of paragraph 22 or 23, wherein the mutant comprises a modification of the peptaibol synthetase gene.

[25] The method of any of paragraphs 22-24, wherein the mutant comprises a modification of the paracelsin synthetase gene.

[26] The method of any of paragraphs 22-25, wherein the mutant comprises a modification of the first terpene cyclase gene.

[27] The method of any of paragraphs 22-26, wherein the mutant comprises a modification of the second terpene cyclase gene.

[28] The method of any of paragraphs 22-27, wherein the mutant comprises a modification of the third terpene cyclase gene.

[29] The method of any of paragraphs 22-28, wherein the mutant comprises a modification of the peptaibol synthetase gene, the paracelsin synthetase gene, the first terpene cyclase gene, the second terpene cyclase gene, and the third terpene cyclase gene.

[30] The method of any of paragraphs 22-29, wherein the *Trichoderma* strain is selected from the group consisting of *Trichoderma harzianum*, *Trichoderma koningii*, *Trichoderma longibrachiatum*, *Trichoderma reesei*, and *Trichoderma viride*.

[31] The method of any of paragraphs 22-30, wherein the *Trichoderma* strain is *Trichoderma reesei*.

[32] The method of any of paragraphs 22-31, wherein the mutant strain produces at least 25% less of one or more of the enzymes selected from the group consisting of the peptaibol synthetase, the paracelsin synthetase, the first terpene cyclase, the second terpene cyclase, and the third terpene cyclase compared to the parent *Trichoderma* strain when cultivated under identical conditions.

[33] The method of any of paragraphs 22-32, wherein the mutant strain is completely deficient in one or more of the enzymes selected from the group consisting of the peptaibol synthetase, the paracelsin synthetase, the first terpene cyclase, the second terpene cyclase, and the third terpene cyclase compared to the parent *Trichoderma* strain when cultivated under identical conditions.

[34] The method of any of paragraphs 22-33, wherein the peptaibol synthetase gene encodes a polypeptide having peptaibol synthetase activity selected from the group consisting of: (a) a polypeptide comprising an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 2; (b) a polypeptide encoded by a polynucleotide that hybridizes under at least low stringency conditions, at least medium stringency conditions, at least medium-high stringency conditions, at least high stringency conditions, or at least very high stringency conditions with SEQ ID NO: 1 or the cDNA sequence thereof; or the full-length complement thereof; and (c) a polypeptide encoded by a polynucleotide comprising a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1 or the cDNA sequence thereof.

[35] The method of any of paragraphs 22-34, wherein the peptaibol synthetase gene encodes a polypeptide having peptaibol synthetase activity comprising or consisting of SEQ ID NO: 2.

[36] The method of any of paragraphs 22-35, wherein the paracelsin synthetase gene encodes a polypeptide having paracelsin synthetase activity selected from the group consisting of: (a) a polypeptide comprising or consisting of an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4; (b) a polypeptide encoded by a polynucleotide that hybridizes under at least low stringency conditions, at least medium stringency conditions, at least medium-high stringency conditions, high stringency conditions, or very high stringency conditions with SEQ ID NO: 3 or the cDNA sequence thereof; or the full-length complement thereof; and (c) a polypeptide encoded by a polynucleotide comprising or consisting of a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3 or the cDNA sequence thereof.

[37] The method of any of paragraphs 22-36, wherein the paracelsin synthetase gene encodes a polypeptide having paracelsin synthetase activity comprising or consisting of SEQ ID NO: 4.

[38] The method of any of paragraphs 22-37, wherein the first terpene cyclase gene encodes a polypeptide having terpene cyclase activity selected from the group consisting of: (a) a polypeptide comprising an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 6; (b) a polypeptide encoded by a polynucleotide that hybridizes under at least low stringency conditions, at least medium stringency conditions, at least medium-high stringency conditions, at least high stringency conditions, or at least very high stringency conditions with SEQ ID NO: 5 or the genomic DNA sequence thereof; or the full-length complement thereof; and (c) a polypeptide encoded by a polynucleotide comprising a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 5 or the genomic DNA sequence thereof.

[39] The method of any of paragraphs 22-38, wherein the first terpene cyclase gene encodes a polypeptide having terpene cyclase activity comprising or consisting of SEQ ID NO: 6.

[40] The method of any of paragraphs 22-39, wherein the second terpene cyclase gene encodes a polypeptide having terpene cyclase activity selected from the group consisting of: (a) a polypeptide comprising or consisting of an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 8; (b) a polypeptide encoded by a polynucleotide that hybridizes under at least low stringency conditions, at least medium stringency conditions, at least medium-high stringency conditions, at least high stringency conditions, or at least very high stringency conditions with SEQ ID NO: 7 or the genomic DNA sequence thereof; or the full-length complement thereof; and (c) a polypeptide encoded by a polynucleotide comprising or consisting of a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 7 or the genomic DNA sequence thereof.

[41] The method of any of paragraphs 22-40, wherein the second terpene cyclase gene encodes a polypeptide having terpene cyclase activity comprising or consisting of SEQ ID NO: 8.

[42] The method of any of paragraphs 22-41, wherein the third terpene cyclase gene encodes a polypeptide having terpene cyclase activity selected from the group consisting of: (a) a polypeptide comprising an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10; (b) a polypeptide encoded by a polynucleotide that hybridizes under at least low stringency conditions, at least medium stringency conditions, at least medium-high stringency conditions, at least high stringency conditions, or at least very high stringency conditions with SEQ ID NO: 9 or the genomic DNA sequence thereof; or the full-length complement thereof; and (c) a polypeptide encoded by a polynucleotide comprising a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9 or the genomic DNA sequence thereof.

[43] The method of any of paragraphs 22-42, wherein the third terpene cyclase gene encodes a polypeptide having terpene cyclase activity comprising or consisting of SEQ ID NO: 10.

[44] A method for obtaining a mutant of a parent *Trichoderma* strain, comprising: modifying one or more genes selected from the group consisting of a peptaibol synthetase gene, a paracelsin synthetase gene, a first terpene cyclase gene, a second terpene cyclase gene, and a third terpene cyclase gene; and identifying a mutant strain from step (a) wherein one or more of the genes are modified rendering the mutant strain deficient in the production of one or more of the enzymes selected from the group consisting of a peptaibol synthetase, a paracelsin synthetase, a first terpene cyclase, a second terpene cyclase, and a third terpene cyclase compared to the parent *Trichoderma* strain when cultivated under identical conditions.

[45] The method of paragraph 44, wherein the mutant comprises a modification of the peptaibol synthetase gene.

[46] The method of paragraph 44 or 45, wherein the mutant comprises a modification of the paracelsin synthetase gene.

[47] The method of any of paragraphs 44-46, wherein the mutant comprises a modification of the first terpene cyclase gene.

[48] The method of any of paragraphs 44-47, wherein the mutant comprises a modification of the second terpene cyclase gene.

[49] The method of any of paragraphs 44-48, wherein the mutant comprises a modification of the third terpene cyclase gene.

[50] The method of any of paragraphs 44-49, wherein the mutant comprises a modification of the peptaibol synthetase gene, the paracelsin synthetase gene, the first terpene cyclase gene, the second terpene cyclase gene, and the third terpene cyclase gene.

[51] The method of any of paragraphs 44-50, wherein the *Trichoderma* strain is selected from the group consisting of *Trichoderma harzianum*, *Trichoderma koningii*, *Trichoderma longibrachiatum*, *Trichoderma reesei*, and *Trichoderma viride*.

[52] The method of any of paragraphs 44-51, wherein the *Trichoderma* strain is *Trichoderma reesei*.

[53] The method of any of paragraphs 44-52, wherein the mutant strain produces at least 25% less of one or more of the enzymes selected from the group consisting of the peptaibol synthetase, the paracelsin synthetase, the first terpene cyclase, the second terpene cyclase, and the third terpene cyclase compared to the parent *Trichoderma* strain when cultivated under identical conditions.

[54] The method of any of paragraphs 44-53, wherein the mutant strain is completely deficient in one or more of the enzymes selected from the group consisting of the peptaibol synthetase, the paracelsin synthetase, the first terpene cyclase, the second terpene cyclase, and the third terpene cyclase compared to the parent *Trichoderma* strain when cultivated under identical conditions.

[55] The method of any of paragraphs 44-54, wherein the peptaibol synthetase gene encodes a polypeptide having peptaibol synthetase activity selected from the group consisting of: (a) a polypeptide comprising an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 2; (b) a polypeptide encoded by a polynucleotide that hybridizes under at least low stringency conditions, at least medium stringency conditions, at least medium-high stringency conditions, at least high stringency conditions, or at least very high stringency conditions with SEQ ID NO: 1 or the cDNA sequence thereof; or the full-length complement thereof; and (c) a polypeptide encoded by a polynucleotide comprising a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1 or the cDNA sequence thereof.

[56] The method of any of paragraphs 44-55, wherein the peptaibol synthetase gene encodes a polypeptide having peptaibol synthetase activity comprising or consisting of SEQ ID NO: 2.

[57] The method of any of paragraphs 44-56, wherein the paracelsin synthetase gene encodes a polypeptide having paracelsin synthetase activity selected from the group consisting of: (a) a polypeptide comprising or consisting of an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4; (b) a polypeptide encoded by a polynucleotide that hybridizes under at least low stringency conditions, at least medium stringency conditions, at least medium-high stringency conditions, at least high stringency conditions, or at least very high stringency conditions with SEQ ID NO: 3 or the cDNA sequence thereof; or the full-length complement thereof; and (c) a polypeptide encoded by a polynucleotide comprising or consisting of a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3 or the cDNA sequence thereof.

[58] The method of any of paragraphs 44-57, wherein the paracelsin synthetase gene encodes a polypeptide having paracelsin synthetase activity comprising or consisting of SEQ ID NO: 4.

[59] The method of any of paragraphs 44-58, wherein the first terpene cyclase gene encodes a polypeptide having terpene cyclase activity selected from the group consisting of: (a) a polypeptide comprising an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 6; (b) a polypeptide encoded by a polynucleotide that hybridizes under at least low stringency conditions, at least medium stringency conditions, at least medium-high stringency conditions, high stringency conditions, or very high stringency conditions with SEQ ID NO: 5 or the genomic DNA sequence thereof; or the full-length complement thereof; and (c) a polypeptide encoded by a polynucleotide comprising a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 5 or the genomic DNA sequence thereof.

[60] The method of any of paragraphs 44-59, wherein the first terpene cyclase gene encodes a polypeptide having terpene cyclase activity comprising or consisting of SEQ ID NO: 6.

[61] The method of any of paragraphs 44-60, wherein the second terpene cyclase gene encodes a polypeptide having terpene cyclase activity selected from the group consisting of: (a) a polypeptide comprising or consisting of an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 8; (b) a polypeptide encoded by a polynucleotide that hybridizes under at least low stringency conditions, at least medium stringency conditions, at least medium-high stringency conditions, at least high stringency conditions, or at least very high stringency conditions with SEQ ID NO: 7 or the genomic DNA sequence thereof; or the full-length complement thereof; and (c) a polypeptide encoded by a polynucleotide comprising or consisting of a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 7 or the genomic DNA sequence thereof.

[62] The method of any of paragraphs 44-61, wherein the second terpene cyclase gene encodes a polypeptide having terpene cyclase activity comprising or consisting of SEQ ID NO: 8.

[63] The method of any of paragraphs 44-62, wherein the third terpene cyclase gene encodes a polypeptide having terpene cyclase activity selected from the group consisting of: (a) a polypeptide comprising an amino acid sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10; (b) a polypeptide encoded by a polynucleotide that hybridizes under at least low stringency conditions, at least medium stringency conditions, at least medium-high stringency conditions, at least high stringency conditions, or at least very high stringency conditions with SEQ ID NO: 9 or the genomic DNA sequence thereof; or the full-length complement thereof; and (c) a polypeptide encoded by a polynucleotide comprising a nucleotide sequence having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9 or the genomic DNA sequence thereof.

[64] The method of any of paragraphs 44-63, wherein the third terpene cyclase gene encodes a polypeptide having terpene cyclase activity comprising or consisting of SEQ ID NO: 10.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties.

What is claimed is:

1. A method of producing a heterologous polypeptide, comprising: cultivating a mutant of a parent *Trichoderma reesei* strain in a medium for the production of the heterologous polypeptide, wherein the mutant strain comprises a polynucleotide encoding the heterologous polypeptide and a peptaibol synthetase gene and a paracelsin synthetase gene, wherein the peptaibol synthetase gene and the paracelsin synthetase gene are modified rendering the mutant strain deficient in the production of a peptaibol synthetase, and a paracelsin synthetase compared to the parent *Trichoderma reesei* strain when cultivated under identical conditions, wherein the heterologous polypeptide is selected from the group consisting of an acetylmannan esterase, acetylxylan esterase, aminopeptidase, alpha-amylase, arabinanase, arabinofuranosidase, carbohydrase, carboxypeptidase, catalase, cellobiohydrolase, cellulase, cellulose inducing protein, chitinase, coumaric acid esterase, cyclodextrin glycosyltransferase, cutinase, cyclodextrin glycosyltransferase, deoxyribonuclease, endoglucanase, esterase, expansin, feruloyl esterase, AA9 polypeptide, alpha-galactosidase, beta-galactosidase, glucocerebrosidase, glucose oxidase, alpha-glucosidase, beta-glucosidase, glucuronidase, glucuronoyl esterase, haloperoxidase, hemicellulase, invertase, isomerase, laccase, ligase, lipase, mannanase, mannosidase, mutanase, oxidase, pectinolytic enzyme, peroxidase, phospholipase, phytase, phenoloxidase, polyphenoloxidase, proteolytic enzyme, ribonuclease, swollenin, alpha-1,6-transglucosidase, transglutaminase, urokinase, xylanase, and beta-xylosidase.

2. The method of claim 1, further comprising recovering the heterologous polypeptide from the cultivation medium.

3. The method of claim 1, wherein the peptaibol synthetase gene encodes a polypeptide having peptaibol synthetase activity selected from the group consisting of: (a) a polypeptide comprising an amino acid sequence having at least 60% sequence identity to SEQ ID NO: 2; (b) a polypeptide encoded by a polynucleotide that hybridizes under at least low stringency conditions with SEQ ID NO: 1 or the cDNA sequence thereof; or the full-length complement thereof; (c) a polypeptide encoded by a polynucleotide comprising a nucleotide sequence having at least 60% sequence identity to SEQ ID NO: 1 or the cDNA sequence thereof; and (d) a polypeptide comprising or consisting of SEQ ID NO: 2.

4. The method of claim 1, wherein the paracelsin synthetase gene encodes a polypeptide having paracelsin synthetase activity selected from the group consisting of: (a) polypeptide comprising or consisting of an amino acid sequence having at least 60% sequence identity to SEQ ID NO: 4; (b) a polypeptide encoded by a polynucleotide that hybridizes under at least low stringency conditions with SEQ ID NO: 3 or the cDNA sequence thereof; or the full-length complement thereof; (c) a polypeptide encoded by a polynucleotide comprising or consisting of a nucleotide sequence having at least 60% sequence identity to SEQ ID NO: 3 or the cDNA sequence thereof; and (d) a polypeptide comprising or consisting of SEQ ID NO: 4.

* * * * *

SEQUENCE LISTING

```
<160> NUMBER OF SEQ ID NOS: 28

<210> SEQ ID NO 1
<211> LENGTH: 50787
<212> TYPE: DNA
<213> ORGANISM: Trichoderma reesei

<400> SEQUENCE: 1
cgatggggca acttgtgtct tatcaatcta atctagttgc tgcccatgag actctaaact      60
aactaggaac agaataagga aagcaaaaca tgtaagaagc cagtcaaata gactagaatg     120
aagaagaaac cgaacagaac aaataatacg agtaaaccga gacaaaggag aaaaagcacg     180
agaaaaaaag aaaagagtat caaaagtccc cgttcatcct gcaagcgtat gcacgcgtcg     240
aatcgtgcca tcccgctgta cattgccaaa tccttcctcc gaagactgga taaagccaat     300
cttcttcata taacgcacgt tgctgtggac agccttctgg gactgctcgc acacatgcgt     360
tcccgcattg gccagcgttg caaagtctcg cggcagaccg agctgaccga ggaagtgctg     420
caccggccac aggggatgcg tgttgccaac cgtattcatc gaggccaggg cgcgttcagt     480
ccattcttgc caggtaaccg gcttgcacgg ggcgtccagc tcggcattga cacggtccca     540
gaagtcggac attgtcattc ctcttgccag taggttgaat ggcttgatgg aatcggcaaa     600
gagtggaccg aggacgttcg atgcgactac gcccacgtct tgcatgacca tccagtgatc     660
agatgcttcc tcggggtagg cctggatcga tgccgccgta gagacgacac gccagacaaa     720
gtcgtcgacg ttggaaacgc cattctcggc ccttccgatg atacgaccgg gcttgactgt     780
cgacacgcgg ttctgtgtgc tggggaggct gttggccatc ttcgtgataa cagcttcaca     840
gacaaacttg gactgagagt agccattgga accactgaga agcgctgcgg aaacggctgg     900
gttctctgct ggatccgtaa aggcaccgcc cgacacaaag acaaacttgg gctggcacgg     960
cgatgtggcc gttgccatga gcaggtcgac agttgagttg acgttgggag cgctcagcgt    1020
ctcatagttg gcgttccagt tgacagatgc tccgttgtga atgatggcat cgatgttggc    1080
ttctgattct gacactccag agaggcgctg ccattgtgct tctgtaagac cgagacgcgt    1140
cttggagagg tcgccgagcc agatttccag cttcgcttca tcttcatcac gccaccagcc    1200
tgcaatcttg gccgtctctc tgattcgatc catccctgt gctagtgttt tcgagcggac    1260
atggacagct atcgacctga ttgctggatt ttcaaccaac cgtctgagaa tctcggtgcc    1320
gaggaaacca gtagctccgg tcaggaagac cgtggcttgg tcaggcagtg tagttgtggg    1380
attctcaagg agggctcgcg ggtgctgcat ccagggcgag ttggcaatct cgttaacctt    1440
ggccatgagg tcgacttgcg catctgggtg atctgcctct gcagcccgt tctccgcgct    1500 ctgggagatg aatttggcca tgttgctgat tgtcgtgtgc ttgctgttca acagggtgct    1560
cccgagggac actccaaact tgtcaaggac aagcctcgag acgttgacga tgcgaatgga    1620
gtcgccgccc agctggtaaa agttgtcgtc cacgctgatg cttctctgg gtagttcgag    1680 gacatctgcc cactctgctc ggagccagtg ttcgaggtct gttgagacgt cgcggaaagg    1740
```

```
tagacgctgg ccggccaaat gaactgccag gtcttccgaa gagagacctg ccgccgtctg   1800
caggagtgct tttctgtcaa gctttccgga ggtgttgagc ggcatggact cgacggcaat   1860
gaaatactgg ggaaccatat gactcggcaa gacagtagag aggtctgaag ccagctggga   1920
gaagagctcc tgcagcttgc tgctatgatt caatacccgt atgtttgacg catcgctggg   1980
gctcgtgtcg ctggagaagc taacaaaggc gacgagggac tcatgggtgt catgacggat   2040
cttgtcgaca accgcatgtt cgacatcatg tgattggagc ttaatttgat actcaatctc   2100
acccaactca atacgttggc ctcgaatctt gacctgcgta tccttgcggc cgaggtaatg   2160
aaggcttcca tccgggttat atcggactag atcgccagtc ttgtagaacc gtcgtcttcc   2220
aacgtcaacg gtatcaggaa gccacttgac gttacttatg aatgcgttgt ttgtcttttc   2280
ttcatcgtta atgtagccac gagacaaggc atctccttgt accagaagct cgccaacgca   2340
cccaatggga gtaagttcat cgtggttctc tgggttgaca acccaacaat gatgagcaaa   2400
cccacgacca atggtagtgg ctgatgtggc atcgtcagtg tatcgttgga ggcaggacgc   2460
gacgcaggtc tcagtaggtc cgtatgcgtt ccaaaggctg acgttctgac gccacgagtc   2520
cacaatgtcc ctggatggag cttcaccacc aagtatcagt gtcttcagcg agggtaccgt   2580
ctgtggatca agtgtcttcg cgaatgtcgg agtcagaagg gcagtgttga cgtgggcttg   2640
ccccatgaag cttgccgcat gctggatgcg ctccgcgtcg gtgggaacgc acacagtgcc   2700
tcctgatatc aaggtggcga agatttcgag gattgacgca tcaaacacat agctagagaa   2760
ttggaaggtc ctcgaatccc tagtaacatg gataactttg cacagcctga cgaggaagct   2820
ggatatggcc ctgtgttcga taatgacacc cttgggtttt ccggtcgaac cagaggtaaa   2880
caggatgtac atggctttgc tgggactgga cctggcagcc ttgagtttcc gtgaggcgga   2940
ggcccgacca tttggtcttg agaaaaaggc cgacgaaagc tcaatgttgt ttctggtcat   3000
gcccgcacac tctttggctg tactagggga tacgatcatg tactgggcac ttgtttcgtc   3060
gatcaaggct tgtcgtcgac tgagcggatg gctcgggtct agcggtagga agacaccgcc   3120
agccttgatg atgcccatca tgacaatgat ggaccacacg gatttctcat agcaaaaggg   3180
tacgatggct tccgatttga cgcccagttg gatgagatgc aaagctagct cgtccgataa   3240
ctgatcgact tctgcatatg tcatgctgcc ggccgttgaa tacagagcct ctttatgcgg   3300
tatctttgca acctgcctgg agaacaagtc atggacgcag gcttctatcg gtgcaatgtc   3360
gaagctgttc cacttggttg cctgctcagt atcccagggg ctcgcagggg agagttctga   3420
cagtgtcttg tcaccattct tctggagctg ctccagaacg taggagaact gctcggccag   3480
cgcgttcact tgagaatggt tgacgagatc agtttggtag atgatactca gctggacatc   3540
gttttcgagc agctgacact gcacgacaag cggatagctg aagtagtctc caaggagctc   3600
accttcagcg aagccttccg cagccacggg ataaaatacg gtggattcag tcccgctgtc   3660
agttggagtg aactgctgag ccggctgaac gatgaggagg ttggtaaagt tgcacgcctc   3720
cttggcgtca gtgctgattc ttgagatgtt cgccagcccg tactgctcgt gggcgaccat   3780
ctcaaaggct tgatcttgca ttgactgaag aagggcggaa atcttttgcc gcttgtcaag   3840
ctgaacgcgt ataggaaccg tagcaagagc gagaccaggc atttcgtcaa tgccctgcac   3900
ggcagcttgt cgcccagaca cggtcgtgcc gaagcaaatg tcatcgtcat gttcgtactg   3960
cgccagcaag atcgcccaag cagtgcgaat gatagtagct ctggtaatgg aggagcccga   4020
cggccgctgc aggtggactg tcttgtctag catgccggca atcttttgtg tggtagatga   4080
```

-continued

| | | | | |
|---|---|---|---|---|
| cggcttgttt | tgtgtagcca | ccacagggaa | cgtgccgcgt | tgacgccac gaagttgggt 4140 |
| agaccagtag | tcgcgggaat | tctcctggtc | gagctccatg | atgtacttga cgaagctggt 4200 |
| atacgggaga | atcgatggcg | gctctgtctg | ggagtacatg | gcgagcaacg ttcgtagcac 4260 |
| aatggacaac | gtccatccat | cgaagatggt | gtgatggatg | ttgactgcaa agtattgatc 4320 |
| gctgccctgc | ttgatgattg | caaatcgaca | cagcggcgac | ccgtaagtca tggtgcagtt 4380 |
| ctctttggat | aggaggaatg | aacgcagatc | ggtgtaagtg | gaaggccagt gaactggctc 4440 |
| ttgaatcaca | gcctggactg | cagtgcttcc | cgagaggacg | atccgtgtgc gaaggttgct 4500 |
| gcagtatcga | atagtttgct | cccaggccag | tttgaagcgg | tcaatatcca catgtggtgc 4560 |
| aagacgatag | acgtgttttg | cgatataggg | tcctggctgg | ctgatggtca aggccatcaa 4620 |
| tcctgtctga | aggtctgtgc | aagggtagat | atcttctatc | tcggccaagt ctgaaagttt 4680 |
| acactgcgtc | tgcacagccc | tcagagcgct | ctgtttatca | ctggtcggta tgaggccgaa 4740 |
| ccgttcgact | tcgtgagccg | tggatgacgg | agaagcgtcg | agctggatgg cctctgccat 4800 |
| cgccgagaga | cgcgggtagt | tgaatatcat | tgccaccgtg | aggccaatgt tctgtcgctg 4860 |
| ggcgaaggag | accagctcaa | tggcactgat | tgaatctccg | ccgagatgga ggaagctgtc 4920 |
| gtgcttgcca | atggctgata | catcgctgat | tttgagaact | tgggcccaaa ggctctgcag 4980 |
| ctctagctcc | atgggagttg | taggcgatac | gtagtcactg | gcgctcggtg taaagcgtag 5040 |
| gcggtcttga | acagagacac | ttcgaccaag | ctccacgaat | gagcggcgat tcaccttgcc 5100 |
| tgaggttgtc | tgttctggtt | tgccttcgaa | gatcaagtat | gaagaaggaa tcatgtacga 5160 |
| aggtaaactt | tcttccaagg | ccaaatcaag | acgagagatg | acgctttgag cctgttctga 5220 |
| aactgtgtgc | atcaactgaa | gagcctctga | ccgagacgtc | atctcgtcgt cggtataccca 5280 |
| caggaatgcc | agaaggatgt | cgtgggcatt | ctcatcatct | gccttgagga tgtcgacgat 5340 |
| gacggccatg | ttgtcaggca | gtagctcatg | gatgcgcgac | tcaatctcac cgagctcgac 5400 |
| acgctggccg | tgtagcttga | cttgagtatc | cttgcggccc | atgtagtcga acgtgccgtc 5460 |
| ggcgttgcgg | cggaccaaat | cgcctgtgcg | atacactctc | tttcttcctc ctggaagcca 5520 |
| atccacgtct | tccatccaac | tggcggcaac | ttcaggggctt | acgttcaagt agccgcgggc 5580 |
| aagcatagga | ccctcgataa | gaagctcgcc | aacacacccc | acaggcacaa gctgccgaag 5640 |
| attgcctggt | tcaacgaccc | agaaggcact | ggaaataggc | cttccaaggt tagtcgatcg 5700 |
| acccaatttg | ccaacggtgg | gattccacgc | gcagatggat | gcctccgccg gtccatacag 5760 |
| accatgtagg | tcgacgtgat | gcacccagcg | atccgcgcac | ttcttgctaa tggcctcacc 5820 |
| accaaggcac | accactttca | tatcagggat | atcagtagga | gataagaggt cggcaactgt 5880 |
| aggagtcagg | aagacccagt | tggcctttga | agaccgcatg | gcacccgcta ggtcgttcat 5940 |
| cctgtcgtgg | tcagatggga | tgcagagaca | ggctccgcgc | atcaaagaca cgagacagtc 6000 |
| gaggatgccg | acatcgaagg | tgtaggccga | aaattggaag | actcgtgtac ccggtccaat 6060 |
| gccaaggaga | ttgccgtatg | cgtcgctgga | cgagaccagg | tttctgtgtt cgatgaccat 6120 |
| gccctttggt | ttgcctgtcg | agccagaggt | aaacaggatc | acgctcgcat tatcgggtcg 6180 |
| tacattggaa | atcactggtt | tcgttgggct | agggagcccc | gaaagcatct cctcatcaac 6240 |
| aaagaagaca | tcgacgccaa | ggccctcgag | cactttgcca | ctagtcgggc tagacatagc 6300 |
| gagagtggca | tgcgtgtctt | caatgatgcc | cttcagtctg | gctgccggag cggcagggtc 6360 |
| aagagggaca | aaagcgccgc | cggccatttc | gatggccacc | atggcaataa cggcccaagc 6420 |
| tgacttgggg | aagcacagaa | gaaccagggt | ttcaggacca | actccgcgtt cctgtaactc 6480 |

```
gattgccaag cgcgaagcaa atgttcctac ctgggagtag gtgagttctg catcccacga   6540
cgcaatggca acatcatctg gtcgagactg gatgttttct tgaatggccc agtgggtaca   6600
agtgttgcta gaaggctcca aacggctgga ctcgactgct tgttggaggt cccaggggct   6660
gagaagtgag actgagctca gaggcgcatt cactgcttcc ttcgccacga gttgttgaat   6720
gacgtggttc aaatgcgatg acagagcaat gacccgagct tccgacagca ctgtagaatc   6780
gtagaaaaag ttcagtctga actcttcagg atagagactg ctgatgatca cgaggggata   6840
gttgaagtag ccgtccatgg agtccatcgt gagatcgctt gcggacgcgt caacaacgaa   6900
gatactctcg ccatgatcgt ctccagctcc atgtgcaggg gctgacaa ctaagagact     6960 cgagaaatcg caaacctccc tcgcttcagc gctgaccttg gcaatattct gcaagccata   7020
ttgctcgtac gggatcatgg atgtgctcag gctctgaatg tcttggacaa atcttgatat   7080
aggcgcctga ttgtctagcc gggctctgat ggggacggtg gcaatcattg gccagatat    7140 catctcagct cctggaatcg gggcttgacg gcctgaaacc gtcgctccga acactgcctc   7200
gctactgtcg cagtatcggg caaggacaat agcccacgcg gctcgaagaa tcgacgcttg   7260
cgtgatagaa gtcttcatgg atctggagaa tggaattgtt gagctgaacc gcttgctttc   7320
catgatgcct ggggcagttc ggcgagatgg gaacgaagcg cgctttgcac cagccagttc   7380
ttgtgtccag tacgatgcga ccttgtcatt atcgagctct ttcacggatt tgatgaaaga   7440
ggagaaaggt cggacttcgg gtgcgtacat gccctggtaa gctgagaaca gcgctgtgaa   7500
catgactttc atggtccaac catcgtaaat ggagtggtgg gctgaccaca caaaatagtt   7560
ttcacccttc tcagacacga tagagtacca gcagagagga gttccgtaac ccatcttcag   7620
attgcgcgac gatccagtca ttgactcgag ggtttcattg tcggcaggca cccattgact   7680
gtcacgatca aggactatct gcgtcatgac gccatccaag acgacaatcc gggttcgaag   7740
attgtcacaa atatcaacca ccgagtccca cgcagccctg aacatgggta tgtccacaaa   7800
gctggagaga tgatgggcat aggtagcaac ataggaccct ggctgcttgg cggtaagggc   7860
tatgaggcct tcttgcagag aactgcatgg atacgcatcc gtgatggttc ggtccttcgc   7920
caggccgcac aattttcggg cgtcctcccc gagtacaagg cgcttctgtg cttcaggcaa   7980
cagactgaat ggctctggag gagagtctgc tggctccata ccatcttgac tcagaacagc   8040
ctttgcggct acagccagta gtctgggatc atcaaacaca tcctgtacag tcagagtaat   8100
gccctcttcc tttgctgttg agacaaggta tatagccatt atcgaatcgc ctcccagctg   8160
gaagaaggtg tcatctctgc cgatggactc cattggcaag ttcatgatct cagcccagat   8220
caactgcagg cgctgctcca tttcggtctc tggctgccgt ttttcgctgt gtaacaacga   8280
atacatcgct agctgatccc tatcgagagt cgagaggtgc gtctgcagaa gctttctatc   8340
cagcttggtc gaagcaatga acggcatgaa ggcacatggg atgaacaagg tcgggatcat   8400
gtatcgggga agggcaatac ccaattcccc aacaagggca atcagctggt tctgtaagct   8460
ctcgtcggtg gataagaata gagtctccga agcatcggtc ttgacgccgg ctgtcttcgt   8520
ttcgtctgtg aagcaaatgt aggcaacaag actggagccg ttgtcgcccc tgacgacgtc   8580
aacagccact tgacgcacac cgatcagtga ttgttggata ttgtattcga tttcactcaa   8640
ttcaacacgc aatcctcgaa tcttgatctg cgtatccttg cgcgttgaaa actcgattgt   8700
tccgtcggca ttataccgac atagatcgcc tgacttgtag aatctgttcc agtgtgattc   8760
gtctggacgg ggagcccact cggcagcggg cagaatgctg gtattggtgc gttccgggtc   8820
```

```
tgcgagatat tcctgcaaca gagtcgggcc ttgaataacg acttccccaa ccgtgccaat    8880
aggggcaaga aacccagaat cgggatcgac aatccagcaa aagccgccga cagggcgtcc    8940
cacagtgaga ggcgactcgt caactgactt ccactcatgt agagtactga agacacaagt    9000
ctcagcaggt ccccagccgt tgatgagacg acgaaccttt ccgaaccagg ctgtcaacac    9060
atcgcgagga actgcctcgc ctgcaagcag taggacttcc agcccaggga catcgtccgg    9120
gtttagggtc cgcacaaacg aaggcgtcaa gaaagcccag ttgacgttca tgtcctgcat    9180
aaacttggac aaatcattca tcctagcatg ctcggatgga atgcatagac aggcgcctgt    9240
gataagggga gccacaattt ctccaatcga caagtcgaaa acgaaggctg caaactgtag    9300
catacgcact tccggtccaa gtctgagcct cttggcaatc gccttctggc ttgtacacac    9360
ggacccatgt tgcattacga ggccctttgg cgtgccggta ctgccagagg taaagaggac    9420
gtaggcaata tcgcctgaag aggctctctc tgtagggccc tgtcggctgt tgacctgttt    9480
ctgaagctgc ttgtcgaatt caggcgtaat ctggatcgcg gactcgacga gggtggagca    9540
aagatcgcta ttgtctggcg agcagagtgc aaacttagcc cgcgtttgac tgacgacttg    9600
ttgaagacgc tgtaggggt gtgatgggtc caagggaacc caggccgcgc cagttttgtt    9660
gatagccagg atagatacaa aatgccagac tgacttctca aagcatacgt gtatcaagtc    9720
gtttgtcttg atctcgtgtg tttgtaccag gtaatttgca agtcggttag ccgcctggtt    9780
cagctgggca taactgaagt caccgtccca agagcggatg ccatggcat caggacgttg    9840
agcagcctga tcttcaacaa gggtgtggaa acaggaatca acgatctcgg gggtgtccac    9900
attgaacttg cgtgattgtt cgatatccca ctggagacg agagacat cacgtagcat    9960
ctggctgggc tttgactcag ccaactgggc aatcacatgc ttcagctgct cggacaatgc    10020
gacgatttgc tgctccgcaa tgcagtgagg gttgtagatc aggacgattc tcatgaagtc    10080
gtcgctcaga tgggcttgga ggacaagcgg atatgagaaa tagttctgca ttccatctgc    10140
gctgtcatct gtgtcctcga caccaaccag aagagcatct tcgccagtgt tttccagatg    10200
tgaaagcatc tttagaggtt gaataaccaa taggctggta aagtcacaag cttcgtcggc    10260
gtctggattg agcttgcgaa tactctgcag gccaaattgt tcgaaaggaa tcgcgtcgct    10320
tgctcgtgtt tggacttcct ccaggaactt tgtcgtcggt tgatcatggt caagatggat    10380
ccggacgggt atagttgcaa tcactggccc aggcatttgt gtcaagcctg ggagcgatgc    10440
ttggcgccct gaaaccgtcg cgccaaagca aacgtcggtg ctatcgcaat agcgagcaag    10500
gactagtgcc caagcggcac gcacaattgt agctgttgtg atggtggtgt tgctcttgga    10560
aagttcaagt tccgctgtca ttgtacgcga agcttcgggc ttgcttgtag acgtaattgg    10620
aacgagggg aatgtcgcct ttcgagcgtt ctcaagctgc cttgcccaga atcgccggc    10680
ggcctcgtga tcgagttcca ttgtgtactt gatgaagtgt gagtaaggaa ccgtggtggc    10740
aggctcgaga cccttgtagg ctcggtggaa ttcctccaag atgatagaca atgtccagcc    10800
atcatagacg gcgtgatgaa ggttgaaaga gaaatagact tcgtcaccgt ccttgaagat    10860
ggcagatcgg cagagccgtg agccgtaacc catttccatg gttcgggtct gctgcaaata    10920
gctccgaagg gtcattcgtt ctgtggaatc ccagacagta tctcccttca caacgacctg    10980
gagggagata gcacccagtc ggatgattct ggtacgcagg ttagggaaac tattgacaat    11040
ctgttcccat gctgccttca gaaggctaac atccacatga cacgggatgc gatagttgta    11100
cttggcaatg tatgatccag gctgcttaac agccaatgcc atcaaacctt cttgcatctt    11160
ggaacacgga tagcaatctt caaccgccat gtctcgagaa agttcgaggc cgaactcttc    11220
```

```
agcgctttcg gtgatcatat cgcgctgtgg ttcatcaaga agagcaaatg gttcgatggg    11280
ggtaaaagct tgagagcttc catcactgat gaaagaagct ttcgatgcaa tagacaacag    11340
tcgaccgtct tcgaaaatct gactgactgt gagcgcgact ccttggtcac gagcagcagc    11400
aacgagccgg atagccgcaa tggaatcacc gccaatactc aggaagctgt cgtcacgacc    11460
aatcgtttcc ataggaatac ccaagacatc agcccagatg gcctgtagct tgccctccat    11520
aggggtttgc ggcatggtct ttttgctatt caccagtgaa taggcggcca gctggtcctt    11580
cgtaaggctt gatgtaagtc ctcgcaacgt ctttcgatcc agcttgccag acgtggcagt    11640
tggcatatgc ttgcattgaa tgaagagggc gggaaccatg tattctggaa gcagaacctt    11700
gagttcgcca accatggttg cgagacgctg ctgtgtttct tctcccaaga ccatgaagat    11760
atcatcgaga gaattactcg agacgtcgac agtggcatcg ccgaagcaaa agtaagcaac    11820
caggtttgag actgagccag acttgaagac atcaaccacg acttgatggg cttcggggaa    11880
ggtctccttg atgcgatatt caacttcacc caactccaca cgaaggccgc gaattttaac    11940
ttgcgtatcc tttcgcgagt agaacctgat agtgccgtca gggttgtaag aacaaagatc    12000
cccggacttg taaaagcgag tccagtgctg cgtatcagga tacattgccc agtcaggtcg    12060
accttccagg attgcagcct tgctcttctc ggcgtcgccc agatactcgc gcaacaacgt    12120
gggaccctgc acaataagct caccaacagt tccagtcggc gcaagtttcc atggatcttc    12180
tggatcaaca atccagcaga acccacccac tggctttcca atcgtcaaag ctgactcttc    12240
tgaagatctc cattcgtgca ttgcgctcat gacgcatgtc tccgacgggc cccaagcatt    12300
gaagaatctc acttttccaa tccattcttc aaatagggcg cgtgggacag cctcgccacc    12360
aagggctacc aattctacac ttggcacatc ctcaggcctc aaggtctgta ggaaggacgg    12420
ggtaaggaat aaccaattga tgccggtgtc gttaacgtac tccttcagtc tgttcatacg    12480
gtcttcttcg gacggaatgc acacacaggc accgtacatc atggctgcga gcatctcgct    12540
gatcgaatag tcaaacacat aggcagcgaa ttgcaggatc ttgacacttg gcgtgaaccc    12600
gaagcgtttg ccagcagcca tctgactcgt acagagggca ccgtgttcca tgattaggcc    12660
tttgggtaca cctgtgcttc cagaagtgaa caagacatag cgcgcgtgct tcggagtgac    12720
taaaacgtcc ggaccttgag agctactgaa gcccttctta cagagatcag aatccaggga    12780
agaagagacg acaacaacag atgtaactaa ttgggagcat ctttccacat tgtcctgaga    12840
cgccagtgca actcgcgcct ttgtctgggc tgttacctgt tgatggcgtt gcagagggtg    12900
tgagggatcg atagggaccc aagcggcgcc gactttgttg attgccaaga tggctacagc    12960
ataccaggcc gatttggtaa agcacacttg gaccaggtcg tgagctttga ctccgatgtc    13020
catgactaga tgatgagcca gcctgttggc tgctttgttc aactcgtcat aggtaagcac    13080
cttatcccag cccagtatgg caacagcgtc tggacgtatc tctgcctggc actcaatgag    13140
atcgtgcaag caagagtcaa tgatttccgg tggatcttcc ctgttggcct tttctgcgaa    13200
tttgacatcc cagtcgcaag tcagagacag atctccaagc agtgactgcg gcttggcaat    13260
tagctgcctc atgatgtgtt ccatctgatg agatatggcc agaacctgag actctggcaa    13320
gacgttcgag tcatagatga acatcaactt gatgtcttcg cccatgacgt gcccctggat    13380
gacgagaggg tacgtgaagt aattctgcaa agagctttcc tcttgtgact caacctcgac    13440
gggctgaagc agtgcatgct caccattgat caagtgctgc atcggttgaa caaccaacaa    13500
gctcgagaag ttgcacacct cttgagccct aggactgatt ttctggattt cctggaggcc    13560
```

-continued

```
aaactgctcg tagggaatca tcttcagggc ctggctttgt atggtgtcaa gatagtccga    13620
aacgctccgg tgcttgtcta atcggacacg gataggcacg gtagcaacag caggcccagg    13680
catatcgggc aatcctggaa caggggcttg gcggccagag acagtagcac cgaagcagac    13740
atcatccgtc tcacagtatc ttgcgaggag cattgcccat gcagcccgaa tgaccgtagc    13800
tttggtggcc gacaagtcgg tcatattggg caactgcata cctcgctcca ggcttttgct    13860
agagttcgag ctggtctttg agagcggagg atacgcggcc cggcttgcac cgtcaagctg    13920 tgcccccccaa tagtttcttg tctcttcgtg attgaggttg ccgacgtatg caacgaacct    13980
gttgtacgat tgtagagacg gcggggaccg gccatcatac attgaatgaa ggacgtccat    14040
catgagacgc attgtccaac cgtcaaagat ggagtggtgc aaagcccaca caaagtagac    14100
ctcgtcccca tccatgacaa tcgcacctcg actcaatcgc gagccataag ccatgtttga    14160
cgaacctaga gcgtgcatgt acgactgcag ctcctgtcct tgtacttcat cccatgcgaa    14220
atcattctca aggacgagtt ggacggtttg gctcccgacc ataacaactc ttgtgcgcaa    14280
gttgtcgcag agttttacca tatcttcaaa tgcagatcgg aacctcaaaa cgtcgacagt    14340
acgaccgagg cggtagacga attttgcaac atagcttcca ggctgtttct ctgtaagagc    14400
cagaagacct tcctgcatct tggtcgaagg gtaagcatct cgaaggacaa catcatcagc    14460
caagtggtaa ttttgtcgca aatcttggct agaaagtaat tgctgggttt gttcatcgat    14520
gaggccaaat tggggganttt ctgcagcttg accgcttctc gtgaggctga tcgccttcgc    14580
ggcaacggct aatagcctgg ggtcatcaaa gatatccgcc accgaaagcc caatgttgga    14640
gttctgagca gcagtgacga agtgaatggc gatgattgaa tcgccaccaa tctgcaggaa    14700
gctgtcatcc cgaccaatgg atgtagcagg gacgttcagt agctcggccc aaatgagctg    14760
tatccgtttt tccatctccg tctccggacc ctgcttctcc aggtcggaga gcgtatactt    14820
ggatagatcc tcaaggctta gagaagacgc catagccttc agcttcttgc gatctagctt    14880
gtcagaggtt gtggatggaa ggtacttgca agggacgaat attgacggga ccatataggg    14940
gggtagagta gccttcagac gtccttccaa ggctctgaaa gccttctgca tgcgagaggt    15000
cggttgtagg aacacttcac cgctcgatcc actactctca atgtctggct gctcgattcc    15060
agacttgaag ctgacaaaag ctatgagact tgcgccagta gtgctcttca agacttcaac    15120
agcagcctcg cagacatcat ccagcttgtc gcggatatga tgctcaatat ctccaatctc    15180
gacccggaag ccgcgtatct tgacttgcgt atccctgcgg ccaccgaaga caaggttgcc    15240
atcagagttg tagaagcata gatcaccagt tcggtagagt cggttccagt gttgggcatc    15300
tggttgaggc gcccagctgg gtctgggtat aagggcagcc tttgttcgtt cgggctcatc    15360
cagatattca cgtagtagtg ttgggccctg gatagccacc tctcccattg tgccgaatgg    15420
cgcaagggac tgaggcatct caggatcgac aatccagcag aagccgccca ccggacggcc    15480
gataaccagc gacgaagtct cagcagacgt ccactcatgc acagcactga tgacacaggc    15540
ctctgcaggg ccccaggcgt tgatcagtcg cacttttcca aaccatgtga ggcacaagtc    15600 ctggggaca gcttcaccac ctagtaaaag gagttctaga ctagggacgt ctgcgggctg    15660
gattgtgcgg gcgaatacgg gtgtgaggaa agcccaatta atttgacgct ttcgaatgaa    15720
agtcgcaata ttctccatgc gttctcggtc cgagggaatg caaacacaag ctccggagat    15780
cagtggtcca atagattctc cgagagacat gtcgaaaacg taggaagcaa attgcatgat    15840
tcgcacactc gaggtcatct tgagtctggt agcaagagcc gtttggctgg tgctgagtga    15900
ttggtgctct ataacaaaac cctttggcgt tccagtactg ccagaggtaa acagaatgta    15960
```

```
ggcaggactg cgaggcgata ttgcgagcgg tttgaatggt tctgacacag aacggcccag    16020
ttgttgatcc agctcagccg tgacttcgac cacgtctgtg acgagtttgg cacagagttc    16080
ggcattactg ggtgatacca acgccaggcg agccttggtc tggagaacaa tctggcgcaa    16140
acgcgcttcg ggctgggatg gctccaaggg aacccaagca gctccagcct tgttgatcgc    16200
gaatattgac acgaaatgcc aagcagactt cccaaagcag acactgacaa atcaccagg    16260 cttgacacca tgactgtgga tgagatggta tgctagtctg tccgaagcgg cagccaagtc    16320
gctgtacgtg agttccgcat cgcatgccaa gattgctggt gcttgtgggg agatctgagc    16380
ttgtttgtca atcaactcat gcacgcatga actgataatc tccggcacct cgctattgac    16440
agctaaagcc aattcaaggt cgtgagatga agcgatcaag atagactcga gggaagtgcc    16500
agcgcccgaa gcgagctggt gaatgacatg gccaagctgt tcggataagg cttgaacctg    16560
gcgctctgtc aaaacatttc gatcgtatgc cactgcaatt tttaccttat caccatacaa    16620
gtggccttgt acaatcaggg gatagttgaa gaagttgttc agggagtcag agagaccttc    16680
ggtcacctct gcagcagaaa gcagttcctt gctctcctcg ctgttggcaa tgtggcgtat    16740
gggctggacg accagcaaac ttgagaactg gcacgcttca taggcgtctc tgctgagttt    16800
cgtgatgttc tgtagaccga attgttcgta cggaatcatt cctactgcgc cctgttggac    16860
gctctgtaag aaatctgata cgggctgttg acgatccagt ctgactcgta caggaaccgt    16920
cgcaatcacc ggccctacca tgtcaacgat tccaggaacg ggagcctgac ggcctgaggt    16980
ggcgatgccg aagcatacat cgtcagtgtc acaatatctc gcaaggacaa tggcccaggc    17040
ggatcgaatg acggttgcta acgtcacatt gagtttgctg gcatcgacaa agccaattgg    17100
tgtttccaaa acacaagtag caactacttt gtcgtgggtg ttatgcagcg aaggcaattg    17160
tgctggcttg gcatcatgta gagcatctct ccaataagca gaggcagcct cctcatctat    17220
ctgcaaaaga tactggataa aacgagagta aggagtcaag acaggagttt caaggccgaa    17280
gtacgctttg tgcaagatgc ccaggataac ttgtgtggac aggccgtcga aaactgtatg    17340
atgcatggcc cagaaaaaga acacactccg ctgctcgtct tcaacaaacg caaattgaca    17400
caatgctgaa ccgtatgtca ttttgatcgt ctgagcatat cgtagtacag cttgtagatc    17460
gtgatacggt agcggctctg aactcgactc gggattcagt acgatttgga atgtcgactt    17520
ggccgatgtg ttgatgattc tgctgcgcaa actggcacaa atatgcatag tctgcttcca    17580
agctgacttg aaacgagcca catcgacgtg gtcaggaagg cggtagagat atttggcgac    17640
gtaactgcca ggttgcttga cggataacgc cattaagccc tcttgaagct tggtacaagg    17700
gtaagagtct tcgatgatag cactgtcagg cagcgagcac tgatctcggg cttcagccag    17760
gatggtactg gactcccctg ccggaagcat atcgaacggc cggatctcac tgtatacagt    17820
caactcatcc tcgacgatgg cgctggccat ttgctcgaga cgaggagatt gaaaaatcgt    17880
cgcgactgtc agatcgagac cttgcagttg ggctttcgac accagctgaa tagcagatat    17940
cgaatcgcca ccgaggcgta agaagctgtc gttcttgcaa atatcatcag gttcaatacg    18000
gagaatctgt gcccatagct cgcgtaactt gaattccatg ggtgtagttg ggagcacgcg    18060
gaagctggta tcaggagcaa agcgcagacg ctcttgagca gtgatatgct gggcttggcc    18120
agtcaaagac cggcgattga tcttgcccgt tgtggtttgc tccggcttcc cactgaagag    18180
gaggtaagag gacggaatca tgtatgaggg caaaattgtg ttcagagacg tatccaagtg    18240
caaaaccatg gctcgcgctt catccgatac ggtgtccacg agacgggctg gcgaggcaga    18300
```

```
gcttccatca gagttccaga tgaaagccaa caaggtagcc ggggcgtcat tgtctttaac   18360
aacgtccaca atcgcagcca tgttttgcgg caagaactcc tgaattcggg tctcaatctc   18420
tcccagctcg acacgctgac cgtgaagctt aacctgggta tctttgcggc cgatgtagtc   18480
gaacgtacca tccgcattcc gcctgacgag atcaccggtt cgataagctc tcctaggtcg   18540
gttgtcacca ggaagccagt caacgccttc aagccagttg gcggcgacct cggccgtcac   18600
attcagatac ccccgagcaa gcattggacc ctcgataaga agttcaccaa tacagccgat   18660
tggcaccagt gatttcgggt cattgacatt aacaacccaa aacgcactgg atatgggtg    18720 tccgagattc gtggggcgcc ctgatctccc tactaccgag ttccatgcac agatagacgc   18780
ttcggctggg ccatagaggc catgcaggct cacatggcca acccacctgt cagcacactt   18840
cttggtaatg gcttcgccac ccagacagac agtcttcaaa gtagggactt ccaccgggtt   18900
gaggaggtct gcaacagttg gcgtgaggaa tacccaatcg gctttagacg cagtaatggc   18960
ggccgcaagg ttgttcagac ggtcatgatc ggatggaatg cagatgcagg cacctctcat   19020
cagcgtcaca agacaatcca ggacaccaac gtcgaacgtg tatgcggaga attgaacac    19080 ccgggtgccg gcttcaatct tcaaatcggc accgtaggca tcgctcgagg aacagatact   19140
tctgtgctca ataatcatgc cctttggctt gccagtgcta ccagatgtaa agaggatgac   19200
gctggcgttg gtaggcctag cctctgaccg caggtcgaac tcggctggca gctcggagat   19260
actttgatcg tccactgtaa cagctttcat gccaagtgac tgaagtaatc cttgacactc   19320
tgagctggtt atagccagcg tagctcccgt atcctggaga attccttgta atctggctgg   19380
cgaggcacca ggatcgaggg gaataaaggc acctccggcc atttgaacag ccaccatagc   19440
gaccacagcc cacttcgatt tgtggaagca gagagggacc aatgactcag gtccaacatc   19500
aagctcttgc aatcttgcag ctaagcgcgc gacatgtttt ccaagctgag cataggtcag   19560
gtctccatcc catgaggaga tagcgatctg gtcaggctgt aatctgactt ggtcttggat   19620
caaccagtgt gtgcatgatt ccgttgcagg gcgaagacga gacgcatcga cggccttttg   19680
cagttcccac gagccgatca gggaaatatc cttctgcatg ccgctgttat tgagaagctg   19740
gtgtgtgaca tgctctatgt gatgagacaa cgcttctatc tggtccttgc caaggacatc   19800
ggagttgtaa aagagccgct gctcaatagc cttctcgcca atgccactga tgatgacgag   19860
agggtagttg aaatagcctt gcatagcctt ttccgtctcg tcctgttccg tctcgctgtg   19920
tgagagaatt gccttttgagt catccccgcc ggcaggatca tgagctggtg gttgaatgac   19980
aaggagactg gaaaattcac aagcctcctt cgcatcagaa ctaagcttgg caatattctg   20040
caatccgagc tgctcatagg gaatcatgga ggatgcttgt gattgaacat cactcaaaaa   20100
ctgagaaaca gggccgttct tatcgagtcg gacacgaact ggaacagttg cgatcatcgg   20160
cccgacgatt gattcaacac cctggacagg ggcctgtctg ccggagacgg ttgtaccaaa   20220
agtgacatcg tcggtatcgc aataccgggc aaggacgact gcccaagcag cccgaacaac   20280
tgtggccttt gttacaggga tattcaaggt ctctggtagc acaatggtcg aatggtacac   20340
atccgtcctg gccgcggaga tggagcgttg gctggtcggg aattctgccc gctttgaccc   20400
agctagctcc ttggtccaga attctgcggc cttttccggtg tcaatattcc tgtagtagtt   20460
gatgaaggag gaataaggcc gaacaggaga cagggaatcg ccatagtagg ctgaatacag   20520
ggtgctgaat aggatccgca tcgtccagcc atcgtagatg gagtgatggg ctgaccagac   20580
gaaataatcc ctgtcaccat catgaacgat agcacaggaa gagagagccg ttccatatgt   20640
catcttcaag ttctcggatg aatcaagaac tgaggacaaa gtctgattct ccgtagatcg   20700
```

```
ccactggttt ccacctcgaa cgacgatttg aacagactcc ccatccaagt gaatgatgcg   20760
agtgcggagg ttggagcaga tatcggacat ctggttccag gcagcaacaa atcgcgagat   20820
atcgacatgc ctaggtaacc ggaacacata gttcgccacg taagatccag gctgtttagc   20880
agtgagagcc atcagaccct cttgtagtga agtacaaggg tagcagtctt caatcacctg   20940
ctcttcggat aagcagcatt gtttgcgaac atcatcacta aagactgcat ccctcagtct   21000
gtcggttacc atgctaagtg gcgcgacatg agtttccaac tggtcagttg tcttcgtagc   21060
cttcaatgac agagccacca atctggggtc atcaaacaca tccttcacct gaaaggaaat   21120
tcccatttct cgggcgcgag aggccaactg aatggccaag atggagtctc cgccaacctg   21180
caagaaactg tcgtctcggc caatggaagc agcagggatg cccaaaacat ctgcccaaag   21240
agcttgaagt tgaatttcca tctctgtttc gggctcgcgt ttctggctgt tgaggagagc   21300
gtaagcattc cgctgctcgt cattcagcga gtccatcagg tggcgcagag tctttctgtc   21360
aagcttggtg gacgtaatgg aaggcataaa tctgcaaggg atgaagagag aaggaatcat   21420
gtaagtaggc aacgcgatcc ggagctcgcc aagcatgatg gcaatccttt ggcgaaggtc   21480
agtcgtgatg gctgcaaata agccatctgc agtgaatagt tcatccgcag atggattctt   21540
catctcgtca ctgaagcaaa tgtaagcgac gagattcgac cgaccctcct tttggtacac   21600
gtcgacaacg acttgtcgca cgccgtccag aatctcgcga acataatgct caacttcccc   21660
gagttcgacc cttaggccac ggatcttgat ctgcgtgtcc ttgcgactgc tgaaaacaat   21720
tgtgccgtcg ggaccatagt acccaaggtc accagactta tagaacttat tccaattctt   21780
ggagtccggc cgcggcgccc atgttggcag agagtataca gttgagtcct tgtgcgttc    21840 gacatcggca aggtactcgc gtaggatcgt gggaccctgt atgacaatct ctccaagtgt   21900
tcctgtcgga gtgagacgct ggggatcttc cgggttgacg atccagcaga accctccaac   21960
ggggcggcca acgacaagtg gtgattcatc tacagaagac cattcatgaa gtgtgctgaa   22020
gcaacatgtc tcagcaggac cccagccatt gacaagacgg actttgccaa accaagtggt   22080
cagcacgtcc cgaggcactg cttcaccggc taagagcaaa agctgcagag caggcatgtc   22140
ttccggaacc agggtcctca caaaggccgg cgttagatac gcccaggtaa ccttcgtgtc   22200
gttgacaaat tccttcaatc cgttcattcg agtgtcctct gatggaacac agatgcatgc   22260
accgaaaatc agaggcccga tgatttcacc aatagagaga tcgaacacga aagccgcaaa   22320
ctgtagcatc cggacctcag acgtcaggtt gagcctcttg gctatggccg tctggcttgt   22380
gcaaacagca ccatgttcca tcactaggcc cttcggtttg cctgtgcttc cagacgtaaa   22440
gagcacgtac accgcgtgat tcggcgtaac ggcaacagct ggaccttcgt cgccattttc   22500
cgtgacggcc aatctctggt cgagcttatc atcaagtcga acgacgttct caagaagggt   22560
tgagcacagc ttttcattgc gtgccgacga caacacaagg gtcgcccgcg tctggtcgac   22620
cacttgccgt agcctttgct ctggatacga gggatccaat ggaacccacg ccgcacccgc   22680
cttattgatg gcaacaattg caacaaagtg ccaaagagac ttttcaaagc acacatgaac   22740
aaggtcgtca ggccgaatgt catagttctt cacaagatga cgcgccagtc gatttgcaga   22800
tttgttgagt tggctatagg ttaagtcgcc gtcccaggca gacactgcca aggcgtttgg   22860
cgcccggtgg gcctgggctt caatgagctt gtggacgcag gagtcgatta tctctggcac   22920
ttcagagttg aactcaacag actgcttaac atcccactca gacgtgatag agaggtcttt   22980
cagcaatagg tcgggatgtg aagccagctg agaaacaaca tgctggaact gatgcgagag   23040
```

```
cgtaataagc tgctgttcag agagagagaa cttgttgtag atgaagacaa gcttgtcccc    23100
atcatcatga aggtgagctt ggatgacgag agggtaagtg aaatagcttt ctagtgcttc    23160
gtccgccgac tcatcggacc gcgcaacaag gagggcatcg ccagctccat tgatgtgcga    23220
cagaatctgc cttggttgaa tcacaagcaa gcttgaaaag tcacaggcgt ctttagcatc    23280
gtcgctcaac ttggcaatgt tgtgcagacc gaactgctca tatgcaacca tttccattgc    23340
ctgtgactga atgtcctcta ggaagtcgga gatcggtttg ccaccatctt caagatggat    23400
tcgaacggga atcgtcgcaa tgactggacc aggcatttcg gccaagccag gaactggcgc    23460
ttgccggccc gacaccgttg taccaaaaca aatatcgttg gcatcacagt agcgagccag    23520
tacgattgcc caggcagcgc gcaaaatggt tgcctttgta gtaccagcgg aaatcttggg    23580
aatttgcatc tccgactcga ggtatcccgt gctgttcgcg ttggctggct gctcgcctgg    23640
agtgagacgg ttgggatagc ttgccttctt tgcgttgcga agttggctaa gccaatactc    23700
gcttgccgat gcttgatccg aatcgagagt atactggatg aaccgggaat atggactgag    23760
ttcggcaacc gcatcgccgt gatatgcgct atccagcgtc tcgagcacca gacgcattgt    23820
ccagccgtca aagaccgcgt gatgcatagt caagatgaag cgagtgctcc catcttgggt    23880
aatcagagca taacgacaca gtcgggaacc atattccatc ctaatatcgc gtgaagcctc    23940
aaggaagcca tccaaagagc cctcttgcgt ggactcccac tcgaaatcgt tctggagcac    24000
aacctggata gaggctccgt cgatattcag gattcgagtc cgcaggttgg gacacatctc    24060
aaccgttctt tgccacgcag ccttgaagct gtcaatgtca gccgatttag aaaggcggta    24120
gtggaatgtg ccaatgtaag agcccggctt ttgcacagct agggccatta gaccttcttg    24180
aagcttcgag caagggaatg catcttcgat actcatacta tggctcaagc caaggcaaga    24240
tttggcttcg tctgtttgaa ggaagtccaa ctcagcttct tccagcatac caaacggttc    24300
aacgtcgccg aagtcatcgt catcatcagc gatgacttcg gctttcgcgg ccacactgag    24360
aaggcgagca tcttggaaca cgtccctggc gctgatactg atgccgctct cacgagctgc    24420
agagacgagc aagatgactg acatcgaatc gcctccaatc tggaggaagt tatcatccct    24480
tccaatcgat tcggctggga tatgcaaaat gtcagcccag acttgctgca atcttgcctc    24540
cattgtcgtt tcgagagcac gtttagtact tccgacgagg gagtactgtt cgaactgctc    24600
tctagacagc gacgtggcca tctgcacaag gagcttccgg tctagcttgg ttgacgttcc    24660
aatcggcata tgttgacagg ggatgaaagt tgtgggaatc atataaggcg gtagaacacc    24720
tttgagaaga gagatcaaat catggatttg aggcgcagca ttgttatcca agggtgcgaa    24780
tatcgccttt ccgtcagggc ctgttccaag atgggaagaa agagtctcgt tgctgaagct    24840
gtaaaaagct actagttgag acgcttcgtc ccgcttcata acgtcgaccg cgacttggcg    24900
agcaccagaa aggttcgtga tgatctgttg ctcaatctcg tgcaactcga tacgaagtcc    24960
acggatcttg acctgggtat ctttacgacc agcaaactcg attgtaccat ctggattgta    25020
atgtcccagg tctccagttc tatagaagcg atcccagcct ctcaattcac gattgggtac    25080
ccaatacgga agagaagaca caatgacctc gtcggtcttg gctggattag ccaggtattc    25140
cctgaagaga gttgggccct ggtagacaat ttcgccaaca catccggtgg gaacaagttt    25200
cctgggatcg tttggatcta cgatccacca attacccaag atagaccgcc caatggtcct    25260
gggagagtcg tttggaccag tccatggatg gagggaagcg atgacacatg tctctgttgg    25320
accccaggca ttgtatagcc gtagctttcc gaaccacgtt gatacaatat ctgacgcggc    25380
agcctcgcct cccacaagaa gtacttgaag gcaaggtatg tcttccggct tcaagctacg    25440
```

```
cgcaacagtt ggggtagcga atgcggcgtt tacagaagct ttgaccatgt agcctgtcag   25500
gttgttcatc tgttcgtccc aagatggcat acatatgcag ccaccgacaa gcagcgttgc   25560
gataatttcg aagatgcacg cgtcgaagac aaaggaagca aactggagcg ttctggattg   25620
atctgtgagg ccaacgttga gagctaaggc cgtctgcgat gtacacaagg acccgtgttc   25680
gatgacgacg cccttgggca tgcctgttgt tccggatgtg aagatgatgt aggcagcatc   25740
tgatggagag acgtcgacat tgggtcggtg cttaagcacg tcctttgtag acaaggcctg   25800
gtccaaccta gatgacacct cgagaacgaa aggcgtcaga ttggtacact ttgatgtgtt   25860
tgtcggagaa gccaagatca gctccgcgcc agtctgcgag atgatctgct ggtaccgctg   25920
aacaggatga gtgggatcaa gtggcgacca ggtcgcgcca gctttgttga tggccaagat   25980
ggcgacgata taccaagctg acttgtcaaa acagacgtgt acaacatcgc ccttcttgac   26040
gtggaagttg ttgatcaggt gatgcgataa cctattggcg caaatatcca gctgttggta   26100
cgtgaaacgg gcgtcgcaag catctacggc gagtgtggcc ggatgcttga gcgtctcgtc   26160
ttcaatcaga gagtggacgc atcgctcgat agtcgtgggt gggactccgt tggctgaggc   26220
ggcaaagtcg acttcccaag gcacctcagc gagcatttgc gacagtgact gattgggaga   26280
aacaagaagc tgttcaaaca catgcttgaa ggcgtgagag agaccttgca cctgatgttc   26340
aggcacgact gatggatcgt aatacagatc gaggtcgacg ctatcgtcag ccagcatgca   26400
ttgagcaacc aggggatagc tcagataacc ctggagcatt tccactttgc tgcttccctc   26460
aaggtctgtt gcgaagctga gcaggttgct ctcgtgagtc agtttttgca ccggctgcac   26520
aacgaccaat gacttgaagt cacaagcggc cttggctgca tcgttgaggt tcgagatgtt   26580
cttcagcccg aattgctcat gtggaatcat gtcaaaggct tggttctgga cacttcgtaa   26640
gaatgtcgat acagactgct ggtcgtctat ctggacacga atcggcacag tagcgacaac   26700
gaggccaggg atggactcca ggccaggga c tgcagcttga cggccagaaa cacttgagcc   26760
aaagcacaca tcattgacac cgctatatct ggccagcaca atagcccaag cagctcgtat   26820
aatcgcagct tttgtgatgg agctgttgga cgattgtcgg attccgacgg tgattgactg   26880
aagcctcgtt tgtttcgact cgattttgcc gccctcgctc accgttggaa agctcatggg   26940
cttggcaccc tccaactgag aagtccaaaa ttcggctgag atatcagaat caatacccat   27000
gatatacttg acgaatcgag agtacgggta aagcggagac acatccaatg cagtgtaata   27060
gctctgcaaa gtgctgagca tcagcggaac tgaccagcca tcgtaaattg aatggtgtag   27120
ccggaggcag aagtaattgg cgccatcatg ctcaatcaga gagtagtcac acagcggcaa   27180
gccataatca acttcaaggt cttgctggcc atggcttggc aacatcgtct tctcctcgtc   27240
attccagcga cagccgtttc tgacaacgac ttggatggtg ctgttattta tgacgatgat   27300
acgggttcgc aagtttgcac acgcttccac ggttcggttc catgcggcga taaagcgtga   27360
aacgtcggta ccctctccaa ggcggtagcg gaacctggct atatacgcgc tggttgctt   27420 caaagttgta ttcaagaggc cctcttggag cggagtgcaa gggtaggcat cttcaatagc   27480
ttggccctcc gtcagtttgc attgaagttc tgcatcgccc cctgatatag ccttgtggat   27540
agactggggt accaagctga atggcggaac ttcatcagat gatatgacgt ggccgtcagc   27600
cagagccatt ttggtggcaa cagcatgtag ccttgggtcg tcggagatgt ccgtgacaga   27660
gatggggaag ccaatctttc gagctatcga aaccagttgg attgcaacaa ctgaatcacc   27720
gccgatctgg aagaagttgt catgacgacc gatggattcg gcaggaatac ttagcacttc   27780
```

```
tgcccataga gactgaagca gcaattccat ctcggttgat gggggttcct tggcagcgtc   27840
ggttaacgag taaccggtaa gttggtctcg atcaagcata gctgtgaact gtcggagcga   27900
ctttctgtcc agcttgacgg aggtgatgga cggcatgaac ttgcaggtaa tgaacagcgt   27960
cggtatcatg taaagtggca ggcttgtcct cagctgtgcc actgcctcgg atatcaatcg   28020
ttgcgtgtca tctgtgagcg gcgcaaagac ttcgtcagct gtcgcggtgg aagaaatctt   28080
tctgagttcc gaagtgaagc agatgtacgc gaccagagta tggccattgt cagtgttgac   28140
gacttccact gcaacttgat ggatggacaa agcttgtgaa atgcgatgct caatctcccc   28200
agcctcaatt ctctgacctc ggatcttgat ttgcgtgtcc ctgcgagaac agtactggat   28260
ggtgccgtcc gggttataat agcaaaggtc acccgtctta tacagtcggt tccagccaac   28320
aagcccttga cgaggaaccc agcttggcat atctgtaacg actgcctcct tggttttgtc   28380
gggagctgca aggtactcac ggaggagcgt tggaccctgg acaacaagtt cccccacaac   28440
accgatggcg gctagctggc tggtatgctt cgaatcaaca atccaacagc agctgcccac   28500
cggcttacca attttgagat cgactcttc tgcagactgc cactcatgtg tactgctgat   28560
cacgcaggtt tctgtcggtc cccagccgtt gataaggcgc accttgccaa tccacgtgtt   28620
gaagatgtcc agagtgggag cttctccggt aacgacgagt gcttctaagc tctgtgcatc   28680
ctcaggactt agtgtccgta ggaaagaagg tgtaagcaaa gtccaattga cggagttctg   28740
gttaatgaag gtagcgaggt cgttcatcct tgtccagtcc gacggaatac agacacaggc   28800
gcctaacatc agcgtcgcaa agatctctgt gactgagggg tcaaaggtaa cgctgtgaa    28860 ttggagcatt cggtcattgc ttttcaggcc gaatctcttt gacaacgcgg tctgactggt   28920
gcacacagcg gcatgctcta ggacgatgcc ctttggagta cctgtcgaac cagacgtgaa   28980
caggacatat gcggcgttgc gaggagttac cggaatactc gggttatctg aactgatacc   29040
cttgctaacc agctgatcat cactcgcgct gttcacttcg agcacacgct cgacgacctt   29100
tccacataaa gccgcattgc ctgacgaggc caacgcaagc ttcgcacctg tctggctgac   29160
aatttgtcga agccgctgtt cgggatgtga gggatcgaag ggaacccaag ctgcaccagc   29220
tttgttgatg gctaagaccg atatcacatg ccagatggac ttctcaaagc acacgtggac   29280
gagatcctct atttggagag agtacctgtc tatcagatga tgggataagc ggttggcggc   29340
actgttgagt tggctgtagg taagctctcc atcccaagca gaaacagcaa ttgcgtcagg   29400
acgttgttca gcttgagcct cgataagtgt gtggatgcat gagtcgatga agtcaggtat   29460
ctcttggttg aagctgatgg ccttttccag gtcccaggag gaggcaagtg ttaccgctct   29520
taggggtgcg aagcgcagcg acgtaagctg acagacaaca tggctcaatt ggtgagcaag   29580
tgcttcagcc tgagcctcaa caagcgcgtt agacttgtag atgatggata gtctgacgga   29640
gtcatcgcca agatgtgctt gaacaacgag tggaaagctg tagaacttgt gaaccatgtc   29700
ggctggactt tcaacttcga cgtctgcggt cacaaggacg ttgtcaccct cctcgttctc   29760
tgtctccgtt ggctggataa gcaggagact cgagaactgg caagcttgtt tggcatcagg   29820
accaagcttc gcaatattct gcaagccgta ttgctcaaat gagatcattt ccagtgcctg   29880
atcttgtaca gcctcaagga agcaagacac agattgatca aagtccaagc gaactcgaac   29940
tggaacagtg gcaagggtag gcccaaccat gtcgataacg tcggggaccg gcgcttggcg   30000
acccgataga gacattccaa agcagacatc gtcagtactg caatatcgag atagtaccag   30060
agcccaagca gctcggatca atgttgcagt cgttatgttt gacttgggca tcttgggtag   30120
gtcaacaact ttctcgagaa tgcttgtggt agtctcagag ttcgggatac cattcgtggc   30180
```

```
tgggaagttg gagtgctcgc agttctcgag ctgcgcgttc caataccgtc cagcattgtc    30240
aacatccaga gatttgacat attggataaa gcgagcatac gagggaagag gcgacacttc    30300
aaggccagag taaaccttct gcagcacggt gaaaatgttt cggttggaca agccatcaaa    30360
tacagcgtga tgaaccgacc aaaagaagaa gcatcgccca tcattttgtt taacaatggt    30420
accaagtgag agcctcaatg cgtagcccat ctcaacagag cggtgcaact gaatagcttc    30480
ttcgacatct cgtccatcaa cagcgggttc gtcgttaaga accacttgga tgggcgtctc    30540
attgacgtaa acaatccgtg tgcgcaggct ggtgcagatt tcaacagttt cgcccacgc    30600 tgttttgaag gaatcgacgt tgacatgatc gggaaggcga tagacaaact tcgcaatgta    30660
tgagcgaggc tgcttgacgg ccagggccat gaggccttcc tgtaggctcg tacatggata    30720
ggcatcgaca gcgtgcgaca atgagccttg gtcacgcaca gcctggatga tcgcctcttt    30780
aggaatacta gagaccaact tgaatggctg tatgtcatcg acgagagagt tggcggtcac    30840
agagacagcg tgggccattt gttccagctg tggtttgtgg aagatggtag ccacactcag    30900
agcaagacca tgcttctgag cgagcgtgac aagccggatt gcactgatgg aatcgccacc    30960
aatgcgcatg aaactgtccc gtttgctgat atcttcagcg ttcacgtgga gaacctctgc    31020
ccagagatcg cggagtttga actccatggg ctctgtcggc gtttccttct cttcattacc    31080
aggaccaaaa cgtgaccgat catcgtagga gatattctga gccagctcaa ggagagaacg    31140
tctgtcgact tttccagatg tggtttgatt cggtttgccg tggaaaatga gatagcatga    31200
gggaatcata tgtgatggca gagtagtgga caaagacatg tctacatcgg aaatcaagat    31260
acgctgctcg tcggataggc taccgatgag ttccaagggc gaggggctgt tggatgtcgc    31320
gctgtcggtg taccataaga aagccatgag gctgtcttgc cgttgctcat cgacagattt    31380
gacaacatca ataatggcag acatcccagc tggaagaact tgatgaagct ggtgttcgat    31440
ctcgccgagt tccacgcgct ggccatggag cttgacctgc gtatctttac gaccgatata    31500
gtcgaaagtc ccatcagcgt ttcggcgcac caagtcgcca gttcgatagg ctctgttcgg    31560
aaagtcatga ggcagccagc ctgctgtgaa gtattcgatc caattggcag cttgcttttc    31620
atcgacattg aggtagcccc gggcaagcaa tgaaccctgg attagcaact ctccgatgca    31680
tccaacaggg gcgagcctgt gaatatcggt aggctcaaca acccagaaag cacttgcaag    31740
cggcttccct agattagttg acttgccgga ccggcccacg gtagggttcc aggcacatat    31800
agaggcctca gcagggccgt agaggccgtg tagctcaacg tggtctttcc atctggcagc    31860
agtcttctgg ttgatcgcct ctccgcccag acacactaca cgaagtgtcg gtacgtcggc    31920
aggattgagg aggtcagcaa ccgtaggcgt caggaatacc caatttgctt gagtcttgtt    31980
gatggcacca gataggtcgt tgagtcgatc ctcttctgaa gggatacaga ggcaaccgcc    32040
acgcatgagt gtaacgagag tatctagaat accgacgtcg aacgtgtagg ctgaaaactg    32100
aaaaacgcgg ctaccaggtc caatcagcag gtcagaacca tatgcatttg ccgaagagca    32160
gagggtatca tgctgaatga ccatgccctt cggtcgacct gtactgccag atgtgaaaag    32220
aacaacggct gcatcagacg ggcagtcagt ttgctgtact ggagtagcag cctcaggcaa    32280
ggtggcaaca aaagaatcat cgataacgac aacaggaatg tcaaggcctg acataaccga    32340
tgcgcagcac gggcttgtca gagcaattgt cgccttaatg tcgtcgagca cactgctgat    32400
tcgtgtccgt ggtgccttcg ggtcaagcgg aacgaaagca ccaccgcca gttccacagc    32460 gaccatcgtc acgacggccc agacggactt ggggaaacat ataggcacaa aggtctcgcg    32520
```

```
ccctatgcca agctgtcgta gcttagctgc caggcgggtg accaagcttc caagctcact    32580
ataggtaagc tcgccgtccc atgagactac agctggagag gtgggatagg tgcggatcgc    32640
atcttgaata agccagtgag tgcaagactg gacgggaagc ttcagtgtct ggcaatccct    32700
agcatgcttc acgtcccagt cgctcactag agagatatct ccgagacaaa catcgttggc    32760
aagctgctga acaacatgct cgatctggta agagagggct tcaacttgct tttcggccag    32820
cactcctgga ttgaagaaca agcgctgctc aacgttgtcg ccggctatcc cgtagatgag    32880
aacaagagga tagttaaagt atgagtccat cgtgtcttcg gtcagggcac tttcagcttc    32940
cccagcaaga agtatggcct cctcggagtc cgcttgagat gaagcgggag ctggataac     33000 gagcaagcta gaaaaactgc atgcttccct tgcatcagag ctgacattgg cgatattctg    33060
tattccatat tgttcatagg gaatcacgtc tgtcgtctga ttctgaacgc caagaaggaa    33120
ttcggaagtt ttcatctggc tatcaagatg aacacggacc gggatagtgg caattgctag    33180
tccaggcatt gcttctaagc ccggaactgg cgcttggcga ccagacacgg tcgtgccaaa    33240
ggtgagatca tcactgtcgc agtaacgtgc aagaacaatc gcccaggccg cacgcaagat    33300
agatgcttta gtgatggatg accttttccct tacaggagaa gcaatggttc tccggtgtac    33360
ctgggtaggc tggccatcag ttcccatgtt ggtaccgttg agaggaggga atgaggcccg    33420
ctttgagccc tgaagttcgt tagcccagaa gttcgtggca gcatcatgat cgagagacaa    33480
tgtgtatttg acgaaggcgt tgtatgcctg cagcggtgat ggctctacgt ttctgtagat    33540
gctctccagg gtactcagaa tgagacgaat ggtccaacca tcgtaaatgg catgatgagc    33600
tgaccagaca aagtagctgg tgtctgcttc ctgcactgtt gcgtaccaac agagaggcgt    33660
accatagctc atttgaaggc ctcggtccga gcggacaagg gaagagagtg tctccttgtc    33720
ggttgcctcc caggaggctg ggtcctttag aaggacctgg atcgatgaat catcaaagag    33780
aatgattctt gtgcgtaaag cgccgcaaag ctcgacagtc ttcatccacg cggctttgaa    33840
gcgacctata tcgacttggc tggccagcct gtatacatat ttagcaacat atgaccccg     33900 ctgcttcaca gagagtgcca tgagaccctc ttggattgaa gtagcaggat aggcgtcatc    33960
aatggcactc tgtgcaatgc cacattgctc agctgcttgc atgacgattg cgtctcgagt    34020
cggcggcggc agaagactga atggcgcaat ttggttgtcc ctcccctcag ctttaccact    34080
gaagaccgcc ttcgcagcta ttgcgagtaa cctggaatcg tcaaagacgt ctttcacact    34140
gatgaccagg ccctcagccc gcgctgtaga caccaggtgt atagcagaga tcgaatctcc    34200
gccaatctgc aagaagctgt catcgcgacc gattgaatca gccggtatgc tcagaataga    34260
tgcccagagt gattggaact ttcgctccat gtccgtctca gggggtctct tgttatcatc    34320
agaaagcgaa tacatagaga tttgatcctg ggtcaggaga gaggcaactt gacgaagcgc    34380
cgtcctgtcg agttttgtcg atgtgatgga aggcatatac ctgcaaacga tgaaaagggt    34440
cggaatcatg tagtttggaa tggacaccct caatttgccg accatagcag ctagtaaggg    34500
tcgaacttcg actgttatag gcatgagaat gtcgtccatg ctattctctg agctcgtcga    34560
ggagcgagtc tcttcagtga agcaaaggta cgagaccaag cgggagccac catcggatgt    34620
cgagatgtca acggctacct ggcaaatgcc ttccaggctc tcgcgaatcc ggtattcaac    34680
ttcgctaagt tcgacacgta agccgcggat cttgacttga gtatctctgc gactacaaaa    34740
ctcgattgtc ccgtccggat tgtacatggc caaatctcct gatttataga agcgtgtcca    34800
ctgcgatgcc ttttgcagcg cccaatcggg caaaacgtt accgttgagg atgctgttcg     34860
ttcagcgtca tccaggtatt cgcgaaggag cgttgggcct tgcagcatga tttcacccac    34920
```

```
ggttccaatc ggggccagct ggtcagaacg ctcagggtcc acgatccagc agaaagcccc   34980
aactggccta cccaccgtca atggagaatc ctgaggctgc cattcatgca gcgtactgaa   35040
cacgcatgtt tcagctggac cccagccgct gatgaatcgc aacttgccaa cccaaacgtc   35100
aaagacatct cgaggagtga cctctccaca cagcagcagt agctccagtc ctgggacatc   35160
ttccggcttg agaacgcgaa caaatgaagg cgttaggtat gcccagttga cactagcatc   35220
cctgatgaag ccagcaacgt cgttcatgcg ggcctgctct gaaggaacac aaacacaggc   35280
accagagata agtggtgcaa ctatttctcc gatagagaga tcgaacacga acgccgcaaa   35340
ttgaagcatc cggaccttgg aatggaggcc agcctgcga acaatggctc tctgactgct   35400
gcagacggat cgatgttcca taacgagacc tttcgggacg ccggtgctac ccgatgtaaa   35460
caggacataa gctgcgttag caggcgaaac cttggtggtc ggcgggttct gactgaaagc   35520
agcaccattg cgtgatagtt gttgatctag agaagcagaa acctcaatga caattggtat   35580
cagatccttg caaagagagg cgtgagattc agatatcaac accatctgag ccttcgtttg   35640
cttgacaatc tgaccgagcc gttccagtgg atgagagggg tcaagaggaa cccatgcggc   35700
gccggccttg ttgatagcca aaatggacac gaaataccaa gccgacttct cgaaacacac   35760
atggatgagt tcgtccggct taatcgcgtg ctgagatata agatgatatg ctaagcgatt   35820
cgctgcagtc tccagctcgg cgtatgtgaa gctaccgtcc catgcgcaga tcgccatggc   35880
gtcaggtgtc tgacgggctt gacgctcaaa gagctgatga aagcagccat cgacggcttc   35940
tggcacctcg gaattgaact tcatcgcctg ttgaaggtcc catgaggatg tcgttgcgat   36000
ggagccaaca tttgactgca acttgaggac aagctcccct gcaacatggt ggaattggtg   36060
cgataacgcg acaatttgct cttcgggcag gatggcagag ttgtagatga gaacgagttc   36120
cgtcgattca tcgtacagat gccctgaac aacgagggga taactgaagt agttttgaag   36180
agcatactct cctgtctcaa ccttcccatc agctgcaatg aggatagcgt cttggtcacc   36240
agcagggtcc aaggcttcct tcggctgaac aactagcaag ctagagaagt cgcaggcctc   36300
cttagcacaa gcatgcagtt tgctgatgtt ctgcagacca aactgttcaa attcgaccat   36360
cgccagggct tgttcttgga cctcctgcag gaaggcggcg accgatttct gttgaggcac   36420
tcggattcgt aatggaactg tcgcaatggc tgggcctggc atgtctatta tgccactcac   36480
cggggcttgt cgaccggaaa ttgttgttcc aaagcagata tcgtctgtct cgcaataacg   36540
ggtaagaagt aaggcccatg tagcacgaag aattgtagcc cttgtgaagc cagttgcgct   36600
cagatctgga agtttgatat tcgtcaccat tgaccgatag ccgtttgaat actcaggaag   36660
cttcccgctc gtattggggg ggaacgaggc cttcttggca tcccaaagct gttccaccca   36720
gtagtcagca gcagattggg ggttgatagc caaggtgtat tcaatgaaac gagaataggg   36780
cgtcaaagct gtggtcttca ttcccttata cacgttatcg agcgtggcga ggacaactcg   36840
tatagaccag ccatcgaaga tagcgtggtg catggtccag atgaagtgcg tctggttgtt   36900
ctcgtcctta atcaacgcat atcggcaaag gcgagatcca tactcaactt ccagatgctc   36960
aattgactga aggtaagact tcaaagtcat acccttcgta tcgtcccaag tgtagtcgct   37020
tatgactacc tgaaccgacg agcccttgag gtgaacaact cttgttcgca ggatgccgca   37080
tagccgtaca gtcttgtccc aggcggcttt gaaggcggag ggatccacgt tctctgctaa   37140
gcggtagtga aagctcgtga tatacgatcc aggctgtttc actgccagga ccataagacc   37200
ttcttgcagg tttgtgcacg gatagccgtc ctcaatcttc atcgagcgag tcaatttcag   37260
```

```
ctcctttctc aatcgcggcg ccaagagggc gtctcgaatg tgcggctcca ataacgcaaa    37320
cggctttgca gaaatggcgg aattggcgga gctagagtca acttcgatag gcgctgcgtt    37380
caaagcgaca gaggaaagtc gagaatcctt gaagatatcg ttcgctcgaa gctcgatacc    37440
atgctcgcgg gccagggcaa tgaggcgaat aatggctatg gaatcgccac cgattgccaa    37500
gaaactgtca tgccttccaa tcgattcagc agggactttg agaacatcgg cccaaagctg    37560
ctgcaaactg tgctccattg gggtctctgg actggacttg gcctcggtca ccgcatacag    37620
ggagtattgc tcaaaggcct gcctatccaa tgccgcagca agacgacgca agagtttcct    37680
gtccatcttg gaggatgtca cgagtggcat cttcttgcaa ggaatgaaga aggtaggtac    37740
catgtagctt ggaagagcag aagccaagaa accgtgcatc gcctctaaat cgctcctcag    37800
atctgccgtc gacggaagga agatatcttc cgttgccaca tcaccagtca tgctagccgg    37860
aatggtatcc gtattctgac agataaaggc aactagatga gtaccagctt cgaacttgag    37920
cgcttcaaca gcgacttggc atggaccttc caagttgttc cgaatgtggt gttcgatctc    37980
acccaattcg acacggagac cgcggatctt gatctgacca tctttgcgac tattgtatct    38040
aatggtgccg tctgcgttat aggtagccag atctccagac ttgtagaatc gaccaaacac    38100
ctcgcggttg gaacccagt gaggaagcga ggtaacagtg gcggcagccg ttttctccgg    38160
gttctccaaa tattcgagaa gcaggttggg cccttggacc acgatttcac caacggtgcc    38220
tactgggctt agctgatgag ggtcattagg gttgacgatc cagcagtttc cacaaattgg    38280
gcgtccaatg gtcagatgag agagttcagt agctgtgtat tcatgtacca tggcgatgac    38340
cgttgtttcc gttgggcccc agacgttgaa cagccgcacc ttaccgagcc aactgttgac    38400
gacttctttg cttggagcct caccaccaag agtcacaagc tctaagcaag gcacgtcttc    38460
cggtctgata atgctggcca ctgacggtgt caggaatgcc caggtaacgt tcctttcgcg    38520
tatgaaagct ggcaatgaat tcatctgtgt atcccatgaa gggatgcaaa cacaggcgcc    38580
tgaaataagg ggactgtaga tctcaaaaag tgaggcatcg aacacgaaag aggagaattg    38640
aagcatcctg acaccgtcat gcatctcgag tctctgactc aaagcgactt ggctgctgca    38700
gatagcgcgg tgctgaatca cgacaccttt gggaacccct gtggatccag aggtgaagat    38760
gatgtatgcg acatcatcgg ggctgacctt cacactgggc ttaaccgcat cattgagtgg    38820
tagcctggac atgaactctc cgttgacctc gaggacactg gtggtcacgc ccatgagctt    38880
gggcacgttt gcaagggaac aaagagccaa agttgccttg gtctgaccaa cgatattctg    38940
atgacgatcc gttggatgtg ctggatcaag aggcacccaa gcggcaccaa tcttgttgat    39000
tgctaggatc gccacaataa accaggcgga tttgtcgaag cagactatga ctaggtcacc    39060
agccttcact ttgagcgtgc tcaggagata cgtcgccagc ttgtcggcat tttcatcaag    39120
ttcggaataa gtgaaatcag cgtcccaaga agagaccgca ggagactcag ggttcagttt    39180
tgttcgctgt tcaatcagcg tgtgaatgca tgactcaaca acgagaggtt tgtcggggtt    39240
ggaggcgtga gcaaagtcaa tacccccattg actagtcatt gacaaatttc cgagcggctc    39300
cttataccga aggttcagct cctgcaagac atgctcgaac tggttgcata gaccctgaag    39360
ctgaagatcg gagagtacat cagcatcgta gtacagcgtc atgacagcct ggtcctgcat    39420
caaatcacat tctaccgtca aaggatagtt gaagaagtcc tctatccaat tctcaatgct    39480
tgtttcatca ttggaatcag tggtgaagag ctctccctgg actttccga tctcatgttg    39540 tctcgactgg acaacaaaca agctggtgaa gtcggttgcg tgtttggcac tatcactgag    39600
cttcgatatg ttctgaaggc caaactgttc ataagccacc atctcggagg cctgcgtctg    39660
```

```
gatattctgc agatattcgg aaacatgttg tgaacgatct agacgaactc tcacagggac   39720
tgttgcaatc gttgggccag cgatgttgac gaggtcctga acaggcgcct gtcgacctga   39780
cgtagttgcg ccgaagcaaa tatcttcgcc ttcacagtac atgctgagga caagcgccca   39840
agcgcctcga agtacagagg cttttgtgac agaggagttg ggttgagttg gtaccgctag   39900 cttctcttc atgatctgag tcttctgagc cgttgacgtc ttgttgccag ttgtgacttt   39960
ggcgggtggg aatgaagccc tctgagcacc ttctagctcc ataagccagt agtccttagc   40020
cgcctttgga tcaagctgtg acaggtattg cacaaaattg gcgaatgggc gaatgggcgg   40080
aagaggctcc tgtgcataca gccgttggag aacgtcaagt ttgatctgca ttgtccagcc   40140
atcgaagata gcatgatggg caacccaaat aaagtacgtc gacccgtttg aacaactcag   40200
gattgcatgc cgcgaaagtc gcgagccata gccatattg aggctggtca accccttcat   40260
gtaggactgg agggtttgac catcagtctc ttcccataag ccatcatgcg agaccacagc   40320
ctgtagtgat acatctccgt gctgaacgat cctcgtcctc aaactactac aggccttgat   40380
ggtacgttcc caggagtcct tgaaacgatc aagatcaacg ccgtccgcca gtttatatgc   40440
ccgtctggca atgtaggagc ctggacgcgt cgcagtcaaa gccatgagac cctcttgcag   40500
cggcgtacaa gggattatgt cttcaagttc ttgttcgttc gcaagtccac actgccgccg   40560
aatcgaggcg tgtaaagact ccacctctgt cgcttcaatc atgctgaacg gttgagcgtc   40620
agtatgctgt gactgcctga tggtcatgca ggcagccatt gaagccagtt gaggctcttt   40680 gaaagatgttt gcaatgggaa gcaggatgtc ctctcgtgca gcaaggttcg aaagatggat   40740
tgcggagatg gaatcacccc caacctcgaa aaagttgtcg aatttggaga tatcttctgt   40800
atcgatcttg agcacttgag cccagagact ctgaatcttg agctccattt ccgtcgtggg   40860
tgggactttg tcttggcgtg caatggaaaa gctagatatt ctttcgcgag gcatgctggt   40920
tgcgagttca cgcagagttc ttctgtcgat cttgtttgac gatgtatgag gcacatctct   40980
cattgggaag atgatgctgg gaatcatgta gcctggtagg acacgtcgaa gctcctggat   41040
gagggcctgg aaggaagaga cgtatatctc attgctgata aattcggcat aaggatcctc   41100
agcatccgtc ggggtattat cgcacaagta gttgtgaat gtgacaaagg caatgatcat   41160
cttgcctgct tcacgctcaa tgagatccac cacaacatgc tgtacatctg caaggtttgc   41220
tttgatgtgt tattcaatct caccgagctc cagtcgctga ccacgtaact tgacttgcgt   41280
gtcttgtcgt ccgaagaact ccaccgttcc gtcggggttg aatctcgcga gatcaccagt   41340
cttgtaggct attggtctat cactctctgt ttgagtaggc agccagtcaa gggaatcgac   41400
aaaggaggct ttggtcttct cctcgttgtt gatatagcca cgcgcaattg catggccctc   41460
aacaagtagt tcaccaacac atcccactgg cgtaaggcga tcatggttgt ccggctccac   41520
gatgaacagc cggtgagtaa atggacgtcc aatagtcatg ggtgagtcgt cctgagactt   41580
gaaggggtgg ccagcacaat tgacacaagc ttccgcaggt ccataggcat ttatcagctc   41640
aactctcccg tgccatgttt tgaggatatc cttcgtggta gcctctccgc cgatagcgac   41700
tgtctgtaga gtggggagag tatcgggatc gagagttctg atgaatgatg gcgtcaagca   41760
cgccaaggtg actcgtgctt tagtcataaa gcgccatgct ctgtccatcc tctcggtttc   41820
tgtaggaata cagagcgtag ctccaaggat gagagtcagg aagatatcca acacgctaac   41880
gtcaaagacg tagctcgcga attggaagac tcgtgaagac ttcttgaaat tgaacatatc   41940
agaatgcttc aacagcgaag tgcaagccgc cgagtgcgtg acgagcaagc cttttggctt   42000
```

-continued

```
tcccgtagag ccagaagtgt acagaacata cgcagcgtta tgaggctccg gtttcttgta   42060
gttactcagc gaatgatagt ccacaggcgt ctcgggagca agtgctaaca atgaggaaga   42120
cacctggatg gtgtgcggcg ccatgctttc acaagatgcc gccatcgatg gcgaggagac   42180
tatcacttta gcattcacct cctgaaccaa ggcttgcctt cgtgattctg gatgtgtagg   42240
atcaagaggc atgtatgcac cacccgcctt caagatacca atcattccaa ccacagccca   42300
gatggacttt tgcatgcaga tgggcacaat tgtctcaggc tggacgttgt attgcaaaag   42360
ctgacttgca acatgatcag acaggcgatc caaggcagcg tacgtgagcg atccttcggt   42420
agagaacaag gcctcatcat cggggcataa tttagcccgc tgagagatta ggtcatgcat   42480
acagtgtttt tggaccacaa tctcgtgaga gttccagtcc aagctctgct gaagatccca   42540
cgggcttgct ctggatacat ctcgaagaag cgttctcttg tccagagatg caagttgttg   42600
aatgatatgg tcgagctggt tggataacgc aagcacttgg aactcggaaa taacgtctgc   42660
atcatataca aactcaagct cgacgctgtc atccccagg tggcattgga ggataagagg   42720
ataattgtag tagtcttcca tcgactgcca tgccaaacgc tgttcctccc tggtggagat   42780
aaggatcgct tcgtttccgt tggaaccggt tgtcaggtcc tttggctgaa caaccatgag   42840
actggtaaaa ttgcatgcgt cctttgcatc agagccaatt ctggctatgt tctgtagccc   42900
gaattgctca tgtgccacca tatcattcga ttgcttctga acatcacgaa gaaagtcgga   42960
cagtgactga tcggggttca gccgaactcg gactgggagc gtcgaaacaa ccaggccaag   43020
aacgctctcc acaccgacaa gaggagcgtt gcgaccagaa acggaggcac caaagcaaat   43080
gtcatctgtg ctgcagtatc ttgcaaggag catagcccac gcagctcgta gataggtcgc   43140
tctcgtaata gtcccgtttg tcgtctgtgg tatcttaacc tctttcgctg agatttgaac   43200
gtttctcttg cttttggcaa ctgctatatc gtctcttggt aaaggaaaca cagcacgtct   43260
cgctccatcc atttgtgcct tccagtacgt cttcgaagtc tcaaagtcga gttgcagcgt   43320
gtaccgcacg aacgccgagt aggggggccag tctcggcact tcactgtctc tgtagatcgc   43380
gtgcaacgcc tggaccatga gagccagagt ccacccatca agattaaat ggtgcatgat   43440 tgcaacgaaa tagcaatcgc tattgtcacc atggacgagt gcaaagcggg cgagccgtga   43500
tccgtaggac atgcggatac tattcgcttg tctcaaaaag acgtctatgc cttgattgtc   43560
tgtgacttcc cattgcgcag gttctttgac gatgacctgg atagagtcca ggctgctgag   43620
ctggacgatc ctggtgcgca aattgctgca acggcaact gttcgctccc aagacgcctt   43680
gaagtgaccg atgtcgacat gcctcggaac cttaaacacc atcttcgaaa cgtatgctcc   43740
cggttgtttc gtggtcagcg ccatcagtcc ttcctgtagt ttagtacaag ggaacgcatc   43800
gtcgactgca tcccaactgg gcaagccgca cagcttaagc agttcatctt gcatcactga   43860
gtcgatctgg ccgggctcaa gaaggccaaa tggcgctaca attggagccg aatgggagtc   43920
tccgtcggca gaagttgcga tgcagccac tcgccacagt cgtggatcgt cgaagacatc   43980
ctggacagag agagatatcc cagcctggcg ggcatcggcc acaaaatgga tcacagcaat   44040
tgaatcaccg ccaatctgca agaagctatc gtctcttcca atggcttcca gtggcatttt   44100
cagccgtttc gcccaaagcg cttgcaactt gctctccatt gccgtttctg gtgggttctt   44160
gacagtatca acaagcgagt aggtggacag gccgtcggga cccagcaatt cgatctggtt   44220
cttcaacgta cgcctgtcca gcttggtcga cgtaatcgat ggcatgtatt tgcatggcac   44280
gaagaatgac ggtatcatgt atcttggaag attcacggat aggtgaccaa tcatgctgac   44340
gatctggctc ttcaactggc tggtgacagg gaggaacatt gcggcgcctt catcggccgc   44400
```

```
ggcgttaact gtcgtcacca ttcttgtttc attgctgaag caaaagaagg caatcaagct    44460
tgaaccacca tcggtggtga ccatgtccac cccaacctgg cagactcctt caagggatgc    44520
cttgatctgg tgctctacct ctcccaactc gactcgaaga cctcggatct tgatttgggt    44580
gtcttttcgt gtgacaaaga cgagagttcc atccggattg tatttacaca aatcgccaga    44640
cttgtagaat cgattccaat ccgctagatt acggtagggc gcccagtccg gcagtgacct    44700
gaccgtcgcc gcttcagtct tttcaggatc cgccagatat tctttgagca acgttggccc    44760
ctggatgaca acttcaccca cggttccaat aggtgctaga acgtgtgggt tttcggggtc    44820
gacaagccaa cagaagccac ccacaggtct gccgatggtc aaagaggatt cgtcaagcga    44880
tgtccattcg tgcagtgtac tgaacacgca cgtctcggct ggtccccatc cattaacaag    44940
acggaccttg ccaaaccatg tctctagcac atcacgtcct acagcctcgc ctgcaagcag    45000
catcagatcg agaccaggga gggtgtccgg gttaagcgtg cgggagaatg aaggagtaag    45060
gtaaacccag ttgatcttca tgtcgcgtat gtactcaacg agcccattca ttcgaacctc    45120
ttcagacggc acacatatgg tagctccggc aacccatgga ccgacaatct cgccaattga    45180
catgtcaaag acgtatgatg caaattgaag cattctgata tccgacgtca tgcctagcct    45240
tctgacagcg gacgtttggc tcgtgcaaac agcctgatgc tgcatgacaa agcctttggg    45300
ggtcccagtc cttccagagg taaaaagcac ataagcggca gcgctcgggg acactcgagg    45360
cagtcccttg ctacctcgtc tctccgcaat cagcatgtcg tcaagatcag cagagacctc    45420
aatgatatgc tcaaccagtt cagagcaaag agcagcattg ctggacgaag tcaacgcaag    45480
ttttgcatta gttcgcgcga cgatttgctt ttggcgttgg accgggtgag acgggtcgag    45540 agggcccaa gcagctccag ctttgttaat cgccaggatg gagatcatga accatgctga    45600
cttttcaaag caaacgtgaa cgagatcgcc cagttgcacc tgagccgcag agttgctgat    45660
cagatagtga gcaagtctat cagcggcaag gttcagctgt tcatatgtca atgtcatgtc    45720
ccatgcacag acggcagtag catctggtcg cttgagggca tggcgttcaa tgatctcgtg    45780
aaggcatgag gaaacaattt caggctcttc actgttccat tccctgacac gttgcaaatc    45840
ccattggctg gatgaagtga cagacttcag aggtatatca tctggctgaa gaagctgctg    45900
gataacgtgt tcgaaatgat ggaataacgc tcccagctgg tcctcattca agatgtcatc    45960
ataataggtg aactcgagat caatggcatc atttccaagt cgggtttgca gaaccaatgg    46020
ataattgaaa tagttgcgca tggcttcctc cgaaatcgtc ttctccaccg ggccttgctg    46080
gaggatcgag ttcaaggaag agcaggccac tgaagagaga tgctgggttg gttgaattac    46140
caataaattg gcaaaatcac acacttcctt tgcattcggg ccaagtttgg agatgttctg    46200
taacccgtac tgttcgtgag caaccatgtg agacgcgtgc gactgaatgt gctgcaggaa    46260
ctcagagatg agcatgtcgc gcttcacatg aatgcgcaca ggtaccgtgg cgatcatcgg    46320
accaggaatc tcgttcaagc cgggaacggg ggcttgtcgg ccagagagcg tcataccaaa    46380
gcaaacatcg tcagagccgc agtactgagc aagaacaagt gcccaggcag cgcggataat    46440
ggtagcggtt tgatcgatg ctttggagtt gcggaacggc atggacttcg tgaagacgcg    46500
atcccgagat gttggagata tagaagcaac agggaactgg gaccgttgtg caccatccag    46560
ttctttcctc cagtactcgc gggaacggtt agagtcgagc gatccaatgt accgaatgaa    46620
gttcgaatat ggcggcgggg gttcaattga gtgcatgctg tgataggcat tctgaaggga    46680
atcgagaaca atcttcatgc tcagaccgtc aaaaaccgcg tggtgaacga tccagacaaa    46740
```

```
gtagatatcg ccgttctctt gatgcaagag tgtactccga ctaaggcaat ctccgtagct   46800
catagtaaaa ctgcgagact ccttcagata ttcgttcacg tcgacattgt acactggagc   46860
atcccatgca gtgtcagtgg caaccacaaa ttgccaggct tgcgagttga ccagaacaat   46920
cctcgaccga agactgccac agtgtttgac gactgtgtcc caggagaccc tgaaccgatc   46980
aaggtcaaca tgcggcatga ctttataaac ttgtcgatga atgtacgatc caggttgcct   47040
gagtcccagt gccatgaatc cctcttgcag tgtggtgcaa gggtatatat cctccagtgc   47100
ttcagcagcg agacggcatt gtctctggat gttcaattcg acatcgtccc tatcctcgct   47160
agaaatcaag ctgaacggtt tagcgttgtt gatttcctca gcatcgtcga tcaccgcaac   47220
agcagccatg cgtacaagct cgggattctc cgtcacatcc gtcggtgaca gacggattcc   47280
atgtcgatag gcagccgttg caagctcagt tgtggtaagg gaatcgccac cgagaagaaa   47340
gaagttgtgg tgcttgccaa tatcctcaac gcggatttgg atgacgttgc gaagtacatc   47400
tgcccaaatg gcccgcaaga tgagctccaa gtccgtctct ggtgtctcgt cggccgagag   47460
gttgcaaggc gttcttgacg cggatctctt gaggatctgt gctcgcctat cctttgcaga   47520
caagtgcatc ttgttcgcat ccgcaaggtc gctgtcattg tcatcgccgt agttccatgg   47580
gtaacggggc aggccagaga gtgcttgtcc cgtaaacaag gtgtccaggc tcaaagccac   47640
agagttctgc cagaggcggc caatcgccga gagaaggctc gccaagcagt ccgtctctct   47700
ggactgagat gagatgtagt tgcaagacag actggcagca gagcagattt gggatagcgg   47760
accagacaga gtggagtgag gtccaatctc aaggaaaaga ccatgtgtag gagtggtgtc   47820
gagaatggac atgactgcag aagagaagcg gacgggagaa accaggttat tgacaaagta   47880
atgggggcca aagtccttgg cagaggtcag gattgtgttg ctgacactcg acatgaagac   47940
ggcattccgc gttgtttgct gcgtcgaagt gattccttcg ctttgtagaa ggcgcagaaa   48000
ttcggcagag actgtttcca tgtggtggga atggaaagct gtgtcgacac gcaacttccg   48060
cgtggtaact tgtggtctgg acagctggat cgaagccatg atatcctcca cgacgccgcg   48120
gtcgccagag attgtcgtgc tcgtcgggct gttttcgcag gccactacgg ctccatcccg   48180
caggaactct cttgtctctt cagcgctgag gccggccacc gccatagccc cgtcgcatac   48240
gctcatcgca gcggcatagc catagtaata ggccacgacg gttgcctcct tcaggttcag   48300
gtagcctgcc gcgtaggctg cggcaatctc accactggag tggccaacga cagcttccgc   48360
cttgagtccg agtcgctcgt actgatgaaa gagtgcgacc tgtagagcgg tcgagaccac   48420
acaagccgtt tcaacagagt tgatccgaca aagagggtcg ctggctgatc gctggatctc   48480
ctcctcgatc gtccaggagg gtggcgtttt cagttgacgc aagatgctat ccatactctt   48540
gatgtcattt ctgaacgcat cgatccgaag aagctctttt cccatgcctg cccattgcgc   48600
tccttgacca ctgaacacca tcgtgataga cgggggagca actgggcatt tggcggggct   48660
cgctgtgctg aggcatacgc catcgttccc aatgatagaa aatgctcggt gatcaagagc   48720
ttctcggcga atagctcgag tgtaggcaat gtcagagacg agatgcgggt tcgatctggc   48780
gaagtcgtgg tgaagctgca tctgctggtt gagagacgtc acgttgtttg cagagaacaa   48840
caccagctgt ggcccagcag catcgttgct gccggggat tcatgctgcc gatgcggctc   48900
aatgacgaag tgagattcat gcccggattt tccagcgaag ttgatgcgga ttctttgagc   48960
tcgaccagag ggaaggtcga ggtgcttctg gcttggtgtt tcatctgctg gcttaggtaa   49020
gcgctggacg ttgacaacaa caacagctgg cggcaaacaa aaacactgtt gactcaaatt   49080
cttacccttt gatagagtgg tggctgaata caggacgtcc tgatgctcca aagaggccat   49140
```

```
ggctttgatc agactgacga ggccagatgc actcttcaga tcgccctggt caggctgaga    49200
ggagctccca gcgataagga catcggaaca ctgcatgacc actgttagtt tcacagactc    49260
ttcttccgtg ttcaaatctt acaatccatc tggatgggga aggagactc acttcaacga     49320 cttcagcatc actcgaatcc gaactggcag cgcggatgac ggcctgaata ggatttccat    49380
cgcggactgc atcgctcagc ggcttgatga acactgcaac aaccgcttct ccctcgagat    49440
catccgcagt cgccccggtg gcgatgaggt tgatgcccgc aacgagagcg gcttgggcgc    49500
tgccgtttct gacagccttg caggcttcat caagtgtcac cagcgaggca gagtcttcag    49560
catcctcaat agttaggctg aagagtatgg atggttagcc tccgcgtgtt gcttcaacta    49620
gagcccattt aagactactc acctcggtcc gcggaattca aactgcttgg acacaagctc    49680
aaccgtcgag gcatttccct tctccctggc ctctacgtcc tttcggccag gcatcgccac    49740
gtagcaagcc acggaagcct tttcgccgcg atagttgacc tcacacgcgt cctcgagaca    49800
ctcgtggacg acctcaaaca gcttctgaga atacggatca ctgtcgattc gcccatcagc    49860
tgccattgtg aagaaccgcg cgtcaaacgc gctcaagctt ctgttcagtt ggccgctctt    49920
ctgagcattt gacgcagacc cttcggcaac cagaccaccg accaatgctt gccagaactc    49980
ttcgatgctg tgaataccac cagcaaggcg gagtccaacg ccgcaaatcg cgacgtcaat    50040
ctgctttgca gtattgccgc attgatgctt ggagctttcg atagagccat tggtactacc    50100
tctagctcct ggctcttcag ccggagactt gattccagtc atattaaaag attgtagaaa    50160
gtacttttgt acaagaccga ataataaaat aactaaactt ttcaacagga attgagcatg    50220
taccgacgaa gttgccttgg ccgtgcagct gtgtgggagg caggccgtta taagagaatg    50280
tctctcctca aggatcggca atgcacactc cggctcctac taatacttat gacagtatta    50340
cctacacaca gtggcacaat atgtagccaa tgattgcagc atggctgtta agtcaatgtc    50400
tcacagagtt ttcaacactt acgtgtagta tgcagcttta cccgagttca cggggagggc    50460
cccctgtcga cttaccgcca ttgtcccacc tatcaaaaca ccattctctc aacttcggcc    50520
agggatccag gctattatca gctacgtatc attaaaggta atggtatggc atatacagag    50580
tcggggcaga cgttgcctca tcgttgagga tggacatcat catcagccgc cgacgccacc    50640
agctcaaggc cacatgtagt tctggctgtg acttgatgtt tcagtgcgga tgcataggta    50700
tacagagtat tgatccgtcg atcttacata ctacgagcaa atagtagctg ctggcgtttg    50760
ttgtttggac gcctgtagaa cagccat                                       50787
```

<210> SEQ ID NO 2
<211> LENGTH: 16534
<212> TYPE: PRT
<213> ORGANISM: Trichoderma reesei

<400> SEQUENCE: 2

Met Ala Val Leu Gln Ala Ser Lys Gln Gln Thr Pro Ala Ala Thr Ile
1               5                   10                  15

Cys Ser Tyr Leu Asp Pro Trp Pro Lys Leu Arg Glu Trp Cys Phe Asp
                20                  25                  30

Arg Trp Asp Asn Gly Ala Met Leu Gln Ser Leu Ala Thr Tyr Cys Ala
            35                  40                  45

Thr Ser Pro Ala Glu Glu Pro Gly Ala Arg Gly Ser Thr Asn Gly Ser
        50                  55                  60

Ile Glu Ser Ser Lys His Gln Cys Gly Asn Thr Ala Lys Gln Ile Asp
65                  70                  75                  80

```
Val Ala Ile Cys Gly Val Gly Leu Arg Leu Ala Gly Gly Ile His Ser
                85                  90                  95

Ile Glu Glu Phe Trp Gln Ala Leu Val Gly Gly Leu Val Ala Glu Gly
            100                 105                 110

Ser Ala Ser Asn Ala Gln Lys Ser Gly Gln Leu Asn Arg Ser Leu Ser
        115                 120                 125

Ala Phe Asp Ala Arg Phe Phe Thr Met Ala Ala Asp Gly Arg Ile Asp
    130                 135                 140

Ser Asp Pro Tyr Ser Gln Lys Leu Phe Glu Val Val His Glu Cys Leu
145                 150                 155                 160

Glu Asp Ala Cys Glu Val Asn Tyr Arg Gly Leu Lys Ala Ser Val Ala
                165                 170                 175

Cys Tyr Val Ala Met Pro Gly Arg Lys Asp Val Glu Ala Arg Glu Lys
            180                 185                 190

Gly Asn Ala Ser Thr Val Glu Leu Val Ser Lys Gln Phe Glu Phe Arg
        195                 200                 205

Gly Pro Ser Leu Thr Ile Glu Asp Ala Glu Asp Ser Ala Ser Leu Val
    210                 215                 220

Thr Leu Asp Glu Ala Cys Lys Ala Val Arg Asn Gly Ser Ala Gln Ala
225                 230                 235                 240

Ala Leu Val Ala Gly Ile Asn Leu Ile Ala Thr Gly Ala Thr Ala Asp
                245                 250                 255

Asp Leu Glu Gly Glu Ala Val Val Ala Val Phe Ile Lys Pro Leu Ser
            260                 265                 270

Asp Ala Val Arg Asp Gly Asn Pro Ile Gln Ala Val Ile Arg Ala Ala
        275                 280                 285

Ser Ser Asp Ser Ser Asp Ala Glu Val Val Glu Cys Ser Asp Val Leu
    290                 295                 300

Ile Ala Gly Ser Ser Ser Gln Pro Asp Gln Gly Asp Leu Lys Ser Ala
305                 310                 315                 320

Ser Gly Leu Val Ser Leu Ile Lys Ala Met Ala Ser Leu Glu His Gln
                325                 330                 335

Asp Val Leu Tyr Ser Ala Thr Thr Leu Ser Lys Ala Val Val Val Val
            340                 345                 350

Asn Val Gln Arg Leu Pro Lys Pro Ala Asp Glu Thr Pro Ser Gln Lys
        355                 360                 365

His Leu Asp Leu Pro Ser Gly Arg Ala Gln Arg Ile Arg Ile Asn Phe
    370                 375                 380

Ala Gly Lys Ser Gly His Glu Ser His Phe Val Ile Glu Pro His Arg
385                 390                 395                 400

Gln His Glu Ser Pro Ala Ser Asn Asp Ala Ala Gly Pro Gln Leu Val
                405                 410                 415

Leu Phe Ser Ala Asn Asn Val Thr Ser Leu Asn Gln Gln Met Gln Leu
            420                 425                 430

His His Asp Phe Ala Arg Ser Asn Pro His Leu Val Ser Asp Ile Ala
        435                 440                 445

Tyr Thr Arg Ala Ile Arg Arg Glu Ala Leu Asp His Arg Ala Phe Ser
    450                 455                 460

Ile Ile Gly Asn Asp Gly Val Cys Leu Ser Thr Ala Ser Pro Ala Lys
465                 470                 475                 480

Cys Pro Val Ala Pro Pro Ser Ile Thr Met Val Phe Ser Gly Gln Gly
                485                 490                 495
```

-continued

```
Ala Gln Trp Ala Gly Met Gly Lys Glu Leu Leu Arg Ile Asp Ala Phe
                500                 505                 510

Arg Asn Asp Ile Lys Ser Met Asp Ser Ile Leu Arg Gln Leu Lys Thr
            515                 520                 525

Pro Pro Ser Trp Thr Ile Glu Glu Ile Gln Arg Ser Ala Ser Asp
        530                 535                 540

Pro Leu Cys Arg Ile Asn Ser Val Glu Thr Ala Cys Val Val Ser Thr
545                 550                 555                 560

Ala Leu Gln Val Ala Leu Phe His Gln Tyr Glu Arg Leu Gly Leu Lys
                565                 570                 575

Ala Glu Ala Val Val Gly His Ser Ser Gly Glu Ile Ala Ala Ala Tyr
            580                 585                 590

Ala Ala Gly Tyr Leu Asn Leu Lys Glu Ala Thr Val Val Ala Tyr Tyr
        595                 600                 605

Tyr Gly Tyr Ala Ala Ala Met Ser Val Cys Asp Gly Ala Met Ala Val
        610                 615                 620

Ala Gly Leu Ser Ala Glu Glu Thr Arg Glu Phe Leu Arg Asp Gly Ala
625                 630                 635                 640

Val Val Ala Cys Glu Asn Ser Pro Thr Ser Thr Thr Ile Ser Gly Asp
                645                 650                 655

Arg Gly Val Val Glu Asp Ile Met Ala Ser Ile Gln Leu Ser Arg Pro
            660                 665                 670

Gln Val Thr Thr Arg Lys Leu Arg Val Asp Thr Ala Phe His Ser His
        675                 680                 685

His Met Glu Thr Val Ser Ala Glu Phe Leu Arg Leu Leu Gln Ser Glu
        690                 695                 700

Gly Ile Thr Ser Thr Gln Gln Thr Thr Arg Asn Ala Val Phe Met Ser
705                 710                 715                 720

Ser Val Ser Asn Thr Ile Leu Thr Ser Ala Lys Asp Phe Gly Pro His
                725                 730                 735

Tyr Phe Val Asn Asn Leu Val Ser Pro Val Arg Phe Ser Ser Ala Val
            740                 745                 750

Met Ser Ile Leu Asp Thr Thr Pro Thr His Gly Leu Phe Leu Glu Ile
        755                 760                 765

Gly Pro His Ser Thr Leu Ser Gly Pro Leu Ser Gln Ile Cys Ser Ala
        770                 775                 780

Ala Ser Leu Ser Cys Asn Tyr Ile Ser Ser Gln Ser Arg Glu Thr Asp
785                 790                 795                 800

Cys Leu Ala Ser Leu Leu Ser Ala Ile Gly Arg Leu Trp Gln Asn Ser
                805                 810                 815

Val Ala Leu Ser Leu Asp Thr Leu Phe Thr Gly Gln Ala Leu Ser Gly
            820                 825                 830

Leu Pro Arg Tyr Pro Trp Asn Tyr Gly Asp Asp Asn Ser Asp Leu
        835                 840                 845

Ala Asp Ala Asn Lys Met His Leu Ser Ala Lys Asp Arg Arg Ala Gln
        850                 855                 860

Ile Leu Lys Arg Ser Ala Ser Arg Thr Pro Cys Asn Leu Ser Ala Asp
865                 870                 875                 880

Glu Thr Pro Glu Thr Asp Leu Glu Leu Ile Leu Arg Ala Ile Trp Ala
                885                 890                 895

Asp Val Leu Arg Asn Val Ile Gln Ile Arg Val Glu Asp Ile Gly Lys
            900                 905                 910

His His Asn Phe Phe Leu Leu Gly Gly Asp Ser Leu Thr Thr Thr Glu
```

```
                915                 920                 925
Leu Ala Thr Ala Ala Tyr Arg His Gly Ile Arg Leu Ser Pro Thr Asp
    930                 935                 940
Val Thr Glu Asn Pro Glu Leu Val Arg Met Ala Ala Val Ala Val Ile
945                 950                 955                 960
Asp Asp Ala Glu Glu Ile Asn Asn Ala Lys Pro Phe Ser Leu Ile Ser
                965                 970                 975
Ser Glu Asp Arg Asp Asp Val Glu Leu Asn Ile Gln Arg Gln Cys Arg
            980                 985                 990
Leu Ala Ala Glu Ala Leu Glu Asp Ile Tyr Pro Cys Thr Thr Leu Gln
        995                 1000                1005
Glu Gly Phe Met Ala Leu Gly Leu Arg Gln Pro Gly Ser Tyr Ile
    1010                1015                1020
His Arg Gln Val Tyr Lys Val Met Pro His Val Asp Leu Asp Arg
    1025                1030                1035
Phe Arg Val Ser Trp Asp Thr Val Val Lys His Cys Gly Ser Leu
    1040                1045                1050
Arg Ser Arg Ile Val Leu Val Asn Ser Gln Ala Trp Gln Phe Val
    1055                1060                1065
Val Ala Thr Asp Thr Ala Trp Asp Ala Pro Val Tyr Asn Val Asp
    1070                1075                1080
Val Asn Glu Tyr Leu Lys Glu Ser Arg Ser Phe Thr Met Ser Tyr
    1085                1090                1095
Gly Asp Cys Leu Ser Arg Ser Thr Leu Leu His Gln Glu Asn Gly
    1100                1105                1110
Asp Ile Tyr Phe Val Trp Ile Val His His Ala Val Phe Asp Gly
    1115                1120                1125
Leu Ser Met Lys Ile Val Leu Asp Ser Leu Gln Asn Ala Tyr His
    1130                1135                1140
Ser Met His Ser Ile Glu Pro Pro Pro Tyr Ser Asn Phe Ile
    1145                1150                1155
Arg Tyr Ile Gly Ser Leu Asp Ser Asn Arg Ser Arg Glu Tyr Trp
    1160                1165                1170
Arg Lys Glu Leu Asp Gly Ala Gln Arg Ser Gln Phe Pro Val Ala
    1175                1180                1185
Ser Ile Ser Pro Thr Ser Arg Asp Arg Val Phe Thr Lys Ser Met
    1190                1195                1200
Pro Phe Arg Asn Ser Lys Ala Ser Ile Thr Thr Ala Thr Ile Ile
    1205                1210                1215
Arg Ala Ala Trp Ala Leu Val Leu Ala Gln Tyr Cys Gly Ser Asp
    1220                1225                1230
Asp Val Cys Phe Gly Met Thr Leu Ser Gly Arg Gln Ala Pro Val
    1235                1240                1245
Pro Gly Leu Asn Glu Ile Pro Gly Pro Met Ile Ala Thr Val Pro
    1250                1255                1260
Val Arg Ile His Val Lys Arg Asp Met Leu Ile Ser Glu Phe Leu
    1265                1270                1275
Gln His Ile Gln Ser His Ala Ser His Met Val Ala His Glu Gln
    1280                1285                1290
Tyr Gly Leu Gln Asn Ile Ser Lys Leu Gly Pro Asn Ala Lys Glu
    1295                1300                1305
His Leu Ser Ser Val Ala Cys Ser Ser Leu Asn Ser Ile Leu Gln
    1310                1315                1320
```

```
Gln Gly Pro Val Glu Lys Thr Ile Ser Glu Glu Ala Met Arg Asn
1325                1330                1335

Tyr Phe Asn Tyr Pro Leu Val Leu Gln Thr Arg Leu Gly Asn Asp
    1340                1345                1350

Ala Ile Asp Leu Glu Phe Thr Tyr Tyr Asp Asp Ile Leu Asn Glu
1355                1360                1365

Asp Gln Leu Gly Ala Leu Phe His His Phe Glu His Val Ile Gln
    1370                1375                1380

Gln Leu Leu Gln Pro Asp Asp Ile Pro Leu Lys Ser Val Thr Ser
1385                1390                1395

Ser Ser Gln Trp Asp Leu Gln Arg Val Arg Glu Trp Asn Ser Glu
    1400                1405                1410

Glu Pro Glu Ile Val Ser Ser Cys Leu His Glu Ile Ile Glu Arg
1415                1420                1425

His Ala Leu Lys Arg Pro Asp Ala Thr Ala Val Cys Ala Trp Asp
    1430                1435                1440

Met Thr Leu Thr Tyr Glu Gln Leu Asn Leu Ala Ala Asp Arg Leu
1445                1450                1455

Ala His Tyr Leu Ile Ser Asn Ser Ala Ala Gln Val Gln Leu Gly
    1460                1465                1470

Asp Leu Val His Val Cys Phe Glu Lys Ser Ala Trp Phe Met Ile
1475                1480                1485

Ser Ile Leu Ala Ile Asn Lys Ala Gly Ala Ala Trp Ala Pro Leu
    1490                1495                1500

Asp Pro Ser His Pro Val Gln Arg Gln Lys Gln Ile Val Ala Arg
1505                1510                1515

Thr Asn Ala Lys Leu Ala Leu Thr Ser Ser Ser Asn Ala Ala Leu
    1520                1525                1530

Cys Ser Glu Leu Val Glu His Ile Ile Glu Val Ser Ala Asp Leu
1535                1540                1545

Asp Asp Met Leu Ile Ala Glu Arg Arg Gly Ser Lys Gly Leu Pro
    1550                1555                1560

Arg Val Ser Pro Ser Ala Ala Ala Tyr Val Leu Phe Thr Ser Gly
1565                1570                1575

Ser Thr Gly Thr Pro Lys Gly Phe Val Met Gln His Gln Ala Val
    1580                1585                1590

Cys Thr Ser Gln Thr Ser Ala Val Arg Arg Leu Gly Met Thr Ser
1595                1600                1605

Asp Ile Arg Met Leu Gln Phe Ala Ser Tyr Val Phe Asp Met Ser
    1610                1615                1620

Ile Gly Glu Ile Val Gly Pro Trp Val Ala Gly Ala Thr Ile Cys
1625                1630                1635

Val Pro Ser Glu Glu Val Arg Met Asn Gly Leu Val Glu Tyr Ile
    1640                1645                1650

Arg Asp Met Lys Ile Asn Trp Val Tyr Leu Thr Pro Ser Phe Ser
1655                1660                1665

Arg Thr Leu Asn Pro Asp Thr Leu Pro Gly Leu Asp Leu Met Leu
    1670                1675                1680

Leu Ala Gly Glu Ala Val Gly Arg Asp Val Leu Glu Thr Trp Phe
1685                1690                1695

Gly Lys Val Arg Leu Val Asn Gly Trp Gly Pro Ala Glu Thr Cys
    1700                1705                1710
```

```
Val Phe Ser Thr Leu His Glu Trp Thr Ser Leu Asp Glu Ser Ser
1715                1720                1725

Leu Thr Ile Gly Arg Pro Val Gly Gly Phe Cys Trp Leu Val Asp
1730                1735                1740

Pro Glu Asn Pro His Val Leu Ala Pro Ile Gly Thr Val Gly Glu
1745                1750                1755

Val Val Ile Gln Gly Pro Thr Leu Leu Lys Glu Tyr Leu Ala Asp
1760                1765                1770

Pro Glu Lys Thr Glu Ala Ala Thr Val Arg Ser Leu Pro Asp Trp
1775                1780                1785

Ala Pro Tyr Arg Asn Leu Ala Asp Trp Asn Arg Phe Tyr Lys Ser
1790                1795                1800

Gly Asp Leu Cys Lys Tyr Asn Pro Asp Gly Thr Leu Val Phe Val
1805                1810                1815

Thr Arg Lys Asp Thr Gln Ile Lys Ile Arg Gly Leu Arg Val Glu
1820                1825                1830

Leu Gly Glu Val Glu His Gln Ile Lys Ala Ser Leu Glu Gly Val
1835                1840                1845

Cys Gln Val Gly Val Asp Met Val Thr Thr Asp Gly Gly Ser Ser
1850                1855                1860

Leu Ile Ala Phe Phe Cys Phe Ser Asn Glu Thr Arg Met Val Thr
1865                1870                1875

Thr Val Asn Ala Ala Ala Asp Glu Gly Ala Ala Met Phe Leu Pro
1880                1885                1890

Val Thr Ser Gln Leu Lys Ser Gln Ile Val Ser Met Ile Gly His
1895                1900                1905

Leu Ser Val Asn Leu Pro Arg Tyr Met Ile Pro Ser Phe Phe Val
1910                1915                1920

Pro Cys Lys Tyr Met Pro Ser Ile Thr Ser Thr Lys Leu Asp Arg
1925                1930                1935

Arg Thr Leu Lys Asn Gln Ile Glu Leu Leu Gly Pro Asp Gly Leu
1940                1945                1950

Ser Thr Tyr Ser Leu Val Asp Thr Val Lys Asn Pro Pro Glu Thr
1955                1960                1965

Ala Met Glu Ser Lys Leu Gln Ala Leu Trp Ala Lys Arg Leu Lys
1970                1975                1980

Met Pro Leu Glu Ala Ile Gly Arg Asp Asp Ser Phe Leu Gln Ile
1985                1990                1995

Gly Gly Asp Ser Ile Ala Val Ile His Phe Val Ala Asp Ala Arg
2000                2005                2010

Gln Ala Gly Ile Ser Leu Ser Val Gln Asp Val Phe Asp Asp Pro
2015                2020                2025

Arg Leu Trp Arg Val Ala Ala Ile Ala Thr Ser Ala Asp Gly Asp
2030                2035                2040

Ser His Ser Ala Pro Ile Val Ala Pro Phe Gly Leu Leu Glu Pro
2045                2050                2055

Gly Gln Ile Asp Ser Val Met Gln Asp Glu Leu Leu Lys Leu Cys
2060                2065                2070

Gly Leu Pro Ser Trp Asp Ala Val Asp Asp Ala Phe Pro Cys Thr
2075                2080                2085

Lys Leu Gln Glu Gly Leu Met Ala Leu Thr Thr Lys Gln Pro Gly
2090                2095                2100

Ala Tyr Val Ser Lys Met Val Phe Lys Val Pro Arg His Val Asp
```

-continued

```
                2105                2110                2115
Ile Gly His Phe Lys Ala Ser Trp Glu Arg Thr Val Ala Val Cys
    2120                2125                2130
Ser Asn Leu Arg Thr Arg Ile Val Gln Leu Ser Ser Leu Asp Ser
    2135                2140                2145
Ile Gln Val Ile Val Lys Glu Pro Ala Gln Trp Glu Val Thr Asp
    2150                2155                2160
Asn Gln Gly Ile Asp Val Phe Leu Arg Gln Ala Asn Ser Ile Arg
    2165                2170                2175
Met Ser Tyr Gly Ser Arg Leu Ala Arg Phe Ala Leu Val His Gly
    2180                2185                2190
Asp Asn Ser Asp Cys Tyr Phe Val Ala Ile Met His His Leu Ile
    2195                2200                2205
Phe Asp Gly Trp Thr Leu Ala Leu Met Val Gln Ala Leu His Ala
    2210                2215                2220
Ile Tyr Arg Asp Ser Glu Val Pro Arg Leu Ala Pro Tyr Ser Ala
    2225                2230                2235
Phe Val Arg Tyr Thr Leu Gln Leu Asp Phe Glu Thr Ser Lys Thr
    2240                2245                2250
Tyr Trp Lys Ala Gln Met Asp Gly Ala Arg Arg Ala Val Phe Pro
    2255                2260                2265
Leu Pro Arg Asp Asp Ile Ala Val Ala Lys Ser Lys Arg Asn Val
    2270                2275                2280
Gln Ile Ser Ala Lys Glu Val Lys Ile Pro Gln Thr Thr Asn Gly
    2285                2290                2295
Thr Ile Thr Arg Ala Thr Tyr Leu Arg Ala Ala Trp Ala Met Leu
    2300                2305                2310
Leu Ala Arg Tyr Cys Ser Thr Asp Asp Ile Cys Phe Gly Ala Ser
    2315                2320                2325
Val Ser Gly Arg Asn Ala Pro Leu Val Gly Val Glu Ser Val Leu
    2330                2335                2340
Gly Leu Val Val Ser Thr Leu Pro Val Arg Val Arg Leu Asn Pro
    2345                2350                2355
Asp Gln Ser Leu Ser Asp Phe Leu Arg Asp Val Gln Lys Gln Ser
    2360                2365                2370
Asn Asp Met Val Ala His Glu Gln Phe Gly Leu Gln Asn Ile Ala
    2375                2380                2385
Arg Ile Gly Ser Asp Ala Lys Asp Ala Cys Asn Phe Thr Ser Leu
    2390                2395                2400
Met Val Val Gln Pro Lys Asp Leu Thr Thr Gly Ser Asn Gly Asn
    2405                2410                2415
Glu Ala Ile Leu Ile Ser Thr Arg Glu Glu Gln Arg Leu Ala Trp
    2420                2425                2430
Gln Ser Met Glu Asp Tyr Tyr Asn Tyr Pro Leu Ile Leu Gln Cys
    2435                2440                2445
His Leu Gly Asp Asp Ser Val Glu Leu Glu Phe Val Tyr Asp Ala
    2450                2455                2460
Asp Val Ile Ser Glu Phe Gln Val Leu Ala Leu Ser Asn Gln Leu
    2465                2470                2475
Asp His Ile Ile Gln Gln Leu Ala Ser Leu Asp Lys Arg Thr Leu
    2480                2485                2490
Leu Arg Asp Val Ser Arg Ala Ser Pro Trp Asp Leu Gln Gln Ser
    2495                2500                2505
```

```
Leu Asp Trp Asn Ser His Glu Ile Val Val Gln Lys His Cys Met
    2510            2515                2520

His Asp Leu Ile Ser Gln Arg Ala Lys Leu Cys Pro Asp Asp Glu
    2525            2530                2535

Ala Leu Phe Ser Thr Glu Gly Ser Leu Thr Tyr Ala Ala Leu Asp
    2540            2545                2550

Arg Leu Ser Asp His Val Ala Ser Gln Leu Leu Gln Tyr Asn Val
    2555            2560                2565

Gln Pro Glu Thr Ile Val Pro Ile Cys Met Gln Lys Ser Ile Trp
    2570            2575                2580

Ala Val Val Gly Met Ile Gly Ile Leu Lys Ala Gly Gly Ala Tyr
    2585            2590                2595

Met Pro Leu Asp Pro Thr His Pro Glu Ser Arg Arg Gln Ala Leu
    2600            2605                2610

Val Gln Glu Val Asn Ala Lys Val Ile Val Ser Ser Pro Ser Met
    2615            2620                2625

Ala Ala Ser Cys Glu Ser Met Ala Pro His Thr Ile Gln Val Ser
    2630            2635                2640

Ser Ser Leu Leu Ala Leu Ala Pro Glu Thr Pro Val Asp Tyr His
    2645            2650                2655

Ser Leu Ser Asn Tyr Lys Lys Pro Glu Pro His Asn Ala Ala Tyr
    2660            2665                2670

Val Leu Tyr Thr Ser Gly Ser Thr Gly Lys Pro Lys Gly Leu Leu
    2675            2680                2685

Val Thr His Ser Ala Ala Cys Thr Ser Leu Leu Lys His Ser Asp
    2690            2695                2700

Met Phe Asn Phe Lys Lys Ser Ser Arg Val Phe Gln Phe Ala Ser
    2705            2710                2715

Tyr Val Phe Asp Val Ser Val Leu Asp Ile Phe Leu Thr Leu Ile
    2720            2725                2730

Leu Gly Ala Thr Leu Cys Ile Pro Thr Glu Thr Glu Arg Met Asp
    2735            2740                2745

Arg Ala Trp Arg Phe Met Thr Lys Ala Arg Val Thr Leu Ala Cys
    2750            2755                2760

Leu Thr Pro Ser Phe Ile Arg Thr Leu Asp Pro Asp Thr Leu Pro
    2765            2770                2775

Thr Leu Gln Thr Val Ala Ile Gly Gly Glu Ala Thr Thr Lys Asp
    2780            2785                2790

Ile Leu Lys Thr Trp His Gly Arg Val Glu Leu Ile Asn Ala Tyr
    2795            2800                2805

Gly Pro Ala Glu Ala Cys Val Asn Cys Ala Gly His Pro Phe Lys
    2810            2815                2820

Ser Gln Asp Asp Ser Pro Met Thr Ile Gly Arg Pro Phe Thr His
    2825            2830                2835

Arg Leu Phe Ile Val Glu Pro Asp Asn His Asp Arg Leu Thr Pro
    2840            2845                2850

Val Gly Cys Val Gly Glu Leu Leu Val Glu Gly His Ala Ile Ala
    2855            2860                2865

Arg Gly Tyr Ile Asn Asn Glu Glu Lys Thr Lys Ala Ser Phe Val
    2870            2875                2880

Asp Ser Leu Asp Trp Leu Pro Thr Gln Thr Glu Ser Asp Arg Pro
    2885            2890                2895
```

```
Ile Ala Tyr Lys Thr Gly Asp Leu Ala Arg Phe Asn Pro Asp Gly
2900                2905                2910

Thr Val Glu Phe Phe Gly Arg Gln Asp Thr Gln Val Lys Leu Arg
2915                2920                2925

Gly Gln Arg Leu Glu Leu Gly Glu Ile Glu Tyr His Ile Lys Ala
2930                2935                2940

Asn Leu Ala Asp Val Gln His Val Val Asp Leu Ile Glu Arg
2945                2950                2955

Glu Ala Gly Lys Met Ile Ile Ala Phe Val Thr Phe His Asn Tyr
2960                2965                2970

Leu Cys Asp Asn Thr Pro Thr Asp Ala Glu Asp Pro Tyr Ala Glu
2975                2980                2985

Phe Ile Ser Asn Glu Ile Tyr Val Ser Ser Phe Gln Ala Leu Ile
2990                2995                3000

Gln Glu Leu Arg Arg Val Leu Pro Gly Tyr Met Ile Pro Ser Ile
3005                3010                3015

Ile Phe Pro Met Arg Asp Val Pro His Thr Ser Ser Asn Lys Ile
3020                3025                3030

Asp Arg Arg Thr Leu Arg Glu Leu Ala Thr Ser Met Pro Arg Glu
3035                3040                3045

Arg Ile Ser Ser Phe Ser Ile Ala Arg Gln Asp Lys Val Pro Pro
3050                3055                3060

Thr Thr Glu Met Glu Leu Lys Ile Gln Ser Leu Trp Ala Gln Val
3065                3070                3075

Leu Lys Ile Asp Thr Glu Asp Ile Ser Lys Phe Asp Asn Phe Phe
3080                3085                3090

Glu Val Gly Gly Asp Ser Ile Ser Ala Ile His Leu Ser Asn Leu
3095                3100                3105

Ala Ala Arg Glu Asp Ile Leu Leu Pro Ile Ala Asn Ile Phe Lys
3110                3115                3120

Glu Pro Gln Leu Ala Ser Met Ala Ala Cys Met Thr Ile Arg Gln
3125                3130                3135

Ser Gln His Thr Asp Ala Gln Pro Phe Ser Met Ile Glu Ala Thr
3140                3145                3150

Glu Val Glu Ser Leu His Ala Ser Ile Arg Arg Gln Cys Gly Leu
3155                3160                3165

Ala Asn Glu Gln Glu Leu Glu Asp Ile Ile Pro Cys Thr Pro Leu
3170                3175                3180

Gln Glu Gly Leu Met Ala Leu Thr Ala Thr Arg Pro Gly Ser Tyr
3185                3190                3195

Ile Ala Arg Arg Ala Tyr Lys Leu Ala Asp Gly Val Asp Leu Asp
3200                3205                3210

Arg Phe Lys Asp Ser Trp Glu Arg Thr Ile Lys Ala Cys Ser Ser
3215                3220                3225

Leu Arg Thr Arg Ile Val Gln His Gly Asp Val Ser Leu Gln Ala
3230                3235                3240

Val Val Ser His Asp Gly Leu Trp Glu Glu Thr Asp Gly Gln Thr
3245                3250                3255

Leu Gln Ser Tyr Met Lys Gly Leu Thr Ser Leu Asn Met Gly Tyr
3260                3265                3270

Gly Ser Arg Leu Ser Arg His Ala Ile Leu Ser Cys Ser Asn Gly
3275                3280                3285

Ser Thr Tyr Phe Ile Trp Val Ala His His Ala Ile Phe Asp Gly
```

-continued

```
            3290              3295              3300

Trp Thr Met Gln Ile Lys Leu Asp Val Leu Gln Arg Leu Tyr Ala
        3305              3310              3315

Gln Glu Pro Leu Pro Pro Ile Arg Pro Phe Ala Asn Phe Val Gln
        3320              3325              3330

Tyr Leu Ser Gln Leu Asp Pro Lys Ala Ala Lys Asp Tyr Trp Leu
        3335              3340              3345

Met Glu Leu Glu Gly Ala Gln Arg Ala Ser Phe Pro Pro Ala Lys
        3350              3355              3360

Val Thr Thr Gly Asn Lys Thr Ser Thr Ala Gln Lys Thr Gln Ile
        3365              3370              3375

Met Lys Arg Lys Leu Ala Asn Ile Gln Thr Gln Ala Ser Glu Met
        3380              3385              3390

Val Ala Tyr Glu Gln Phe Gly Leu Gln Asn Ile Ser Lys Leu Ser
        3395              3400              3405

Asp Ser Ala Lys His Ala Thr Asp Phe Thr Ser Leu Phe Val Val
        3410              3415              3420

Gln Ser Arg Gln His Glu Ile Gly Lys Ser Gln Gly Glu Leu Phe
        3425              3430              3435

Thr Thr Asp Ser Asn Asp Glu Thr Ser Ile Glu Asn Trp Ile Glu
        3440              3445              3450

Asp Phe Phe Asn Tyr Pro Leu Thr Val Glu Cys Asp Leu Met Gln
        3455              3460              3465

Asp Gln Ala Val Met Thr Leu Tyr Tyr Asp Ala Asp Val Leu Ser
        3470              3475              3480

Asp Leu Gln Leu Gln Gly Leu Cys Asn Gln Phe Glu His Val Leu
        3485              3490              3495

Gln Glu Leu Asn Leu Arg Tyr Lys Glu Pro Leu Gly Asn Leu Ser
        3500              3505              3510

Met Thr Ser Gln Trp Gly Ile Asp Phe Ala His Ala Ser Asn Pro
        3515              3520              3525

Asp Lys Pro Leu Val Val Glu Ser Cys Ile His Thr Leu Ile Glu
        3530              3535              3540

Gln Arg Thr Lys Leu Asn Pro Glu Ser Pro Ala Val Ser Ser Trp
        3545              3550              3555

Asp Ala Asp Phe Thr Tyr Ser Glu Leu Asp Glu Asn Ala Asp Lys
        3560              3565              3570

Leu Ala Thr Tyr Leu Leu Ser Thr Leu Lys Val Lys Ala Gly Asp
        3575              3580              3585

Leu Val Ile Val Cys Phe Asp Lys Ser Ala Trp Phe Ile Val Ala
        3590              3595              3600

Ile Leu Ala Ile Asn Lys Ile Gly Ala Ala Trp Val Pro Leu Asp
        3605              3610              3615

Pro Ala His Pro Thr Asp Arg His Gln Asn Ile Val Gly Gln Thr
        3620              3625              3630

Lys Ala Thr Leu Ala Leu Cys Ser Leu Ala Asn Val Pro Lys Leu
        3635              3640              3645

Met Gly Val Thr Thr Ser Val Leu Glu Val Asn Gly Glu Phe Met
        3650              3655              3660

Ser Arg Leu Pro Leu Asn Asp Ala Val Lys Pro Ser Val Lys Val
        3665              3670              3675

Ser Pro Asp Asp Val Ala Tyr Ile Ile Phe Thr Ser Gly Ser Thr
        3680              3685              3690
```

Gly Val Pro Lys Gly Val Val Ile Gln His Arg Ala Ile Cys Ser
3695            3700                3705

Ser Gln Val Ala Leu Ser Gln Arg Leu Glu Met His Asp Gly Val
3710            3715                3720

Arg Met Leu Gln Phe Ser Ser Phe Val Phe Asp Ala Ser Leu Phe
3725            3730                3735

Glu Ile Tyr Ser Pro Leu Ile Ser Gly Ala Cys Val Cys Ile Pro
3740            3745                3750

Ser Trp Asp Thr Gln Met Asn Ser Leu Pro Ala Phe Ile Arg Glu
3755            3760                3765

Arg Asn Val Thr Trp Ala Phe Leu Thr Pro Ser Val Ala Ser Ile
3770            3775                3780

Ile Arg Pro Glu Asp Val Pro Cys Leu Glu Leu Val Thr Leu Gly
3785            3790                3795

Gly Glu Ala Pro Ser Lys Glu Val Val Asn Ser Trp Leu Gly Lys
3800            3805                3810

Val Arg Leu Phe Asn Val Trp Gly Pro Thr Glu Thr Val Ile
3815            3820                3825

Ala Met Val His Glu Tyr Thr Ala Thr Glu Leu Ser His Leu Thr
3830            3835                3840

Ile Gly Arg Pro Ile Cys Gly Asn Cys Trp Ile Val Asn Pro Asn
3845            3850                3855

Asp Pro His Gln Leu Ser Pro Val Gly Thr Val Gly Glu Ile Val
3860            3865                3870

Val Gln Gly Pro Asn Leu Leu Leu Glu Tyr Leu Glu Asn Pro Glu
3875            3880                3885

Lys Thr Ala Ala Ala Thr Val Thr Ser Leu Pro His Trp Val Pro
3890            3895                3900

Asn Arg Glu Val Phe Gly Arg Phe Tyr Lys Ser Gly Asp Leu Ala
3905            3910                3915

Thr Tyr Asn Ala Asp Gly Thr Ile Arg Tyr Asn Ser Arg Lys Asp
3920            3925                3930

Gly Gln Ile Lys Ile Arg Gly Leu Arg Val Glu Leu Gly Glu Ile
3935            3940                3945

Glu His His Ile Arg Asn Asn Leu Glu Gly Pro Cys Gln Val Ala
3950            3955                3960

Val Glu Ala Leu Lys Phe Glu Ala Gly Thr His Leu Val Ala Phe
3965            3970                3975

Ile Cys Gln Asn Thr Asp Thr Ile Pro Ala Ser Met Thr Gly Asp
3980            3985                3990

Val Ala Thr Glu Asp Ile Phe Leu Pro Ser Thr Ala Asp Leu Arg
3995            4000                4005

Ser Asp Leu Glu Ala Met His Gly Phe Leu Ala Ser Ala Leu Pro
4010            4015                4020

Ser Tyr Met Val Pro Thr Phe Phe Ile Pro Cys Lys Lys Met Pro
4025            4030                4035

Leu Val Thr Ser Ser Lys Met Asp Arg Lys Leu Leu Arg Arg Leu
4040            4045                4050

Ala Ala Ala Leu Asp Arg Gln Ala Phe Glu Gln Tyr Ser Leu Tyr
4055            4060                4065

Ala Val Thr Glu Ala Lys Ser Ser Pro Glu Thr Pro Met Glu His
4070            4075                4080

```
Ser Leu Gln Gln Leu Trp Ala Asp Val Leu Lys Val Pro Ala Glu
4085                4090                4095

Ser Ile Gly Arg His Asp Ser Phe Leu Ala Ile Gly Gly Asp Ser
4100                4105                4110

Ile Ala Ile Ile Arg Leu Ile Ala Leu Ala Arg Glu His Gly Ile
4115                4120                4125

Glu Leu Arg Ala Asn Asp Ile Phe Lys Asp Ser Arg Leu Ser Ser
4130                4135                4140

Val Ala Leu Asn Ala Ala Pro Ile Glu Val Asp Ser Ser Ser Ala
4145                4150                4155

Asn Ser Ala Ile Ser Ala Lys Pro Phe Ala Leu Leu Glu Pro His
4160                4165                4170

Ile Arg Asp Ala Leu Leu Ala Pro Arg Leu Arg Lys Glu Leu Lys
4175                4180                4185

Leu Thr Arg Ser Met Lys Ile Glu Asp Gly Tyr Pro Cys Thr Asn
4190                4195                4200

Leu Gln Glu Gly Leu Met Val Leu Ala Val Lys Gln Pro Gly Ser
4205                4210                4215

Tyr Ile Thr Ser Phe His Tyr Arg Leu Ala Glu Asn Val Asp Pro
4220                4225                4230

Ser Ala Phe Lys Ala Ala Trp Asp Lys Thr Val Arg Leu Cys Gly
4235                4240                4245

Ile Leu Arg Thr Arg Val Val His Leu Lys Gly Ser Ser Val Gln
4250                4255                4260

Val Val Ile Ser Asp Tyr Thr Trp Asp Asp Thr Lys Gly Met Thr
4265                4270                4275

Leu Lys Ser Tyr Leu Gln Ser Ile Glu His Leu Glu Val Glu Tyr
4280                4285                4290

Gly Ser Arg Leu Cys Arg Tyr Ala Leu Ile Lys Asp Glu Asn Asn
4295                4300                4305

Gln Thr His Phe Ile Trp Thr Met His His Ala Ile Phe Asp Gly
4310                4315                4320

Trp Ser Ile Arg Val Val Leu Ala Thr Leu Asp Asn Val Tyr Lys
4325                4330                4335

Gly Met Lys Thr Thr Ala Leu Thr Pro Tyr Ser Arg Phe Ile Glu
4340                4345                4350

Tyr Thr Leu Ala Ile Asn Pro Gln Ser Ala Ala Asp Tyr Trp Val
4355                4360                4365

Glu Gln Leu Trp Asp Ala Lys Lys Ala Ser Phe Pro Pro Asn Thr
4370                4375                4380

Ser Gly Lys Leu Pro Glu Tyr Ser Asn Gly Tyr Arg Ser Met Val
4385                4390                4395

Thr Asn Ile Lys Leu Pro Asp Leu Ser Ala Thr Gly Phe Thr Arg
4400                4405                4410

Ala Thr Ile Leu Arg Ala Thr Trp Ala Leu Leu Leu Thr Arg Tyr
4415                4420                4425

Cys Glu Thr Asp Asp Ile Cys Phe Gly Thr Thr Ile Ser Gly Arg
4430                4435                4440

Gln Ala Pro Val Ser Gly Ile Ile Asp Met Pro Gly Pro Ala Ile
4445                4450                4455

Ala Thr Val Pro Leu Arg Ile Arg Val Pro Gln Gln Lys Ser Val
4460                4465                4470

Ala Ala Phe Leu Gln Glu Val Gln Glu Gln Ala Leu Ala Met Val
```

```
             4475                4480                4485
Glu Phe Glu Gln Phe Gly Leu Gln Asn Ile Ser Lys Leu His Ala
        4490                4495                4500
Cys Ala Lys Glu Ala Cys Asp Phe Ser Ser Leu Leu Val Val Gln
        4505                4510                4515
Pro Lys Glu Ala Leu Asp Pro Ala Gly Asp Gln Asp Ala Ile Leu
        4520                4525                4530
Ile Ala Ala Asp Gly Lys Val Glu Thr Gly Glu Tyr Ala Leu Gln
        4535                4540                4545
Asn Tyr Phe Ser Tyr Pro Leu Val Val Gln Gly His Leu Tyr Asp
        4550                4555                4560
Glu Ser Thr Glu Leu Val Leu Ile Tyr Asn Ser Ala Ile Leu Pro
        4565                4570                4575
Glu Glu Gln Ile Val Ala Leu Ser His Gln Phe His His Val Ala
        4580                4585                4590
Arg Glu Leu Val Leu Lys Leu Gln Ser Asn Val Gly Ser Ile Ala
        4595                4600                4605
Thr Thr Ser Ser Trp Asp Leu Gln Gln Ala Met Lys Phe Asn Ser
        4610                4615                4620
Glu Val Pro Glu Ala Val Asp Gly Cys Phe His Gln Leu Phe Glu
        4625                4630                4635
Arg Gln Ala Arg Gln Thr Pro Asp Ala Met Ala Ile Cys Ala Trp
        4640                4645                4650
Asp Gly Ser Phe Thr Tyr Ala Glu Leu Asp Thr Ala Ala Asn Arg
        4655                4660                4665
Leu Ala Tyr His Leu Ile Ser Gln His Ala Ile Lys Pro Asp Glu
        4670                4675                4680
Leu Ile His Val Cys Phe Glu Lys Ser Ala Trp Tyr Phe Val Ser
        4685                4690                4695
Ile Leu Ala Ile Asn Lys Ala Gly Ala Ala Trp Val Pro Leu Asp
        4700                4705                4710
Pro Ser His Pro Leu Glu Arg Leu Gly Gln Ile Val Lys Gln Thr
        4715                4720                4725
Lys Ala Gln Met Val Leu Ile Ser Glu Ser His Ala Ser Leu Cys
        4730                4735                4740
Lys Asp Leu Ile Pro Ile Val Ile Glu Val Ser Ala Ser Leu Asp
        4745                4750                4755
Gln Gln Leu Ser Arg Asn Gly Ala Ala Phe Ser Gln Asn Pro Pro
        4760                4765                4770
Thr Thr Lys Val Ser Pro Ala Asn Ala Ala Tyr Val Leu Phe Thr
        4775                4780                4785
Ser Gly Ser Thr Gly Val Pro Lys Gly Leu Val Met Glu His Arg
        4790                4795                4800
Ser Val Cys Ser Ser Gln Arg Ala Ile Val Arg Arg Leu Gly Leu
        4805                4810                4815
His Ser Lys Val Arg Met Leu Gln Phe Ala Ala Phe Val Phe Asp
        4820                4825                4830
Leu Ser Ile Gly Glu Ile Val Ala Pro Leu Ile Ser Gly Ala Cys
        4835                4840                4845
Val Cys Val Pro Ser Glu Gln Ala Arg Met Asn Asp Val Ala Gly
        4850                4855                4860
Phe Ile Arg Asp Ala Ser Val Asn Trp Ala Tyr Leu Thr Pro Ser
        4865                4870                4875
```

```
Phe Val Arg Val Leu Lys Pro Glu Asp Val Pro Gly Leu Glu Leu
    4880                4885                4890

Leu Leu Leu Cys Gly Glu Val Thr Pro Arg Asp Val Phe Asp Val
    4895                4900                4905

Trp Val Gly Lys Leu Arg Phe Ile Ser Gly Trp Gly Pro Ala Glu
    4910                4915                4920

Thr Cys Val Phe Ser Thr Leu His Glu Trp Gln Pro Gln Asp Ser
    4925                4930                4935

Pro Leu Thr Val Gly Arg Pro Val Gly Ala Phe Cys Trp Ile Val
    4940                4945                4950

Asp Pro Glu Arg Ser Asp Gln Leu Ala Pro Ile Gly Thr Val Gly
    4955                4960                4965

Glu Ile Met Leu Gln Gly Pro Thr Leu Leu Arg Glu Tyr Leu Asp
    4970                4975                4980

Asp Ala Glu Arg Thr Ala Ser Ser Thr Val Thr Cys Leu Pro Asp
    4985                4990                4995

Trp Ala Leu Gln Lys Ala Ser Gln Trp Thr Arg Phe Tyr Lys Ser
    5000                5005                5010

Gly Asp Leu Ala Met Tyr Asn Pro Asp Gly Thr Ile Glu Phe Cys
    5015                5020                5025

Ser Arg Arg Asp Thr Gln Val Lys Ile Arg Gly Leu Arg Val Glu
    5030                5035                5040

Leu Ser Glu Val Glu Tyr Arg Ile Arg Glu Ser Leu Glu Gly Ile
    5045                5050                5055

Cys Gln Val Ala Val Asp Ile Ser Thr Ser Asp Gly Gly Ser Arg
    5060                5065                5070

Leu Val Ser Tyr Leu Cys Phe Thr Glu Glu Thr Arg Ser Ser Thr
    5075                5080                5085

Ser Ser Glu Asn Ser Met Asp Asp Ile Leu Met Pro Ile Thr Val
    5090                5095                5100

Glu Val Arg Pro Leu Leu Ala Ala Met Val Gly Lys Leu Arg Val
    5105                5110                5115

Ser Ile Pro Asn Tyr Met Ile Pro Thr Leu Phe Ile Val Cys Arg
    5120                5125                5130

Tyr Met Pro Ser Ile Thr Ser Thr Lys Leu Asp Arg Thr Ala Leu
    5135                5140                5145

Arg Gln Val Ala Ser Leu Leu Thr Gln Asp Gln Ile Ser Met Tyr
    5150                5155                5160

Ser Leu Ser Asp Asp Asn Lys Arg Pro Pro Glu Thr Asp Met Glu
    5165                5170                5175

Arg Lys Phe Gln Ser Leu Trp Ala Ser Ile Leu Ser Ile Pro Ala
    5180                5185                5190

Asp Ser Ile Gly Arg Asp Asp Ser Phe Leu Gln Ile Gly Gly Asp
    5195                5200                5205

Ser Ile Ser Ala Ile His Leu Val Ser Thr Ala Arg Ala Glu Gly
    5210                5215                5220

Leu Val Ile Ser Val Lys Asp Val Phe Asp Asp Ser Arg Leu Leu
    5225                5230                5235

Ala Ile Ala Ala Lys Ala Val Phe Ser Gly Lys Ala Glu Gly Arg
    5240                5245                5250

Asp Asn Gln Ile Ala Pro Phe Ser Leu Leu Pro Pro Pro Thr Arg
    5255                5260                5265
```

```
Asp Ala Ile Val Met Gln Ala Ala Glu Gln Cys Gly Ile Ala Gln
    5270            5275            5280

Ser Ala Ile Asp Asp Ala Tyr Pro Ala Thr Ser Ile Gln Glu Gly
    5285            5290            5295

Leu Met Ala Leu Ser Val Lys Gln Arg Gly Ser Tyr Val Ala Lys
    5300            5305            5310

Tyr Val Tyr Arg Leu Ala Ser Gln Val Asp Ile Gly Arg Phe Lys
    5315            5320            5325

Ala Ala Trp Met Lys Thr Val Glu Leu Cys Gly Ala Leu Arg Thr
    5330            5335            5340

Arg Ile Ile Leu Phe Asp Asp Ser Ser Ile Gln Val Leu Leu Lys
    5345            5350            5355

Asp Pro Ala Ser Trp Glu Ala Thr Asp Lys Glu Thr Leu Ser Ser
    5360            5365            5370

Leu Val Arg Ser Asp Arg Gly Leu Gln Met Ser Tyr Gly Thr Pro
    5375            5380            5385

Leu Cys Trp Tyr Ala Thr Val Gln Glu Ala Asp Thr Ser Tyr Phe
    5390            5395            5400

Val Trp Ser Ala His His Ala Ile Tyr Asp Gly Trp Thr Ile Arg
    5405            5410            5415

Leu Ile Leu Ser Thr Leu Glu Ser Ile Tyr Arg Asn Val Glu Pro
    5420            5425            5430

Ser Pro Leu Gln Ala Tyr Asn Ala Phe Val Lys Tyr Thr Leu Ser
    5435            5440            5445

Leu Asp His Asp Ala Ala Thr Asn Phe Trp Ala Asn Glu Leu Gln
    5450            5455            5460

Gly Ser Lys Arg Ala Ser Phe Pro Pro Leu Asn Gly Thr Asn Met
    5465            5470            5475

Gly Thr Asp Gly Gln Pro Thr Gln Val His Arg Arg Thr Ile Ala
    5480            5485            5490

Leu Pro Val Arg Glu Arg Ser Ser Ile Thr Lys Ala Ser Ile Leu
    5495            5500            5505

Arg Ala Ala Trp Ala Ile Val Leu Ala Arg Tyr Cys Asp Ser Asp
    5510            5515            5520

Asp Leu Thr Phe Gly Thr Thr Val Ser Gly Arg Gln Ala Pro Val
    5525            5530            5535

Pro Gly Leu Glu Ala Met Pro Gly Leu Ala Ile Ala Thr Ile Pro
    5540            5545            5550

Val Arg Val His Leu Asp Ser Gln Met Lys Thr Ser Glu Phe Leu
    5555            5560            5565

Leu Gly Val Gln Asn Gln Thr Thr Asp Val Ile Pro Tyr Glu Gln
    5570            5575            5580

Tyr Gly Ile Gln Asn Ile Ala Asn Val Ser Ser Asp Ala Arg Glu
    5585            5590            5595

Ala Cys Ser Phe Ser Ser Leu Leu Val Ile Gln Pro Pro Ala Ser
    5600            5605            5610

Ser Gln Ala Asp Ser Glu Glu Ala Ile Leu Leu Ala Gly Glu Ala
    5615            5620            5625

Glu Ser Ala Leu Thr Glu Asp Thr Met Asp Ser Tyr Phe Asn Tyr
    5630            5635            5640

Pro Leu Val Leu Ile Tyr Gly Ile Ala Gly Asp Asn Val Glu Gln
    5645            5650            5655

Arg Leu Phe Phe Asn Pro Gly Val Leu Ala Glu Lys Gln Val Glu
```

```
              5660               5665               5670
Ala Leu Ser Tyr Gln Ile Glu His Val Gln Gln Leu Ala Asn
        5675               5680               5685

Asp Val Cys Leu Gly Asp Ile Ser Leu Val Ser Asp Trp Asp Val
        5690               5695               5700

Lys His Ala Arg Asp Cys Gln Thr Leu Lys Leu Pro Val Gln Ser
        5705               5710               5715

Cys Thr His Trp Leu Ile Gln Asp Ala Ile Arg Thr Tyr Pro Thr
        5720               5725               5730

Ser Pro Ala Val Val Ser Trp Asp Gly Glu Leu Thr Tyr Ser Glu
        5735               5740               5745

Leu Gly Ser Leu Val Thr Arg Leu Ala Ala Lys Leu Arg Gln Leu
        5750               5755               5760

Gly Ile Gly Arg Glu Thr Phe Val Pro Ile Cys Phe Pro Lys Ser
        5765               5770               5775

Val Trp Ala Val Val Thr Met Val Ala Val Glu Leu Ala Gly Gly
        5780               5785               5790

Ala Phe Val Pro Leu Asp Pro Lys Ala Pro Arg Thr Arg Ile Ser
        5795               5800               5805

Ser Val Leu Asp Asp Ile Lys Ala Thr Ile Ala Leu Thr Ser Pro
        5810               5815               5820

Cys Cys Ala Ser Val Met Ser Gly Leu Asp Ile Pro Val Val Val
        5825               5830               5835

Ile Asp Asp Ser Phe Val Ala Thr Leu Pro Glu Ala Ala Thr Pro
        5840               5845               5850

Val Gln Gln Thr Asp Cys Pro Ser Asp Ala Ala Val Val Leu Phe
        5855               5860               5865

Thr Ser Gly Ser Thr Gly Arg Pro Lys Gly Met Val Ile Gln His
        5870               5875               5880

Asp Thr Leu Cys Ser Ser Ala Asn Ala Tyr Gly Ser Asp Leu Leu
        5885               5890               5895

Ile Gly Pro Gly Ser Arg Val Phe Gln Phe Ser Ala Tyr Thr Phe
        5900               5905               5910

Asp Val Gly Ile Leu Asp Thr Leu Val Thr Leu Met Arg Gly Gly
        5915               5920               5925

Cys Leu Cys Ile Pro Ser Glu Glu Asp Arg Leu Asn Asp Leu Ser
        5930               5935               5940

Gly Ala Ile Asn Lys Thr Gln Ala Asn Trp Val Phe Leu Thr Pro
        5945               5950               5955

Thr Val Ala Asp Leu Leu Asn Pro Ala Asp Val Pro Thr Leu Arg
        5960               5965               5970

Val Val Cys Leu Gly Gly Glu Ala Ile Asn Gln Lys Thr Ala Ala
        5975               5980               5985

Arg Trp Lys Asp His Val Glu Leu His Gly Leu Tyr Gly Pro Ala
        5990               5995               6000

Glu Ala Ser Ile Cys Ala Trp Asn Pro Thr Val Gly Arg Ser Gly
        6005               6010               6015

Lys Ser Thr Asn Leu Gly Lys Pro Leu Ala Ser Ala Phe Trp Val
        6020               6025               6030

Val Glu Pro Thr Asp Ile His Arg Leu Ala Pro Val Gly Cys Ile
        6035               6040               6045

Gly Glu Leu Leu Ile Gln Gly Ser Leu Leu Ala Arg Gly Tyr Leu
        6050               6055               6060
```

Asn Val Asp Glu Lys Gln Ala Ala Asn Trp Ile Glu Tyr Phe Thr
6065            6070                6075

Ala Gly Trp Leu Pro His Asp Phe Pro Asn Arg Ala Tyr Arg Thr
6080            6085                6090

Gly Asp Leu Val Arg Arg Asn Ala Asp Gly Thr Phe Asp Tyr Ile
6095            6100                6105

Gly Arg Lys Asp Thr Gln Val Lys Leu His Gly Gln Arg Val Glu
6110            6115                6120

Leu Gly Glu Ile Glu His Gln Leu His Gln Val Leu Pro Ala Gly
6125            6130                6135

Met Ser Ala Ile Ile Asp Val Val Lys Ser Val Asp Glu Gln Arg
6140            6145                6150

Gln Asp Ser Leu Met Ala Phe Leu Trp Tyr Thr Asp Ser Ala Thr
6155            6160                6165

Ser Asn Ser Pro Ser Pro Leu Glu Leu Ile Gly Ser Leu Ser Asp
6170            6175                6180

Glu Gln Arg Ile Leu Ile Ser Asp Val Asp Met Ser Leu Ser Thr
6185            6190                6195

Thr Leu Pro Ser His Met Ile Pro Ser Cys Tyr Leu Ile Phe His
6200            6205                6210

Gly Lys Pro Asn Gln Thr Thr Ser Gly Lys Val Asp Arg Arg Ser
6215            6220                6225

Leu Leu Glu Leu Ala Gln Asn Ile Ser Tyr Asp Asp Arg Ser Arg
6230            6235                6240

Phe Gly Pro Gly Asn Glu Glu Lys Glu Thr Pro Thr Glu Pro Met
6245            6250                6255

Glu Phe Lys Leu Arg Asp Leu Trp Ala Glu Val Leu His Val Asn
6260            6265                6270

Ala Glu Asp Ile Ser Lys Arg Asp Ser Phe Met Arg Ile Gly Gly
6275            6280                6285

Asp Ser Ile Ser Ala Ile Arg Leu Val Thr Leu Ala Gln Lys His
6290            6295                6300

Gly Leu Ala Leu Ser Val Ala Thr Ile Phe His Lys Pro Gln Leu
6305            6310                6315

Glu Gln Met Ala His Ala Val Ser Val Thr Ala Asn Ser Leu Val
6320            6325                6330

Asp Asp Ile Gln Pro Phe Lys Leu Val Ser Ser Ile Pro Lys Glu
6335            6340                6345

Ala Ile Ile Gln Ala Val Arg Asp Gln Gly Ser Leu Ser His Ala
6350            6355                6360

Val Asp Ala Tyr Pro Cys Thr Ser Leu Gln Glu Gly Leu Met Ala
6365            6370                6375

Leu Ala Val Lys Gln Pro Arg Ser Tyr Ile Ala Lys Phe Val Tyr
6380            6385                6390

Arg Leu Pro Asp His Val Asn Val Asp Ser Phe Lys Thr Ala Trp
6395            6400                6405

Ala Lys Thr Val Glu Ile Cys Thr Ser Leu Arg Thr Arg Ile Val
6410            6415                6420

Tyr Val Asn Glu Thr Pro Ile Gln Val Val Leu Asn Asp Glu Pro
6425            6430                6435

Ala Val Asp Gly Arg Asp Val Glu Glu Ala Ile Gln Leu His Arg
6440            6445                6450

```
Ser Val Glu Met Gly Tyr Ala Leu Arg Leu Ser Leu Gly Thr Ile
6455                6460                6465

Val Lys Gln Asn Asp Gly Arg Cys Phe Phe Trp Ser Val His
6470                6475                6480

His Ala Val Phe Asp Gly Leu Ser Asn Arg Asn Ile Phe Thr Val
6485                6490                6495

Leu Gln Lys Val Tyr Ser Gly Leu Glu Val Ser Pro Leu Pro Ser
6500                6505                6510

Tyr Ala Arg Phe Ile Gln Tyr Val Lys Ser Leu Asp Val Asp Asn
6515                6520                6525

Ala Gly Arg Tyr Trp Asn Ala Gln Leu Glu Asn Cys Glu His Ser
6530                6535                6540

Asn Phe Pro Ala Thr Asn Gly Ile Pro Asn Ser Glu Thr Thr Thr
6545                6550                6555

Ser Ile Leu Glu Lys Val Val Asp Leu Pro Lys Met Pro Lys Ser
6560                6565                6570

Asn Ile Thr Thr Ala Thr Leu Ile Arg Ala Ala Trp Ala Leu Val
6575                6580                6585

Leu Ser Arg Tyr Cys Ser Thr Asp Asp Val Cys Phe Gly Met Ser
6590                6595                6600

Leu Ser Gly Arg Gln Ala Pro Val Pro Asp Val Ile Asp Met Val
6605                6610                6615

Gly Pro Thr Leu Ala Thr Val Pro Val Arg Val Arg Leu Asp Phe
6620                6625                6630

Asp Gln Ser Val Ser Cys Phe Leu Glu Ala Val Gln Asp Gln Ala
6635                6640                6645

Leu Glu Met Ile Ser Phe Glu Gln Tyr Gly Leu Gln Asn Ile Ala
6650                6655                6660

Lys Leu Gly Pro Asp Ala Lys Gln Ala Cys Gln Phe Ser Ser Leu
6665                6670                6675

Leu Leu Ile Gln Pro Thr Glu Thr Glu Asn Glu Glu Gly Asp Asn
6680                6685                6690

Val Leu Val Thr Ala Asp Val Glu Val Glu Ser Pro Ala Asp Met
6695                6700                6705

Val His Lys Phe Tyr Ser Phe Pro Leu Val Val Gln Ala His Leu
6710                6715                6720

Gly Asp Asp Ser Val Arg Leu Ser Ile Ile Tyr Lys Ser Asn Ala
6725                6730                6735

Leu Val Glu Ala Gln Ala Glu Ala Leu Ala His Gln Leu Ser His
6740                6745                6750

Val Val Cys Gln Leu Thr Ser Leu Arg Phe Ala Pro Leu Arg Ala
6755                6760                6765

Val Thr Leu Ala Ser Ser Trp Asp Leu Glu Lys Ala Ile Ser Phe
6770                6775                6780

Asn Gln Glu Ile Pro Asp Phe Ile Asp Ser Cys Ile His Thr Leu
6785                6790                6795

Ile Glu Ala Gln Ala Glu Gln Arg Pro Asp Ala Ile Ala Val Ser
6800                6805                6810

Ala Trp Asp Gly Glu Leu Thr Tyr Ser Gln Leu Asn Ser Ala Ala
6815                6820                6825

Asn Arg Leu Ser His His Leu Ile Asp Arg Tyr Ser Leu Gln Ile
6830                6835                6840

Glu Asp Leu Val His Val Cys Phe Glu Lys Ser Ile Trp His Val
```

```
              6845                6850                6855

Ile Ser Val Leu Ala Ile Asn Lys Ala Gly Ala Ala Trp Val Pro
    6860                6865                6870

Phe Asp Pro Ser His Pro Glu Gln Arg Leu Arg Gln Ile Val Ser
    6875                6880                6885

Gln Thr Gly Ala Lys Leu Ala Leu Ala Ser Ser Gly Asn Ala Ala
    6890                6895                6900

Leu Cys Gly Lys Val Val Glu Arg Val Leu Glu Val Asn Ser Ala
    6905                6910                6915

Ser Asp Asp Gln Leu Val Ser Lys Gly Ile Ser Ser Asp Asn Pro
    6920                6925                6930

Ser Ile Pro Val Thr Pro Arg Asn Ala Ala Tyr Val Leu Phe Thr
    6935                6940                6945

Ser Gly Ser Thr Gly Thr Pro Lys Gly Ile Val Leu Glu His Ala
    6950                6955                6960

Ala Val Cys Thr Ser Gln Thr Ala Leu Ser Lys Arg Phe Gly Leu
    6965                6970                6975

Lys Ser Asn Asp Arg Met Leu Gln Phe Thr Ala Phe Thr Phe Asp
    6980                6985                6990

Pro Ser Val Thr Glu Ile Phe Ala Thr Leu Met Leu Gly Ala Cys
    6995                7000                7005

Val Cys Ile Pro Ser Asp Trp Thr Arg Met Asn Asp Leu Ala Thr
    7010                7015                7020

Phe Ile Asn Gln Asn Ser Val Asn Trp Thr Leu Leu Thr Pro Ser
    7025                7030                7035

Phe Leu Arg Thr Leu Ser Pro Glu Asp Ala Gln Ser Leu Glu Ala
    7040                7045                7050

Leu Val Val Thr Gly Glu Ala Pro Thr Leu Asp Ile Phe Asn Thr
    7055                7060                7065

Trp Ile Gly Lys Val Arg Leu Ile Asn Gly Trp Gly Pro Thr Glu
    7070                7075                7080

Thr Cys Val Ile Ser Ser His Glu Trp Gln Ser Ala Glu Glu
    7085                7090                7095

Ser Tyr Leu Lys Ile Gly Lys Pro Val Gly Ser Cys Cys Trp Ile
    7100                7105                7110

Val Asp Ser Lys His Thr Ser Gln Leu Ala Ala Ile Gly Val Val
    7115                7120                7125

Gly Glu Leu Val Val Gln Gly Pro Thr Leu Leu Arg Glu Tyr Leu
    7130                7135                7140

Ala Ala Pro Asp Lys Thr Lys Glu Ala Val Val Thr Asp Met Pro
    7145                7150                7155

Ser Trp Val Pro Arg Gln Gly Leu Val Gly Trp Asn Arg Leu Tyr
    7160                7165                7170

Lys Thr Gly Asp Leu Cys Tyr Tyr Asn Pro Asp Gly Thr Ile Gln
    7175                7180                7185

Tyr Cys Ser Arg Arg Asp Thr Gln Ile Lys Ile Arg Gly Gln Arg
    7190                7195                7200

Ile Glu Ala Gly Glu Ile Glu His Arg Ile Ser Gln Ala Leu Ser
    7205                7210                7215

Ile His Gln Val Ala Val Glu Val Val Asn Thr Asp Asn Gly His
    7220                7225                7230

Thr Leu Val Ala Tyr Ile Cys Phe Thr Ser Glu Leu Arg Lys Ile
    7235                7240                7245
```

Ser Ser Thr Ala Thr Ala Asp Glu Val Phe Ala Pro Leu Thr Asp
7250                7255                7260

Asp Thr Gln Arg Leu Ile Ser Glu Ala Val Ala Gln Leu Arg Thr
7265                7270                7275

Ser Leu Pro Leu Tyr Met Ile Pro Thr Leu Phe Ile Thr Cys Lys
7280                7285                7290

Phe Met Pro Ser Ile Thr Ser Val Lys Leu Asp Arg Lys Ser Leu
7295                7300                7305

Arg Gln Phe Thr Ala Met Leu Asp Arg Asp Gln Leu Thr Gly Tyr
7310                7315                7320

Ser Leu Thr Asp Ala Ala Lys Glu Pro Pro Ser Thr Glu Met Glu
7325                7330                7335

Leu Leu Leu Gln Ser Leu Trp Ala Glu Val Leu Ser Ile Pro Ala
7340                7345                7350

Glu Ser Ile Gly Arg His Asp Asn Phe Phe Gln Ile Gly Gly Asp
7355                7360                7365

Ser Val Val Ala Ile Gln Leu Val Ser Ile Ala Arg Lys Ile Gly
7370                7375                7380

Phe Pro Ile Ser Val Thr Asp Ile Ser Asp Asp Pro Arg Leu His
7385                7390                7395

Ala Val Ala Thr Lys Met Ala Leu Ala Asp Gly His Val Ile Ser
7400                7405                7410

Ser Asp Glu Val Pro Pro Phe Ser Leu Val Pro Gln Ser Ile His
7415                7420                7425

Lys Ala Ile Ser Gly Gly Asp Ala Glu Leu Gln Cys Lys Leu Thr
7430                7435                7440

Glu Gly Gln Ala Ile Glu Asp Ala Tyr Pro Cys Thr Pro Leu Gln
7445                7450                7455

Glu Gly Leu Leu Asn Thr Thr Leu Lys Gln Pro Gly Ala Tyr Ile
7460                7465                7470

Ala Arg Phe Arg Tyr Arg Leu Gly Glu Gly Thr Asp Val Ser Arg
7475                7480                7485

Phe Ile Ala Ala Trp Asn Arg Thr Val Glu Ala Cys Ala Asn Leu
7490                7495                7500

Arg Thr Arg Ile Ile Val Ile Asn Asn Ser Thr Ile Gln Val Val
7505                7510                7515

Val Arg Asn Gly Cys Arg Trp Asn Asp Glu Glu Lys Thr Met Leu
7520                7525                7530

Pro Ser His Gly Gln Gln Asp Leu Glu Val Asp Tyr Gly Leu Pro
7535                7540                7545

Leu Cys Asp Tyr Ser Leu Ile Glu His Asp Gly Ala Asn Tyr Phe
7550                7555                7560

Cys Leu Arg Leu His His Ser Ile Tyr Asp Gly Trp Ser Val Pro
7565                7570                7575

Leu Met Leu Ser Thr Leu Gln Ser Tyr Tyr Thr Ala Leu Asp Val
7580                7585                7590

Ser Pro Leu Tyr Pro Tyr Ser Arg Phe Val Lys Tyr Ile Met Gly
7595                7600                7605

Ile Asp Ser Asp Ile Ser Ala Glu Phe Trp Thr Ser Gln Leu Glu
7610                7615                7620

Gly Ala Lys Pro Met Ser Phe Pro Thr Val Ser Glu Gly Gly Lys
7625                7630                7635

```
Ile Glu Ser Lys Gln Thr Arg Leu Gln Ser Ile Thr Val Gly Ile
         7640                7645                7650

Arg Gln Ser Ser Asn Ser Ser Ile Thr Lys Ala Ala Ile Ile Arg
         7655                7660                7665

Ala Ala Trp Ala Ile Val Leu Ala Arg Tyr Ser Gly Val Asn Asp
         7670                7675                7680

Val Cys Phe Gly Ser Ser Val Ser Gly Arg Gln Ala Ala Val Pro
         7685                7690                7695

Gly Leu Glu Ser Ile Pro Gly Leu Val Val Ala Thr Val Pro Ile
         7700                7705                7710

Arg Val Gln Ile Asp Asp Gln Ser Val Ser Thr Phe Leu Arg
         7715                7720                7725

Ser Val Gln Asn Gln Ala Phe Asp Met Ile Pro His Glu Gln Phe
         7730                7735                7740

Gly Leu Lys Asn Ile Ser Asn Leu Asn Asp Ala Ala Lys Ala Ala
         7745                7750                7755

Cys Asp Phe Lys Ser Leu Val Val Val Gln Pro Val Gln Lys Leu
         7760                7765                7770

Thr His Glu Ser Asn Leu Leu Ser Phe Ala Thr Asp Leu Glu Gly
         7775                7780                7785

Ser Ser Lys Val Glu Met Leu Gln Gly Tyr Leu Ser Tyr Pro Leu
         7790                7795                7800

Val Ala Gln Cys Met Leu Ala Asp Asp Ser Val Asp Leu Asp Leu
         7805                7810                7815

Tyr Tyr Asp Pro Ser Val Val Pro Glu His Gln Val Gln Gly Leu
         7820                7825                7830

Ser His Ala Phe Lys His Val Phe Glu Gln Leu Leu Val Ser Pro
         7835                7840                7845

Asn Gln Ser Leu Ser Gln Met Leu Ala Glu Val Pro Trp Glu Val
         7850                7855                7860

Asp Phe Ala Ala Ser Ala Asn Gly Val Pro Pro Thr Thr Ile Glu
         7865                7870                7875

Arg Cys Val His Ser Leu Ile Glu Asp Glu Thr Leu Lys His Pro
         7880                7885                7890

Ala Thr Leu Ala Val Asp Ala Cys Asp Ala Arg Phe Thr Tyr Gln
         7895                7900                7905

Gln Leu Asp Ile Cys Ala Asn Arg Leu Ser His His Leu Ile Asn
         7910                7915                7920

Asn Phe His Val Lys Lys Gly Asp Val Val His Val Cys Phe Asp
         7925                7930                7935

Lys Ser Ala Trp Tyr Ile Val Ala Ile Leu Ala Ile Asn Lys Ala
         7940                7945                7950

Gly Ala Thr Trp Ser Pro Leu Asp Pro Thr His Pro Val Gln Arg
         7955                7960                7965

Tyr Gln Gln Ile Ile Ser Gln Thr Gly Ala Glu Leu Ile Leu Ala
         7970                7975                7980

Ser Pro Thr Asn Thr Ser Lys Cys Thr Asn Leu Thr Pro Phe Val
         7985                7990                7995

Leu Glu Val Ser Ser Arg Leu Asp Gln Ala Leu Ser Thr Lys Asp
         8000                8005                8010

Val Leu Lys His Arg Pro Asn Val Asp Val Ser Pro Ser Asp Ala
         8015                8020                8025

Ala Tyr Ile Ile Phe Thr Ser Gly Thr Thr Gly Met Pro Lys Gly
```

-continued

```
                  8030                8035                8040
Val Val Ile Glu His Gly Ser Leu Cys Thr Ser Gln Thr Ala Leu
        8045                8050                8055
Ala Leu Asn Val Gly Leu Thr Asp Gln Ser Arg Thr Leu Gln Phe
        8060                8065                8070
Ala Ser Phe Val Phe Asp Ala Cys Ile Phe Glu Ile Ile Ala Thr
        8075                8080                8085
Leu Leu Val Gly Gly Cys Ile Cys Met Pro Ser Trp Asp Glu Gln
        8090                8095                8100
Met Asn Asn Leu Thr Gly Tyr Met Val Lys Ala Ser Val Asn Ala
        8105                8110                8115
Ala Phe Ala Thr Pro Thr Val Ala Arg Ser Leu Lys Pro Glu Asp
        8120                8125                8130
Ile Pro Cys Leu Gln Val Leu Leu Val Gly Gly Glu Ala Ala Ala
        8135                8140                8145
Ser Asp Ile Val Ser Thr Trp Phe Gly Lys Leu Arg Leu Tyr Asn
        8150                8155                8160
Ala Trp Gly Pro Thr Glu Thr Cys Val Ile Ala Ser Leu His Pro
        8165                8170                8175
Trp Thr Gly Pro Asn Asp Ser Pro Arg Thr Ile Gly Arg Ser Ile
        8180                8185                8190
Leu Gly Asn Trp Trp Ile Val Asp Pro Asn Asp Pro Arg Lys Leu
        8195                8200                8205
Val Pro Thr Gly Cys Val Gly Glu Ile Val Tyr Gln Gly Pro Thr
        8210                8215                8220
Leu Phe Arg Glu Tyr Leu Ala Asn Pro Ala Lys Thr Asp Glu Val
        8225                8230                8235
Ile Val Ser Ser Leu Pro Tyr Trp Val Pro Asn Arg Glu Leu Arg
        8240                8245                8250
Gly Trp Asp Arg Phe Tyr Arg Thr Gly Asp Leu Gly His Tyr Asn
        8255                8260                8265
Pro Asp Gly Thr Ile Glu Phe Ala Gly Arg Lys Asp Thr Gln Val
        8270                8275                8280
Lys Ile Arg Gly Leu Arg Ile Glu Leu His Glu Ile Glu Gln Gln
        8285                8290                8295
Ile Ile Thr Asn Leu Ser Gly Ala Arg Gln Val Ala Val Asp Val
        8300                8305                8310
Met Lys Arg Asp Glu Ala Ser Gln Leu Val Ala Phe Tyr Ser Phe
        8315                8320                8325
Ser Asn Glu Thr Leu Ser Ser His Leu Gly Thr Gly Pro Asp Gly
        8330                8335                8340
Lys Ala Ile Phe Ala Pro Leu Asp Asn Asn Ala Ala Pro Gln Ile
        8345                8350                8355
His Asp Leu Ile Ser Leu Leu Lys Gly Val Leu Pro Pro Tyr Met
        8360                8365                8370
Ile Pro Thr Thr Phe Ile Pro Cys Gln His Met Pro Ile Gly Thr
        8375                8380                8385
Ser Thr Lys Leu Asp Arg Lys Leu Leu Val Gln Met Ala Thr Ser
        8390                8395                8400
Leu Ser Arg Glu Gln Phe Glu Gln Tyr Ser Leu Val Gly Ser Thr
        8405                8410                8415
Lys Arg Ala Leu Glu Thr Thr Met Glu Ala Arg Leu Gln Gln Val
        8420                8425                8430
```

-continued

Trp Ala Asp Ile Leu His Ile Pro Ala Glu Ser Ile Gly Arg Asp
8435                 8440                 8445

Asp Asn Phe Leu Gln Ile Gly Gly Asp Ser Met Ser Val Ile Leu
8450                 8455                 8460

Leu Val Ser Ala Ala Arg Glu Ser Gly Ile Ser Ile Ser Ala Arg
8465                 8470                 8475

Asp Val Phe Gln Asp Ala Arg Leu Leu Ser Val Ala Ala Lys Ala
8480                 8485                 8490

Glu Val Ile Ala Asp Asp Asp Asp Phe Gly Asp Val Glu Pro
8495                 8500                 8505

Phe Gly Met Leu Glu Glu Ala Glu Leu Asp Phe Leu Gln Thr Asp
8510                 8515                 8520

Glu Ala Lys Ser Cys Leu Gly Leu Ser His Ser Met Ser Ile Glu
8525                 8530                 8535

Asp Ala Phe Pro Cys Ser Lys Leu Gln Glu Gly Leu Met Ala Leu
8540                 8545                 8550

Ala Val Gln Lys Pro Gly Ser Tyr Ile Gly Thr Phe His Tyr Arg
8555                 8560                 8565

Leu Ser Lys Ser Ala Asp Ile Asp Ser Phe Lys Ala Ala Trp Gln
8570                 8575                 8580

Arg Thr Val Glu Met Cys Pro Asn Leu Arg Thr Arg Ile Leu Asn
8585                 8590                 8595

Ile Asp Gly Ala Ser Ile Gln Val Val Leu Gln Asn Asp Phe Glu
8600                 8605                 8610

Trp Glu Ser Thr Gln Glu Gly Ser Leu Asp Gly Phe Leu Glu Ala
8615                 8620                 8625

Ser Arg Asp Ile Arg Met Glu Tyr Gly Ser Arg Leu Cys Arg Tyr
8630                 8635                 8640

Ala Leu Ile Thr Gln Asp Gly Ser Thr Arg Phe Ile Leu Thr Met
8645                 8650                 8655

His His Ala Val Phe Asp Gly Trp Thr Met Arg Leu Val Leu Glu
8660                 8665                 8670

Thr Leu Asp Ser Ala Tyr His Gly Asp Ala Val Ala Glu Leu Ser
8675                 8680                 8685

Pro Tyr Ser Arg Phe Ile Gln Tyr Thr Leu Asp Ser Asp Gln Ala
8690                 8695                 8700

Ser Ala Ser Glu Tyr Trp Leu Ser Gln Leu Arg Asn Ala Lys Lys
8705                 8710                 8715

Ala Ser Tyr Pro Asn Arg Leu Thr Pro Gly Glu Gln Pro Ala Asn
8720                 8725                 8730

Ala Asn Ser Thr Gly Tyr Leu Glu Ser Glu Met Gln Ile Pro Lys
8735                 8740                 8745

Ile Ser Ala Gly Thr Thr Lys Ala Thr Ile Leu Arg Ala Ala Trp
8750                 8755                 8760

Ala Ile Val Leu Ala Arg Tyr Cys Asp Ala Asn Asp Ile Cys Phe
8765                 8770                 8775

Gly Thr Thr Val Ser Gly Arg Gln Ala Pro Val Pro Gly Leu Ala
8780                 8785                 8790

Glu Met Pro Gly Pro Val Ile Ala Thr Ile Pro Val Arg Ile His
8795                 8800                 8805

Leu Glu Asp Gly Gly Lys Pro Ile Ser Asp Phe Leu Glu Asp Ile
8810                 8815                 8820

Gln Ser Gln Ala Met Glu Met Val Ala Tyr Glu Gln Phe Gly Leu
    8825                8830                8835

His Asn Ile Ala Lys Leu Ser Asp Asp Ala Lys Asp Ala Cys Asp
    8840                8845                8850

Phe Ser Ser Leu Leu Val Ile Gln Pro Arg Gln Ile Leu Ser His
    8855                8860                8865

Ile Asn Gly Ala Gly Asp Ala Leu Leu Val Ala Arg Ser Asp Glu
    8870                8875                8880

Ser Ala Asp Glu Ala Leu Glu Ser Tyr Phe Thr Tyr Pro Leu Val
    8885                8890                8895

Ile Gln Ala His Leu His Asp Asp Gly Asp Lys Leu Val Phe Ile
    8900                8905                8910

Tyr Asn Lys Phe Ser Leu Ser Glu Gln Gln Leu Ile Thr Leu Ser
    8915                8920                8925

His Gln Phe Gln His Val Val Ser Gln Leu Ala Ser His Pro Asp
    8930                8935                8940

Leu Leu Leu Lys Asp Leu Ser Ile Thr Ser Glu Trp Asp Val Lys
    8945                8950                8955

Gln Ser Val Glu Phe Asn Ser Glu Val Pro Glu Ile Ile Asp Ser
    8960                8965                8970

Cys Val His Lys Leu Ile Glu Ala Gln Ala His Arg Ala Pro Asn
    8975                8980                8985

Ala Leu Ala Val Ser Ala Trp Asp Gly Asp Leu Thr Tyr Ser Gln
    8990                8995                9000

Leu Asn Lys Ser Ala Asn Arg Leu Ala Arg His Leu Val Lys Asn
    9005                9010                9015

Tyr Asp Ile Arg Pro Asp Asp Leu Val His Val Cys Phe Glu Lys
    9020                9025                9030

Ser Leu Trp His Phe Val Ala Ile Val Ala Ile Asn Lys Ala Gly
    9035                9040                9045

Ala Ala Trp Val Pro Leu Asp Pro Ser Tyr Pro Glu Gln Arg Leu
    9050                9055                9060

Arg Gln Val Val Asp Gln Thr Arg Ala Thr Leu Val Leu Ser Ser
    9065                9070                9075

Ala Arg Asn Glu Lys Leu Cys Ser Thr Leu Leu Glu Asn Val Val
    9080                9085                9090

Arg Leu Asp Asp Lys Leu Asp Gln Arg Leu Ala Val Thr Glu Asn
    9095                9100                9105

Gly Asp Glu Gly Pro Ala Val Ala Val Thr Pro Asn His Ala Val
    9110                9115                9120

Tyr Val Leu Phe Thr Ser Gly Ser Thr Gly Lys Pro Lys Gly Leu
    9125                9130                9135

Val Met Glu His Gly Ala Val Cys Thr Ser Gln Thr Ala Ile Ala
    9140                9145                9150

Lys Arg Leu Asn Leu Thr Ser Glu Val Arg Met Leu Gln Phe Ala
    9155                9160                9165

Ala Phe Val Phe Asp Leu Ser Ile Gly Glu Ile Gly Pro Leu
    9170                9175                9180

Ile Ser Gly Ala Cys Ile Cys Val Pro Ser Glu Asp Thr Arg Met
    9185                9190                9195

Asn Gly Leu Lys Glu Phe Val Asn Asp Thr Lys Val Thr Trp Ala
    9200                9205                9210

Tyr Leu Thr Pro Ala Phe Val Arg Thr Leu Val Pro Glu Asp Met

-continued

```
            9215                9220                9225
Pro Ala Leu Gln Leu Leu Leu Ala Gly Glu Ala Val Pro Arg
        9230                9235                9240
Asp Val Leu Thr Thr Trp Phe Gly Lys Val Arg Leu Val Asn Gly
        9245                9250                9255
Trp Gly Pro Ala Glu Thr Cys Cys Phe Ser Thr Leu His Glu Trp
        9260                9265                9270
Ser Ser Val Asp Glu Ser Pro Leu Val Gly Arg Pro Val Gly
        9275                9280                9285
Gly Phe Cys Trp Ile Val Asn Pro Glu Asp Pro Gln Arg Leu Thr
        9290                9295                9300
Pro Thr Gly Thr Leu Gly Glu Ile Val Ile Gln Gly Pro Thr Ile
        9305                9310                9315
Leu Arg Glu Tyr Leu Ala Asp Val Glu Arg Thr Lys Asp Ser Thr
        9320                9325                9330
Val Tyr Ser Leu Pro Thr Trp Ala Pro Arg Pro Asp Ser Lys Asn
        9335                9340                9345
Trp Asn Lys Phe Tyr Lys Ser Gly Asp Leu Gly Tyr Tyr Gly Pro
        9350                9355                9360
Asp Gly Thr Ile Val Phe Ser Ser Arg Lys Asp Thr Gln Ile Lys
        9365                9370                9375
Ile Arg Gly Leu Arg Val Glu Leu Gly Glu Val Glu His Tyr Val
        9380                9385                9390
Arg Glu Ile Leu Asp Gly Val Arg Gln Val Val Asp Val Tyr
        9395                9400                9405
Gln Lys Glu Gly Arg Ser Asn Leu Val Ala Tyr Ile Cys Phe Ser
        9410                9415                9420
Asp Glu Met Lys Asn Pro Ser Ala Asp Glu Leu Phe Thr Ala Asp
        9425                9430                9435
Gly Leu Phe Ala Ala Ile Thr Thr Asp Leu Arg Gln Arg Ile Ala
        9440                9445                9450
Ile Met Leu Gly Glu Leu Arg Ile Ala Leu Pro Thr Tyr Met Ile
        9455                9460                9465
Pro Ser Leu Phe Ile Pro Cys Arg Phe Met Pro Ser Ile Thr Ser
        9470                9475                9480
Thr Lys Leu Asp Arg Lys Thr Leu Arg His Leu Met Asp Ser Leu
        9485                9490                9495
Asn Asp Glu Gln Arg Asn Ala Tyr Ala Leu Leu Asn Ser Gln Lys
        9500                9505                9510
Arg Glu Pro Glu Thr Glu Met Glu Ile Gln Leu Gln Ala Leu Trp
        9515                9520                9525
Ala Asp Val Leu Gly Ile Pro Ala Ala Ser Ile Gly Arg Asp Asp
        9530                9535                9540
Ser Phe Leu Gln Val Gly Gly Asp Ser Ile Leu Ala Ile Gln Leu
        9545                9550                9555
Ala Ser Arg Ala Arg Glu Met Gly Ile Ser Phe Gln Val Lys Asp
        9560                9565                9570
Val Phe Asp Asp Pro Arg Leu Val Ala Leu Ser Leu Lys Ala Thr
        9575                9580                9585
Lys Thr Thr Asp Gln Leu Glu Thr His Val Ala Pro Leu Ser Met
        9590                9595                9600
Val Thr Asp Arg Leu Arg Asp Ala Val Phe Ser Asp Asp Val Arg
        9605                9610                9615
```

```
Lys Gln Cys Cys Leu Ser Glu Glu Val Ile Glu Asp Cys Tyr
         9620              9625              9630

Pro Cys Thr Ser Leu Gln Glu Gly Leu Met Ala Leu Thr Ala Lys
         9635              9640              9645

Gln Pro Gly Ser Tyr Val Ala Asn Tyr Val Phe Arg Leu Pro Arg
         9650              9655              9660

His Val Asp Ile Ser Arg Phe Val Ala Ala Trp Asn Gln Met Ser
         9665              9670              9675

Asp Ile Cys Ser Asn Leu Arg Thr Arg Ile Ile His Leu Asp Gly
         9680              9685              9690

Glu Ser Val Gln Ile Val Val Arg Gly Gly Asn Gln Trp Arg Ser
         9695              9700              9705

Thr Glu Asn Gln Thr Leu Ser Ser Val Leu Asp Ser Ser Glu Asn
         9710              9715              9720

Leu Lys Met Thr Tyr Gly Thr Ala Leu Ser Ser Cys Ala Ile Val
         9725              9730              9735

His Asp Gly Asp Ser Asp Tyr Phe Val Trp Ser Ala His His Ser
         9740              9745              9750

Ile Tyr Asp Gly Trp Thr Met Arg Ile Leu Phe Ser Thr Leu Tyr
         9755              9760              9765

Ser Ala Tyr Tyr Gly Asp Ser Leu Ser Pro Val Arg Pro Tyr Ser
         9770              9775              9780

Ser Phe Ile Asn Tyr Tyr Arg Asn Ile Asp Thr Gly Lys Ala Ala
         9785              9790              9795

Glu Phe Trp Thr Lys Glu Leu Ala Gly Ser Lys Arg Ala Glu Phe
         9800              9805              9810

Pro Thr Ser Gln Arg Ser Ile Ser Ala Ala Arg Thr Asp Val Tyr
         9815              9820              9825

His Ser Thr Ile Val Leu Pro Glu Thr Leu Asn Ile Pro Val Thr
         9830              9835              9840

Lys Ala Thr Val Val Arg Ala Ala Trp Ala Val Val Leu Ala Arg
         9845              9850              9855

Tyr Cys Asp Thr Asp Val Thr Phe Gly Thr Thr Val Ser Gly
         9860              9865              9870

Arg Gln Ala Pro Val Gln Gly Val Glu Ser Ile Val Gly Pro Met
         9875              9880              9885

Ile Ala Thr Val Pro Val Arg Val Arg Leu Asp Lys Asn Gly Pro
         9890              9895              9900

Val Ser Gln Phe Leu Ser Asp Val Gln Ser Gln Ala Ser Ser Met
         9905              9910              9915

Ile Pro Tyr Glu Gln Leu Gly Leu Gln Asn Ile Ala Lys Leu Ser
         9920              9925              9930

Ser Asp Ala Lys Glu Ala Cys Glu Phe Ser Ser Leu Leu Val Ile
         9935              9940              9945

Gln Pro Pro Ala His Asp Pro Ala Gly Gly Asp Asp Ser Lys Ala
         9950              9955              9960

Ile Leu Ser His Ser Glu Thr Glu Gln Asp Glu Thr Glu Lys Ala
         9965              9970              9975

Met Gln Gly Tyr Phe Asn Tyr Pro Leu Val Ile Ile Ser Gly Ile
         9980              9985              9990

Gly Glu Lys Ala Ile Glu Gln Arg Leu Phe Tyr Asn Ser Asp Val
         9995             10000             10005
```

```
Leu Gly  Lys Asp Gln Ile Glu  Ala Leu Ser His His  Ile Glu His
    10010            10015                10020

Val Thr  His Gln Leu Leu Asn  Asn Ser Gly Met Gln  Lys Asp Ile
    10025            10030                10035

Ser Leu  Ile Gly Ser Trp Glu  Leu Gln Lys Ala Val  Asp Ala Ser
    10040            10045                10050

Arg Leu  Arg Pro Ala Thr Glu  Ser Cys Thr His Trp  Leu Ile Gln
    10055            10060                10065

Asp Gln  Val Arg Leu Gln Pro  Asp Gln Ile Ala Ile  Ser Ser Trp
    10070            10075                10080

Asp Gly  Asp Leu Thr Tyr Ala  Gln Leu Gly Lys His  Val Ala Arg
    10085            10090                10095

Leu Ala  Ala Arg Leu Gln Glu  Leu Asp Val Gly Pro  Glu Ser Leu
    10100            10105                10110

Val Pro  Leu Cys Phe His Lys  Ser Lys Trp Ala Val  Val Ala Met
    10115            10120                10125

Val Ala  Val Gln Met Ala Gly  Gly Ala Phe Ile Pro  Leu Asp Pro
    10130            10135                10140

Gly Ala  Ser Pro Ala Arg Leu  Gln Gly Ile Leu Gln  Asp Thr Gly
    10145            10150                10155

Ala Thr  Leu Ala Ile Thr Ser  Ser Glu Cys Gln Gly  Leu Leu Gln
    10160            10165                10170

Ser Leu  Gly Met Lys Ala Val  Thr Val Asp Asp Gln  Ser Ile Ser
    10175            10180                10185

Glu Leu  Pro Ala Glu Phe Asp  Leu Arg Ser Glu Ala  Arg Pro Thr
    10190            10195                10200

Asn Ala  Ser Val Ile Leu Phe  Thr Ser Gly Ser Thr  Gly Lys Pro
    10205            10210                10215

Lys Gly  Met Ile Ile Glu His  Arg Ser Ile Cys Ser  Ser Ser Asp
    10220            10225                10230

Ala Tyr  Gly Ala Asp Leu Lys  Ile Glu Ala Gly Thr  Arg Val Phe
    10235            10240                10245

Gln Phe  Ser Ala Tyr Thr Phe  Asp Val Gly Val Leu  Asp Cys Leu
    10250            10255                10260

Val Thr  Leu Met Arg Gly Ala  Cys Ile Cys Ile Pro  Ser Asp His
    10265            10270                10275

Asp Arg  Leu Asn Asn Leu Ala  Ala Ala Ile Thr Ala  Ser Lys Ala
    10280            10285                10290

Asp Trp  Val Phe Leu Thr Pro  Thr Val Ala Asp Leu  Leu Asn Pro
    10295            10300                10305

Val Glu  Val Pro Thr Leu Lys  Thr Val Cys Leu Gly  Gly Glu Ala
    10310            10315                10320

Ile Thr  Lys Lys Cys Ala Asp  Arg Trp Val Gly His  Val Ser Leu
    10325            10330                10335

His Gly  Leu Tyr Gly Pro Ala  Glu Ala Ser Ile Cys  Ala Trp Asn
    10340            10345                10350

Ser Val  Val Gly Arg Ser Gly  Arg Pro Thr Asn Leu  Gly His Pro
    10355            10360                10365

Ile Ser  Ser Ala Phe Trp Val  Val Asn Val Asn Asp  Pro Lys Ser
    10370            10375                10380

Leu Val  Pro Ile Gly Cys Ile  Gly Glu Leu Leu Ile  Glu Gly Pro
    10385            10390                10395

Met Leu  Ala Arg Gly Tyr Leu  Asn Val Thr Ala Glu  Val Ala Ala
```

```
                10400               10405               10410
Asn Trp  Leu Glu Gly Val Asp  Trp Leu Pro Gly Asp  Asn Arg Pro
    10415               10420               10425
Arg Arg  Ala Tyr Arg Thr Gly  Asp Leu Val Arg Arg  Asn Ala Asp
    10430               10435               10440
Gly Thr  Phe Asp Tyr Ile Gly  Arg Lys Asp Thr Gln  Val Lys Leu
    10445               10450               10455
His Gly  Gln Arg Val Glu Leu  Gly Glu Ile Glu Thr  Arg Ile Gln
    10460               10465               10470
Glu Phe  Leu Pro Gln Asn Met  Ala Ala Ile Val Asp  Val Val Lys
    10475               10480               10485
Asp Asn  Asp Ala Pro Ala Thr  Leu Leu Ala Phe Ile  Trp Asn Ser
    10490               10495               10500
Asp Gly  Ser Ser Ala Ser Pro  Ala Arg Leu Val Asp  Thr Val Ser
    10505               10510               10515
Asp Glu  Ala Arg Ala Met Val  Leu His Leu Asp Thr  Ser Leu Asn
    10520               10525               10530
Thr Ile  Leu Pro Ser Tyr Met  Ile Pro Ser Ser Tyr  Leu Leu Phe
    10535               10540               10545
Ser Gly  Lys Pro Glu Gln Thr  Thr Thr Gly Lys Ile  Asn Arg Arg
    10550               10555               10560
Ser Leu  Thr Gly Gln Ala Gln  His Ile Thr Ala Gln  Glu Arg Leu
    10565               10570               10575
Arg Phe  Ala Pro Asp Thr Ser  Phe Arg Val Leu Pro  Thr Thr Pro
    10580               10585               10590
Met Glu  Phe Lys Leu Arg Glu  Leu Trp Ala Gln Ile  Leu Arg Ile
    10595               10600               10605
Glu Pro  Asp Asp Ile Cys Lys  Asn Asp Ser Phe Leu  Arg Leu Gly
    10610               10615               10620
Gly Asp  Ser Ile Ser Ala Ile  Gln Leu Val Ser Lys  Ala Gln Leu
    10625               10630               10635
Gln Gly  Leu Asp Leu Thr Val  Ala Thr Ile Phe Gln  Ser Pro Arg
    10640               10645               10650
Leu Glu  Gln Met Ala Ser Ala  Ile Val Glu Asp Glu  Leu Thr Val
    10655               10660               10665
Tyr Ser  Glu Ile Arg Pro Phe  Asp Met Leu Pro Ala  Gly Glu Ser
    10670               10675               10680
Ser Thr  Ile Leu Ala Glu Ala  Arg Asp Gln Cys Ser  Leu Pro Asp
    10685               10690               10695
Ser Ala  Ile Ile Glu Asp Ser  Tyr Pro Cys Thr Lys  Leu Gln Glu
    10700               10705               10710
Gly Leu  Met Ala Leu Ser Val  Lys Gln Pro Gly Ser  Tyr Val Ala
    10715               10720               10725
Lys Tyr  Leu Tyr Arg Leu Pro  Asp His Val Asp Val  Ala Arg Phe
    10730               10735               10740
Lys Ser  Ala Trp Lys Gln Thr  Met His Ile Cys Ala  Ser Leu Arg
    10745               10750               10755
Ser Arg  Ile Ile Asn Thr Ser  Ala Lys Ser Thr Phe  Gln Ile Val
    10760               10765               10770
Leu Asn  Pro Glu Ser Ser Ser  Glu Pro Leu Pro Tyr  His Asp Leu
    10775               10780               10785
Gln Ala  Val Leu Arg Tyr Ala  Gln Thr Ile Lys Met  Thr Tyr Gly
    10790               10795               10800
```

-continued

Ser Ala Leu Cys Gln Phe Ala Phe Val Glu Asp Glu Gln Arg Ser
        10805            10810            10815

Val Phe Phe Trp Ala Met His His Thr Val Phe Asp Gly Leu
        10820            10825            10830

Ser Thr Gln Val Ile Leu Gly Ile Leu His Lys Ala Tyr Phe Gly
        10835            10840            10845

Leu Glu Thr Pro Val Leu Thr Pro Tyr Ser Arg Phe Ile Gln Tyr
        10850            10855            10860

Leu Leu Gln Ile Asp Glu Glu Ala Ala Ser Ala Tyr Trp Arg Asp
        10865            10870            10875

Ala Leu His Asp Ala Lys Pro Ala Gln Leu Pro Ser Leu His Asn
        10880            10885            10890

Thr His Asp Lys Val Val Ala Thr Cys Val Leu Glu Thr Pro Ile
        10895            10900            10905

Gly Phe Val Asp Ala Ser Lys Leu Asn Val Thr Leu Ala Thr Val
        10910            10915            10920

Ile Arg Ser Ala Trp Ala Ile Val Leu Ala Arg Tyr Cys Asp Thr
        10925            10930            10935

Asp Asp Val Cys Phe Gly Ile Ala Thr Ser Gly Arg Gln Ala Pro
        10940            10945            10950

Val Pro Gly Ile Val Asp Met Val Gly Pro Val Ile Ala Thr Val
        10955            10960            10965

Pro Val Arg Val Arg Leu Asp Arg Gln Gln Pro Val Ser Asp Phe
        10970            10975            10980

Leu Gln Ser Val Gln Gln Gly Ala Val Gly Met Ile Pro Tyr Glu
        10985            10990            10995

Gln Phe Gly Leu Gln Asn Ile Thr Lys Leu Ser Arg Asp Ala Tyr
        11000            11005            11010

Glu Ala Cys Gln Phe Ser Ser Leu Leu Val Val Gln Pro Ile Arg
        11015            11020            11025

His Ile Ala Asn Ser Glu Glu Ser Lys Glu Leu Leu Ser Ala Ala
        11030            11035            11040

Glu Val Thr Glu Gly Leu Ser Asp Ser Leu Asn Asn Phe Phe Asn
        11045            11050            11055

Tyr Pro Leu Ile Val Gln Gly His Leu Tyr Gly Asp Lys Val Lys
        11060            11065            11070

Ile Ala Val Ala Tyr Asp Arg Asn Val Leu Thr Glu Arg Gln Val
        11075            11080            11085

Gln Ala Leu Ser Glu Gln Leu Gly His Val Ile His Gln Leu Ala
        11090            11095            11100

Ser Gly Ala Gly Thr Ser Leu Glu Ser Ile Leu Ile Ala Ser Ser
        11105            11110            11115

His Asp Leu Glu Leu Ala Leu Ala Val Asn Ser Glu Val Pro Glu
        11120            11125            11130

Ile Ile Ser Ser Cys Val His Glu Leu Ile Asp Lys Gln Ala Gln
        11135            11140            11145

Ile Ser Pro Gln Ala Pro Ala Ile Leu Ala Cys Asp Ala Glu Leu
        11150            11155            11160

Thr Tyr Ser Asp Leu Ala Ala Ala Ser Asp Arg Leu Ala Tyr His
        11165            11170            11175

Leu Ile His Ser His Gly Val Lys Pro Gly Asp Phe Val Ser Val
        11180            11185            11190

```
Cys Phe  Gly Lys Ser Ala Trp  His Phe Val Ser Ile  Phe Ala Ile
    11195            11200                11205

Asn Lys  Ala Gly Ala Ala Trp  Val Pro Leu Glu Pro  Ser Gln Pro
    11210            11215                11220

Glu Ala  Arg Leu Arg Gln Ile  Val Leu Gln Thr Lys  Ala Arg Leu
    11225            11230                11235

Ala Leu  Val Ser Pro Ser Asn  Ala Glu Leu Cys Ala  Lys Leu Val
    11240            11245                11250

Thr Asp  Val Val Glu Val Thr  Ala Glu Leu Asp Gln  Gln Leu Gly
    11255            11260                11265

Arg Ser  Val Ser Glu Pro Phe  Lys Pro Leu Ala Ile  Ser Pro Arg
    11270            11275                11280

Ser Pro  Ala Tyr Ile Leu Phe  Thr Ser Gly Ser Thr  Gly Thr Pro
    11285            11290                11295

Lys Gly  Phe Val Ile Glu His  Gln Ser Leu Ser Thr  Ser Gln Thr
    11300            11305                11310

Ala Leu  Ala Thr Arg Leu Lys  Met Thr Ser Ser Val  Arg Ile Met
    11315            11320                11325

Gln Phe  Ala Ser Tyr Val Phe  Asp Met Ser Leu Gly  Glu Ser Ile
    11330            11335                11340

Gly Pro  Leu Ile Ser Gly Ala  Cys Val Cys Ile Pro  Ser Asp Arg
    11345            11350                11355

Glu Arg  Met Glu Asn Ile Ala  Thr Phe Ile Arg Lys  Arg Gln Ile
    11360            11365                11370

Asn Trp  Ala Phe Leu Thr Pro  Val Phe Ala Arg Thr  Ile Gln Pro
    11375            11380                11385

Ala Asp  Val Pro Ser Leu Glu  Leu Leu Leu Leu Gly  Gly Glu Ala
    11390            11395                11400

Val Pro  Gln Asp Leu Cys Leu  Thr Trp Phe Gly Lys  Val Arg Leu
    11405            11410                11415

Ile Asn  Ala Trp Gly Pro Ala  Glu Ala Cys Val Ile  Ser Ala Val
    11420            11425                11430

His Glu  Trp Thr Ser Ala Glu  Thr Ser Ser Leu Val  Ile Gly Arg
    11435            11440                11445

Pro Val  Gly Gly Phe Cys Trp  Ile Val Asp Pro Glu  Met Pro Gln
    11450            11455                11460

Ser Leu  Ala Pro Phe Gly Thr  Met Gly Glu Val Ala  Ile Gln Gly
    11465            11470                11475

Pro Thr  Leu Leu Arg Glu Tyr  Leu Asp Glu Pro Glu  Arg Thr Lys
    11480            11485                11490

Ala Ala  Leu Ile Pro Arg Pro  Ser Trp Ala Pro Gln  Pro Asp Ala
    11495            11500                11505

Gln His  Trp Asn Arg Leu Tyr  Arg Thr Gly Asp Leu  Cys Phe Tyr
    11510            11515                11520

Asn Ser  Asp Gly Asn Leu Val  Phe Gly Gly Arg Arg  Asp Thr Gln
    11525            11530                11535

Val Lys  Ile Arg Gly Phe Arg  Val Glu Ile Gly Asp  Ile Glu His
    11540            11545                11550

His Ile  Arg Asp Lys Leu Asp  Asp Val Cys Glu Ala  Ala Val Glu
    11555            11560                11565

Val Leu  Lys Ser Thr Thr Gly  Ala Ser Leu Ile Ala  Phe Val Ser
    11570            11575                11580

Phe Lys  Ser Gly Ile Glu Gln  Pro Asp Ile Glu Ser  Ser Gly Ser
```

-continued

```
        11585               11590               11595

Ser Gly Glu Val Phe Leu Gln Pro Thr Ser Arg Met Gln Lys Ala
        11600               11605               11610

Phe Arg Ala Leu Glu Gly Arg Leu Lys Ala Thr Leu Pro Pro Tyr
        11615               11620               11625

Met Val Pro Ser Ile Phe Val Pro Cys Lys Tyr Leu Pro Ser Thr
        11630               11635               11640

Thr Ser Asp Lys Leu Asp Arg Lys Lys Leu Lys Ala Met Ala Ser
        11645               11650               11655

Ser Leu Ser Leu Glu Asp Leu Ser Lys Tyr Thr Leu Ser Asp Leu
        11660               11665               11670

Glu Lys Gln Gly Pro Glu Thr Glu Met Glu Lys Arg Ile Gln Leu
        11675               11680               11685

Ile Trp Ala Glu Leu Leu Asn Val Pro Ala Thr Ser Ile Gly Arg
        11690               11695               11700

Asp Asp Ser Phe Leu Gln Ile Gly Gly Asp Ser Ile Ile Ala Ile
        11705               11710               11715

His Phe Val Thr Ala Ala Gln Asn Ser Asn Ile Gly Leu Ser Val
        11720               11725               11730

Ala Asp Ile Phe Asp Asp Pro Arg Leu Leu Ala Val Ala Ala Lys
        11735               11740               11745

Ala Ile Ser Leu Thr Arg Ser Gly Gln Ala Ala Glu Ile Pro Gln
        11750               11755               11760

Phe Gly Leu Ile Asp Glu Gln Thr Gln Gln Leu Leu Ser Ser Gln
        11765               11770               11775

Asp Leu Arg Gln Asn Tyr His Leu Ala Asp Asp Val Val Leu Arg
        11780               11785               11790

Asp Ala Tyr Pro Ser Thr Lys Met Gln Glu Gly Leu Leu Ala Leu
        11795               11800               11805

Thr Glu Lys Gln Pro Gly Ser Tyr Val Ala Lys Phe Val Tyr Arg
        11810               11815               11820

Leu Gly Arg Thr Val Asp Val Leu Arg Phe Arg Ser Ala Phe Glu
        11825               11830               11835

Asp Met Val Lys Leu Cys Asp Asn Leu Arg Thr Arg Val Val Met
        11840               11845               11850

Val Gly Ser Gln Thr Val Gln Leu Val Leu Glu Asn Asp Phe Ala
        11855               11860               11865

Trp Asp Glu Val Gln Gly Gln Glu Leu Gln Ser Tyr Met His Ala
        11870               11875               11880

Leu Gly Ser Ser Asn Met Ala Tyr Gly Ser Arg Leu Ser Arg Gly
        11885               11890               11895

Ala Ile Val Met Asp Gly Asp Glu Val Tyr Phe Val Trp Ala Leu
        11900               11905               11910

His His Ser Ile Phe Asp Gly Trp Thr Met Arg Leu Met Met Asp
        11915               11920               11925

Val Leu His Ser Met Tyr Asp Gly Arg Ser Pro Pro Ser Leu Gln
        11930               11935               11940

Ser Tyr Asn Arg Phe Val Ala Tyr Val Gly Asn Leu Asn His Glu
        11945               11950               11955

Glu Thr Arg Asn Tyr Trp Gly Ala Gln Leu Asp Gly Ala Ser Arg
        11960               11965               11970

Ala Ala Tyr Pro Pro Leu Ser Lys Thr Ser Ser Asn Ser Ser Lys
        11975               11980               11985
```

```
Ser Leu Glu Arg Gly Met Gln   Leu Pro Asn Met Thr   Asp Leu Ser
    11990           11995                 12000

Ala Thr Lys Ala Thr Val Ile   Arg Ala Ala Trp Ala   Met Leu Leu
    12005           12010                 12015

Ala Arg Tyr Cys Glu Thr Asp   Asp Val Cys Phe Gly   Ala Thr Val
    12020           12025                 12030

Ser Gly Arg Gln Ala Pro Val   Pro Gly Leu Pro Asp   Met Pro Gly
    12035           12040                 12045

Pro Ala Val Ala Thr Val Pro   Ile Arg Val Arg Leu   Asp Lys His
    12050           12055                 12060

Arg Ser Val Ser Asp Tyr Leu   Asp Thr Ile Gln Ser   Gln Ala Leu
    12065           12070                 12075

Lys Met Ile Pro Tyr Glu Gln   Phe Gly Leu Gln Glu   Ile Gln Lys
    12080           12085                 12090

Ile Ser Pro Arg Ala Gln Glu   Val Cys Asn Phe Ser   Ser Leu Leu
    12095           12100                 12105

Val Val Gln Pro Met Gln His   Leu Ile Asn Gly Glu   His Ala Leu
    12110           12115                 12120

Leu Gln Pro Val Glu Val Glu   Ser Gln Glu Glu Ser   Ser Leu Gln
    12125           12130                 12135

Asn Tyr Phe Thr Tyr Pro Leu   Val Ile Gln Gly His   Val Met Gly
    12140           12145                 12150

Glu Asp Ile Lys Leu Met Phe   Ile Tyr Asp Ser Asn   Val Leu Pro
    12155           12160                 12165

Glu Ser Gln Val Leu Ala Ile   Ser His Gln Met Glu   His Ile Met
    12170           12175                 12180

Arg Gln Leu Ile Ala Lys Pro   Gln Ser Leu Leu Gly   Asp Leu Ser
    12185           12190                 12195

Leu Thr Cys Asp Trp Asp Val   Lys Phe Ala Glu Lys   Ala Asn Arg
    12200           12205                 12210

Glu Asp Pro Pro Glu Ile Ile   Asp Ser Cys Leu His   Asp Leu Ile
    12215           12220                 12225

Glu Cys Gln Ala Glu Ile Arg   Pro Asp Ala Val Ala   Ile Leu Gly
    12230           12235                 12240

Trp Asp Lys Val Leu Thr Tyr   Asp Glu Leu Asn Lys   Ala Ala Asn
    12245           12250                 12255

Arg Leu Ala His His Leu Val   Met Asp Ile Gly Val   Lys Ala His
    12260           12265                 12270

Asp Leu Val Gln Val Cys Phe   Thr Lys Ser Ala Trp   Tyr Ala Val
    12275           12280                 12285

Ala Ile Leu Ala Ile Asn Lys   Val Gly Ala Ala Trp   Val Pro Ile
    12290           12295                 12300

Asp Pro Ser His Pro Leu Gln   Arg His Gln Gln Val   Thr Ala Gln
    12305           12310                 12315

Thr Lys Ala Arg Val Ala Leu   Ala Ser Gln Asp Asn   Val Glu Arg
    12320           12325                 12330

Cys Ser Gln Leu Val Thr Ser   Val Val Val Val Ser   Ser Ser Leu
    12335           12340                 12345

Asp Ser Asp Leu Cys Lys Lys   Gly Phe Ser Ser Ser   Gln Gly Pro
    12350           12355                 12360

Asp Val Leu Val Thr Pro Lys   His Ala Ala Tyr Val   Leu Phe Thr
    12365           12370                 12375
```

-continued

| | | | | | | | | | | | |
|---|---|---|---|---|---|---|---|---|---|---|---|
| Ser | Gly 12380 | Ser | Thr | Gly | Val 12385 | Pro | Lys | Gly | Leu | Ile 12390 | Met | Glu | His | Gly |
| Ala 12395 | Leu | Cys | Thr | Ser | Gln 12400 | Met | Ala | Ala | Gly | Lys 12405 | Arg | Phe | Gly | Phe |
| Thr 12410 | Pro | Ser | Val | Lys | Ile 12415 | Leu | Gln | Phe | Ala | Ala 12420 | Tyr | Val | Phe | Asp |
| Tyr 12425 | Ser | Ile | Ser | Glu | Met 12430 | Leu | Ala | Ala | Met | Met 12435 | Tyr | Gly | Ala | Cys |
| Val 12440 | Cys | Ile | Pro | Ser | Glu 12445 | Glu | Asp | Arg | Met | Asn 12450 | Arg | Leu | Lys | Glu |
| Tyr 12455 | Val | Asn | Asp | Thr | Gly 12460 | Ile | Asn | Trp | Leu | Phe 12465 | Leu | Thr | Pro | Ser |
| Phe 12470 | Leu | Gln | Thr | Leu | Arg 12475 | Pro | Glu | Asp | Val | Pro 12480 | Ser | Val | Glu | Leu |
| Val 12485 | Ala | Leu | Gly | Gly | Glu 12490 | Ala | Val | Pro | Arg | Ala 12495 | Leu | Phe | Glu | Glu |
| Trp 12500 | Ile | Gly | Lys | Val | Arg 12505 | Phe | Phe | Asn | Ala | Trp 12510 | Gly | Pro | Ser | Glu |
| Thr 12515 | Cys | Val | Met | Ser | Ala 12520 | Met | His | Glu | Trp | Arg 12525 | Ser | Ser | Glu | Glu |
| Ser 12530 | Ala | Leu | Thr | Ile | Gly 12535 | Lys | Pro | Val | Gly | Gly 12540 | Phe | Cys | Trp | Ile |
| Val 12545 | Asp | Pro | Glu | Asp | Pro 12550 | Trp | Lys | Leu | Ala | Pro 12555 | Thr | Gly | Thr | Val |
| Gly 12560 | Glu | Leu | Ile | Val | Gln 12565 | Gly | Pro | Thr | Leu | Leu 12570 | Arg | Glu | Tyr | Leu |
| Gly 12575 | Asp | Ala | Glu | Lys | Ser 12580 | Lys | Ala | Ala | Ile | Leu 12585 | Glu | Gly | Arg | Pro |
| Asp 12590 | Trp | Ala | Met | Tyr | Pro 12595 | Asp | Thr | Gln | His | Trp 12600 | Thr | Arg | Phe | Tyr |
| Lys 12605 | Ser | Gly | Asp | Leu | Cys 12610 | Ser | Tyr | Asn | Pro | Asp 12615 | Gly | Thr | Ile | Arg |
| Phe 12620 | Tyr | Ser | Arg | Lys | Asp 12625 | Thr | Gln | Val | Lys | Ile 12630 | Arg | Gly | Leu | Arg |
| Val 12635 | Glu | Leu | Gly | Glu | Val 12640 | Glu | Tyr | Arg | Ile | Lys 12645 | Glu | Thr | Phe | Pro |
| Glu 12650 | Ala | His | Gln | Val | Val 12655 | Val | Asp | Val | Phe | Lys 12660 | Ser | Gly | Ser | Val |
| Ser 12665 | Asn | Leu | Val | Ala | Tyr 12670 | Phe | Cys | Phe | Gly | Asp 12675 | Ala | Thr | Val | Asp |
| Val 12680 | Ser | Ser | Asn | Ser | Leu 12685 | Asp | Asp | Ile | Phe | Met 12690 | Val | Leu | Gly | Glu |
| Glu 12695 | Thr | Gln | Gln | Arg | Leu 12700 | Ala | Thr | Met | Val | Gly 12705 | Glu | Leu | Lys | Val |
| Leu 12710 | Leu | Pro | Glu | Tyr | Met 12715 | Val | Pro | Ala | Leu | Phe 12720 | Ile | Gln | Cys | Lys |
| His 12725 | Met | Pro | Thr | Ala | Thr 12730 | Ser | Gly | Lys | Leu | Asp 12735 | Arg | Lys | Thr | Leu |
| Arg 12740 | Gly | Leu | Thr | Ser | Ser 12745 | Leu | Thr | Lys | Asp | Gln 12750 | Leu | Ala | Ala | Tyr |
| Ser 12755 | Leu | Val | Asn | Ser | Lys 12760 | Lys | Thr | Met | Pro | Gln 12765 | Thr | Pro | Met | Glu |
| Gly | Lys | Leu | Gln | Ala | Ile | Trp | Ala | Asp | Val | Leu | Gly | Ile | Pro | Met |

-continued

|  |  |  |  |  |  |  |  |  |  |
|---|---|---|---|---|---|---|---|---|---|
| 12770 | | | 12775 | | | | 12780 | | |
| Glu | Thr | Ile | Gly | Arg | Asp | Asp | Ser | Phe | Leu | Ser | Ile | Gly | Gly | Asp |
| | 12785 | | | | 12790 | | | | 12795 |
| Ser | Ile | Ala | Ala | Ile | Arg | Leu | Val | Ala | Ala | Arg | Asp | Gln | Gly |
| | 12800 | | | | 12805 | | | | 12810 |
| Val | Ala | Leu | Thr | Val | Ser | Gln | Ile | Phe | Glu | Asp | Gly | Arg | Leu | Leu |
| | 12815 | | | | 12820 | | | | 12825 |
| Ser | Ile | Ala | Ser | Lys | Ala | Ser | Phe | Ile | Ser | Asp | Gly | Ser | Ser | Gln |
| | 12830 | | | | 12835 | | | | 12840 |
| Ala | Phe | Thr | Pro | Ile | Glu | Pro | Phe | Ala | Leu | Leu | Asp | Glu | Pro | Gln |
| | 12845 | | | | 12850 | | | | 12855 |
| Arg | Asp | Met | Ile | Thr | Glu | Ser | Ala | Glu | Glu | Phe | Gly | Leu | Glu | Leu |
| | 12860 | | | | 12865 | | | | 12870 |
| Ser | Arg | Asp | Met | Ala | Val | Glu | Asp | Cys | Tyr | Pro | Cys | Ser | Lys | Met |
| | 12875 | | | | 12880 | | | | 12885 |
| Gln | Glu | Gly | Leu | Met | Ala | Leu | Ala | Val | Lys | Gln | Pro | Gly | Ser | Tyr |
| | 12890 | | | | 12895 | | | | 12900 |
| Ile | Ala | Lys | Tyr | Asn | Tyr | Arg | Ile | Pro | Ser | His | Val | Asp | Val | Ser |
| | 12905 | | | | 12910 | | | | 12915 |
| Leu | Leu | Lys | Ala | Ala | Trp | Glu | Gln | Ile | Val | Asn | Ser | Phe | Pro | Asn |
| | 12920 | | | | 12925 | | | | 12930 |
| Leu | Arg | Thr | Arg | Ile | Ile | Arg | Leu | Gly | Ala | Ile | Ser | Leu | Gln | Val |
| | 12935 | | | | 12940 | | | | 12945 |
| Val | Val | Lys | Gly | Asp | Thr | Val | Trp | Asp | Ser | Thr | Glu | Arg | Met | Thr |
| | 12950 | | | | 12955 | | | | 12960 |
| Leu | Arg | Ser | Tyr | Leu | Gln | Gln | Thr | Arg | Thr | Met | Glu | Met | Gly | Tyr |
| | 12965 | | | | 12970 | | | | 12975 |
| Gly | Ser | Arg | Leu | Cys | Arg | Ser | Ala | Ile | Phe | Lys | Asp | Gly | Asp | Glu |
| | 12980 | | | | 12985 | | | | 12990 |
| Val | Tyr | Phe | Ser | Phe | Asn | Leu | His | His | Ala | Val | Tyr | Asp | Gly | Trp |
| | 12995 | | | | 13000 | | | | 13005 |
| Thr | Leu | Ser | Ile | Ile | Leu | Glu | Glu | Phe | His | Arg | Ala | Tyr | Lys | Gly |
| | 13010 | | | | 13015 | | | | 13020 |
| Leu | Glu | Pro | Ala | Thr | Thr | Val | Pro | Tyr | Ser | His | Phe | Ile | Lys | Tyr |
| | 13025 | | | | 13030 | | | | 13035 |
| Thr | Met | Glu | Leu | Asp | His | Glu | Ala | Ala | Gly | Asp | Phe | Trp | Ala | Arg |
| | 13040 | | | | 13045 | | | | 13050 |
| Gln | Leu | Glu | Asn | Ala | Arg | Lys | Ala | Thr | Phe | Pro | Ser | Val | Pro | Ile |
| | 13055 | | | | 13060 | | | | 13065 |
| Thr | Ser | Thr | Ser | Lys | Pro | Glu | Ala | Ser | Arg | Thr | Met | Thr | Ala | Glu |
| | 13070 | | | | 13075 | | | | 13080 |
| Leu | Glu | Leu | Ser | Lys | Ser | Asn | Thr | Thr | Ile | Thr | Thr | Ala | Thr | Ile |
| | 13085 | | | | 13090 | | | | 13095 |
| Val | Arg | Ala | Ala | Trp | Ala | Leu | Val | Leu | Ala | Arg | Tyr | Cys | Asp | Ser |
| | 13100 | | | | 13105 | | | | 13110 |
| Thr | Asp | Val | Cys | Phe | Gly | Ala | Thr | Val | Ser | Gly | Arg | Gln | Ala | Ser |
| | 13115 | | | | 13120 | | | | 13125 |
| Leu | Pro | Gly | Leu | Thr | Gln | Met | Pro | Gly | Pro | Val | Ile | Ala | Thr | Ile |
| | 13130 | | | | 13135 | | | | 13140 |
| Pro | Val | Arg | Ile | His | Leu | Asp | His | Asp | Gln | Pro | Thr | Thr | Lys | Phe |
| | 13145 | | | | 13150 | | | | 13155 |
| Leu | Glu | Glu | Val | Gln | Thr | Arg | Ala | Ser | Asp | Ala | Ile | Pro | Phe | Glu |
| | 13160 | | | | 13165 | | | | 13170 |

```
Gln Phe Gly Leu Gln Ser Ile Arg Lys Leu Asn Pro     Asp Ala Asp
13175               13180                 13185

Glu Ala Cys Asp Phe Thr Ser Leu Leu Val Ile Gln     Pro Leu Lys
13190               13195                 13200

Met Leu Ser His Leu Glu Asn Thr Gly Glu Asp Ala     Leu Leu Val
13205               13210                 13215

Gly Val Glu Asp Thr Asp Asp Ser Ala Asp Gly Met     Gln Asn Tyr
13220               13225                 13230

Phe Ser Tyr Pro Leu Val Leu Gln Ala His Leu Ser     Asp Asp Phe
13235               13240                 13245

Met Arg Ile Val Leu Ile Tyr Asn Pro His Cys Ile     Ala Glu Gln
13250               13255                 13260

Gln Ile Val Ala Leu Ser Glu Gln Leu Lys His Val     Ile Ala Gln
13265               13270                 13275

Leu Ala Glu Ser Lys Pro Ser Gln Met Leu Arg Asp     Val Ser Leu
13280               13285                 13290

Val Ser Gln Trp Asp Ile Glu Gln Ser Arg Lys Phe     Asn Val Asp
13295               13300                 13305

Thr Pro Glu Ile Val Asp Ser Cys Phe His Thr Leu     Val Glu Asp
13310               13315                 13320

Gln Ala Ala Gln Arg Pro Asp Ala Met Ala Ile Arg     Ser Trp Asp
13325               13330                 13335

Gly Asp Phe Ser Tyr Ala Gln Leu Asn Gln Ala Ala     Asn Arg Leu
13340               13345                 13350

Ala Asn Tyr Leu Val Gln Thr His Glu Ile Lys Thr     Asn Asp Leu
13355               13360                 13365

Ile His Val Cys Phe Glu Lys Ser Val Trp His Phe     Val Ser Ile
13370               13375                 13380

Leu Ala Ile Asn Lys Thr Gly Ala Ala Trp Val Pro     Leu Asp Pro
13385               13390                 13395

Ser His Pro Leu Gln Arg Leu Gln Gln Val Val Ser     Gln Thr Arg
13400               13405                 13410

Ala Lys Phe Ala Leu Cys Ser Pro Asp Asn Ser Asp     Leu Cys Ser
13415               13420                 13425

Thr Leu Val Glu Ser Ala Ile Gln Ile Thr Pro Glu     Phe Asp Lys
13430               13435                 13440

Gln Leu Gln Lys Gln Val Asn Ser Arg Gln Gly Pro     Thr Glu Arg
13445               13450                 13455

Ala Ser Ser Gly Asp Ile Ala Tyr Val Leu Phe Thr     Ser Gly Ser
13460               13465                 13470

Thr Gly Thr Pro Lys Gly Leu Val Met Gln His Gly     Ser Val Cys
13475               13480                 13485

Thr Ser Gln Lys Ala Ile Ala Lys Arg Leu Arg Leu     Gly Pro Glu
13490               13495                 13500

Val Arg Met Leu Gln Phe Ala Ala Phe Val Phe Asp     Leu Ser Ile
13505               13510                 13515

Gly Glu Ile Val Ala Pro Leu Ile Thr Gly Ala Cys     Leu Cys Ile
13520               13525                 13530

Pro Ser Glu His Ala Arg Met Asn Asp Leu Ser Lys     Phe Met Gln
13535               13540                 13545

Asp Met Asn Val Asn Trp Ala Phe Leu Thr Pro Ser     Phe Val Arg
13550               13555                 13560
```

-continued

| | | | | | | | | | | | |
|---|---|---|---|---|---|---|---|---|---|---|---|
| Thr | Leu 13565 | Asn | Pro | Asp | Asp 13570 | Val | Pro | Gly | Leu | Glu 13575 | Val | Leu | Leu | Leu |
| Ala | Gly 13580 | Glu | Ala | Val | Pro 13585 | Arg | Asp | Val | Leu | Thr 13590 | Ala | Trp | Phe | Gly |
| Lys | Val 13595 | Arg | Arg | Leu | Ile 13600 | Asn | Gly | Trp | Gly | Pro 13605 | Ala | Glu | Thr | Cys |
| Val | Phe 13610 | Ser | Thr | Leu | His 13615 | Glu | Trp | Lys | Ser | Val 13620 | Asp | Glu | Ser | Pro |
| Leu | Thr 13625 | Val | Gly | Arg | Pro 13630 | Val | Gly | Gly | Phe | Cys 13635 | Trp | Ile | Val | Asp |
| Pro | Asp 13640 | Ser | Gly | Phe | Leu 13645 | Ala | Pro | Ile | Gly | Thr 13650 | Val | Gly | Glu | Val |
| Val | Ile 13655 | Gln | Gly | Pro | Thr 13660 | Leu | Leu | Gln | Glu | Tyr 13665 | Leu | Ala | Asp | Pro |
| Glu | Arg 13670 | Thr | Asn | Thr | Ser 13675 | Ile | Leu | Pro | Ala | Ala 13680 | Glu | Trp | Ala | Pro |
| Arg | Pro 13685 | Asp | Glu | Ser | His 13690 | Trp | Asn | Arg | Phe | Tyr 13695 | Lys | Ser | Gly | Asp |
| Leu | Cys 13700 | Arg | Tyr | Asn | Ala 13705 | Asp | Gly | Thr | Ile | Glu 13710 | Phe | Ser | Thr | Arg |
| Lys | Asp 13715 | Thr | Gln | Ile | Lys 13720 | Ile | Arg | Gly | Leu | Arg 13725 | Val | Glu | Leu | Ser |
| Glu | Ile 13730 | Glu | Tyr | Asn | Ile 13735 | Gln | Gln | Ser | Leu | Ile 13740 | Gly | Val | Arg | Gln |
| Val | Ala 13745 | Val | Asp | Val | Val 13750 | Arg | Gly | Asp | Asn | Gly 13755 | Ser | Ser | Leu | Val |
| Ala | Tyr 13760 | Ile | Cys | Phe | Thr 13765 | Asp | Glu | Thr | Lys | Thr 13770 | Ala | Gly | Val | Lys |
| Thr | Asp 13775 | Ala | Ser | Glu | Thr 13780 | Leu | Phe | Leu | Ser | Thr 13785 | Asp | Glu | Ser | Leu |
| Gln | Asn 13790 | Gln | Leu | Ile | Ala 13795 | Leu | Val | Gly | Glu | Leu 13800 | Gly | Ile | Ala | Leu |
| Pro | Arg 13805 | Tyr | Met | Ile | Pro 13810 | Thr | Leu | Phe | Ile | Pro 13815 | Cys | Ala | Phe | Met |
| Pro | Phe 13820 | Ile | Ala | Ser | Thr 13825 | Lys | Leu | Asp | Arg | Lys 13830 | Leu | Leu | Gln | Thr |
| His | Leu 13835 | Ser | Thr | Leu | Asp 13840 | Arg | Asp | Gln | Leu | Ala 13845 | Met | Tyr | Ser | Leu |
| Leu | His 13850 | Ser | Glu | Lys | Arg 13855 | Gln | Pro | Glu | Thr | Glu 13860 | Met | Glu | Gln | Arg |
| Leu | Gln 13865 | Leu | Ile | Trp | Ala 13870 | Glu | Ile | Met | Asn | Leu 13875 | Pro | Met | Glu | Ser |
| Ile | Gly 13880 | Arg | Asp | Asp | Thr 13885 | Phe | Phe | Gln | Leu | Gly 13890 | Gly | Asp | Ser | Ile |
| Met | Ala 13895 | Ile | Tyr | Leu | Val 13900 | Ser | Thr | Ala | Lys | Glu 13905 | Glu | Gly | Ile | Thr |
| Leu | Thr 13910 | Val | Gln | Asp | Val 13915 | Phe | Asp | Asp | Pro | Arg 13920 | Leu | Leu | Ala | Val |
| Ala | Ala 13925 | Lys | Ala | Val | Leu 13930 | Ser | Gln | Asp | Gly | Met 13935 | Glu | Pro | Ala | Asp |
| Ser | Pro 13940 | Pro | Glu | Pro | Phe 13945 | Ser | Leu | Leu | Pro | Glu 13950 | Ala | Gln | Lys | Arg |
| Leu | Val | Leu | Gly | Glu | Asp | Ala | Arg | Lys | Leu | Cys | Gly | Leu | Ala | Lys |

```
            13955               13960              13965

Asp Arg Thr Ile Thr Asp Ala Tyr Pro Cys Ser Ser Leu Gln Glu
    13970               13975              13980

Gly Leu Ile Ala Leu Thr Ala Lys Gln Pro Gly Ser Tyr Val Ala
    13985               13990              13995

Thr Tyr Ala His His Leu Ser Ser Phe Val Asp Ile Pro Met Phe
    14000               14005              14010

Arg Ala Ala Trp Asp Ser Val Val Asp Ile Cys Asp Asn Leu Arg
    14015               14020              14025

Thr Arg Ile Val Val Leu Asp Gly Val Met Thr Gln Ile Val Leu
    14030               14035              14040

Asp Arg Asp Ser Gln Trp Val Pro Ala Asp Asn Glu Thr Leu Glu
    14045               14050              14055

Ser Met Thr Gly Ser Ser Arg Asn Leu Lys Met Gly Tyr Gly Thr
    14060               14065              14070

Pro Leu Cys Trp Tyr Ser Ile Val Ser Glu Lys Gly Glu Asn Tyr
    14075               14080              14085

Phe Val Trp Ser Ala His His Ser Ile Tyr Asp Gly Trp Thr Met
    14090               14095              14100

Lys Val Met Phe Thr Ala Leu Phe Ser Ala Tyr Gln Gly Met Tyr
    14105               14110              14115

Ala Pro Glu Val Arg Pro Phe Ser Ser Phe Ile Lys Ser Val Lys
    14120               14125              14130

Glu Leu Asp Asn Asp Lys Val Ala Ser Tyr Trp Thr Gln Glu Leu
    14135               14140              14145

Ala Gly Ala Lys Arg Ala Ser Phe Pro Ser Arg Arg Thr Ala Pro
    14150               14155              14160

Gly Ile Met Glu Ser Lys Arg Phe Ser Ser Thr Ile Pro Phe Ser
    14165               14170              14175

Arg Ser Met Lys Thr Ser Ile Thr Gln Ala Ser Ile Leu Arg Ala
    14180               14185              14190

Ala Trp Ala Ile Val Leu Ala Arg Tyr Cys Asp Ser Ser Glu Ala
    14195               14200              14205

Val Phe Gly Ala Thr Val Ser Gly Arg Gln Ala Pro Ile Pro Gly
    14210               14215              14220

Ala Glu Met Ile Ser Gly Pro Met Ile Ala Thr Val Pro Ile Arg
    14225               14230              14235

Ala Arg Leu Asp Asn Gln Ala Pro Ile Ser Arg Phe Val Gln Asp
    14240               14245              14250

Ile Gln Ser Leu Ser Thr Ser Met Ile Pro Tyr Glu Gln Tyr Gly
    14255               14260              14265

Leu Gln Asn Ile Ala Lys Val Ser Ala Glu Ala Arg Glu Val Cys
    14270               14275              14280

Asp Phe Ser Ser Leu Leu Val Val Gln Pro Pro Ala His Gly Ala
    14285               14290              14295

Gly Asp His Gly Glu Ser Ile Phe Val Val Asp Ala Ser Ala
    14300               14305              14310

Ser Asp Leu Thr Met Asp Ser Met Asp Gly Tyr Phe Asn Tyr Pro
    14315               14320              14325

Leu Val Ile Ile Ser Ser Leu Tyr Pro Glu Glu Phe Arg Leu Asn
    14330               14335              14340

Phe Phe Tyr Asp Ser Thr Val Leu Ser Glu Ala Arg Val Ile Ala
    14345               14350              14355
```

-continued

```
Leu Ser  Ser His Leu Asn His  Val Ile Gln Gln Leu  Val Ala Lys
    14360        14365                 14370

Glu Ala  Val Asn Ala Pro Leu  Ser Ser Val Ser Leu  Leu Ser Pro
    14375        14380                 14385

Trp Asp  Leu Gln Gln Ala Val  Glu Ser Ser Arg Leu  Glu Pro Ser
    14390        14395                 14400

Ser Asn  Thr Cys Thr His Trp  Ala Ile Gln Glu Asn  Ile Gln Ser
    14405        14410                 14415

Arg Pro  Asp Asp Val Ala Ile  Ala Ser Trp Asp Ala  Glu Leu Thr
    14420        14425                 14430

Tyr Ser  Gln Val Gly Thr Phe  Ala Ser Arg Leu Ala  Ile Glu Leu
    14435        14440                 14445

Gln Glu  Arg Gly Val Gly Pro  Glu Thr Leu Val Leu  Leu Cys Phe
    14450        14455                 14460

Pro Lys  Ser Ala Trp Ala Val  Ile Ala Met Val Ala  Ile Glu Met
    14465        14470                 14475

Ala Gly  Gly Ala Phe Val Pro  Leu Asp Pro Ala Ala  Pro Ala Ala
    14480        14485                 14490

Arg Leu  Lys Gly Ile Ile Glu  Asp Thr His Ala Thr  Leu Ala Met
    14495        14500                 14505

Ser Ser  Pro Thr Ser Gly Lys  Val Leu Glu Gly Leu  Gly Val Asp
    14510        14515                 14520

Val Phe  Phe Val Asp Glu Glu  Met Leu Ser Gly Leu  Pro Ser Pro
    14525        14530                 14535

Thr Lys  Pro Val Ile Ser Asn  Val Arg Pro Asp Asn  Ala Ser Val
    14540        14545                 14550

Ile Leu  Phe Thr Ser Gly Ser  Thr Gly Lys Pro Lys  Gly Met Val
    14555        14560                 14565

Ile Glu  His Arg Asn Leu Val  Ser Ser Ser Asp Ala  Tyr Gly Asn
    14570        14575                 14580

Leu Leu  Gly Ile Gly Pro Gly  Thr Arg Val Phe Gln  Phe Ser Ala
    14585        14590                 14595

Tyr Thr  Phe Asp Val Gly Ile  Leu Asp Cys Leu Val  Ser Leu Met
    14600        14605                 14610

Arg Gly  Ala Cys Leu Cys Ile  Pro Ser Asp His Asp  Arg Met Asn
    14615        14620                 14625

Asp Leu  Ala Gly Ala Met Arg  Ser Ser Lys Ala Asn  Trp Val Phe
    14630        14635                 14640

Leu Thr  Pro Thr Val Ala Asp  Leu Leu Ser Pro Thr  Asp Ile Pro
    14645        14650                 14655

Asp Met  Lys Val Val Cys Leu  Gly Gly Glu Ala Ile  Ser Lys Lys
    14660        14665                 14670

Cys Ala  Asp Arg Trp Val His  His Val Asp Leu His  Gly Leu Tyr
    14675        14680                 14685

Gly Pro  Ala Glu Ala Ser Ile  Cys Ala Trp Asn Pro  Thr Val Gly
    14690        14695                 14700

Lys Leu  Gly Arg Ser Thr Asn  Leu Gly Arg Pro Ile  Ser Ser Ala
    14705        14710                 14715

Phe Trp  Val Val Glu Pro Gly  Asn Leu Arg Gln Leu  Val Pro Val
    14720        14725                 14730

Gly Cys  Val Gly Glu Leu Leu  Ile Glu Gly Pro Met  Leu Ala Arg
    14735        14740                 14745
```

```
Gly Tyr Leu Asn Val Ser Pro Glu Val Ala Ala Ser Trp Met Glu
             14750             14755             14760

Asp Val Asp Trp Leu Pro Gly Gly Arg Lys Arg Val Tyr Arg Thr
             14765             14770             14775

Gly Asp Leu Val Arg Arg Asn Ala Asp Gly Thr Phe Asp Tyr Met
             14780             14785             14790

Gly Arg Lys Asp Thr Gln Val Lys Leu His Gly Gln Arg Val Glu
             14795             14800             14805

Leu Gly Glu Ile Glu Ser Arg Ile His Glu Leu Leu Pro Asp Asn
             14810             14815             14820

Met Ala Val Ile Val Asp Ile Leu Lys Ala Asp Glu Asn Ala
             14825             14830             14835

His Asp Ile Leu Leu Ala Phe Leu Trp Tyr Thr Asp Asp Glu Met
             14840             14845             14850

Thr Ser Arg Ser Glu Ala Leu Gln Leu Met His Thr Val Ser Glu
             14855             14860             14865

Gln Ala Gln Ser Val Ile Ser Arg Leu Asp Leu Ala Leu Glu Glu
             14870             14875             14880

Ser Leu Pro Ser Tyr Met Ile Pro Ser Ser Tyr Leu Ile Phe Glu
             14885             14890             14895

Gly Lys Pro Glu Gln Thr Thr Ser Gly Lys Val Asn Arg Arg Ser
             14900             14905             14910

Phe Val Glu Leu Gly Arg Ser Val Ser Val Gln Asp Arg Leu Arg
             14915             14920             14925

Phe Thr Pro Ser Ala Ser Asp Tyr Val Ser Pro Thr Thr Pro Met
             14930             14935             14940

Glu Leu Glu Leu Gln Ser Leu Trp Ala Gln Val Leu Lys Ile Ser
             14945             14950             14955

Asp Val Ser Ala Ile Gly Lys His Asp Ser Phe Leu His Leu Gly
             14960             14965             14970

Gly Asp Ser Ile Ser Ala Ile Glu Leu Val Ser Phe Ala Gln Arg
             14975             14980             14985

Gln Asn Ile Gly Leu Thr Val Ala Met Ile Phe Asn Tyr Pro Arg
             14990             14995             15000

Leu Ser Ala Met Ala Glu Ala Ile Gln Leu Asp Ala Ser Pro Ser
             15005             15010             15015

Ser Thr Ala His Glu Val Glu Arg Phe Gly Leu Ile Pro Thr Ser
             15020             15025             15030

Asp Lys Gln Ser Ala Leu Arg Ala Val Gln Thr Gln Cys Lys Leu
             15035             15040             15045

Ser Asp Leu Ala Glu Ile Glu Asp Ile Tyr Pro Cys Thr Asp Leu
             15050             15055             15060

Gln Thr Gly Leu Met Ala Leu Thr Ile Ser Gln Pro Gly Ser Tyr
             15065             15070             15075

Ile Ala Lys His Val Tyr Arg Leu Ala Pro His Val Asp Ile Asp
             15080             15085             15090

Arg Phe Lys Leu Ala Trp Glu Gln Thr Ile Arg Tyr Cys Ser Asn
             15095             15100             15105

Leu Arg Thr Arg Ile Val Leu Ser Gly Ser Thr Ala Val Gln Ala
             15110             15115             15120

Val Ile Gln Glu Pro Val His Trp Pro Ser Thr Tyr Thr Asp Leu
             15125             15130             15135

Arg Ser Phe Leu Leu Ser Lys Glu Asn Cys Thr Met Thr Tyr Gly
```

-continued

```
              15140               15145               15150

Ser Pro  Leu Cys Arg Phe Ala   Ile Ile Lys Gln Gly   Ser Asp Gln
    15155               15160               15165

Tyr Phe  Ala Val Asn Ile His   His Thr Ile Phe Asp   Gly Trp Thr
    15170               15175               15180

Leu Ser  Ile Val Leu Arg Thr   Leu Leu Ala Met Tyr   Ser Gln Thr
    15185               15190               15195

Glu Pro  Pro Ser Ile Leu Pro   Tyr Thr Ser Phe Val   Lys Tyr Ile
    15200               15205               15210

Met Glu  Leu Asp Gln Glu Asn   Ser Arg Asp Tyr Trp   Ser Thr Gln
    15215               15220               15225

Leu Arg  Gly Val Lys Arg Gly   Thr Phe Pro Val Val   Ala Thr Gln
    15230               15235               15240

Asn Lys  Pro Ser Ser Thr Thr   Gln Lys Ile Ala Gly   Met Leu Asp
    15245               15250               15255

Lys Thr  Val His Leu Gln Arg   Pro Ser Gly Ser Ser   Ile Thr Arg
    15260               15265               15270

Ala Thr  Ile Ile Arg Thr Ala   Trp Ala Ile Leu Leu   Ala Gln Tyr
    15275               15280               15285

Glu His  Asp Asp Asp Ile Cys   Phe Gly Thr Thr Val   Ser Gly Arg
    15290               15295               15300

Gln Ala  Ala Val Gln Gly Ile   Asp Glu Met Pro Gly   Leu Ala Leu
    15305               15310               15315

Ala Thr  Val Pro Ile Arg Val   Gln Leu Asp Lys Arg   Gln Lys Ile
    15320               15325               15330

Ser Ala  Leu Leu Gln Ser Met   Gln Asp Gln Ala Phe   Glu Met Val
    15335               15340               15345

Ala His  Glu Gln Tyr Gly Leu   Ala Asn Ile Ser Arg   Ile Ser Thr
    15350               15355               15360

Asp Ala  Lys Glu Ala Cys Asn   Phe Thr Asn Leu Leu   Ile Val Gln
    15365               15370               15375

Pro Ala  Gln Gln Phe Thr Pro   Thr Asp Ser Gly Thr   Glu Ser Thr
    15380               15385               15390

Val Phe  Tyr Pro Val Ala Ala   Glu Gly Phe Ala Glu   Gly Glu Leu
    15395               15400               15405

Leu Gly  Asp Tyr Phe Ser Tyr   Pro Leu Val Val Gln   Cys Gln Leu
    15410               15415               15420

Leu Glu  Asn Asp Val Gln Leu   Ser Ile Ile Tyr Gln   Thr Asp Leu
    15425               15430               15435

Val Asn  His Ser Gln Val Asn   Ala Leu Ala Glu Gln   Phe Ser Tyr
    15440               15445               15450

Val Leu  Glu Gln Leu Gln Lys   Asn Gly Asp Lys Thr   Leu Ser Glu
    15455               15460               15465

Leu Ser  Pro Ala Ser Pro Trp   Asp Thr Glu Gln Ala   Thr Lys Trp
    15470               15475               15480

Asn Ser  Phe Asp Ile Ala Pro   Ile Glu Ala Cys Val   His Asp Leu
    15485               15490               15495

Phe Ser  Arg Gln Val Ala Lys   Ile Pro His Lys Glu   Ala Leu Tyr
    15500               15505               15510

Ser Thr  Ala Gly Ser Met Thr   Tyr Ala Glu Val Asp   Gln Leu Ser
    15515               15520               15525

Asp Glu  Leu Ala Leu His Leu   Ile Gln Leu Gly Val   Lys Ser Glu
    15530               15535               15540
```

```
Ala Ile Val Pro Phe Cys Tyr  Glu Lys Ser Val Trp  Ser Ile Ile
    15545            15550                15555

Val Met Met Gly Ile Ile Lys  Ala Gly Gly Val Phe  Leu Pro Leu
    15560            15565                15570

Asp Pro Ser His Pro Leu Ser  Arg Arg Gln Ala Leu  Ile Asp Glu
    15575            15580                15585

Thr Ser Ala Gln Tyr Met Ile  Val Ser Pro Ser Thr  Ala Lys Glu
    15590            15595                15600

Cys Ala Gly Met Thr Arg Asn  Asn Ile Glu Leu Ser  Ser Ala Phe
    15605            15610                15615

Phe Ser Arg Pro Asn Gly Arg  Ala Ser Ala Ser Arg  Lys Leu Lys
    15620            15625                15630

Ala Ala Arg Ser Ser Pro Ser  Lys Ala Met Tyr Ile  Leu Phe Thr
    15635            15640                15645

Ser Gly Ser Thr Gly Lys Pro  Lys Gly Val Ile Ile  Glu His Arg
    15650            15655                15660

Ala Ile Ser Ser Phe Leu Val  Arg Leu Cys Lys Val  Ile His Val
    15665            15670                15675

Thr Arg Asp Ser Arg Thr Phe  Gln Phe Ser Ser Tyr  Val Phe Asp
    15680            15685                15690

Ala Ser Ile Leu Glu Ile Phe  Ala Thr Leu Ile Ser  Gly Gly Thr
    15695            15700                15705

Val Cys Val Pro Thr Asp Ala  Glu Arg Ile Gln His  Ala Ala Ser
    15710            15715                15720

Phe Met Gly Gln Ala His Val  Asn Thr Ala Leu Leu  Thr Pro Thr
    15725            15730                15735

Phe Ala Lys Thr Leu Asp Pro  Gln Thr Val Pro Ser  Leu Lys Thr
    15740            15745                15750

Leu Ile Leu Gly Gly Glu Ala  Pro Ser Arg Asp Ile  Val Asp Ser
    15755            15760                15765

Trp Arg Gln Asn Val Ser Leu  Trp Asn Ala Tyr Gly  Pro Thr Glu
    15770            15775                15780

Thr Cys Val Ala Ser Cys Leu  Gln Arg Tyr Thr Asp  Asp Ala Thr
    15785            15790                15795

Ser Ala Thr Thr Ile Gly Arg  Gly Phe Ala His His  Cys Trp Val
    15800            15805                15810

Val Asn Pro Glu Asn His Asp  Glu Leu Thr Pro Ile  Gly Cys Val
    15815            15820                15825

Gly Glu Leu Leu Val Gln Gly  Asp Ala Leu Ser Arg  Gly Tyr Ile
    15830            15835                15840

Asn Asp Glu Glu Lys Thr Asn  Asn Ala Phe Ile Ser  Asn Val Lys
    15845            15850                15855

Trp Leu Pro Asp Thr Val Asp  Val Gly Arg Arg Arg  Phe Tyr Lys
    15860            15865                15870

Thr Gly Asp Leu Val Arg Tyr  Asn Pro Asp Gly Ser  Leu His Tyr
    15875            15880                15885

Leu Gly Arg Lys Asp Thr Gln  Val Lys Ile Arg Gly  Gln Arg Ile
    15890            15895                15900

Glu Leu Gly Glu Ile Glu Tyr  Gln Ile Lys Leu Gln  Ser His Asp
    15905            15910                15915

Val Glu His Ala Val Val Asp  Lys Ile Arg His Asp  Thr His Glu
    15920            15925                15930
```

-continued

| | | | | | | | | | | |
|---|---|---|---|---|---|---|---|---|---|---|
| Ser | Leu | Val | Ala | Phe | Val | Ser | Phe | Ser | Ser | Asp | Thr | Ser | Pro | Ser |
| | 15935 | | | | 15940 | | | | 15945 | |

Asp Ala Ser Asn Ile Arg Val Leu Asn His Ser Ser Lys Leu Gln
    15950              15955              15960

Glu Leu Phe Ser Gln Leu Ala Ser Asp Leu Ser Thr Val Leu Pro
    15965              15970              15975

Ser His Met Val Pro Gln Tyr Phe Ile Ala Val Glu Ser Met Pro
    15980              15985              15990

Leu Asn Thr Ser Gly Lys Leu Asp Arg Lys Ala Leu Leu Gln Thr
    15995              16000              16005

Ala Ala Gly Leu Ser Ser Glu Asp Leu Ala Val His Leu Ala Gly
    16010              16015              16020

Gln Arg Leu Pro Phe Arg Asp Val Ser Thr Asp Leu Glu His Trp
    16025              16030              16035

Leu Arg Ala Glu Trp Ala Asp Val Leu Glu Leu Pro Arg Glu Ser
    16040              16045              16050

Ile Ser Val Asp Asp Asn Phe Tyr Gln Leu Gly Gly Asp Ser Ile
    16055              16060              16065

Arg Ile Val Asn Val Ser Arg Leu Val Leu Asp Lys Phe Gly Val
    16070              16075              16080

Ser Leu Gly Ser Thr Leu Leu Asn Ser Lys His Thr Thr Ile Ser
    16085              16090              16095

Asn Met Ala Lys Phe Ile Ser Gln Ser Ala Glu Asn Gly Ala Ala
    16100              16105              16110

Glu Ala Asp His Pro Asp Ala Gln Val Asp Leu Met Ala Lys Val
    16115              16120              16125

Asn Glu Ile Ala Asn Ser Pro Trp Met Gln His Pro Arg Ala Leu
    16130              16135              16140

Leu Glu Asn Pro Thr Thr Thr Leu Pro Asp Gln Ala Thr Val Phe
    16145              16150              16155

Leu Thr Gly Ala Thr Gly Phe Leu Gly Thr Glu Ile Leu Arg Arg
    16160              16165              16170

Leu Val Glu Asn Pro Ala Ile Arg Ser Ile Ala Val His Val Arg
    16175              16180              16185

Ser Lys Thr Leu Ala Gln Gly Met Asp Arg Ile Arg Glu Thr Ala
    16190              16195              16200

Lys Ile Ala Gly Trp Trp Arg Asp Glu Asp Glu Ala Lys Leu Glu
    16205              16210              16215

Ile Trp Leu Gly Asp Leu Ser Lys Thr Arg Leu Gly Leu Thr Glu
    16220              16225              16230

Ala Gln Trp Gln Arg Leu Ser Gly Val Ser Glu Glu Ala Asn
    16235              16240              16245

Ile Asp Ala Ile Ile His Asn Gly Ala Ser Val Asn Trp Asn Ala
    16250              16255              16260

Asn Tyr Glu Thr Leu Ser Ala Pro Asn Val Asn Ser Thr Val Asp
    16265              16270              16275

Leu Leu Met Ala Thr Ala Thr Ser Pro Cys Gln Pro Lys Phe Val
    16280              16285              16290

Phe Val Ser Gly Gly Ala Phe Thr Asp Pro Ala Glu Asn Pro Ala
    16295              16300              16305

Val Ser Ala Ala Leu Leu Ser Gly Ser Asn Gly Tyr Ser Gln Ser
    16310              16315              16320

Lys Phe Val Cys Glu Ala Val Ile Thr Lys Met Ala Asn Ser Leu

```
                     16325              16330              16335
Pro Ser  Thr Gln Asn Arg Val  Ser Thr Val Lys Pro  Gly Arg Ile
         16340              16345              16350
Ile Gly  Arg Ala Glu Asn Gly  Val Ser Asn Val Asp  Asp Phe Val
         16355              16360              16365
Trp Arg  Val Val Ser Thr Ala  Ala Ser Ile Gln Ala  Tyr Pro Glu
         16370              16375              16380
Glu Ala  Ser Asp His Trp Met  Val Met Gln Asp Val  Gly Val Val
         16385              16390              16395
Ala Ser  Asn Val Leu Gly Pro  Leu Phe Ala Asp Ser  Ile Lys Pro
         16400              16405              16410
Phe Asn  Leu Leu Ala Arg Gly  Met Thr Met Ser Asp  Phe Trp Asp
         16415              16420              16425
Arg Val  Asn Ala Glu Leu Asp  Ala Pro Cys Lys Pro  Val Thr Trp
         16430              16435              16440
Gln Glu  Trp Thr Glu Arg Ala  Leu Ala Ser Met Asn  Thr Val Gly
         16445              16450              16455
Asn Thr  His Pro Leu Trp Pro  Val Gln His Phe Leu  Gly Gln Leu
         16460              16465              16470
Gly Leu  Pro Arg Asp Phe Ala  Thr Leu Ala Asn Ala  Gly Thr His
         16475              16480              16485
Val Cys  Glu Gln Ser Gln Lys  Ala Val His Ser Asn  Val Arg Tyr
         16490              16495              16500
Met Lys  Lys Ile Gly Phe Ile  Gln Ser Ser Glu Glu  Gly Phe Gly
         16505              16510              16515
Asn Val  Gln Arg Asp Gly Thr  Ile Arg Arg Val His  Thr Leu Ala
         16520              16525              16530
Gly

<210> SEQ ID NO 3
<211> LENGTH: 69518
<212> TYPE: DNA
<213> ORGANISM: Trichoderma reesei

<400> SEQUENCE: 3
atggcgccga acactacgta cgaagatggg aacaaatccc tcatcccaat tgccatctgc       60
ggcgttggca tccggcttcc tggtggcatt cgcaatgccg agcaactctg ggagtccctc      120
gtcaacgacc gtgttcagcc gcgtgtggat ggcaatgaag aggaagaact agacgctgtt      180
gatgcttcgt tcttctcctt gaccgaggca gagctcgaga gctgcagccc tctgcagcgg      240
aagctcttgg aggtgactcg tgagtgtttt gaggatgcgt gcgagatcga cttccggggc      300
gaggatgctc gtgtgggctg ctatgccggt agtattggag aggacgatgt gtcgatggtg      360
tcactgaagc atgatttggg aggcccgagg ttcgtttact atccggactg ctgtcctccc      420
tcccccctt  gagtataatt tctgggttgc taacgagttt tttggctta  gcatggcgat      480
tagagagtcg acgtcgtcat ttctcgtggc tctgcatgag gcttgctccg ctgttcgatc      540
tggcagtgcc aaatctgcag ttgttctggg agctgcccag aatggcgctg tgggaggcga      600
ggccgtgtca gctgtatata tcaagacact gcctgatgcc atgcgcagag caacccaat       660
tcgcgccatc attcgagctt ctagcattat gacgctcagt ggccgaagtt ctgtggctga      720
ggcccatgag gagctcattc gcgaggccta cgatgccgcg ggcctagata tccgatcagc      780
ccttgtagtt gaggtgggtg taacaatgac ctgattgaag catcatgaac gagagaatgt      840
```

-continued

```
ctaatatgct aacttgaatg ataactagtg gagcggagat gccgaagctg aagtctctgc    900
aattaacagc gcctttggcg agcagggtat ctatttgacc aagggtgcgt cgggcttgac    960
gagcttggtc aaggccgtgg taacattgga gaaccggaca atctctccga atattgtatc   1020
tggtaagttt catgctgctc aagtccgccg aaaagtcagg cccaagtctc taacgtaaag   1080
aaacatcagc atcctctacc cccggagcgc tcgtagctac gcaggccatt ccgttcccgc   1140
atgatcgcgc agagagagcc agcatcattg cctctgacgc tgagggacac agcgctcatg   1200
ttatcgtcga ctctcacccc cggcctactc cgcgagtatc tgagtcccgg ccgcaacttg   1260
ttctgttctc tgcgaacaac ccagcttctt tggctaagca gatcgagctg caccgcctgt   1320
atgctgaatc tcacccagac gatgctgccg acatcgccta tactcgcgct ctccgacgcg   1380
aggctctgga ctacaaggca ttctccatcc tttcgaactc atccttcgtc aacacttcca   1440
actacgccaa gtcttccgcg cgggctccgg ccatcaccat ggtgttcaac ggccagggtg   1500
ctcagtgggc gggaatgggc aaggagctca tcttgaccga ctcaagcttc agggaagaca   1560
tcaggaagat ggatctggtt ctgaagggac tgaacatacc cgcaacctgg tcgattgaag   1620
aggagcttct ccgtgatgct gccgaccccg acaacaggat caacacctca agttctcct   1680
accctctcag cacggcgctt cagattgccc tggtcaactg tttcaaacgc cttggtgtta   1740
cgcccaaggc cgtcgttggt cactccagtg gtgagattgc tgctgcctat gctgcgggct   1800
ttctctcttt cgaagacgcc atcacagtcg cttactacta cggccatatt actaccaggg   1860
accagaagga cggtgccatg ggcgtggtaa gcttaggtgc agaggaaacg gaggggtttc   1920
tcgagcaggg cgtggtcatt gcttgtgaga actcacccac tagcaccacc atttccggcg   1980
accgtgaggc ggttgagcga gtcttgaagt ttgtcaaggc agcaaagcct gaggtgactg   2040
ctcgtctgct gaaggttgat actgcgtatc actctgaaca catgactcag cttgccgatg   2100
agctgcttga ccttttgacg gcggagaaga ttgcttcgca tgcaaccagg aagagcgagg   2160
ccatctttat ttctaccgtc agcgagaagg ttctgaagga gaagagcgag tttggagcag   2220
cgtactgggt ctccaacctg gtgtcacctg tccgcttcag ctcgtccgtc tccaacctcc   2280
tcggcatgtc atctgaggaa actctgttcc tggaagttgg acctcattct gccctctccg   2340
tgcctctgtc ccagatctgt gccgctgcag atgtccgatg caattatgtc tcgtcccaaa   2400
ctcgtggggc tgatagtgca gtgagctttc tctctgctgt tggaaggctg tggcaggagt   2460
cggctgtgcc gaatctcgcc ccttttgttct cccacggcag ggcaatttct gggttacctc   2520
agtatccctg gagttacgga acctctgatg aggactccga tgctactgct ctatctgccc   2580
gtgagaagcg ggctcgtgtc tttgcagagg acagctctct ggagagcgag ctcgccgacg   2640
aagaggctcc taccactgag gtggagattg ttcttcgagc tgtctgggtt gagatcctcc   2700
gggatgtgaa ccgaatccgt aagcaggaca ttggaaagaa gcacaacttc ttcctgcttg   2760
gcggcgactc tctcacaacc atcgagcttg ttactgctgc ttatcaatac ggcattcgtc   2820
tgagtccggc agccgtatcg gacaacgctg agcttgccca gatggcagct gtggcaacca   2880
tcgaacacga cagcgcaatg atggctgaga caaagccctt cagcttgatt agcagtgaaa   2940
aggttgatga tatcaagcac cagatccgga aggagtgcaa gcttgcccct accgagacta   3000
ttgaggatat ctatccttgc acgactctcc aggaaggttt catggccctg gtatgaagc    3060
agcctggctc ttacatccac agagtcgtgt acaagctgat gccagaaatt gatgttgatc   3120
aattcaaggc ttcctgggag gccaccatca gccaatgcgg aagcttgcgt tcgcgagtag   3180
cccttctcgg cggtcgagct ctccaagctg tgatgacgga agatattgct tgggagcagc   3240
```

```
ctgctccagg cctggacatc aacgcttatc tcaaccgaac gcgaagcatc agcatgagct    3300
acggcgagcg cctgagcaga catgccctgg tacgagacag caatggcggc gtctactttg    3360
tgtggctcat tcaccacgcc gtgtttgacg gtctcaccat gcgaatcgtc ctggacgccc    3420
tctacaacgc ttatcatggc aatgacgcca aagccttgcg tccgtactcc aactttatcc    3480
gctatgtcga atccattgat tccgccgcgt ctaccgagta ctggcaaaag cagcttgatg    3540
gtgctcagcg cgctcacttc ccgcccgcga gactgtctgc cacatctgaa gaccgagtca    3600
tgaagaggac tatgcctttc cataacgcga agacctcttc cgtgaccacc gctacgattc    3660
ttcgtgcggc ttgggctctc cttcttgcgc gctactgcga ctctgatgat gtgtgctttg    3720
gtactacact gtcgggtcgt caggctgcgg tgcccggatt gaacgagatt ccaggaccca    3780
tgattgcgac tgtgcctatc cgagtcaaga ttgatcgtgg catgactgtg tcctctttcc    3840
tcgagaagat tcagacacaa gcggcagaca tggtggccca tgagcagtac ggtcttcaga    3900
acatctcgaa actgtcccag gacgccgagg aggcatgcga cttttccaac ctcatcgtca    3960
ttcagccaaa caaccatctg acgtccatgg ctgatactgc ttctgatgcc atcttgcagc    4020
agggatcccg cgaaaaggct ctctcggaag aggctatgcg caattacttc aactatcccc    4080
tcgttttgca gcctcgcatt ggcgaggaca gcatcgagct ggacttgacg tattacgctg    4140
atgccatcac tgagggccag cttgaggctc tgtgtgttca ctacgagcac attgttcagc    4200
aattgcttgc tccgacggac atgcccctca gtgacctttc ggtatctggc tcgtgggacc    4260
tggaagaggc gatcaaggcc aacgacgaaa caccagagat tgtcgacatg tgtcttcatc    4320
agcttattga gagacagtcg aaggcaaacc ccgatgcccc tgctattcat gcctgggata    4380
tggagctgtc ttactcgcaa ctcgatcgtg ctgccaaccg cctcgctcat catctcgtca    4440
agtcctgtgg cgtcaaggat caggacttcg tccacgtctg ctttgagaaa tcggcctggt    4500
ttttcgtgtc tgttattgct gtcaataagg ctggtgctac ctgggttccc ttggatccct    4560
cgcacccgct gcagaggcag caacaggttg tctcgcagac aaaggcgacg ctggccttgg    4620
cttcccctag caatgtcgag atgtgttctg agttggtcaa taccgtcgtt gaggtgtctt    4680
cagccctgga tgagaagcta tctaagaccg aagagagctc ttacgaccca gtacgcaatg    4740
tgtcaccaga taatgcagcc tatgttctgt ttacttctgg aagtactgga acgccaaagg    4800
gtctggtcat gcagcacagg gctgtctgca cctcgcagac cgctattacc aagcgcctgg    4860
aaatgacctc tagcgtaagg atgcttcaat ttgcatcctt tgtcttcgat ctctctatcg    4920
gtgagattgt tggtccctgg gtggttggcg gctgtctctg cgttccgtct gaggaaacga    4980
ggatgaacaa cctggtggac ttcatcaaca cgatgcaagt caactgggcc tatctgacgc    5040
cctcgtttac gcgcactttg aaccctgacg acgttccagg cttggatttg ctgttgtttg    5100
ctggcgaggc tgttggccga gatgtgtttg aagcttggtt tggcaaggtg cggctgatca    5160
atggttgggg ccctgccgaa acttgtgtct tctcaaccct ccacgagtgg aagagcttcg    5220
aggaatctcc gttgacggtc ggtaagccgg ttggcggata ctgctggatt gttgatccgc    5280
atgatccgca gcgattagcc cctgtcggaa cccttggaga agttgtcatc caggggccga    5340
cggttcttcg cgagtatctg gctgatacta ccaagactga ggcctcgctg gtgcgtagcc    5400
tccccgagtg ggtgccaaac cgtacagctg cgcactggga tcgatttac aagtcgggtg    5460
acctgtgtcg gtacaatgcg gacggcacca ttgagtttgg atctcgtaag gatagccagg    5520
ttaagattcg aggccttcgt gtcgagcttg gagaaatcga gcatcatatc cgcgagtctc    5580
```

```
tggaaggcgt caagcaggtc gctgttgatg tggcaaaggg agatggtggc gcgatcatcg    5640
tgtcctactt ctcctttacc gacgaaaccc gcactgctgg caagaactcc gagacgagcg    5700
tcagagatgt gttcgtcccg atgactcctg agctccagag tcaactgaca gccttggttg    5760
gccagctgag cgttacactt cctcgataca tgatcccgac gctatttatc ccctgccact    5820
acatgccctt tatcacttcg acaaagttgg atatgaagct cctgcgactg caatgtcca     5880 atcttggtaa ggacgacatt gcgaggtatt cccttgtgga tagcaagaag cgtgctccgg    5940
aaacggagat ggagactcgt atccaggcga tctgggcgga tctcctgaag ctgtcgcccg    6000
agttcatcgg tcgagatgat agcttttga gaatgggcgg tgactctatt gctgccatct     6060
attttgtgtc tgcggctcgc gatgccggta tttccatcgc tgtgaaggac gttttcgacg    6120 accccgatt gttccaggtg gcctccaagg ctaccctcct ctccaacgcg gccgttctt      6180 ctcagactga gccctttacc ctgcttccag aatcgttgag caaactcatg caaagcgatg    6240
ctattcgatc tcgctacggc ctgggacagc gccagacgat cgaggacgcc tatccttgca    6300
cccccctcca ggaaggtctc atggccctga ctgccaagca acgcggctca tacgtctcgc    6360
aatggttcta ccgaatgcct agacatatcg ataccgccaa gttcaaggct gcttggaacg    6420
aggccgttga gcgaaatgcc actctgagga ctcgtatcat gctggaggaa ggttctgcag    6480
tgcaagctgt catttcgaat gacggcgatt gggaagacac tgagggactc aaccttgagt    6540
ccttcaaaga cgtaatctct cagctggaca ttggctatgg aactcgtctg accagatttg    6600
ctcttgttga ggaccatgat gacacttact ttgtctggat catccaccat gctatcaacg    6660
acggctggag catgcgcatc gtcctcgata gcgtttacaa cagctactac ggtcagaagg    6720
tcgcctccct gacgccttac tccaacttca tcaactacct gagtaatata gatggcgagg    6780
cagcggcaaa cttctggcga tcgaacctgg ctggtgctca acggcctatc tatcctgctg    6840
ctggcagcta ctcaactgct gacagctctg gagactcaac ccgtgttgtc gatcgcttgg    6900
tgtccttttc cagccatgaa gacgcctcca ttaccatggc cactattatt cgagcggcct    6960
gggcaattgt gcttggcaag cattgtgacg ccagcgatgt ctgctatggc gcgacggttt    7020
ctggtcgcca ggctgatatg gacggcctct tgtcaactcc cggtgctgtc attgccaccg    7080
tcccaatccg agtcccttg gaagctgatc agcctgtgag ccagatgctg caggacttgc     7140
agggtcacgg tctggatatg gttccctatg agcagtatgg tctgcccaac atcgccaaac    7200
tgagcccgga ggcccgcgag gcttgtgact ttacctcccct gctggtaatt cagcccaagg   7260
aacaggagag ctccatcttc aactccaaaa atggtctgct gcagtcggat gctgaagaag    7320
atcacctgtt gattgagtct atggacaagt acttcaacta tccattggtc atgctcagct    7380
acatgacaga agacagcgtg aatcagaggt ttatatataa gcctgacatg ctgtccgagg    7440
ctgaagtcga ggccctctct tatcagtttg aatacgtcgt ccagcagctt ctgagtcctg    7500
accaaaagct tatcagcgac atctctcttg ttggagagcg tgagattcag catgccgctg    7560
acgtatctcg atatcgcccc gccaccgagt cttgcactca ctgggagatt tacaagcaga    7620
ttgaagccca gccagatgcc cctgcctttg actcctggga cgccaagctc atataccgtg    7680
aagtcggtgt tttggctact cgcttggccg ctaagttgca gagacttggt gttggatcgg    7740
acgttatggt gcccatttcg ttccccaaga gcaccccggc catgatcacc atggttgcta    7800
tccagatggc tggtggtgct cttgtgccgc ttgaccctgc agctccattg gcccgtctgc    7860
aaagtatcgt ttctgatacg caggcgaagc tcatcgtcac ccatccttct ctcgaggaga    7920
aacttcaaga gcttggcgtg gacctcctga ttgtggacct gtccatgttg gataagttgc    7980
```

```
ccgatcccag caccaagttc atctcgtcag atgccacgcc agagagtctt tacgctgtct   8040
tgtttacgtc tggctctacc ggcaagccca agggcattcg cattccgcat agcagtctct   8100
gctctgtaag cgatgcccat gctgcggaaa ccggcgttgg gcctggcagc agagtgttcc   8160
agttttcggc ttacacgttc gatatcggca ttctcgatgt cttggtcact ctcatgcgcg   8220
gtggctgcgt ctgtgtgcct tcggaccacg atcgcctcaa caacctcgcg ggcgtcatca   8280
gtgctctcca ggccaactgg gttttcttga cgcctactgt cgccgacatg ctcaacccag   8340
cagacgtccc ttgtttgaca accatcaacc tgggaggcga agccgtcaac aagaagtcat   8400
ccgagaggtg gcagggctac actactctga acggcctttg cggtcctgct gaggcctcga   8460
tttgcgctcg caacgcggat gtgcacaacg gtgcatctac taacttgggc tttcctctgt   8520
ccagtgcttt ctgggctgtc gagccaaacg acccaagccg tcttgtgccc atcggctgta   8580
tcggcgagtt gctcatccag agtcctatct tggcttacgg atacctcaat gccgatgcaa   8640
agaataatgc aaattggctg gaggatatga catacgactg gcttccagcc aatgggccaa   8700
agcgagccta tcgaactggt gatttggttt gccgcaaccc tgatggcacg ttcgagtaca   8760
tgggccgaag ggacaaccag gtcaagatcc gtggccagcg tgtcgagctg ggtgagatcg   8820
aatatactgt cctgaccaac cttcccggcg cgaagcagat cctggtggat gtcattaaca   8880
atgacgaagc cggtctcagc ctcatcacct atttatgctt caacgacgac accaagggca   8940
gcgacaagaa cctggaggat atcttcctga ccaccactcc cgagatgaag cagaagttct   9000
ctgacatgct tggccaactg cacatcaccc ttcctcacta catgattccg accatcttcg   9060
ttccgtgcaa gtacatgcct atcaacactt cagctaagct ggaccgcaag gctctccgcg   9120
cttgtgcggc tgtcctgagc aaagacgagc tggcggctta cacgctctct gatgatgagg   9180
acaagcaacc acccgagacc ccgatggaag caaggctgca gcagatctgg gcggacactc   9240
tcaagatttc gcctggctct attggccgcg gctccaactt tttgcgcttg ggtggtgatt   9300
ccattgcagc catttacagc gtgatggctg cgaatgaggc tggaatcatc ttgacagtga   9360
aggacatctt tgacgacccg cgattgtcaa aggttgctct caaggctgtt gaggtcagtg   9420
gagatgtagc ccagcaaaac gccgtcattg agcctttcag ccttcttgac gcacacagac   9480
gcaactgggc catgagcgac gaggttcatg gcttgtgcaa gctgcttccg caccagactg   9540
ttgaagatgc tttccctact accagcttcc aagagggcct catggctatg gctgtgaagc   9600
agccgggatc ttacattgca aaacacgttt acaagatccc caagcatgtt gatctccagc   9660
tcttcaagga ggcttgggag cagactgtga agctgtgcgg cattctgcgt accaggatcg   9720
tgctcaacca ggggtcgtct attcaggttg ttatcaaaga cgatgttgcc tgggatgtga   9780
cttacggcca ggacgtagtc tcctatatcg actcaacaag gaacattgag atgacctatg   9840
gctcacgcct gtgtcgctat gcccttatcg aggagcgcag cggcgacaga tactttgtct   9900
ggaccattca ccacactgcc tttgacggtt ggacgatgca aatcattctt gagactctgc   9960
aaagtgtcta tcgtcaacag aacccctctc cacctcgggc atactcccac ttcatccggt  10020
acacgtccga gattgaccaa gccgaagcca aggacttttg gtcttctcaa ctccaggatg  10080
ctcgtcgtgc tgcttcccca gctgccggct cgtcttccgc cccgtcgacc actcgcgtca  10140
tgaagaagag gatctcaatt cccagcctgg aggagacatc catcacaaag ccatcaattc  10200
tgcgcgctgc tttgggctat tgttcttggc cggtatagcga tgccgatgat atctgcttcg  10260
ggacaacaat ttccggtcgt caagctcctc tggcaggcat gactgagatt gccggccctg  10320
```

```
ccgtagccac ggtgcccgtc agggtccgtc tcgatggttc aaagcctgtg gcccagttcc   10380
tccatgacat ccagagccag gcctctgaga tggtagccta cgagcagttt ggtttgcaga   10440
atattgccaa ggtcagcgaa agtgctcggg aggcttgtga cttctcaagc ttgcttgtca   10500
tccagcccgg ccacttcctg cagtatggcg atgaaagcac tgatgcaatt ctcattggcg   10560
acgacaagag cattgaggag gaggtcatgc agaactactt cacgtatccc ctcatcgtgg   10620
aaggtgtctt gtacgaagac catgttgagc ttcttgtgat ttacaatgcc aacgtcttgg   10680
ccgagtcgca aatcactgcc ttgacgtatc acttcgagca tgtcacccag cagcttgcta   10740
gccaggaggg tcttgtgatc ggggatgtct ctgtttccgg ttcttgggat ctggagcaga   10800
gtctccaagc aaacaacgag gttcctgaaa ttgtcgactc ttgtatccac gagttggtcg   10860
aaaaacaggc cctcgaacgt cccggcgccc ctgctgttgt gggttgggac cgggttttca   10920
cctatgctga actcaacgag gccgctaacc ggttggccca tcatctcacg cagacctttg   10980
ccatcaaagc cgatgagctg attcatgttt gctttgaaaa gtcggcatgg cattttgtcg   11040
cgatcctggc tattaataaa gctggtgccg gatgggttcc ccttgatccg tcacatcctg   11100
agcagcggtt gcgccagatt gccagccaga cccgggcaag aatcatacta acatcaccgg   11160
ccaatttgga tatttgtgcc cgtcttggct tgtctgtcat tgagatcagc ccgttctttg   11220
atcagaagct tatcaagagc ggcatgaata gcagcgctgg gccagacgtc aaggtgacgc   11280
ctcgtaacat tgcttacgtc ctcttttacct ccggttctac tggtactcct aagggactgg   11340
tcatggaaca tggctctgta tgcacgtcac agaccgctat cagccggaga ctcggattga   11400
ctgccgatgt tcgtatgctg cagtttgcag cctttgtttt cgatcttcct atcggtgaaa   11460
tcgttgcgcc actgatttca ggtgcttctt tgcacatccc tgacgaaaac actcgattga   11520
atgacctgcc caacttcatc cagaagaaac aaatcaattg ggccttcctt accccgcgt   11580 tcgcccgcac tctgaagcca gaagacgtcc ctgctctaga cctcttattg ctagcaggag   11640
aagccgttag tcgcgatgtg tttgaaagct ggttcggaaa ggtcagactt atcaatggct   11700
ggggcccagc tgagacgtgc gttttctcga ctcttcatga gtggaggtct atcaacgaga   11760
gtcccctaac tgtcggccgg ccggtcggcg gtttctgctg gattgtcgat ccggaacacc   11820
ctgacaagct ggctcccacg ggcaccgtcg gcgaggtcgt tatccaaggc ccgaccctgc   11880
ttcgggaata ccttgcagac gctgagagga ccaagctgtc gaccgtctat gacttgcccg   11940
cttgggcacc ccgccgcgag ttacagcatt ggagccgatt ctacaagtcc ggtgacttgt   12000
gttactacaa cccggatggt accatcgaat tctcaactcg taaggatacg cagatcaaga   12060
ttcgcggcct tcgtgttgaa ttgggcgaaa tcgagcacca cctgcagctt gcccttgatg   12120
acattcgtca ggtcgccgtc gacgtgttta agggtgaaag tggctcaaat ctcgtggcct   12180
acttctgctt caacgaggag agcaagacgg ctgatgctcg tgttgcgggt gacgataagg   12240
gtcctttcat gcccatcgat gaagaccttc aagcccgcct tattgcagcc tcgggtgaat   12300
tgagggttgt tcttccgtcc tacatggtgc caaccttctt cattccctgt agctatatgc   12360
caaccagcac atcgaccaag cttgaccgca aggagctgaa gcggtatacc gctgccttat   12420
ccgtcgaaga gctatcgaaa tactcccttg tcgatggcaa aaagagggca cccgagactc   12480
cgatggaaag ccagttacag cagatatggg ctgaaatttt gaacattcct atggagtcgg   12540
ttggacgcga tgcagcttc cttggcctcg gcggtgactc tatcacgcc atccacttgg   12600 ttaacgtcat gcgggaagag ggtatctcgt tgaccgtcaa ggacatcttt gatgaccctc   12660
gcctgctgtc tgtcgccagc aaggctataa ccaccgagga ggtacttgaa ctcgatgaga   12720
```

```
ttgagccatt cagcctcctg gaaaaggaga tccgtgatgc tgttctatca gaggatcttc    12780
gacaagaact caagctcgcc aagtgccagc ttgtcgagga tgcttatcca tgcagcaagc    12840
tccaggaagg ccttatggtc ctttctgtga agcagcccgg atcatacgtc gccaagtaca    12900
cctatcgtct tcctgcccat gtcgaccttc aacgcttcaa ggaggcgtgg gagtacacct    12960
cgtctgctgt tgaagcactc cgaactcgtc ttgtcatgat tgacggttct tgtgtccagg    13020
tcgtcatcaa cgaggagatc ccctgggaga ctacaaagac ggatgatatt cgatcggcca    13080
tagcatcggc tcagtctctc cgcatgacat acggctcatc tctgtcgcgc tacacaatcc    13140
tcgaggacca agacggcagc aactatttca tgtgggctgt ccaccactct gtccatgatg    13200
gttggtcgat gaggatagtc ctggagacgt tgcggcgaga gtatgagggc cgggcatcgg    13260
ccccggttat gccctacaac ggattcattc gctataccct tggtctcgac ctggaggccg    13320
ctgctgagta ttggagcagc cagctggata acgccaagcg ggccagtttc cctgctgctg    13380
ccactacctc tagcgaaacg aagcacatca cgcgaatgat gacaaagtct attccattcc    13440
ctgcttccat gaacccagcc atcacaaagg ccacagtttt gcgagctgct tgggccgtca    13500
tcctagctcg ttactgcgat acagacgatg tcacgtttgg gtctaccatt tctggtaggc    13560
aggcggcagt tccaggcctg accgagatgg ctggtccagc tgttgccact gttcccgtcc    13620
gtatccgtct cgataagcag cagcgcgtgt ccaaattcct tcaaggtgta cagagtcaag    13680
cctctgagat gatcccttc gaacaatttg gcctgcagag catctccagg cttggtgctg    13740
atgcgaggga tgcgtgcgac tttacttccc tgatgctagt tcaacccatg cagcatcttg    13800
ctggcgagga tctcgacagt gtcatggtgc ctgctcttga acaagagaca caagaggatc    13860
aattgcagaa ttacttctca taccctcttg ttctgcaggg ccatatccat gacgatcgag    13920
ttgagctcgt cttgatctac gactctgtcg ttcttccaga accacagctt gttgccttgt    13980
cacatcagtt caatggcgtt gtccagcagc ttctcagcgg caaggattgc aagcttggcg    14040
aaatctcagt ggcgagcccc tgggatctcg accttgcaca ggcttccaac ggcgatggcc    14100
ctgaaatcgt tgatgattgt gctcatctca taatcgagcg gcaaacgaag cagactcccc    14160
atgcccatgc tgtacatgct tgggatggct cactcaccta cagtgagctt gatcttgctg    14220
ccaacaggct cgccaatctc ttgatccaac gtcacggggt caaggtcggc gatgtcgttc    14280
atgtgtgctt tgaaaagtct cttttggtatg tggtttcggt cctggccatc aacaaggctg    14340
gagctgcttg ggtgccaatg gacccggcac acccattcca acggcttcaa caggttgcca    14400
gtcaaactgg tgcaaagctc gcgctctcat ctgctatcca cagcccctg tgctccaagc    14460 ttctggacac ggttgttgaa gtgtcctcaa acctggatga gcagttgaag agtgacgaga    14520
ccatcagtca tgtcaagcca accactaagg tgacccccaa cgacgctgtc tacctgctct    14580
ttacttccgg tagtactggc gttcctaagg gtatcattat ggaacatgcc tctctttgca    14640
ccagccagcg tgatatcgca aagagactcg gcctgactag cagcgtcaga atgcttcaat    14700
tctcgtcctt tgtctttgac gtttccgtgg gagaaatcat gctttcccctt atgcatggtg    14760 gttgcatttg cataccatct gaccacgatc gtctcaacaa cttggatgga ttcatccgag    14820
acgccgaggt gacctgggca ttcctgacac catcgttttgc acgcacactc cgccctcaag    14880
acgttccatc ccttgagctc attgtccttg ccggagagcc cgtcagccag gacgtcttg    14940 acctctggtt cggtaaggca aggcttgtca atggttgggg acctgctgag acttgcgttc    15000
tgagtgctat ccacgaatgg aaatccgcag acgaatcgcc gttgaccatc ggacgttcgg    15060
```

-continued

```
ttggaagctt tgcctggatt gtcgacgcag agaattcgaa ccgtctagcc ccggttggat    15120
gtatcggaga aatcgtcatg caggggccta ctctcctccg tgagtacttg gctgacccgg    15180
ccaagacggc ctcatcgacc atgacctctt tgccgaactg ggcaccccgc gccaatgaca    15240
agaaatgggg tcgtttctat aagactggcg atctgggttt ctacaaccct gatggaacga    15300
tccactactc tggccgcaag gatacacagg tcaagatccg tggtcttcgc gttgagcttg    15360
gtgaagttga gcatcacatt cggaatgcac ttgaatccat ccgacaggtt gccgttgatg    15420
tgttccgaac agaaaccgga acgaacctcg tctcatacat ctgctttagc agcgagacga    15480
aaactcccgg accaaacacc gaccccaatg tgatgacgtt tttcctctac atgactcgga    15540
acgtccagag cgatttgaac atcgccatca acaagctcaa cgccctgctg cctagctaca    15600
tgatcccaac ttactggatt ccttgtgact acatgccgct gatttcctcc ggcaagttgg    15660
acagggtcaa gctccgcaag cagatggctg cgttgactca ggaggagctg gaggcctatt    15720
cactgactga tgccgacaag cgcgctccgg acacagccat ggaagtgcga ctgcaaagca    15780
tgtgggctga gatcttgaac attcccgctc agaccattgg caaggacgac aacttcctcc    15840
gtattggtgg tgactcaatc gctgctatca gattggtctc gatggctcgc gagcgcggca    15900
tcaccctcac ggtcaatggc attttgaag atccgcgcct gtcatctatg gctgccactg    15960
ccggggcggc tgatggggat gatgagcttc tgactcctat tcctgctttc tccctcctgg    16020
atgcagcac tcgagacccg atccaggctc ccagcatcta ccaagacttg ggcctgaatg    16080
tcacacagcg gatcgaggac gcatatccaa ccaccaagct ccaagaaggc ctcatggccc    16140
tctccgccaa gcagcccgga tcgtacattg ccaagttcct ctatcgtatt cccaagcaca    16200
ttgaagtcgc tcgcttcaag gatgcctgga cgcacggt tgatgcttgt cccaaccttc    16260
gcacccggat cctcctcacc gaaggaggcc acagcacgca gcttgtgatt agccacgatt    16320
tcgagtggga tctcgtcgag aatgaagacc ttcactccta tctccagctg actcaggact    16380
ttgagatggg ttacggttcg cagctttctc ggtacgcgct gatcaagcac acggatggcg    16440
agacgtactt catgtggagc gtgcatcacg ctgtttcga tggtctgtct actcagaacg    16500
tattgaacat tcttgagaag gcctatcaag gcaaagacgt cctagaaacg cctccgtatg    16560
cccgcttcat caagtatacc cttggactgg atgcagaggc tgcagcaaca tactggagag    16620
aacaattaca gagctctcgc aaggccactt tccctgcgtc aagtgaagta tccaacaagc    16680
ctggcgccac tcgtgtcctt gaacgatcca tcgagctgcc caagatggcc tcatcgggca    16740
ttactctcgc caccgttgtt cggtctgctt gggccatggt cctcgcacgc tacagcgatt    16800
cggaagatgt cacctttggt acaagcatct caggccgtca ggccccagta cccgagttga    16860
tggacatggt tggacccatc atcgcaaccg tccctgtgag ggtccgcgta gaccaagcgc    16920
agctggctac tgacttcctt caagctgtcc agaggcagac actcgaaatg gttccctacg    16980
agcagttcgg tctacagagt atagccaagg tcagcgaaga cgccaaggag gcttgtgact    17040
ttacttcgct cttggtgatt cagcctatgc aacacgtgtc cgactctgaa tccgccgatt    17100
ctgtccttgt acacgcagat ggagcgctaa aggaggaggc cgaatcgatg gagaactatt    17160
tctcgtaccc cctcattgtc caggctcatc tgtatgagga ccgcatcaac attgttctca    17220
tctacgactc gactatcctg gccaagacac agctagaagc cctctctcaa cagcttggac    17280
atgttatgtg ccagcttgcg gcagccactg acgagaaatc gttgggatcg gtatccatta    17340
cttctgactg gatctggag cgcgctgttt catttaacag tgacgttcct gaaatcgttg    17400
atgcttgtgt gcatgacctt gttgcacgtc aggctgagct tcgaccagat tctgtcgcta    17460
```

```
tatctgcgtg ggatgccgag ctcacatata gccagcttaa cctcgctgcc aatagactgg   17520
cgaaccacat catcacagcc tatgggatca agcctaatga cttcattcac gtgtgttttg   17580
agaagtcagc ttggcacttt gttgccattt tggctatcaa taaggctgga gccgcttggg   17640
tgcctcttga ctcttctcat ccagagcagc gtcttcgtca agtggttagc cagacgaatg   17700
ccaggctggt tttgacgtct cctagcaact ccacgctttg ttccggacta cttgcagacg   17760
tccttgaagt cacaccagca ttggaccaaa agctagctgc aacagttggc tcccaggctc   17820
ccaaggtcgc tgtgacgcct gaacatgctg tgtatgctct gttcacctcc ggatctaccg   17880
gtacccctaa gggcctcgtt atgcagcacc gagctgtttg cacctcgcag acggccattg   17940
ccaaacggtt aggtctgtca tcggacattc gacaacttca attcgctgcg ttcgttttcg   18000
atctatccat tggtgagatt atcgcgccat taatcagcgg agcttgcgtt tgtgttcctt   18060
ctgaagacgt ccggatgaac agcattaccg agtacattcg tgaccagcgc atcaactggg   18120
cattcttgac cccttcgtac gttcgtacct tacggccaaa ggatgtacct ggcctggaac   18180
tacttcttct tgccggtgaa gctgtaccta aggagatcct taacacatgg ttcgggaaat   18240
tgcgccttgt caacggctgg gggccagccg agacctgtgt cttcagtacc ctgcacgaat   18300
ggaagtcagt cgacgaaagt cctcttaccg ttggcaagcc agttggaggc ttctgctggg   18360
ttgtcgaccc ggagaacccc cataagctag cccctgttgg cactttgggc gaggttgtca   18420
tccaaggtcc gaccttactt cgcgagtatc tggctgatcc agaacgtacc gcggcttcct   18480
cagccacagc ccctgactgg gcaccgcagc ctgactccaa gcattggggg cgcctttaca   18540
aatctggtga tctctgctcc tacaaccctg atggaactct tgagttctcg tccagaaagg   18600
acacacagat caagattcga ggccttcgtg tggagttggg tgaggtggaa caccacatcc   18660
aaacggcgat gcgcggcctg cgccagattg ctgttgacgt ttacaagggc gagagcggaa   18720
cgaatcttgt ggcttatctg tgctttaccg acgagacccg agcctcttct gctgaccaca   18780
gcccattcat gtccgtcgac aagaagcttc agaaccaact gaatgctttg gtcggcgaat   18840
tgggagttac gctgccgcgg tatatgatcc ccacgcttta catacccgt agcttcatgc    18900 cgtcaatcac gtcgaccaag ctggaccgca atgaattgcg ccgtcgtacc gccagcctca   18960
cccgcgatga actgtctcaa tattccctgc tgggaggcaa caagagggct ccggaaaccg   19020
acgtggagcg cgcgcttcaa cggatctggt ccggcatctt gggcctctcg ccggacgcaa   19080
ttggccgaga cgacagcttc ctcggtctgg gaggtgactc gattactgcg atacagcttg   19140
ttggggtttg tcgtgatcaa ggcatttctc tgtcggtcaa ggatatcttc aacgaccctc   19200
ggcttatcgc tgtggccaag gctgctcagt cgctgagctc tgttgacgat gtcgctattg   19260
agcctttcgg cctgttggat gatgaactgc gtcgtctcgc tacgagtgaa accgccaggg   19320
ctcagtgcca tcttgcaaca gaagccgtca tcgaggacgc ctatccttgc acaaagttcc   19380
aagaaggcct tatggctctc tccatcaagt ctcctggatc atatgttgcc aagtatgcct   19440
atcggctggc ggatgatgtt gacattgagc agttcaagtc aagctggaag aagaccgttt   19500
ctctctgccc tacactgcgc acacgcatcg tgcttcttgg tgaccgctgc gtgcagttgg   19560
ttgtcaagga ggatgcagag tttgtatcat ctaccgcttc aagcttcgag tcagccatgc   19620
ttgaagctcg taatgtgcaa atgacatacg gcacgccgct gtcacagtat actctgttcc   19680
aaggagaaga tggcttctac ttcatctggg ttgttcatca tacggttcac gacgatgga   19740 ccatgcgtct tgtgcttgaa acgctgcaga acctccacca gggctcgacc accagctcgc   19800
```

```
tgaagccgta ttcaaacttc atcaagtatg cgatggatgt tgtgcaagac ccggctgtcg    19860
agaaatactg gtcgcagcag ctggatggag cagtccaggc gtcctatccc cctcgcccaa    19920
ggtctgacaa gcagcacaag gcagttaccc gcatgatgac caagactatc caagtgccaa    19980
acaacactca gtcttcagtt accatggcga ctctcctgcg tgccacctgg gctatcatcc    20040
ttgctcgtta ctccaacact gacgatatct gctttgccac gacggtgtct ggccgtcaag    20100
cctctgtttc ggacatcttg cagatacccg ggcctatcgt tgcgactatc ccagtgcgcg    20160
tacgactcaa tggccagcag actgtgctgg aatatttgga gagtgtgcag catcaagcta    20220
cacagatgat tccccacgag caatacgggt tgcaaaacat ttccaggatc tcagaaaaca    20280
tcagcgatgc cattgacttc tcaagtctac tggtcatcca gcctcgatcg cacctggact    20340
ctggcaatgg tgacggaagc aatgagaaca ttcttattcc taccgttgag gacgatgaag    20400
ctgtagcaga ccttctgcaa gattacttca cgtatcctct ggttattcag ggcaacctgt    20460
tagatgacca tatcgacctg ctcctgacct acgatagcac tgtcctgtcc gaggtcgagc    20520
tcagccgatt ggctgtgcaa ttcgaacacg ttgctcagca gctcctggat tccgatcatg    20580
tcaagctggg agatctctcg ttggtgcccc cgcaagacgt tcaacaggcc attgcgtgga    20640
acacagaaga ccccgagatc gttgaagatt gcatccacac aattggtcga acgacaagcca   20700
tttctactcc ggatgccatc gccatcgact cttgggatgg aagctgacg tacgcccagt     20760
tagacgaggc tgcgacacgt ttatctcatc acctcatcaa gacatatgat gtcgccctg     20820
atgatcttgt ccttctcttg ttcgggaaat cgttgtggta catcatctcg acaattgccg    20880
tcaacaaggc tggagcagcc tgggttcccc ttgacccagc tcaccccatg cagcgtctgc    20940
agcaagttac cagacagacg aaagctcagg tgattctcgc gtcatctctg caatgcgagc    21000
tggctcaaga actgctgaac actgttgttg aagtcagcca agccctggac gatgccctca    21060
ccacggcagg ctccacgctc cgcactccag atgccatggt ttcctccaga gacaaggcct    21120
atgtcctgtt cacttccggc agcaccgag tgccaaaagg tatcgtgatc agccacggat     21180
ctgtctgcac gagtcaaaact gctatttcta gccgtctggg cctgcacagc ggtgttcgga   21240
tgctccagtt ctctgccttc gtcttcgatg tctctgttgg cgagatatat ggctcgttaa    21300
tccgcggcgc ttgcgttgtt ataccatccg acgagattcg catgaatgac ctgaccagat    21360
tcatgcggga gaaagaggtc acttgggcat gtttcacccc ttcattcatc gagactcttc    21420
atccagctga tctggaaaat ctggagctgg tcatcctaga gggtgaacct tctaagagac    21480
atatactaga ggaatggttc ggcaaggtca agctgatcaa tggctggggc cctgcggaaa    21540
cctgtgtatt cagcagtatg cacgagtgga agtcagccac cgaaagccct gttactatcg    21600
gcaagcctgt gggctgcttt gcgtggattc ctgatcccga caatcatcat cgccttgctc    21660
caatcggtac tgttggcgag attgtgctcc agggtccgac actgttgtgc gaatacctcg    21720
atgaccctat gcagacgcag gccagtatcc tcaagtcaat cccaagctgg gctccacgcc    21780
gcgaatcgca gcactggaac cggttctact aaccggcga tctaggctgc tataaccctg     21840
acggaaccct cgcgtatcac ggccggaagg atactcaagt caagattcga ggccttcgcg    21900
tggaattgga tgaggtcgag caccatatcc gcagcctgct aagtgatgtt gttcatgtca    21960
ctgtggacgt tcacaagtcc gaggcaggtt cgagtctggt tgcctatctt gcttacactg    22020
aggagagtgt ggacgacgag gatgcactgt tcctgcccctt gacgaacgag ctgcaaaagg   22080
atctggatgc catgtccagt cagccttagtg tcttgttgcc tcggtatatg gtaccaactc    22140
tctatatccc gtgctcgcac atgcctttcc tgtcatctgg gaagacggat agggctcagt    22200
```

```
tacgcagact tacttccgaa ctaagccaag agcagctcga ggcctatgcg ctggacgata   22260
ccaagaagga ggctgccgaa acagaggctg agttgcgtct tcgagatgtc tgggccaaga   22320
ttctgggcct ttctgctcaa tcaattggtc gtcacgatag cttcttgcgt attggaggcg   22380
attcaattgc agccatccag ctggtcaccg ctgccagaga ggccggcatc atcttctcag   22440
tgaaggatgt ctttgatgac tcccgacttt ggaagctggc tgaatttgcc tcatccaaga   22500
cggaatcgga aaaggttgtg gaggccattg caccattcag cctgcttcgc acttccctca   22560
acgagacagc tgtaactgct attctgcagc agcaatatgg tttgaccgac agtgtcgtcg   22620
ttgaggatgc ctatccctct acgaagcttc aggagggtct tatggccatc tctgctaagc   22680
agcctggaac atatgttgca aagcaggtct acggcctgcc tgagcacgtt gaccttgata   22740
ccttcaaggc agcctgggag cgaacagttg agctttgtgt caatttgagg acgcgtctcg   22800
tcatcgccgg tgatgcaagt gtgcaggtgg ttattcggaa cgaagaaatc gagtgggaga   22860
cttgcaatac aaccgtgcaa gcctacctct cccagcagtt caacatggga tacggttccc   22920
gactgttccg taacggaatc gttcatgagc cctcggggca gaacttcttt gtcctgagca   22980
ttcaccatgc catctttgat ggttggacgc tcccgatgct tatggagaca ctggactctg   23040
cgtatcgcgg cgtcgaagct tccgccctcc gcccatacgc tgagtttgtc aagtatatcc   23100
tggacattga tgaggcagct gctggtgact actggcgagg ccaactccaa gatgccaagc   23160
gtgcctcgtt cccgccgtcg gccccggttc aatcatctca gacgattacc aggatccttg   23220
agaagcccct caacttctct cactcaatca aatccggcat caccaaggca tcagtcctca   23280
gggctgcctg ggccctggtg ttatccaggt attctgatag cgatgatgtg acatttggtg   23340
tcaacgtttc cggacgtaat gccgcagttg caggcattga atcgatgccc ggccttgttg   23400
tcgccacggt cccggtccgc gtgagactgg accccgaaca aacggtttcc caatttgtgg   23460
aaagcattca gtctcaatcg actgatatga tcccttacga gcagttcggt ctacaagaca   23520
tctccaagct tagccccgag gcgaaggacg cttgcgattt ctcatccctc atggtcatcc   23580
agcccatgtc tagcatcgcc aacaacaagt ctgttcttga gcctccccca gaggacaagg   23640
ctgctgctga agagagcttg cagaactact tcacttaccc tctggttatc caagctcacc   23700
tgcatgatga tggtgcggtc aatctgctgc tgatttacga tgcgaatgtg ctctccgagg   23760
atcaacttca agcactatcc atccagtttg atcatgtggt gcaacaatta cttggccaag   23820
attccggggc taagctaagg gatgtcacca ttgccggacc atgggatttg cagcaggcta   23880
tgagttacaa cgtcaaggag cccgggatcg tcaacgcctg tgtacacgag cttattgctc   23940
aacaagcggc ccgagatccc catcacgagg ctatctactc aagcgaaggc acagttacat   24000
atgccacctt ggatcgtctc tccagcctct tggcccacca cctacatgct catggagtac   24060
ggcctgagtc ggtggttcca ttctgcttcg acaagtctgc gtgggccatc atcgcgatgc   24120
tcgctattct gaaggctggt ggtgtttttc tccccttga ccctcacac ccgcgcaacc   24180 gtcgtgaggc tctgatcgag gaagtcggag cagaggtcat gattgtctct ccctcgtcgt   24240
ctgtcacctg cgagggtcta actcccacca tggtagagct gacgactccg ctacttgagc   24300
agctttcatc gacctatgat gccttccagc agattcatcc caagcaaag cctagcaatg   24360 cagcctacgt cctttttaca tcaggctcta ccggcaagcc gaaaggtgtc ttgatggagc   24420
actcgggctt tgccaccagc accctgggac acggccgggt gtataacctt ggcccgactt   24480
ctcgtgtctt ccagtttttcc aactatgtct ttgatggaag cttgggtgag atcttccacca   24540
```

```
cgctctcgtt tggcggcact gtttgtgtgc cctctgagac tgaaagactc caagaagcgc    24600
ctacctttat gcgcaagtcc cgtgttaata ctgccatgtt gacgccttct tttgttcgga    24660
cctttacgcc cgaccaagtc ccgtcgctcc aattgcttgt cctcggtggt gaagcctcgt    24720
caaaagatct catcgagact tggtgcgacc gcctgcgtct tgtcaacggc tatggaccag    24780
ctgaagcttg caattacgcg acaacgcatg acttcaagcc gactgactct cctcgcacga    24840
ttggccgcgg cttcaacagc gcatgttgga ttgttgagcc aaccgactac aataggctga    24900
cccctattgg atgtgtcgga gagttgatta tccaaggaaa tgctcttgct cgcggctaca    24960
tcaacgaccc caagcgcact gcagactcgt ttgtcactgc tgtcgactgt ctgcccagag    25020
acatgatttc cggccctcac aggttctacc tgaccggcga tcttgttcgg tacaactcca    25080
ccggcgaaat ggagtatctt ggtaggaagg atacccaggt caagctccgc ggccaacgtc    25140
ttgagcttgg cgaaatcgag taccaagtca agcagtcatt gcctgagatt gagcacgttg    25200
ctgtcgatgt ggttcatcgc gagaccggcg atgcccttat tgcgttcgtc tcgttcaagg    25260
acacggcttc ttctgcttca agtgacatac tctcccttga tgacgagatg cactctacct    25320
tggccacagt catggagcac ctgaagagct ctcttcctgg ctacatggtg cccagcacta    25380 tccttcccctt gaagaagatg ccattcatta cctcgatgaa agttgatcgg aagaggctta    25440
ttgctgttgc agctgaatta tcgttggaag aacttacctc attctcccctt gtcaagcgtg    25500 actttgctcc gcccaccaca gccatggaga gaagttggc cgacctctgg gctcaagtcc    25560
ttaagattga tgtcggcagc attggcaaga tgatagtttt ccttcagatt ggtggtgatt    25620
ccatcacctc gatccatctg gtcacgcttg cgcaaaagtc tggcatcaat ctgacggtag    25680
ccggcatctt tgacgactct aagttatcat caatggcaca ctcagctggc gaaggcgata    25740
ttgagccagt ttacgaggtg gtgccattcg atatggttgc cacacacaat ctgagctctc    25800
tgatggaaga agtgcgcacc aagtgtgggc tgcccggttc tgcggtgatc gaggatatct    25860
accctgcaac aagcttccag gaaggcctca tggcactggc cgtgaagcag cctggctcct    25920
acattgccaa gcaggtctat cagctgccaa ggggtgttga cgttgctcgc ttcaaggccg    25980
cctgggagac aactgcgcgc atgtgcagca acctccgtac tcggatcgtt cttgctggtg    26040
atgcctctgt ccaggtcatc ttgaaggata ttggctcttg gaagtcact tcaaacatga    26100 cactcaagtc gtatcttcag gcgactcaga agattaacat ggactatggc tctgcgctga    26160
gccgccacgc gctcattgag caggctgatg gcaagaacta ctttgtatgg tcaatccacc    26220
acactgtatt tgatggctgg acgactcgcc tggtactcaa caccttgctc tctgcataca    26280
tgggtgaaca gattgtcccg cttgagccgt atgcccgctt catcaactac gccatcaatc    26340
tcaatatcga tgccgccaag tcctactgga ccgagcagct gttggatgcc aagcgggcat    26400
tattccctgc tgtctccaac gaggtttccc gcaacaagac gtcaaacact cgtgtgctcg    26460
agaaggcctt ggatctgccg caagtgaagc agacctcgat aaccatggcc tcgatcttgc    26520
gcgccacatg gtccatcgtc cttgcccaat actgcgatac agacgacgtg acgttcggca    26580
caacggtatc cggacgacaa gcccctgtat cgggtatcac tgaaatggcc gggccagttg    26640
ttgctactgt ccctgtacgc gttcgactcg acagaaacgc ttcggttcca gagtttctca    26700
agggcatcca gactcaggct tcccagatga ttccatttga acagtttggt ctgcagaata    26760
ttgccaagtt gaatgttgag gccaaggaag cttgcgactt cagatcactc ttggtcatcc    26820
aaccaatgaa gaagctgctt gacactgcg atcgcgaagc catcatggag cctgtttcag    26880
cgactacccg ggatgaggaa gactttatgc aaaactactt ctcttatccc ctcgtcatcc    26940
```

```
aaggccatgt gtatgaggaa tcggtcaatc tggtcctgat ctatgatgcg gacattctgc    27000
ctgagcaaca gctgcttgct ttggctcatc aattcgagca tgtcgcacag caacttgttg    27060
ctaaaggcaa ccgtactacc aagcttggag acgtatctgt gtctggtgct tgggacctgg    27120
atttcgctct gcgtcagaac agcgaggtgc ccgagctcat cgactcttgc ttccacaccc    27180
ttgttgaaca gcaagctgtc gtacggcctg aggctcctgc aatcaacgga tgggatgcca    27240
agttcacgta tgcccagctc aacgaggctg ctaacagatt ggcgaaccac cttgttgcag    27300
agtacgagat caacaacgac gagcttatcc acgtctgctt tgaaaaatct gcttggttct    27360
tcgttgcaat tctagccatc aacaaggccg gcgcagcttg ggttcccta gaccccttccc   27420
acccatctca acgccatcaa caggttgtca accagacaaa ggcccgcctt gccctcgttt    27480
cgacctccca catttcgact tgtgtcgacc ttgtggacga cattctagaa gtatcatcca    27540
caaccgatga gcttcttcgc aagtcgcagt cttctcgcca tggtcctact cgcaaggtct    27600
cgccgtccaa cgctgcgtat gtactctttta cctcgggctc aaccggcaca ccaaagggcc    27660
ttgtcatgga gcacggaagc gtttgcacat cacaaacagc cattgtgaag cgcctgaaca    27720
tgacgcccag tgtcaggatt ctgcaattcg ctgcctttgt gttcgatctg tcgataggcg    27780
aaattgtcgc accactgatt accggtgcat gcatctgcgt gccttcagag cacgccagga    27840
tgaatgcgct gcctgaattc gttcggcaga acaacgtcaa ctgggcctat ctcacgccat    27900
catacattca aacccttagc ccgaaggacg tgcccggcct tgaattggtg ttgcttgccg    27960
gcgaagctgt gagcagggac atcttggatg cttggtttgg caaggttcgt ctggttaatg    28020
gctggggtcc agctgagacg tgtgtgtttt ccactcttca tgagtggcgg tccaaggatg    28080
aagagtctcc tctcacgatt ggccgccccg tgggaggctt cacttggatt gtcgatcccg    28140
aaaaccccca gaagctcgca cccatcggag ttccaggtga agttgtaatc cagggaccaa    28200
caatcctcag ggagtatctg gatgatcctg tccgcacctc agacagcacc gtttacagtc    28260
tccctccttg ggctcctaat cgaggaacca agtggaacag gttctacaag tctggtgatc    28320
tttgctcgta caatgccgac ggaacgatcg agttcatcag tcgcaaagac actcaaatca    28380
agatccgagg ccttcgagtc gaactaggcg aagtcgaaca ccacgtcaag tctgctttgg    28440
acgtccgaca tgttgctgtc gatgtgcttc gatccagcaa tggttcgaac ctggtggcct    28500
acttctgctt cagtgatcag acgagaatga atggtactcg tggaacttct gatggaagcg    28560
gattgtttgc tgagatggac gacgaactgc aaactcgtct tactgccgtg atcggccagt    28620
tgaatatttc gttgccgcgg tatatggtgc cgactttctt catcccttgc cagtacatgc    28680
ctaccattac ctccacgaag ctggatagga actacctgaa acggcaaacc gcggcgctca    28740
gccaggaaga gcttaccatg tattctcttc tacaaggagg gaagaagcgt gcaccagaaa    28800
aagacatgga gaagcaactc cagtctatct ggtctcagat actttccatt ccatctgaga    28860
gcattggcct tgacgatagc ttccttggcc taggcggcga ctcaatcagc gctatccgcc    28920
tcgtggcttt atgccgtgag gaggccgtct cgcttacagc gcaggatatc ttcgacgacc    28980
cacgcctgtt tgctgttgcg gcacgcgccc agaagatgaa cgtagttgtg gaagaatctc    29040
ttgacatcgc tcccttctct ctcctcagcg agaagtccca ggaactggtc aaggccgatg    29100
atgtgcgcgc tcagtgcaac ctgtcctggg aaaccgttgt cgatgcgtac ccctgcactc    29160
ctctgcaaga aggtctcatg gccctctctg tcaagcagcc gggatcgtat atggcaagat    29220
acgtctatcg catgcctcga accgtgaaca ttgcgcggtt caagtggtcc tgggagcgaa    29280
```

```
ccgtttctct ctgcgacaat cttcgcaccc gcatagttct cgtcggcggc agagctacgc    29340
agattgtggt cgatgggcct attgattggg atgtcagcca cgacttggag gcgcatctct    29400
cggccatgaa gtccatcaag atgacctacg gctctgccct ttcgcagatc gccctggtca    29460
aacaggacaa tggcgacatg ttcttcacat gggccgtcca tcactctgtc ttcgacggct    29520
ggacagttcc catcctgttc aatacccctgc aagctgtcta ccagggcgtc aagcccatcc    29580
cacccgctcc atacgctcga ttcatcaaat tcaccatggg tatcgacaac gacaacactg    29640
tccagtactg gaaggatcag ttgcacaatg caaagaaagc cacattccct ccagctgcag    29700
cccagtcggg ctcagtacaa gtgctggaaa catcgatcaa ctacacacag gcgcctggct    29760
cgtctatcac cagagccacc atcttgcgtg cggcatgggc cctcgtccta gcccggtact    29820
ctgagagcaa cgacatcacc ttcggcacca cgatctctgg tcgacaggcg cctgtggatg    29880
agatcaccaa catggctggc ccagctgtgg ccacggtccc tgtgcgagtt cgtcttgaga    29940
aacagcagac tgtatctgcc ttcttacagg gagttcaaag ccaggccatg aagatgattt    30000
cctatgagca gtacggtctg caaaacatct caaaggttag cctggatgcc aaggaggttt    30060
gtgactttac gtccttgttg gtcatccaac ccgttgagga cttggcgtac cttgatgatg    30120
atgctctcct agtcaatgcc ggaccggaac tcactggcga gacagagatg atgcagaact    30180
atttctcgta cccctcatt atccaaggcc atctatatga gaatagcatc aagctgatgc    30240
ttgtgtatga cactcaagtc atttcgacgg gcaagatgga cgcattgtcc caccacttca    30300
acgctgccgt tcaacagctc actcgcaatg gcaacgccct cctagacaat gtatcacttg    30360
cgagtgagtg ggatatggag aaggcaatcg ccttgaatag tggctcacct gatgctattg    30420
aacgctgttt ccacgacatg gttgatgaag tcgctttagt acgaggtgac gctccggccc    30480
tttctggctg ggataaatcc tttacgtaca aggaaatgac tgaggcgacg aaccgtcttg    30540
ctcactatct cgtcaatgat tatggcgtca aagtgggaga tatcattcat gtgtgcttcg    30600
agaagtcggc ttggttcatt atcgcgactc tggccatcaa caaagccggt gcagcctggt    30660
caactctcga cacgtctcac cccatcgagc ggtaccagaa gattgtcagt cagacaggat    30720
caaagctggc gctggcttcc gctgccaact cgtatcgatg tgttggcgtg ttgcctcacg    30780
ttatcgagct tactcctgag cttgatgcta ggcttgccaa gaacacttct tggagcgctt    30840
gcggaccagc tgttgcagtt attcccagcg atatggctta tatcctgttc acctctggat    30900
ctactggtgt gcccaagggt gtggtcattg agcacgccac gctttgcacc agtcaaacgt    30960
ctctgtcaca gactcttggt ttccacgagg aatacaaggt tcttcaattc tcgtctctatt    31020
cgttcgatgc cgcggtgttt gagattgatt caactctcct gactggcgct tgcctgtacg    31080
tgccctcgtg ggacgaacag atgaatgagt tggtgggcta tatccgaaag cacacaatta    31140
cctgcacgct cctgactcca actctggctc gaaccctccg ccccgaggat gttccgtctc    31200
tgaatatgtt gatattgggt ggtgaagctc ccactcgaga tatcctcgat atctggtttg    31260
gcaaattgaa gctcgtcaac ggctggggtc cgaccgaggc atgtgttatc gcgtgcctcc    31320
attcgtggac ttcggtagac gagtctccca gcgtcatcgg tcgaccaatt ggtggctcta    31380
tatgggttgt tgatccggat gatgccactc gcatggcccc cgtgggaacg tcggagaga    31440
ttgcagttca aggccggaac ttgttccgtg gatatctctc tgatcccgtc aaaacggctg    31500
ctgctacagt gacaggcctt ccggagtggg ttccaaagcg tgattcctct gctcactggg    31560
atcgcttcta tctcaccggt gatttgggct tcatcaacga agccggtaac gtcgagtact    31620
gcactcgcaa agacacccag gtcaagattc gaggacagcg actcgagctt ggggagattg    31680
```

| | | | | |
|---|---|---|---|---|
| agcatcatat | ccaagccaac | ctcgaaggtg | ttcgacaggt | cgccgtggac gtcatcaagt 31740 |
| ccgatgctgg | ttctacgctc | gttgcttttg | ttagcttctc | tgatgccacg gaaccaatag 31800 |
| actctgacac | atcggctttc | ctgccacttt | ccggagatct | ccaagcaaca atcaccagcc 31860 |
| tggtgggaac | tctgggcact | ctgatgcctc | gatacatggt | gccaagtgcc tttatcccat 31920 |
| gcgcttacat | gcccctcgca | acgtccacca | agttggaccg | caagaaattg aaagagcttg 31980 |
| ctgcctccct | gagccaggat | gaactgtcta | tctactcgct | cgccaatgaa caaaaggccg 32040 |
| ctcctcagac | tgctatggag | agccgtatcc | aggcgatatg | gtcccaggtc ttaaacgtca 32100 |
| gcatcgattc | tatcggacgc | gacgattcgt | tcctccagat | tggtggtgat tctatcctcg 32160 |
| ctattcagct | cgtttccgtt | gctcgggatg | ccaacgttaa | gattaccgtt ggcgacgtgt 32220 |
| ttgatgatcc | ccggttgctc | gctgttgccg | caaaggccac | tgaacttgac gataacggcg 32280 |
| aggtcattgc | taacatcgag | cctttggcc | ttttggatga | acccttgaag gacctggttc 32340 |
| tgagccagcg | catccaagag | cagtacagcc | ttccaactga | tcgcgagatt gaagatgcct 32400 |
| atccgtgcac | gaagctccag | gagggtctca | tggctctcgc | cgtcaaacag cccggttctt 32460 |
| acattgccaa | gttcctctac | cgcctctcca | gcaacgttga | cgtctcgcat ttcaaggctt 32520 |
| cttgggaaga | gaccgttcgt | ctcctaccca | atttgcgcac | caggatcttc actgccggca 32580 |
| acatgtctat | tcaggccatc | ctcaaggacg | acatctcctg | gcaaccaaca gaaggcgact 32640 |
| ctctgcgatc | atacatgggc | tcagctcaga | actttgagat | gacctatggt tcgccgctgg 32700 |
| ctcgatatgc | cctcatcgag | gacaatggag | atacttattt | cgtcctgtcg atgcaccacg 32760 |
| ctgtctttga | cggttggggc | atcagggtgt | tgatgagcgt | tttccattct gtgttccgca 32820 |
| agcaagcccc | cgttatcgag | ccgtatgtac | gtttcgtgca | gtacaccatg gatgtcaaca 32880 |
| acgatgaagc | ttcagactac | tggcggtctc | agttccaggg | tgcgagacaa accatcttcc 32940 |
| cgcccaatgc | atctgcatca | gagagcagga | agaacagcac | tcagacgtc gaaaagatga 33000 |
| ttgagctgcc | tagcatgaac | aagtcgtcta | tcacaaaggc | caccatgctc cgagctgcct 33060 |
| gggctattgt | cctttccagg | tattgcgaca | gtgacgatgt | tactttcggc atcaccatct 33120 |
| cgggccggca | ggcgcctgta | catggcctaa | tcaacatgac | gggtcctgct atcgcaactg 33180 |
| ttcccgtgcg | tgttgctatg | gatcgcaaga | cggttgtcaa | ggattacctg caggccatcc 33240 |
| agagccaggc | aaatggcatg | gttccctttg | aacaattcgg | cctgcaaaat atctctcgcc 33300 |
| ttagtgctga | ggctaaggat | gcctgcgact | ttggcagtct | ccttgtcatc caacccatcc 33360 |
| aatcactggc | ctacgtcgat | gagagtgcag | acactgtctt | tatcccgctt gacgtggata 33420 |
| aggaggttac | cgataccgtc | cagaattact | tcagctaccc | cttggtcatc caaggccaca 33480 |
| tgcatgaaga | cttcatcaac | cttgtgctca | tctatgacac | aggtgtgtta gcagagagcc 33540 |
| agatggttgc | cttgtctcac | caattcgaga | atgtcctgaa | gcaactcgcg tccaagcccg 33600 |
| atctggagct | gggctctgta | tcaatggctg | gtgactggga | tcttgaattc tccaagagac 33660 |
| agaacagcga | ggttcccgag | atccttgatg | tttgtgttca | tcagcttatt gagaagcaag 33720 |
| ccgctgccca | gccagatgcc | cctgccgtcc | tgagctggga | ccatagcttt acgtacaagc 33780 |
| agctcaacga | agcatccaac | aggctggcac | atctccttgt | caacaaatac cacgtcaagc 33840 |
| ccaacgacct | ggttcacgtt | tgctttgaca | agtgtgcttg | gcatttcgtc gcaataactg 33900 |
| ccatcaacaa | ggttggcgca | gcttgggtgc | cacttgatcc | ctcgcatcct gaaatgcgac 33960 |
| ttcgtcaaat | cgtttcccag | actcgggcca | ctctgactct | tgtgtcttca tctaatgcat 34020 |

```
ctctatgctc ttctcttact gagagggtca tagaagtcaa tgcaagcctt gataacgagc    34080
ttctggcagt ggaaagcggt gaatatggcc cttctgtgga cgtctcctcg cacagcgccg    34140
cctacgtgtt gttcacgtcc ggtagcacgg gcgttccaaa gggtttcgtt atggagcacg    34200
gctctgtatg tacgtcgcag attgctatcg ccaggagact tggactagga ccaaacgttc    34260
ggatgctgca gttcgctgca tttgtctttg acttgtccat cggcgagatc gttggtccgc    34320
tcatctcagg tgcctgcatc tgtgttcctt cagaagacac tcgtataaat ggcatcgttg    34380
ccttcattaa cgagacgaag gttacttggg cctacataac accatccttt gcccgtacaa    34440
tcaagccgtc cgaagtgcct cacctagagc tcctgctact ggctggtgaa gctgtccccc    34500
gggatgtttt cgcaacttgg tttggcagca ctgtccgcct tatcaatggc tgggggccag    34560
ccgagacctg cgtgttctct actctccacg aatggaagtc tgctgatgaa agtcctctga    34620
cagtcggtcg tccggtgggt ggattctgct ggatcgctga ccccgaggat cctagtcgac    34680
ttgcagcaac cggtacccta ggtgaaatcc ttatccaagg acctacaatc cttcgggaat    34740
acctctcaga cgtcgccaga acggaggcta cggtcatcaa gtcccttccg gagtgggctc    34800
ccttccgcaa cgaacctggc tgggatcgga tgtataagtc aggagatctt ggcttctaca    34860
accctgatgg aaccattgaa ttctccagtc gcaaggatac ccaagtcaag atccgtggtc    34920
tgagggtcga gttaggtgaa gttgaacatc acgttcaggt cgctttaccc ggcgttaaac    34980
aaatcgctgt agacgtcttc cagggcgaaa acggtaccaa cctcgtggcc ttcttctcct    35040
tcaatgatga aacccgccaa atccatgaag cagattcgtc cggacctttt gagccgctcg    35100
acgacaactt gcaggatcgc cttactgctg tcgtcggtga gcttagtgta tctctgcccc    35160
gatacatgat tcctaccctc ttcatcccct tgcaagtatat gccgtctatc acgtccacca    35220
agcttgaccg gaacgaactc aagcgtcgca gcacagcact tagccagtct gaactcgctg    35280
tgtattcgtt gcagggcgga aagaagaggg ctcctgagac accaatggag agcctcatcc    35340
aagccctttg gtcagacatc ttgcacgttc cggccgattc tattggccgt gacgacagct    35400
ttttgggcct aggtggcgat tcaattactg caatccacct ggtcagcatt gctcgtgaga    35460
agggcattca acttgttgtg aaggacatct ttgacgatcc tcgtctcttg gccgtgtcca    35520
gtaaagccaa ggagatggac atcgaggctc gacaagagct gcttgaggta tcgccgttca    35580
gtcttctgaa tgctgaaact catgatctcg ctatcggtcc aagtgtcaga cagcaactca    35640
atttgctcga aggccagacg attgacgatg cgtacccctg taccaagctt caggaaggtc    35700
tcatggcctt gtcagttact caaccgggat cctacatcgc gagatatgtc taccgtctat    35760
ccagacaagt cgatgttgct cgcttcaagt ccgcctggga aaccactgtt gctctgcgtg    35820
atatcctacg aacgcggatc gtcatgatta acggcacatg cattcaactg gttgtcaagg    35880
gtggtgtcgt ctgggatctt atcgattccg agagtctgga ggaagctgcc cacaagacgc    35940
actctcacac catgacctat ggctcgcaac tatccagaac ctccatctat gagaccaaga    36000
ctggcgacaa gtacttcctg tggactgttc atcacgccat ccacgacggc tggtctgtgc    36060
ctgtcatctt cagcactctc tatcaagctt atgaaggtct ggaactgggg actcccaagt    36120
cttactccgg cttcatccga tacactttgg agcttgatca ggaggctgct agcaattact    36180
ggagagaaca gctgcaagac gccaagcggg ccagtttccc caaaaccgga ctcacgacaa    36240
aatccgccga caatgagcag aagattcagg tcatgtcgac ttctctcagc ttcccttcat    36300
catccaacga agctgtcact aaggctagcg tcatgaggga tgcctgggcg gttgtccttg    36360
caagatactg cgacagtgat gacgtctgct ttggtgccac catctctgga agacaggcac    36420
```

```
ctgtgcatgg tgtactcgag atggccggcc cggcagttgc aactgtgcct gtgcgtgtga   36480
agctggacaa gggccagagc atccctcagt tccttcaagt catccagaac caagcccatg   36540
agatggttcc atatgagcaa tatggtctac aaagtattgc gaagctggga gcagatgcaa   36600
gagatgcttg cgattttacg tctctcttgc tgatccagcc tgttcagcgc ctttcttcgg   36660
gcgttgcaga tgaggagggc ctcttggttc ctgctcagtc agagatcaag gacatggttc   36720
agaactacta cagctatcct ctcgttatcc agggtcacgt atacgatgac cgagctgatc   36780
tcgttttgat ctacgactca acggttgttc cagagcccca gatgactgct ctttctcacc   36840
actttgacaa tgtggtgcag cagctgttgg ctgtggatgg caagtgggc gacatttctg    36900
ttgctggttc atgggatctt gagcttgcac aaaagtccaa tggcgacgga cccgagatca   36960
ttgaggactg catccactcc atcattgaga gacaggtcca acagaggcca aactcacctg   37020
ccgtcgatgc ttgggacgga cgtctgacct acagccagct ggatcacgcc gccaataggc   37080
tcgctcacct gcttgttgat gactatgcgg ttcaagttgg cgacattgtg cacgtctgct   37140
ttgaaaagtc gatgtggtac attgtggcta ttctcgcgat caacaaggcc ggtgccgcct   37200
gggcacccct cgattctgcg catccttttcc agagactcca ggctgttgct aagcaaaccg   37260
gtgccaaact ggcccttgct tcgactgcaa acgccggact ctgcaagcag cttgtggatc   37320
gtgtgattga agtgtcggca gctctcgacg aaaagctctc gtccaacgcc gtcagcagcg   37380
gaaagggacc tcaagtcaat gtatcccctc tagatgctgc gtatatcctg ttcacatctg   37440
gttccactgg tacaccaaag ggtatcgtga tgcaacatgg agcactctgc acaagtcaaa   37500
cggacatcag tcgatggctg ggccttgacc acaccgtcag gatgctgcaa ttctcatcgt   37560
ttgtgttcga tgtgtctgtc ggtgagatca tggagccgtt gatgaacggt gcctgtgtct   37620
gtgttccttc ggaccacatg cgtctcaaca gcctcgatgt ctttgtccgc gatttcaacg   37680
tgacttgggc gtatctgacc ccgtcattta cgcgcacctt gaagccggaa gacttccctg   37740
gactcgagct tctgttgctt atcggagaag ccgtcactca ggatgtcctc gatacgtggt   37800
ttggtcttcc taacacccgc ttcgtcaacg cttggggtcc tgcagagacg tgcgttttca   37860
gcacactgta tgactggcag tccaatactg agtctccctt gacgattgga cgagctgttg   37920
gtgcgtatgt gtgggttgtg gatgctgaga tccccagcg gctcgctcct acaggctgct   37980
taggcgaaat cgtcgttcaa ggccctccac tcctcaggga atatcttgct gatccttcga   38040
aaacggcggc tgctactgtg acggagctcc ctgagtgggc tccccgacga gaattgacca   38100
aatggaaccg cttctaccgg actggtgacc tgggcttcta cagtcatgat ggtctgcttc   38160
actatgccag ccgcaaggac actcaagtca agattcgtgg attgcgtgtt gagttgggcg   38220
aagttgaaca ccatatccga agctcgttgg atggtgttcg ccaggttgct gtcgacgtct   38280
tcaagactga gacgggagcc aacttggtga cctacttctg ctttaccgat gacaccaaga   38340
ctcctggccc tgacaccgat cctgagggca aagatgtgtt catgtctatt gacgctgccc   38400
tacaggagaa gctgggcaac atgttgagca aattgaactc atcactgcct gggtacatga   38460
ttccaacact ctttatccct tgcgactaca tgcctctcat ctcgtctgcc aagttggacc   38520
gtgtcaagct tcgtcgcatc acagccgagc tcagtcaaga tcaactggaa tcctattcgt   38580
tgcttgacac cgataaacgg gcgcccgaga cggaaatgga gattcgtctc cagaagctct   38640
gggctgagat cctcaacctta ccggaatcct cgattggccg agacgacaac ttcctacgaa   38700
ttggtggtga ctcgattgct gctattcgtc ttgtttcaat ggcccgcgac gtcggaatca   38760
```

```
gcctgacagt tgacgacatc ttcaatgacg ctcgtctgat ttcaattgct gccaaagctg   38820
ttgatggcga tgtatatagc tccatcatgg cgccgattga tgcattcagc ctcttgtcac   38880
ccggaactgg agacttggtt ctgccctcag ctctccccga agggcaggtt atcgaagatg   38940
cttacccttg cagcaagctt caagaaggtc tcatggctct cgctgtgaag caaccgggct   39000
catacatcgc caagtatgtc tacaagctcc cagagcatgt ggacgttgtc aagttcaaag   39060
cggcttggga gcgcacagtg gagttgtcca gcatcttgcg cactcgcatc atccagatca   39120
acggccgttc gatccaggtt gtcatcaatg gtgatgtaac ctgggatgag actgatggca   39180
gcttgcagcc gtgccttgct cgtgctcaat ctctcgagat gggctacggt gatcgtcttt   39240
gccagtacgc tctcattcga gatggcaaca gcacatattt catgtggaat gtgcaccatg   39300
ctgtcattga tggtctgtca actcaaaaca ttctggccac gcttttcagg ctctacagcg   39360
gcatcgacgt gttgtcagtt cccccatttg cgcgcttcat caagtacatt ctcggtctcg   39420
atgaagaggt cacagccaac tattggaaga cgcagctgtc caacgcccgc aaggccattt   39480
tcccgccctc aaaggatgcc tccaatgaca agccagaggc tactcgaacg ttggagacgt   39540
ctattgatct tccttccagc atcaagaact caaccatcac aatggccaca gttgtccgat   39600
ctgcctgggc catcgtgctt gcgaggtact gtgagactga cgatgtgaca tttggtacta   39660
caatctcagg tcggcaggct cctatccccg aggtcatgga aatggtcggt cctattattg   39720
ccaccgtgcc agtccgcgtc cgtattgatc gccgtcagct cgtctcggag ttcctcgaag   39780
gcgtgcagaa gcaagctgtg gagatgacgg cctttgaaca gtacggcctt caaaatatcg   39840
ccaggctgag tgaggacgcg cgtgatgctt gtgactttgg cagtcttctc gtggtccagc   39900
ctatgcagca tcttggtggc gccggcaacg acgatgccat cttggtcgat gctgcaattc   39960
cggacaatag ttctgctgag tctctccgga actatttctc ttatcccctt gtcatccagg   40020
ctcacttgta cgatgatcat gtcaaccttg tgctggtcta cgactcgaac gtcatcccag   40080
aggctcgact ggtggcatta tcgcatcacc tcagtcatgt tatgacacag ttgaccacca   40140
ctgagccagc tgccttggac actgtgtcag tctcttcgcc atatgacgtc cagaaggcat   40200
tgtcattcaa tactgaagtc ccagaggtca ttgacgcctg cattcatgaa ttgttcgaac   40260
aacaggccag tttgcgtccg caagcgccag ctattgccgc ttgggacggc aacttaacct   40320
acgacgagct taacaaagca gctaacaagt tggctcacca cctcgtcaac gtctatggtg   40380
tcaagcctaa cgatttcgta cacgtttgct tcgagaaatc agcttggtac atcgtctcga   40440
tccttgcaat caacaaagct ggcgccactt gggtcccctt ggatccctcc caccctgagc   40500
aacgatggca gtctatcatc agccaaacaa aggccactct tgctctggtc tcgccgggta   40560
gtgttggccc cctatcacgc ttgatcgaca atgttgtcgc ggttgattcg aacctcgata   40620
gcttgcttcc tgaacatgac gcggcacgag gcctcagtgt gtcaatctcc cctagtacag   40680
ctgcatacgt gctgttttact tcgggttcaa ccggcactcc caagggattc atcatcgagc   40740
acaggtcgat atgcacaagc cagaaggcgt tcaacaagag gctacgctac catgaaaacg   40800
tgcgcgtctt acactttgcg gctactgttt tcgatctctc gattggtgaa atcatcatgt   40860
cgcttctaaa aggagcgtgt ctatgtgttc cttctgagca cactcgattg aatggcatcg   40920
tcgactttat ccgcgacatg aagatcaatt ggctctatct cacgccctct ttcttgcgaa   40980
cgatagatcc aagccaggtt cccaatgtcg aattgattct cctggcaggc gaagctgtgc   41040
cgcgcgaggt tttcgagacc tggtacggac gcgttcgtct gttgaacggc tggggtccag   41100
cggaaacatg tgtcacgagc gccatccatg agtttgaatc tgctgacgac tcaccgttga   41160
```

```
ccgtcggtcg ccctgtgggt ggcttctgct ggattgttga tccagagaac ccacagcttc   41220
ttgcgccgac agggaccgtg ggcgaggtcg tcatccaagg accaacattg cttcgcgagt   41280
atttggataa ccccgaaaag acgcaagaga caacagtcta tgagctacct gactgggcac   41340
cccgtcccga tgagaagaac tggagtaggt tctacaagac gggcgatttg tgcttctaca   41400
acccggatgg cactattgag ttttcctctc gtaaggacac acaggtcaag attcgcggtc   41460
tccgtgtcga gcttggcgaa atcgagtacc atgttcaagc atcgctggaa ggaatccgtc   41520
aaattgctgt ggacgtcgtc aaaaccgaca acggctctca cttggtcgct tatctgtgct   41580
tcaacgatca gatgcgtcaa cctgacgaag ctgaggtcaa cgggccattt acccctatcg   41640
atgctgagct tcaagacaag ctcattggcg cagtcagcat gttgaatgtg acgctcccga   41700
ggtatatgat tccgacattc tatatcccgt gcagctacat gccctacaac acatctggta   41760
agctggatcg aagggagctc aagacgcaaa ctgctgctct aggccagtcc ggactgagca   41820
atttctcact acacggcgtt gataagcgtg ccccgagac gccgatggag attgagctac   41880
agaaggtctg gtcaacggtc ctgtctctcc cgaccgactc gattggccgt gatgatagct   41940
tccttggctt gggcggtgat tcaatcatgg ctatccatct tgtcagcgcg tgccgcgaag   42000
ctggcatctc ccttaccgtc aaggacgttt ttgatgatcc tcgcctgtcc gcggttgctt   42060
ctaaggcttc ccgccttgac tctacggatc aagagacctc cgtcgcgcct ttcagtttgt   42120
tgcccgaccg tatccgcgag atggcgctca gcaacgatgt ccgatcacaa gtttcattgt   42180
ccgccagcga ctcagtggaa gatgcctacc cttgctcaaa actccaggat ggtctgatgg   42240
ccttgtccgt caagcagcga ggctcctatg tcgcacagta tgtgtacaag ctgtcgacca   42300
gtgtcgacct cgagagattc aaggctgctt gggagaagac actccagctt tgtgcaaacc   42360
ttcgcacccg tatcgtcatg cttgatggca tttgcgttca actactgatc gatggcccgg   42420
cggaatggga cgaccaatct ccaacggact gaaggccac tgttgatgcg actcgcactg   42480
acatgaccta cggctctcgt cttaaccgtt ttgctcttgt ccaggatccc gagtttggca   42540
accactttgt ctggtcatca caccacgccg ttcatgacgg ttggacccct agaattgtca   42600
tgaatactct gtacggagtc tatctaaacc aaacggcacc tcgtcttctc ccgtattccg   42660
cctttatccg ctacacagtc aacatcaacg cggacgatgc caatgccttt tggagcgagc   42720
agctgaggaa cgcgaagcgt gccacgtttc caccaatgcc ccgtatcgag tcccatgcta   42780
gcatcactcg catgatgaac aagacgattt ccttccctcc ctccgtcaag acaacgacta   42840
cgaaggctac tattctccgt gctgcttggg ccattctcct agcccgttac tgtgattctg   42900
acgatatcac gtttggaacc acaatttctg gccgtcaagc tcctgtgccg ggcctcacgg   42960
aaatgccagg cccagtcgtt gcaacagtcc cgattcgcgt tcgcattgat gccagccagc   43020
cagtgtctcg cttcctgagc aagatacagt cacaagcaac tgacatgatt gcctatgaac   43080
agttcggtct gcagaacatc atcaagctgg gtgctgacgc taaggatgcc tgcgagttct   43140
cttctcttct cgtcatccag cctcgaactc acttggatgc aattgagagc aaggaagctt   43200
ctgatcccct gatgacgact tcggtggcgg caaagggcgc tgagcaactc atgcaaggct   43260
attttacgta cccccttgtg atccaaggcc acgttttga cgactctatt gagctccttt   43320
tgacgtatga ctcgaccatc ctgtcggaag tcgccatgga agctctttgc catcaatttg   43380
acgttgtctc taaccagctg gtcaaggaat ccaatgaccc tcttggttcc gtcgccgtct   43440
ctggtgaatg ggatctcgag caagcaaaga agtggaacgt tgagaatccc gacatcctcg   43500
```

```
acacatgcat ccacaacctc atcgaagagc aagcacgcat cagaccagac gcaccggcca    43560
tttgcgcttg gaatggtgag atgagctaca gccagctcaa cttcgctgct aacaagcttg    43620
cccatcacct tctcaacgcc ggcgtcaagt ccgaggactt ggtacacgtt tgttttgaga    43680
agtcgctgtg gttctttatc tccattgtcg caattaacaa ggtgggcgca gcttgggtgc    43740
cgcttgattc atctcaccct gagcagcgtc tgcgccaagt cgtgagccag actcgtgccc    43800
aatttgcgtt gtcttctcct accaatgccg ctctttgtgg aagcctcgtc gacaaggtca    43860
tcgaagtgtc acaaggcctc atcgacagtt tcccgtacga tggtgccaat ggaccggcca    43920
tcaaggtacc atcaagcaac gctgcatatg tcctcttcac ttcgggcagc acaggaacgc    43980
caaagggtct tgttatgcag caccaagccg tctgtaccag tcaagccgcc atcgctaaaa    44040
ggcttcgcct gacgcctgat gtgagaattc tccaattcgc cgcatacgtc ttcgatttat    44100
cgattggaga gatcgttgct cccttaatcc atggagcttg tgtatgtgtg ccatcggagg    44160
agatgagaat gaatgggctg aaggaattca tccgggacgc atccatcaac tgggtatttt    44220
tgacgccttc ctttgttcga acgctgcggc ctgaagacgt acccaatctt gatctactgc    44280
tccttgccgg tgaagccgtg ggaagagata tcctcgacac atggttcggt aaggtacgct    44340
tggtcaatgg ctggggtcct gctgaaacgt gtgtcttctc cacgctacac gagtgggctt    44400
ccattgacga gtctccattg actgttggaa cacctgtcgg aggtcactgt tggatcgtgg    44460
acgccgagga ctccagcaag ctggcgccaa tcggctgctt gggtgaagtc gttcttcagg    44520
gcccaacgct acttcgtgag tatcttgctg atcctcagag gagcaaggag gccatcatca    44580
cctcgttgcc gtcatgggcg ccaaagcaag acagtcagcc ttggagccgc ttttacaagt    44640
ccggcgactt gtgctactac aaccctgacg gcacgctcga attctatagc cgcaaggata    44700
cccaggtcaa gattcgtggc ctccgtgtgg aactgggcga ggttgaacac cacattcgtg    44760
aatcgcttga aggtgtccga caggtggctg tagatgtgtt gaagtcagaa acaggtacta    44820
acctggtctc atacctctgc ttcaacgacg actctcagcc cgtctcgtca gagcttcaag    44880
caagcgatgt ctatctcccc cttgatgccg acatccagac tcgcatcacg gccatggttg    44940
gcgagcttag tgtgaccctt ccacggtata tgattcccac gctgttcatt ccttgcaaat    45000
tcatgcctgt cattacctcc accaagttgg acaggaaaac actcaaggca atgacggcgt    45060
ccctagacag ggatcagcta gcacactact cgctgattga tagcaagaag agagctcccg    45120
agaccgagat ggaaacccgc ctccaggtca tctgggccga catcctcggt cttcctgtcg    45180
actcgattgg ccgtgacgat agcttcctcc agattggagg tgattctatt actgcaatct    45240
acttggtgtc taaggcccgt gaagccggca tctcgcttgt tgtcaaggat gtcttttgaag   45300
actcgcgtct gcttgccgtt gcttccaagg ccgtcttctc ggaatacgcc caagaggatc    45360
aggagcccgt cgtacccttc agcctcttga acgaacagac ccgtgccctc gtgcttggcg    45420
gcgaggttcg caaactgtgc ggccttgctg aagatcagat catcgaagat gcttatcctt    45480
gcacgtcact gcaggaaggt ctgatggcct tgaccgtgaa gcaaccgggc tcgtacgttg    45540
ccaagtatgt ttacaagctt gcgcccttcg tcgacgtcga tcgcctcaag gctgcgtgga    45600
gccgcactgt tgagctctgc ggcaacatga gaacgcgaat cgttctgcta aatggctcgc    45660
ctgtccaact gctccttaag gaggacagcc agtggcagtc actggaggcc gagacacttg    45720
cctcagttgc cacgtcttct cgcgacttga tgatgggcta tggatcacct ctttgctggt    45780
acggaattct cgaagagaac gatgctcgat atctggtgtg gtcggccat cattccatct     45840
acgatggctg ggtgatgcgt atcctggtga ctaccctata cacggtatat cacggcgcgg    45900
```

```
aagtcacgcc tttgcagccc tattccggct tcatcaagta caatatggag ctggatagtg   45960
cttcttccgc tgagttttgg cgagagcaat tgtcaggctc caagagggcg gcattcccag   46020
cccgacagcc cgctgccaca tcatcgtcct caacgcagat attcaaatcc agcatcagca   46080
ttggacaagc caaacagagc agcatcacaa aggcctctat tttaagggct gcctgggcta   46140
tcgttcttgc gagatactgc gataccaacg atgttagctt tggtgcgact gtgtcgggtc   46200
gccacgctcc tgtggctggt ctcgagacca tgcccggtcc tatgattgcg actgtcccag   46260
ttcgcgttca cttggatcgt gcttccacca agtcccagtt ccttgcaagc atccaaagcc   46320
aggcccacga gatggttcct tatgaacagt ttggtcttca aaacatctca aaggtaagcc   46380
aggatgctag ggatacttgc gatttctcaa gcttgctcgt catccaaccc cctgcgacca   46440
ccatctcaga agaggactcc aagaccaaca tcctcgtcta tggtgacgcg aacagagcc   46500 gcacggatga cgctatgcaa aactacttca actatcctct cgtcattatc atgaacacct   46560
ttgaggatca cattctgcag cgcttcttct acaacccaga cgtcctggac gaggctcgag   46620
tgtctgcttt gtcgcagcac attggccatg ttgttgagca gcttctggca tcaagcgatg   46680
aagccctcga cagcattgac ctcgtcagcg actgggacgt gcagcacgct gtggaatcca   46740
cacggctgaa gccgtcaacc gagtcatgta cgcattggct catccgagat cgcattgaga   46800
agcagcccag cgatcccgct attgcttctt gggatggcga tctcacatat gaagagttgg   46860
gcgtcttagc atcccgtctt gcgtggaaac ttcaaggcct cggcgttgga cccgagtccc   46920
tcattccatt gtgcttcccc aagtctacct gggcagttgt tgcaatggtt gctattgaga   46980
tggctggtgg tgccttcgtt ccccttgacc ctaaggcgcc tgttgctcgt cttcgtggta   47040
tcattgaaga caccaagtca accctggcag ttgccagccc gtcatgccag gatgctcttc   47100
atgagattgg catcgatgtg ttggccgtcg acgaggctct cctgctggag ttatccgacc   47160
ccgtggaggg cattcagtca aaggcagggc caaaggacgc aagtgttgtg ttgttcacct   47220
caggatcaac cggaaagccc aagggaatgg ttatccagca caacagctta tgctcatctg   47280
gaaatgcgta cggccaggac ctcaacatcg gacctggaac gcgtgtcttc caattctctg   47340
cctatacctt cgacgttggt gtacttgact gcctcgtttc tctcatgcgg ggtgcgacga   47400
tatgcattcc ttcagaccat gctcgcctca atgaccttgc tggagctatg actgcaacca   47460
aggccaattg ggtgttcctt acacctacgg ttgcggatct tctttcacca gcagatgttc   47520
catatctcaa ggtcctctgc ttgggtggtg aagccattag caagaagtgt gcagaccgat   47580
ggatcaacta cactgagctc catggcttat acggccctgc tgaggcttcc atctgtgcct   47640
ggaacccaag tgttggcaag tctgggcggt caaccaacct cggaagaccg atatcatcag   47700
ccttctgggt agtcgagccc aataaccata agcaacttgt ccccgttggt tgtattggtg   47760
agctcttgat cgaagggcca atgctcgctc gaggatatct caacgtcagt gccgacgttg   47820
cttccaactg gatggataac gtcgactggc tcccggaag cgacaagaag agagtctaca   47880
ggacaggtga cttggttcgc cgcaacgctg acggaacgtt tgagtttatg gccgtaaag   47940 atacacaagt gaagctccac ggtcaacgtg ttgagcttgg cgaaatcgag gcccgtatcc   48000
acgaattcct ccccagtgac atggctgcta tcgtcgccgt tgtcaaggac gaacacggcc   48060
atgacagctt gcttgctttc atgtggtaca ccgaaggggt cgttgcctct cgatcgaccg   48120
cccatctcat ggaggttgtc tcagacgagg cgcgtgccac catctctcat gttgactctt   48180
ccctcgaaat ggtgctgcct tcatacatga ttccatcgtc ttatctggta ttcgagggca   48240
```

-continued

```
agcctgaaca aaccgtcaat ggcaaagttg accgaaaagc actgctggct cacgctcaga    48300
acttatcaac acaagatcgt ctgcgattcg cgcctgttgt tggcaagagt gagccaccga    48360 gcaccccat ggagttcagg ctcagagacc tctgggctca ggtgttgcag attgacgctg     48420
agtctattag caagaatgat agcttcctgc gtattggagg tgactctatc agcgcaatcc    48480
agctcgtctc tttggcccag cagaataaca ttggcctcac ggtagctgcc atctttaacg    48540
atcctcgctt atcccacatg gctgaggctg ccaacgttga cgacatcatg cccgtctatg    48600
agactaagcc atttagtatc atcccggctt cggctatgga tgaggttctc gcccaagtac    48660
gctctcagtg cgacaatctc tcagagacag ccatcatcga agatgcttat ccctgcactc    48720
gattacaaga agggttgatg atcctggctg tgaagcaacc tgggtcatac gtcgccaagc    48780
atgtgtatcg cctttctgat aacatcaacg tcgcgcgatt caagcgcgcg tgggatcaga    48840
ccgttgaagc ctgtgcagcg ctgcggacgc gaatcgtcct tgttgacggc tcagcttacc    48900
aagccgtcat caaagactct gtgaaatggc agacagcatc cgacattcgt tcattctcca    48960
tgtctccgga caacactcaa atgggctacg gctcccctct atgccggtac gcgcttattg    49020
agcagaatgg tgagaggtac ttcgtttgga atactcatca cacggtatat gacgggtgga    49080 cttttgcccct gatcatgggc acgcttcacg ctttctacag cggcactgat gcccctccac    49140 tcctcccta ttctggcttc gtcaagtatg tgacggaaat ggactctgcg gctgctagtg     49200
agtattggac tcaacagctt gagggtgcta ggaagactac tttccctcct ggagctgaag    49260
ccgtcaagac caagaaatcg cagatgtcaa ccagggtcat gcgcaacacg gtccaattcc    49320
cacggtcgac taatacgtca atcacgaagg cttctgtcct tcgagccgcc tgggcgattg    49380
tgctcgcacg gtataacgat actgacgatg tctgcttcgg atctacagtc tccggccgcc    49440
atgctcctgt accaggaatc gagcgaatgc ctggccttgc ggtcgcgact gtccctgtcc    49500
gcgtcaagct ggatcagaag cagtccctgg atgccttcat ggagggtatt cagtcgcagg    49560
cctctgagat ggtcgcatat gagcaattcg gcattcagaa catatccaaa ttgaacgcca    49620
aggctaagga ggcttgcgat ttcaccagct tgttggttgt acaaccgacc cagcacatca    49680
cttcgactgg aaacgccagc gaagaagccc tccttactgc cgcagcaacg gacgacattg    49740
ctgctgacga gatgctggac aactatttca actaccccct ggtcctgcag tgttacgtgc    49800
ttgataacca agtcgagctt gtcctcgtct atgactgcga tgtcattgct gagcatcaac    49860
tcgttggctt gtcccaccag ttccagcatg tagttaccca actgcttagc caggatggtc    49920
ctctatctgc tgtttctgta gcaagtgaat gggaccttga gtttgctcag gcgtccaatc    49980
acgatgagcc tgctgttgtt gacgactgca tccacaacat gatcgagcaa cgagccctga    50040
tgaaccccaa cgctgaggcc gtcagtgcct gggacgcccg cttacctac gctgagttgg     50100 accggtctgc taatatactg gcaaaccatc tgatccaatc aaggggcgtt caagtaggcg    50160
acttggtcca cgtgtgcttc gagaagtcgg cttggtatgt cgtatcaatc ttggccatca    50220
acaaagcggg tgcagcttgg attccactgg atccgtcaca tcctgccgaa cgccaccaac    50280
aagtggttgg gcaaactcgc tccagattgg ccctcacgtc gcccgcaaat gctgccaagt    50340
gtgccaacct tgtagccaac gttttggagg tgacagagg gctcctcgat gacctggaaa     50400
cgcaagtcaa ccatgcaagg ccagtcacaa gtgtcggtcc tcaagatgtg gcctatatac    50460
tgttcacgtc cggatcgact ggtgttccca agggcgttgt tatggaacac ggagctctct    50520
gcagtagcca gacgtccatc agcaagcgac ttggctatgc acctggtgtg cggatgcttc    50580
aattcgcctc gtttgtcttc gacgcctgta ttggcgagat aatcgctcca ctgatctcgg    50640
```

```
gctcctgcgt ctgtatcccg tcatgggaga cacagatgaa ctcactgacc agctacatcc   50700
gcgaggaaaa tgttacttgg gccatgctca ccccgtcgtt tgcccgtacc atggatccta   50760
gcgaggtacc ttgcttggag ctcctgatcc tgatcggcga ggctgtcagc cgcgacgtat   50820
tcgagctgtg gttcggcaag ctccgtctac tcaacggttg gggtcctacg gaaacgtgtg   50880
tctttggtgc tctgcacgag tggcagtcca tcgacgaatc tcagatgacc atcggtcaac   50940
cagtcggtgg ttactgctgg atagtcgacc ctgaagatcc gcagagatta gccctacag    51000 gcacctttgg tgaggttgtt attcaagggc ctaatctgct tcgcgagtat cttgccgatg   51060
aggtcaagac ggcttcatca actgttcctg tcctcccaga atgggctccc aacaggcatt   51120
tgcgtcattg aaccggttc tataagacag gcgatctggc gatgtacaac ccagatggaa    51180
ccattcagta ctacagccgc aaggacacgc aggtcaagat ccgaggtttg agagtggaat   51240
tgggcgaagt cgaacaccac gtacgacaga atctcgacgc cgtccaacaa gttgctgtgg   51300
acgtgttcaa gacggattct ggcgtcaacc tcgtttcgtt tgtgtgcttc aacaacgaca   51360
ccctcccggc cagcatgact ggcgatatca ccagcaagga catcatcacg cccttgacgg   51420
gcgagctcaa ggagagcatc aacagccttc tgggtcgtct aaacgtcctc ttaccgggat   51480
acatgattcc tacgttgttc atcccattca aggccatgcc actcgtcaca tctggcaagc   51540
ttgataggaa gcttctgttg aagcttactg cttcgcttga aaggagcag ctagaggaat    51600 atgccctcac tggcggtgac aagagagagc ccgagactga gttggaatac cgcttacagg   51660
agctatgggc tactctgctg aatatgccag cttccgccat tggccgcgat gacagcttcc   51720
tgcggattgg cggtgactca attgccgcca tccgccttgt ctccaaggcc cgtgagagcg   51780
gcatatctct cagtgttgat gacatcttca gtgatcccg cctcctagct gtcgcagcta    51840
aagctaccga ctcagcagct gaaatcgagg atattgtccc aattgagccg ttcagcctca   51900
ttaatgaggc tcaacactcc atggtcctta gcagttcctc ggacttgcac ctgtcagccg   51960
acatggaaat cgaagatgcc taccctgct caaagctcca ggagggtctg atggctttgg    52020
ctgtgaagca acctggctcg tacattgcca agtaccatta ccgcctgcct tcccacatcg   52080
acgtggcccg gttcaagcgt gcctgggaga tgactgttga cgtgtgtgcc aacatgcgga   52140
ctcgcatcat caccgttggt gggatgacga ttcagacggt catcaagaac gacattgctt   52200
gggaggatac tactggtatg actctcatgt cgtatgtacg tgccacccag aagaccgaga   52260
tgggctacgg ttctcgtctc tgccgttacg ccttggtcga agaggagggc caggatgtcc   52320
agtttgtctg gagcattcac cacgccgtct tcgacggttg gacaacgccc atcatcatga   52380
gcgctttaca cagcgcatac agaggtctgg agatgcccaa gattgagaac tacgccaggt   52440
tcatcaagta tacgatggac atcaactacc aagacgccag tgagtattgg atgagggagc   52500
ttcacgacgt gaagaaggct actttcccgt cgtctgtttc cgttgaagca tcggacaagg   52560
gcgatgtcac aaagttcatg gagaccagaa tcgacctgcc ccgaaacgac gtcggtgtca   52620
caaaggccac tattcttcgt gctgcttggg ctgtggtcct tgcacgctac tgcgataccg   52680
atgatgtttg cttcggcaca acaatttcag gtcgacaagc ccctattgcc gggctcatgg   52740
agatgcctgg tccagtcatc gcgactgtgc caatccgcgt tcgattggac cgacagaaga   52800
ccgttgacga cttccttcaa ggcgtgcaag accaagctac caagatggtc gcctacgagc   52860
aattcggcct tcaaagcatc ggcaaactga gcgctgacgc aaaggacgcg tgtgactttt   52920
catcgctcct ggttatccag cctctcccaga ctctgatcta caacgacgat gacgagcagg   52980
```

```
ctctactggc tgcttcagca gctgcggctg acaccaagga ccaggtgatg cagaattact    53040
tctcatatcc attggtcata caagcgcact tgcatgacga tcacatcagc ctggtcttga    53100
tctacaactc tatggcccct tccggaagcc caactgtttgc cctgtcgcag cagttcaagc    53160
acgtcgtgga gcagctagta ttggaacctc agcttagtct cggttctctg tctattgcct    53220
ccggctggga cgttgcacaa tctctcaaat ttaatgccga aatcccagag attgtcgact    53280
cttgtgtcca tcagctcatc gaaaggcaag ctgagatccg ccctgacgca atggcaataa    53340
gggcctggga cgccgaattg acgtatcgag aattcaaccg tgctgcaaat cgtcttgcca    53400
actatctaac ggcatcctac gacatcaagc cggatgagct gatccatgtc tgcttcgaga    53460
agtccgcttg gttctttgtg tctatcctgg ccatcaacaa gtcgggtgcc gcatgggtgc    53520
ccctcgaccc atctcaccca gagcagcgac ttcgacaagt tgtgtctcaa acgcgagcca    53580
ggatagcact tacttcacct tcgaaccgtg acctggttac cggcttggtt gactctgttg    53640
ttactgtgga ctctcagctc gatgtgcaac tgtcaaaggt tgacgagcac agccaaaagg    53700
gcccggaaac agccgtgtcg tcagacaacg ccgtttatgt tctcttcaca tctggatcaa    53760
ctggtacacc caagggcctt gttatgcagc acggctcggt gtgtacgtct cagacggcta    53820
ttgtcaagcg gctaggccta acccctgacg tccgcatgtt gcaatttgct gccttttgtat    53880
ttgacctttc tatcggagag atcattgcac cccttatcac aggcgcctgt ctgtgtatac    53940
cgtcggacca tacgaggatg aatggcctta cacagtatat cagggatacg ggcatcaatt    54000
gggcgttcct tacaccctca ttcatccgga caatcaaccc tgccgaggtt cccggcctgg    54060
aactcgtctt actagctggc gaggccgtcc cgcgggacgt cttgactacc tggtttggca    54120
aggtccgttt ggtcaatggc tgggggcctg ccgagacgtg tgtgttttca acactccacg    54180
agtggcaatc agttaacgag tcacccctta cggttggtag gcctgtcggt ggtttctgct    54240
gggttgttga tcccgaagat cctcatcgcc tagctccgac cggaacgctt ggagaagtcg    54300
tcatacaggg tccgacgttg ctacgagagt atctctctga tcctgaacga acacaggcct    54360
ctacagtgta tgaccttccc aagtgggcac ctcgccccga ctccagacac tggaacaagt    54420
tctacaagtc cggtgatttg tgctattaca accaggacgg cacaatcgaa ttttcgactc    54480
gtaaagacac tcaaatcaaa atccgtggct tacgggtaga gcttggagag gtccagcacc    54540
atatccaaca ggcactgcct tcggccaggc aggtcgccgt ggacgtgtac aggggcgaaa    54600
acggtacgaa cctggtcgcc tatctgtgct tcagcgatga caccgcacg gctggcatca    54660
gcggcggtgc atctgacggc ccattcttgc cgctcagcga agatttgcag tcgacgttgg    54720
cggccgttgt tgggcagctc agcatctcgt tgccccggta tatgattccg accatgttca    54780
tccctgcag ctacatgccc ttcatcacct caacaaagct tgaccgtaat gagctgaaga    54840
agctcacaag ctcactggac aaggcccaga tcgcccagta ctcactcctt ggcggcaaga    54900
aacgctcgcc agaaacgcca atggaagtgt tcctgcagaa gctttggtcc gagctacttg    54960
gtgtgccggt tgagtccatc ggtcgtgatg atagcttcct ggggcttggt ggtgattcca    55020
ttactgccat ccacatggtc agcgctgcca gagaatccgg cgtctcgctt gcagtcaagg    55080
aaatctttga cgatccgcgc ttatcggccg ttgcaagcaa ggctcgcgag attgagcaag    55140
atgagcagac ttcactcgtc gacgctactc ccttctatct ggtagacgaa tctatccgcc    55200
agctggccat tggcgatgaa gttcgacaac tctgtgacct gacaaacaac gaagaagtcg    55260
aagatgccta tccggtaacc atgttccagg agggcctcat ggctctgtca gcgaagcagc    55320
cgggctccta cattgccaag tatgcctata gattgtctga gcacgttgat gttgctcgct    55380
```

```
tcaaggccgc ttgggagact actgtttcat tgtgcccgac tctgcgcacc cgactcgtcc    55440
ttctgaatgg caaatgcacg caggtagtcg tcaaggggga aaccgggtgg cagtctcagg    55500
aacacacgga tgttcacgct gctattcaag acgctcagac ggctgaaatg acctacggct    55560
ctcatctttc tcaagctatc atggtcaacg atgcaagcaa cggaaacaac tacttcatct    55620
ggacagttca ccatgcggtt cacgatggct ggacggtccg tctcatcatg accactttgc    55680
agaatgccta taacaacctc gaggtacctg atctgaaacc gtattccggc ttcattcagt    55740
acctgggatc tatcaaggct gatgacacca tcaacttctg gactcagcag ctacaaggtg    55800
ccagcaaggc gtcttatccg ccatccaagc cagcatccgc acctgagtcg gtcactcgac    55860
tcatcaccaa gacaatccaa gccagctcct cggccaatgc tgccatcaca aaggccacca    55920
tcatgcgggc gacctgggct atactgttag cccgctactg cgataccgac gatgtcactt    55980
taggtacgtc catctctggc cgacaggctc cagtgtctgg cctcatggac atgcccggcc    56040
ctgtggttgc gactgttccc gtacgagtcc gtctggaccg aagtcagaca atcagcaagt    56100
acctccaggc catccagagt caggcccacg agatggtgcc atacgagcag tatggcttga    56160
caaacattgg caagatcaac tctgacttca gagatgtctg tgactttacg agcttgctgg    56220
ttgttcagcc tcgaacgcac ttggattctc gaagcaaggg cacgtctact gagtctgacg    56280
cttcgtcggc cgctctgctt ctgcctgcca atgtcgaagg cggttcggtc gaggacttga    56340
tgcaaggtta cttttcgtat cccttgtta tacaaggcca cctgatgagt gactccattg    56400
agctggtcat tacctatgac tcttccgtcc tctccgaggc atccatggaa gccatgtgtc    56460
atcagtttga gcatgtggct tcgcaactct ttgcggacga gggacgtaca ttgggcgact    56520
tgacggttgc ttcctcctgg gatctcgaac gcgcgagagc ctttaactct gaagccccaa    56580
tggtcatgga tacttgcatc catcacctca ttgaagctca agtcagaaaa actcctgatc    56640
tgccagcggt ctgggcctgg gatgggcagt tgacctaccg ccagcttaac gaagcggcca    56700
accggttagc ccactatctc atcaacgagc acaatgtcca ggttgaagat cttgtccacg    56760
tctgcttcga aaaatctgtt tggcactggg tctctgtgct tgccatcaac aaggctgggg    56820
ccgtatgggt tcctctggac ccatcacacc ctgagcagcg ccttcgccag gttgcctctc    56880
agactcagtc cacgctggct ctgacatcgg atactacgaa gagcctcctg tctcatatta    56940
ttgatcgggt ggtcgaagtc tctcctgcat tgttcgagca gattgatgtc cgactcggtg    57000
aaaaggagcc tcaggtctcg gtctcagcca gcaatgctgc gtacattctc ttcacctctg    57060
gatccacggg tacgcccaag ggtctggtca tgacacacgg tgctttgaca accagtcaga    57120
ccgccatcaa gaagcgaatg ggcaccggca ctcataccag agccctccag tttgcttcgt    57180
acgtgtttga catgtctgtc ggcgaaggct tcgtacagct tatttctggc gcctgcattt    57240
tcattccatc ggagcacacc agaatgaatg gcctgaagca gttcatcacc gaacacagaa    57300
tcaactctct gtggctgacc ccgtccttta tccggactct cagtccagag caagtgccaa    57360
cggttgactt tgtgttcttg gctggtgaag ctattccacg cgacgtgttc accacttggt    57420
gtaccaaggt ccgcttgtgg aacggttggg gccctgctga gacttgcgtc gtcagctcct    57480
tgcacgagtt tacaagcctt gatgagtcgc cattgacaat tggtcgtcct attggagggt    57540
actgctggat tgttgaccct acggaccata cgaagcttgc ccctatcggc acaatgggcg    57600
aggtcgtcat ccaaagtccc acgattctga gggaatacct tgccgacgtc gagcgcacca    57660
aggcctctac ggtatatgag ctacctgagt gggcgccata ccgagaccag gctccttggt    57720
```

```
cacgattctt caagtccggc gatctggcgt catataaccc tgacggtaca ctcgaattcg    57780
ctagccgaaa ggatacccaa gtcaagattc gcggtctgcg tgttgagctt ggagaaatcg    57840
agcatcacgt ccgcagcagc ctcacagacg ctcgtcaagt tgctgttgat gttttcagga    57900
ccgatgccgg cacaagactc attgcgtact tctgctactc tgatgtgacg cgcactgccg    57960
gcaattctca gccggataac gatgacatct tcctgcctgt gacggaagac cttcagagac    58020
agctcaccag catggtcagc cagctgcatg tcacgctgcc tcggtacatg gtgccctcgc    58080
tcttcattcc atgccgttac atgcctttca ttacgtccac caagcttgac aggaaccggt    58140
tgaagaagct tgtttccgag ctcagccaag aagaccatgc ggcgtactcg ttaagcaacg    58200
gcgtcaagcg catgcctgac actgagatgg aggcccgtat gcaggagctt tggtccgtcg    58260
tgttgcacat gcccaaggaa gagattggct gcgatgaaag cttcctgcaa atcggtggtg    58320
attctattac tgccatccag ctcgttacca acgctcgtga ggctggtatc tcaattgctg    58380
tcaaggatat ctttgacgac cctcgccttt cgaagcttgc cctggtggct gcagccaact    58440
ctgatcagag caatgcgtcc acgatagtcg aacccttcag cctcctggga gactccctta    58500
ctaaggaact ggtcacagaa gctgccaagg agcaatgcaa cctcgccggg gatgacctgc    58560
ttgatgatgc ctatccttgc acaaagctac aggaaggtct catggcccct gcaatcaagc    58620
aacccggatc ttacattgcc aagtatgtgt atcaaattcc cgaccacgtc gatgtttcca    58680
gattccgcaa ggcctgggag cgtaccgtcc agagctgtgc caaccttcgc acacgcatgg    58740
tgcttgtcaa cggcattacc gtccaagttc tgctgaagga cgacattgag tgggataaca    58800
ccgacgatac ttcgctcgag acttatgctc gctcaacgct ccacatagag atgggttttg    58860
cccagcgtct gtgtcgctat gccctcattg aagaagagac tggtaactac tttgctttca    58920
gcatccatca taccatcttt gatggttggt ctcttccgct ggtgatgggt accttgtctg    58980
cggcctacta cgatcttgag cttccttctc tgcagtcata tgcagcattc gtcaagtaca    59040
ccatggaact cgatcacggc gtcgcttccg actactggga gaagcagctc aagggtgcca    59100
aacgcgcaag tttcccggcg ccgagcgata agtcagggtc ttctcagacg cgtgtggcga    59160
acaagaccat tggcttcccc aagtcaaaga cgtccatcac aaaggcctct attctgcgcg    59220
ccgcttgggc catcgtattg gcccgctact ctgacagtga tgatgtctgc ttcggcacca    59280
cagtctctgg tcgcaatgcc aatgtggctg gtcttgaggc tatgcctggt cttgtggtcg    59340
ccaccgttcc tgttcgtatt catgttgaca agcagaagcc tctttctgga ttcctgcaag    59400
atgttcagaa gcaggccaat gacatggttg atttcgaaca atttggtatc cagaatatct    59460
ccagacttgg ctccgacgca aaggacgctt gcgacttcac ctctctcctg gctatccaac    59520
ctgtccagca tatgagtgca gacagcggca atcctgctga ccagggtgct attgtcattc    59580
ccgctgcctc gccccatgtt aatgctgagg acatgctgca gaactatttc tcttacccct    59640
tggttattca gtgccacctc atggatgacc atgtgaatct ggtcctcgtc tacgacactg    59700
atgtccttga agagacacag ctgaacgcgc tcatgcagca gttcgaccat gttgtccagc    59760
aactgagtgc ccagggtaat gagccattgg gcgacgtcag tatctcaggg ccttgggatc    59820
ttgaacaagc tctgcagctg aatagcagga acccgacttt gtccacact tgtcttcacg    59880 acatcttctc aaagcatgcg ctgagttctc ctcaccacga ggctatttac tcgtccgaag    59940
gcagccttac ctatggtgaa cttgaccacc tgaccgatat cctcgccacg catctgagct    60000
ctctaggtgc cggcccgag acagtggtgc ccttctgctt cgagaaatcg atgtgggcgg    60060
tggttgccat cctagcaatt cttaaggctg gcgccgcgtt tgtgcccctt gatccttcgc    60120
```

```
atccaaccag ccgtcgcgag gctttggtca aggaagtcag tgctcgcgtg cttgtggctt    60180
cttctagcgc tatcgcctca tgcaaaggaa tgtttgagca cgttgttgag ctgtcaccca    60240
gtgttatggc taagctggcc gcttctgtaa cgcctaggat cctgccaaag gttggaccga    60300
ggaacacggc atatgtcctg ttcacctccg gttcgacggg caagcccaag ggcgttgtta    60360
tgcagcatgg ctcattcagc tctactacta ttggatatgg caaggtgtat aacctgtcac    60420
cgttgtcgag agtgttccag ttctccaact atatctttga tggtagcttg ggcgagatct    60480
ttggtccgtt ggcctttggt ggaacaatct gcatcccag tgaggacgaa cgcctcggta    60540
gtgcccctgc cttcatgagc acgtcaaagg tcaacacagc catgttgacc ccgtcctttg    60600
tgcgaacctt tacgcctgac caggtgccgc atctgacgac ccttgttctt ggcggcgaag    60660
ctgcttccaa gagcaccttg gagatgtggg ttaaccgcgt cactttgtac aacgcgatacg   60720 gaccagctga agcttgcaac tacgcgacta cacacgtctt caagtcaagt tccgagtctc    60780
ctcgtatcat cggatccgga ttcaacggtg cttgttgggt cgttgaacct gataaccaca    60840
acatccttgc ccctataggt tgcacaggag agctggttct gcaaggccac gctctggctc    60900
gcggctatct caatgacaag gcgaagacag agcaatcgtt tgttagcgac attagttctc    60960
ttccatcatc ttcgctgcat gagcctaagc gattctacct cacaggagac ttggtccgct    61020
acaattcaaa cggtaagctc gaatacctgg gacgaaagga ctctcaggtc aaattgcgtg    61080
gtcagcgtct agaactgggt gaaatcgaat acaacatcac tcagtcactc aagagcgtgc    61140
gagacgtcgc tgttgatgtc attcacaaag acaccggtga cttgctagtc gcgttcattt    61200
cgttctctgg caacgcggac gctcagtggg attcggataa cctgcttctg aacctccttg    61260
ctgctgatga gtccatgaga tccctgcttg atggtttgag agagggcttg aaggcctctc    61320
taccaggcta catggtacca agcatcattc tccctcttcg atgcatgcct ttcatcacat    61380
caatgaagct cgacaagaag ccgcttcttt cgcttgccca cagcctctct atcgagtaca    61440
ttgctgccta ctcggcatcc aagagagaaa aggtcgagcc cgcgtctgac ctcgagttca    61500
agctccgtga tctgtgggcg caagtcctca agctagagcc tggcgaaata ggacgcaacg    61560
atgccttcct ggaaattggc ggtgactcga tctctgctat ccacctggtg actgctgcac    61620
agcaagccgg aattagcatt accgttgcaa acatctttgc cgattctcga ctttcatctc    61680
tagcagcttc ggcaaaggtc ggatacgtcg ccaagagctt cgacgtgaag cccttcagca    61740
tgctacccgg tatcagcatc gaagaactga ccagtctggc caagctaaa tgcaatttgc    61800 caaactacct tgcccttgag gatgcttacc cttgcacaag tcttcaggag ggtttgatgg    61860
caattgcaat caagcaacct ggatcctaca tcgccaagca cgtctatcag ttgcccctc    61920 atgtcgatgt tggtcgcttc aagacctcct gggagcgtac tgtcgaggct tgcagcaacc    61980
tgcgtacccg gatcattctt gttgacaaga acatgttca agtcgttgtc aaggatgaca    62040
tctcctggga ctctggcctg gccacggcc tggagtctta catccgcgct tctcaaagcc    62100
ttgatatgaa gtatggatcg cgactttgcc gatatgctct gatccaagat gaggagaccg    62160
gcgacaactt cttctccctc agcgtgcacc acacaatctt tgatggttgg agcttgcctc    62220
ttatcctcgg tacactgaat gctttctacc gcgatactga ggtcccagcc ctgcagcctt    62280
actctggctt tgtcaagtac acccttgacc ttgacgagac ggctgctgtc aactattgga    62340
ccacgcagct gtctggagct aagaaggctg ccttcccgcc cactacggac gtcatcggcc    62400
ccgactctgt caagcctgct tctcagttcc tgaacaaggt cattgagttc ccgcgaacga    62460
```

```
cgaactcatc catcaccaag gcgaccatcc ttcgaacggc atgggccatt gtccttgccc    62520
gctactccga ttcagacgac atctgcttcg gcacaactgt gtctggccgt cacgcgtccg    62580
tccctggtct tgaggctact acaggcttgg tcgttgctac tgtgcctgtc cgcgtccgcc    62640
ttgacacaca gcaatcggta gccaaactcc tccgcgatgt gcagattcaa gcctcggaaa    62700
tggtcgagta cgaacaatat ggcctccaga atatctccaa gattggtgcc gagttcaagg    62760
acgccgttga tttcagcagc ttgctggctg ttcagcctat ccagcacatt ggatcaacgg    62820
gtgaaagctc cgaggaggcc ctcctggtcg ctgctgattc cgaacttctt cgtgccgaag    62880
aggcgctgca gaattacttc aactaccctc tggtcgtcca gtgtcacgta tacgatgaca    62940
tggtcaacct gatgttcatc tatgacccca gcgtcttgtc tgagcaccaa ctccaggcca    63000
tctcacagca ctacgatcac gttgtgcagc agctgctgac gcagagcgaa gaaactctca    63060
gtagcctgtc ccttgcaggc ccttgggacc ttcagcaagt cctcgggtgg aatgccagtg    63120
ctccggaact tatcgaggcc tgtgtccacg acttgatttc cgacaatgcc cagcgcgatc    63180
ccaaccatga agcgatcttt tcgtctgagg gtagcatgac ctatgctgct cttgaccggt    63240
taaccgacgt cctagcaagc catctttgcc agctgggcgt tggtccagag acgattgttc    63300
ccttctgctt cgaaaagtcc atgtgggctg tcgtcgctat tgtcggtatc ctcaaggcgg    63360
gaggtgtctt cgttcccctg gacccttcgc atccgatcaa ccgccgtgaa gccctcgtca    63420
aggaagttgg cgcccaaatc atcattgcat ccgagtcggc cgctgcctcg tgtgctggca    63480
tggctcctcg cattgtccag ctttcgtccg acttcatggc tcgcttatct gccccaagcc    63540
aaaccctcgt cgagcccaga cgccccagcc catcaaatgc agcctatgtg ctgttcactt    63600
ctggctcaac gggcaagcct aaaggtgtgg tcatggaaca ctctgctctg acaacaagca    63660
caatcggtta cggccgcgtc tacgagctca gccctgcatc ccgcgtgttc caattctcca    63720
actacatctt tgacggcagc ttgggtgaga ttctcgcaac actgacctt ggcggtactg    63780 tctgtattcc agacgaagtc gaacgtctgc aggatgctcc aggctttgta cgcaaggccc    63840
agatcaacac tgccatgttg acgccctcgt ttgtccgcac gtttacgcct gaccaggttc    63900
ccagcctcaa gacattggta cttggtggtg agctgctgg tagggacatt cttgatgctt    63960
ggtgcgattg tgtgaagctc atcaatggtt acggacctgc cgaggcttgc aactacgcaa    64020
cgtggcatcc atttcatcg agcagagact cgccgcgtgt catcggaaag gcattcaaca    64080
gttcttgctg ggttgtcgaa ccgaacaacc atcacgcact cactcccgtc ggttgtgttg    64140
gtgaactcgc catccagggc catgtgcttg cccgtgggta catcaatgat ttagagagaa    64200
ccagaagctc ctttgtcacc gagattgctt ccttgtcgtc agtcatcgct ggtcctcagc    64260
gcttctacct gactggtgat ttggtgagat actgcagcga cggctctctc gagtatcttg    64320
gccgtaagga cactcaagtc aagcttcgtg gccaacgtat cgagctcggc gaagttgaat    64380
atcatgtcca gcgagctctt ccagatatcg agcatgcggc tgtggacatc atcactagag    64440
aagctggaca agcccttgtt gcctttgtgt cgtttgcggg cacttacgac gacaatgaga    64500
ctaccagctt ctctgataac ctgatcaagc caagtgacag tcttcgtgct gccatcgtct    64560
cccttctcga caacctcaag gctgtgctcc ccgctttcat gatgcccagt cttgtcttgc    64620
cggtccgaaa catgcccttc atcacatcga tgaagctcga caggaaacaa ctgcgaactc    64680
tcgcaagctc tctgtctcct gaggagctcg ccactttgc tcccagcaag gcagacaagg    64740
ttgagccgac cactgacatg gaactcaagc tgcgcgacct ttgggcccag atccttggga    64800
tcccggcgga agagattggc aagaacgata gcttcctaca aatcggaggt gactccatct    64860
```

```
cagccatcca cttggtgact ctggctcaag aaacgggcat ctcactcacc gtggccacca    64920
tctttgccga cccgagactg tcctcagttg ctgcatcggc ccatctcggc ggtatcagtg    64980
atgcctacga ggctgagccc ttcagtctga tccagcattc tgagagcgat gccatcactc    65040
gtgagattga gcagcagtgc aaactctctg ctggccagtc gatcgaggat gcttacccaa    65100
caaccaagct gcaggaaggt ctcatggcct tgtccgtcaa gcagcccggc tcttacacag    65160
ctcgctacgt gtaccgcctt cctgatcacg tcgatgttga gcgattcaag gcggcttggg    65220
acaagacagt tgaggtttgc cacaaccttc gaacatccat tgttcttgtt ggctacaccg    65280
ctatccaagc cgtcatcaag gacacttcaa ggtcgctgtg ggagcctgcc acgggcgttt    65340
cgctgcagtc ctacatgaag aaggcgattg gatccttcaa catgggctat ggctctcgtc    65400
tctgccgcta tgctctgatt gaagatggcg gcagcactta tttcgcctgg cacattcacc    65460
actcggtgta tgacggttgg acgcacccgc tcatcatggg ctcgctctac gccgcttact    65520
ttggcaccga aatgcctcct ctacggcctt tcgcccgctt cgtaaaatac acgacgagca    65580
tcgaccaaca cgaggccgca gagtactgga gacgccaact tcacgacgcc aggccggctt    65640
cgttccctgc cgttgaccag cagttgactg cttcgaagag caaggctgat gtgacccgaa    65700
tcttgagaaa ggctgtcgac ttccctcgcc tgaccaactc atccatcacc aaggccacaa    65760
tcatgagggc agcttggtct attgtcttgg ctcaatactg cggtgttgac gacgtgtgct    65820
tcgggactac actctcgggc cgtcacgcac cagttccagg attggattct atgcctggtc    65880
ctatgcttgc taccgttcct gtccgaatcc gtttggctca agatcagcca gcatcgcggt    65940
tcctgcaaga cgtccagatt caggccgcag agatggttgc ctatgagcag tttggcctcc    66000
agaatatcgc agctctaagc cctgacgcca aacaagcatg cgacttttcg agcttgctgg    66060
tcatccaacc tgcccaacag cagatttccg acgacaaggc cgtgtctgaa acggacatga    66120
tcctattgcc cggcgactct gaaaactctg ctgaagaatc gatgcagaac tttgccaatt    66180
atcccttggt ccttcaaatt gccatcatgg acagccatgt cgagctgctg ctgatttacg    66240
acaccaatgc tctgaccgaa ttccaggcta cagccatttc tgagcagttt ggcaacgttg    66300
caagacaact cgttgcccaa gatgagactt tgattggtga tgtcaaggta gctggttcat    66360
gggacctgca gaagcagctg gaatggaacc acgaaatcta tggtccttca gaaaccactc    66420
tgcacgatct cttctcgaag caagttgctc gcagacctgc tcaccaagct tgtacagca    66480 gcgaaggaag catgacatac agcaagctgg atcgactgac aactcagctt gcagtctacc    66540
tcagcagtct tggtgttcga cccgaaacca tcgtgccttt ctgcttcgac aagtccatct    66600
gggccattgt cgcgatgatt ggtattctca aggccggtgg tgttttcatg cccttggacc    66660
cgtcctaccc agcaagccgc cgccaggcct tgatagacga ggtcaacgcc cagttcatga    66720
ttgtgtcacc cacaaccgcc cctgactctc aaggcatggt tcaaaacatg attgagctct    66780
cgccatctct gattgccttc ttctctacaa tcgacaccgg cgaccaatcg tttatcaagt    66840
caggtcccaa caatgccgcc tatgtcttgt ttacatcagg ttcaactggc aagccaaagg    66900
gcgtcgtcat tgaccacaag gccatttccg cagccctcct ccgacaacgc gaggcctttt    66960
cattcaacga cgacacaagg acgctgcaat tcgccaactt cgtcttcgac gcttgtatcg    67020
ccgagatctt ctccgcgctg gtggccggtg ctaccgtttg cgtgcccaca gagcacgaac    67080
gtgttcacaa cactgcagct ttcatccgtg aggctcgcat caaccacgcc ttcctgactc    67140 cgaccttat caagactctc tctccggagc agattcccgg tatgaagact gtcattctta    67200
```

```
tgggtgaagc gccctctcaa gaaatcatcg acacctgggc cgacgagatc gaccttcaca    67260
acggctatgg cccagcagag ggctgcgttg gttcgaccaa caacacgtat tcgtcgtcga    67320
tcaaggtatc agtcaccaac gtgggtcgta gctttaccca cggactctgg attgtcgacc    67380
ctgataacca caaccgcctc atgcccatcg gctgcgttgg tgagttgctg ctccagggtt    67440
cgtctctggc acgcggctac atcaacgacg aggaaaagtc aagacagtct ttcatcgatc    67500
aagtcgagtg gctaccagcg aatgtcaatg ttggtgaacg ccgcttctac aagactggtg    67560
acttggttcg ctacactcca gatggatcga tcgagtacgt cagccgaaag gacacgcaag    67620
tcaagatccg cggccagcgt atcgagcttg gcgagatcga ataccacgtc aaacgctcca    67680
acgcttctat tgagcacgtt gttgtcgaca ttactcgaca ggccggccgc gagtctcttc    67740
tcgcctttgt gtgcttcagc tcgcatcaag gacggagag tgcttccaag gagactcgcc    67800
tcacggagct caccagcgaa ctccgcgaga cgctgtctga cattgctaca actatcgcat    67860
cgacgctccc tagccacatg gtgcccaagt atctcatccc tgtcgaccac atgcctcaca    67920
acgctgccgg caagttagac cgaaagatgc ttctcgcatc cattgccaac cttacgccgg    67980
atgatctttc gaaataccct gctggccagc gtctgccctt ccgtgactgc tctaccgacg    68040
tcgagttctg gctccgtaac cagtgggcgt ctacgcttga tcttcctgca gagaccatcg    68100
gaatggatga caacttctac agtctgggcg gtgattctat ccgcattgtc accatttcca    68160
aggctatcct tagccagtat gatgtctcac tcggcatgtc ccttctcaac tcgaagcata    68220
ccacgattgc aaacatggcc aagcacatcg acagcgaacg cagtgggcaa gacggcgcag    68280
aacttggagt cgtcgatatc aacggcgaga tctcatctct ctcacgctcg atcctggctt    68340
ctggtgatct taacgtcgtt tcccactcta agactgagct gcctgagcag gccaccgtct    68400
ttttgactgg tgccactggc ttcctcggtc aagaactcct cagacaactt ctctgcaacg    68460
actccattgc ctccatcatc gccctggtac gatccaagtc tgccaaccac ggaatggacc    68520
gtctccgcga cactgcgaag attgcaggct ggtggcgcga agagtacaca agcaagattg    68580
agatttggtg tggtgatctg agcaagaagc gcatgggcct gagcagttcg caatgggctc    68640
gcctggccgg ccagtccagc aacaacaacg tcgatgccat catccacaac ggtgccatcg    68700
tcaactggaa cgccgactac gacaagatgc gtgccgccaa cgttgattcc acggtggatc    68760
tcctcaaggc taccgtcacc tcgcccgctt cccccaagtt cgtcttcgtc tccggcggca    68820
tcaagtctga tcccaccacc gaccgcacag ctctgggcca gtatctcaac aactcgactg    68880
gctacatcca gaccaagttc gtctccgagg gcatcatcca ggaggtcatc aagaccctcc    68940
cggctgacca gaaccgcatt tccactctca gcccggccg catcatcgga tctcctgaaa    69000
ctggtgtggc caacgtggac gatgtgctgt ggcgaattgt ttccgccgcc gcttctcttg    69060
gagtctatcc tgccgagccc gaggaccatt gggtctacat ctccgacgtt gacactgtgg    69120
catcatccgt gctcagccaa ctttacagca agcagggcat cgctccctac gtcagtgcca    69180
cgggcggcat gccggcaaca gtcttctggg atctcatcaa caaggagctg gacgtcccct    69240
gcgagcctct ttctcaagat gaatggactc accgtgcgtt ggagtcgatg aatcaagtcg    69300
gcgacaagca tcctctgtgg cctgtgcagc acttccttgg caaccttggc actcctcgat    69360
ctgctcaaga cattgagatc gaaggcagtg agcacaagca gtggcacatg gctgtaaaga    69420
tgagcatgcg ctaccttatg aaggtcggct tcattcagac gtccactgat ggctttgctc    69480
agcctcgtcg ggcggacact ttccagcgcc atggctga                           69518
```

<210> SEQ ID NO 4
<211> LENGTH: 20873
<212> TYPE: PRT
<213> ORGANISM: Trichoderma reesei

<400> SEQUENCE: 4

```
Met Ala Pro Asn Thr Thr Tyr Glu Asp Gly Asn Lys Ser Leu Ile Pro
1               5                   10                  15

Ile Ala Ile Cys Gly Val Gly Ile Arg Leu Pro Gly Gly Ile Arg Asn
            20                  25                  30

Ala Glu Gln Leu Trp Glu Ser Leu Val Asn Asp Arg Val Gln Pro Arg
        35                  40                  45

Val Asp Gly Asn Glu Glu Glu Leu Asp Ala Val Asp Ala Ser Phe
    50                  55                  60

Phe Ser Leu Thr Glu Ala Glu Leu Glu Ser Cys Ser Pro Leu Gln Arg
65                  70                  75                  80

Lys Leu Leu Glu Val Thr Arg Glu Cys Phe Glu Asp Ala Cys Glu Ile
                85                  90                  95

Asp Phe Arg Gly Glu Asp Ala Arg Val Gly Cys Tyr Ala Gly Ser Ile
            100                 105                 110

Gly Glu Asp Asp Val Ser Met Val Ser Leu Lys His Asp Leu Gly Gly
        115                 120                 125

Pro Ser Met Ala Ile Arg Glu Ser Thr Ser Ser Phe Leu Val Ala Leu
130                 135                 140

His Glu Ala Cys Ser Ala Val Arg Ser Gly Ser Ala Lys Ser Ala Val
145                 150                 155                 160

Val Leu Gly Ala Ala Gln Asn Gly Ala Val Gly Glu Ala Val Ser
                165                 170                 175

Ala Val Tyr Ile Lys Thr Leu Pro Asp Ala Met Arg Arg Gly Asn Pro
            180                 185                 190

Ile Arg Ala Ile Ile Arg Ala Ser Ser Ile Met Thr Leu Ser Gly Arg
        195                 200                 205

Ile Glu Gly Ala Ser Gly Leu Thr Ser Leu Val Lys Ala Val Val Thr
    210                 215                 220

Leu Glu Asn Arg Thr Ile Ser Pro Asn Ile Val Ser Gly Lys Phe His
225                 230                 235                 240

Ala Ala Gln Val Arg Arg Lys Val Arg Pro Lys Ser Leu Thr Ala Ser
                245                 250                 255

Ile Ile Ala Ser Asp Ala Glu Gly His Ser Ala His Val Ile Val Asp
            260                 265                 270

Ser His Pro Arg Pro Thr Pro Arg Val Ser Glu Ser Arg Pro Gln Leu
        275                 280                 285

Val Leu Phe Ser Ala Asn Asn Pro Ala Ser Leu Ala Lys Gln Ile Glu
    290                 295                 300

Leu His Arg Leu Tyr Ala Glu Ser His Pro Asp Asp Ala Ala Asp Ile
305                 310                 315                 320

Ala Tyr Thr Arg Ala Leu Arg Arg Glu Ala Leu Asp Tyr Lys Ala Phe
                325                 330                 335

Ser Ile Leu Ser Asn Ser Ser Phe Val Asn Thr Ser Asn Tyr Ala Lys
            340                 345                 350

Ser Ser Ala Arg Ala Pro Ala Ile Thr Met Val Phe Asn Gly Gln Gly
        355                 360                 365

Ala Gln Trp Ala Gly Met Gly Lys Glu Leu Ile Leu Thr Asp Ser Ser
    370                 375                 380
```

```
Phe Arg Glu Asp Ile Arg Lys Met Asp Leu Val Leu Lys Gly Leu Asn
385                 390                 395                 400

Ile Pro Ala Thr Trp Ser Ile Glu Glu Leu Leu Arg Asp Ala Ala
            405                 410                 415

Asp Pro Asp Asn Arg Ile Asn Thr Ser Lys Phe Ser Tyr Pro Leu Ser
            420                 425                 430

Thr Ala Leu Gln Ile Ala Leu Val Asn Cys Phe Lys Arg Leu Gly Val
            435                 440                 445

Thr Pro Lys Ala Val Val Gly His Ser Ser Gly Glu Ile Ala Ala Ala
            450                 455                 460

Tyr Ala Ala Gly Phe Leu Ser Phe Glu Asp Ala Ile Thr Val Ala Tyr
465                 470                 475                 480

Tyr Tyr Gly His Ile Thr Thr Arg Asp Gln Lys Asp Gly Ala Met Gly
                485                 490                 495

Val Val Ser Leu Gly Ala Glu Glu Thr Glu Gly Phe Leu Glu Gln Gly
            500                 505                 510

Val Val Ile Ala Cys Glu Asn Ser Pro Thr Ser Thr Ile Ser Gly
            515                 520                 525         Gly

Asp Arg Glu Ala Val Glu Arg Val Leu Lys Phe Val Lys Ala Ala Lys
            530                 535                 540

Pro Glu Val Thr Ala Arg Leu Leu Lys Val Asp Thr Ala Tyr His Ser
545                 550                 555                 560

Glu His Met Thr Gln Leu Ala Asp Glu Leu Leu Asp Leu Leu Thr Ala
                565                 570                 575

Glu Lys Ile Ala Ser His Ala Thr Arg Lys Ser Glu Ala Ile Phe Ile
            580                 585                 590

Ser Thr Val Ser Glu Lys Val Leu Lys Glu Lys Ser Glu Phe Gly Ala
            595                 600                 605

Ala Tyr Trp Val Ser Asn Leu Val Ser Pro Val Arg Phe Ser Ser Ser
            610                 615                 620

Val Ser Asn Leu Leu Gly Met Ser Ser Glu Thr Leu Phe Leu Glu
625                 630                 635                 640

Val Gly Pro His Ser Ala Leu Ser Val Pro Leu Ser Gln Ile Cys Ala
            645                 650                 655

Ala Ala Asp Val Arg Cys Asn Tyr Val Ser Ser Gln Thr Arg Gly Ala
            660                 665                 670

Asp Ser Ala Val Ser Phe Leu Ser Ala Val Gly Arg Leu Trp Gln Glu
            675                 680                 685

Ser Ala Val Pro Asn Leu Ala Pro Leu Phe Ser His Gly Arg Ala Ile
            690                 695                 700

Ser Gly Leu Pro Gln Tyr Pro Trp Ser Tyr Gly Thr Ser Asp Glu Asp
705                 710                 715                 720

Ser Asp Ala Thr Ala Leu Ser Ala Arg Glu Lys Arg Ala Arg Val Phe
            725                 730                 735

Ala Glu Asp Ser Ser Leu Glu Ser Glu Leu Ala Asp Glu Glu Ala Pro
            740                 745                 750

Thr Thr Glu Val Glu Ile Val Leu Arg Ala Val Trp Val Glu Ile Leu
            755                 760                 765

Arg Asp Val Asn Arg Ile Arg Lys Gln Asp Ile Gly Lys Lys His Asn
            770                 775                 780

Phe Phe Leu Leu Gly Gly Asp Ser Leu Thr Thr Ile Glu Leu Val Thr
785                 790                 795                 800

Ala Ala Tyr Gln Tyr Gly Ile Arg Leu Ser Pro Ala Ala Val Ser Asp
```

```
            805                 810                 815
Asn Ala Glu Leu Ala Gln Met Ala Ala Val Ala Thr Ile Glu His Asp
        820                 825                 830

Ser Ala Met Met Ala Glu Thr Lys Pro Phe Ser Leu Ile Ser Ser Glu
        835                 840                 845

Lys Val Asp Asp Ile Lys His Gln Ile Arg Lys Glu Cys Lys Leu Ala
        850                 855                 860

Pro Thr Glu Thr Ile Glu Asp Ile Tyr Pro Cys Thr Thr Leu Gln Glu
865                 870                 875                 880

Gly Phe Met Ala Leu Gly Met Lys Gln Pro Gly Ser Tyr Ile His Arg
                885                 890                 895

Val Val Tyr Lys Leu Met Pro Glu Ile Asp Val Asp Gln Phe Lys Ala
        900                 905                 910

Ser Trp Glu Ala Thr Ile Ser Gln Cys Gly Ser Leu Arg Ser Arg Val
        915                 920                 925

Ala Leu Leu Gly Gly Arg Ala Leu Gln Ala Val Met Thr Glu Asp Ile
        930                 935                 940

Ala Trp Glu Gln Pro Ala Pro Gly Leu Asp Ile Asn Ala Tyr Leu Asn
945                 950                 955                 960

Arg Thr Arg Ser Ile Ser Met Ser Tyr Gly Glu Arg Leu Ser Arg His
                965                 970                 975

Ala Leu Val Arg Asp Ser Asn Gly Gly Val Tyr Phe Val Trp Leu Ile
        980                 985                 990

His His Ala Val Phe Asp Gly Leu Thr Met Arg Ile Val Leu Asp Ala
        995                 1000                1005

Leu Tyr Asn Ala Tyr His Gly Asn Asp Ala Lys Ala Leu Arg Pro
    1010                1015                1020

Tyr Ser Asn Phe Ile Arg Tyr Val Glu Ser Ile Asp Ser Ala Ala
    1025                1030                1035

Ser Thr Glu Tyr Trp Gln Lys Gln Leu Asp Gly Ala Gln Arg Ala
    1040                1045                1050

His Phe Pro Pro Ala Arg Leu Ser Ala Thr Ser Glu Asp Arg Val
    1055                1060                1065

Met Lys Arg Thr Met Pro Phe His Asn Ala Lys Thr Ser Ser Val
    1070                1075                1080

Thr Thr Ala Thr Ile Leu Arg Ala Ala Trp Ala Leu Leu Leu Ala
    1085                1090                1095

Arg Tyr Cys Asp Ser Asp Asp Val Cys Phe Gly Thr Thr Leu Ser
    1100                1105                1110

Gly Arg Gln Ala Ala Val Pro Gly Leu Asn Glu Ile Pro Gly Pro
    1115                1120                1125

Met Ile Ala Thr Val Pro Ile Arg Val Lys Ile Asp Arg Gly Met
    1130                1135                1140

Thr Val Ser Ser Phe Leu Glu Lys Ile Gln Thr Gln Ala Ala Asp
    1145                1150                1155

Met Val Ala His Glu Gln Tyr Gly Leu Gln Asn Ile Ser Lys Leu
    1160                1165                1170

Ser Gln Asp Ala Glu Glu Ala Cys Asp Phe Ser Asn Leu Ile Val
    1175                1180                1185

Ile Gln Pro Asn Asn His Leu Thr Ser Met Ala Asp Thr Ala Ser
    1190                1195                1200

Asp Ala Ile Leu Gln Gln Gly Ser Arg Glu Lys Ala Leu Ser Glu
    1205                1210                1215
```

```
Glu Ala Met Arg Asn Tyr Phe Asn Tyr Pro Leu Val Leu Gln Pro
1220            1225            1230

Arg Ile Gly Glu Asp Ser Ile Glu Leu Asp Leu Thr Tyr Tyr Ala
1235            1240            1245

Asp Ala Ile Thr Glu Gly Gln Leu Glu Ala Leu Cys Val His Tyr
1250            1255            1260

Glu His Ile Val Gln Gln Leu Leu Ala Pro Thr Asp Met Pro Leu
1265            1270            1275

Ser Asp Leu Ser Val Ser Gly Ser Trp Asp Leu Glu Glu Ala Ile
1280            1285            1290

Lys Ala Asn Asp Glu Thr Pro Glu Ile Val Asp Met Cys Leu His
1295            1300            1305

Gln Leu Ile Glu Arg Gln Ser Lys Ala Asn Pro Asp Ala Pro Ala
1310            1315            1320

Ile His Ala Trp Asp Met Glu Leu Ser Tyr Ser Gln Leu Asp Arg
1325            1330            1335

Ala Ala Asn Arg Leu Ala His His Leu Val Lys Ser Cys Gly Val
1340            1345            1350

Lys Asp Gln Asp Phe Val His Val Cys Phe Glu Lys Ser Ala Trp
1355            1360            1365

Phe Phe Val Ser Val Ile Ala Val Asn Lys Ala Gly Ala Thr Trp
1370            1375            1380

Val Pro Leu Asp Pro Ser His Pro Leu Gln Arg Gln Gln Gln Val
1385            1390            1395

Val Ser Gln Thr Lys Ala Thr Leu Ala Leu Ala Ser Pro Ser Asn
1400            1405            1410

Val Glu Met Cys Ser Glu Leu Val Asn Thr Val Val Glu Val Ser
1415            1420            1425

Ser Ala Leu Asp Glu Lys Leu Ser Lys Thr Glu Glu Ser Ser Tyr
1430            1435            1440

Gly Pro Val Arg Asn Val Ser Pro Asp Asn Ala Ala Tyr Val Leu
1445            1450            1455

Phe Thr Ser Gly Ser Thr Gly Thr Pro Lys Gly Leu Val Met Gln
1460            1465            1470

His Arg Ala Val Cys Thr Ser Gln Thr Ala Ile Thr Lys Arg Leu
1475            1480            1485

Glu Met Thr Ser Ser Val Arg Met Leu Gln Phe Ala Ser Phe Val
1490            1495            1500

Phe Asp Leu Ser Ile Gly Glu Ile Val Gly Pro Trp Val Val Gly
1505            1510            1515

Gly Cys Leu Cys Val Pro Ser Glu Glu Thr Arg Met Asn Asn Leu
1520            1525            1530

Val Asp Phe Ile Asn Thr Met Gln Val Asn Trp Ala Tyr Leu Thr
1535            1540            1545

Pro Ser Phe Thr Arg Thr Leu Asn Pro Asp Val Pro Gly Leu
1550            1555            1560

Asp Leu Leu Leu Phe Ala Gly Glu Ala Val Gly Arg Asp Val Phe
1565            1570            1575

Glu Ala Trp Phe Gly Lys Val Arg Leu Ile Asn Gly Trp Gly Pro
1580            1585            1590

Ala Glu Thr Cys Val Phe Ser Thr Leu His Glu Trp Lys Ser Phe
1595            1600            1605
```

```
Glu Glu Ser Pro Leu Thr Val Gly Lys Pro Val Gly Gly Tyr Cys
1610                1615                1620

Trp Ile Val Asp Pro His Asp Pro Gln Arg Leu Ala Pro Val Gly
    1625                1630                1635

Thr Leu Gly Glu Val Val Ile Gln Gly Pro Thr Val Leu Arg Glu
1640                1645                1650

Tyr Leu Ala Asp Thr Thr Lys Thr Glu Ala Ser Leu Val Arg Ser
    1655                1660                1665

Leu Pro Glu Trp Val Pro Asn Arg Thr Ala His Trp Asp Arg
    1670                1675                1680

Phe Tyr Lys Ser Gly Asp Leu Cys Arg Tyr Asn Ala Asp Gly Thr
    1685                1690                1695

Ile Glu Phe Gly Ser Arg Lys Asp Ser Gln Val Lys Ile Arg Gly
    1700                1705                1710

Leu Arg Val Glu Leu Gly Glu Ile Glu His His Ile Arg Glu Ser
    1715                1720                1725

Leu Glu Gly Val Lys Gln Val Ala Val Asp Val Ala Lys Gly Asp
    1730                1735                1740

Gly Gly Ala Ile Ile Val Ser Tyr Phe Ser Phe Thr Asp Glu Thr
1745                1750                1755

Arg Thr Ala Gly Lys Asn Ser Glu Thr Ser Val Arg Asp Val Phe
1760                1765                1770

Val Pro Met Thr Pro Glu Leu Gln Ser Gln Leu Thr Ala Leu Val
    1775                1780                1785

Gly Gln Leu Ser Val Thr Leu Pro Arg Tyr Met Ile Pro Thr Leu
    1790                1795                1800

Phe Ile Pro Cys His Tyr Met Pro Phe Ile Thr Ser Thr Lys Leu
    1805                1810                1815

Asp Met Lys Leu Leu Arg Leu Ala Met Ser Asn Leu Gly Lys Asp
    1820                1825                1830

Asp Ile Ala Arg Tyr Ser Leu Val Asp Ser Lys Lys Arg Ala Pro
    1835                1840                1845

Glu Thr Glu Met Glu Thr Arg Ile Gln Ala Ile Trp Ala Asp Leu
    1850                1855                1860

Leu Lys Leu Ser Pro Glu Phe Ile Gly Arg Asp Ser Phe Leu
    1865                1870                1875

Arg Met Gly Gly Asp Ser Ile Ala Ala Ile Tyr Phe Val Ser Ala
    1880                1885                1890

Ala Arg Asp Ala Gly Ile Ser Ile Ala Val Lys Asp Val Phe Asp
    1895                1900                1905

Asp Pro Arg Leu Phe Gln Val Ala Ser Lys Ala Thr Leu Leu Ser
    1910                1915                1920

Asn Ala Gly Arg Ser Ser Gln Thr Glu Pro Phe Thr Leu Leu Pro
    1925                1930                1935

Glu Ser Leu Ser Lys Leu Met Gln Ser Asp Ala Ile Arg Ser Arg
    1940                1945                1950

Tyr Gly Leu Gly Gln Arg Gln Thr Ile Glu Asp Ala Tyr Pro Cys
    1955                1960                1965

Thr Pro Leu Gln Glu Gly Leu Met Ala Leu Thr Ala Lys Gln Arg
    1970                1975                1980

Gly Ser Tyr Val Ser Gln Trp Phe Tyr Arg Met Pro Arg His Ile
    1985                1990                1995

Asp Thr Ala Lys Phe Lys Ala Ala Trp Asn Glu Ala Val Glu Arg
```

```
                    2000                2005                2010
Asn Ala Thr Leu Arg Thr Arg Ile Met Leu Glu Glu Gly Ser Ala
                2015                2020                2025

Val Gln Ala Val Ile Ser Asn Asp Gly Asp Trp Glu Asp Thr Glu
            2030                2035                2040

Gly Leu Asn Leu Glu Ser Phe Lys Asp Val Ile Ser Gln Leu Asp
            2045                2050                2055

Ile Gly Tyr Gly Thr Arg Leu Thr Arg Phe Ala Leu Val Glu Asp
            2060                2065                2070

His Asp Asp Thr Tyr Phe Val Trp Ile Ile His Ala Ile Asn
            2075                2080                2085

Asp Gly Trp Ser Met Arg Ile Val Leu Asp Ser Val Tyr Asn Ser
            2090                2095                2100

Tyr Tyr Gly Gln Lys Val Ala Ser Leu Thr Pro Tyr Ser Asn Phe
            2105                2110                2115

Ile Asn Tyr Leu Ser Asn Ile Asp Gly Glu Ala Ala Ala Asn Phe
            2120                2125                2130

Trp Arg Ser Asn Leu Ala Gly Ala Gln Arg Pro Ile Tyr Pro Ala
            2135                2140                2145

Ala Gly Ser Tyr Ser Thr Ala Asp Ser Ser Gly Asp Ser Thr Arg
            2150                2155                2160

Val Val Asp Arg Leu Val Ser Phe Ser Ser His Glu Asp Ala Ser
            2165                2170                2175

Ile Thr Met Ala Thr Ile Ile Arg Ala Ala Trp Ala Ile Val Leu
            2180                2185                2190

Gly Lys His Cys Asp Ala Ser Asp Val Cys Tyr Gly Ala Thr Val
            2195                2200                2205

Ser Gly Arg Gln Ala Asp Met Asp Gly Leu Leu Ser Thr Pro Gly
            2210                2215                2220

Ala Val Ile Ala Thr Val Pro Ile Arg Val Pro Leu Glu Ala Asp
            2225                2230                2235

Gln Pro Val Ser Gln Met Leu Gln Asp Leu Gln Gly His Gly Leu
            2240                2245                2250

Asp Met Val Pro Tyr Glu Gln Tyr Gly Leu Pro Asn Ile Ala Lys
            2255                2260                2265

Leu Ser Pro Glu Ala Arg Glu Ala Cys Asp Phe Thr Ser Leu Leu
            2270                2275                2280

Val Ile Gln Pro Lys Glu Gln Glu Ser Ser Ile Phe Asn Ser Lys
            2285                2290                2295

Asn Gly Leu Leu Gln Ser Asp Ala Glu Glu Asp His Leu Leu Ile
            2300                2305                2310

Glu Ser Met Asp Lys Tyr Phe Asn Tyr Pro Leu Val Met Leu Ser
            2315                2320                2325

Tyr Met Thr Glu Asp Ser Val Asn Gln Arg Phe Ile Tyr Lys Pro
            2330                2335                2340

Asp Met Leu Ser Glu Ala Glu Val Glu Ala Leu Ser Tyr Gln Phe
            2345                2350                2355

Glu Tyr Val Val Gln Gln Leu Leu Ser Pro Asp Gln Lys Leu Ile
            2360                2365                2370

Ser Asp Ile Ser Leu Val Gly Glu Pro Thr Ser Leu Gln Ala Asn
            2375                2380                2385

Asn Glu Val Pro Glu Ile Val Asp Ser Cys Ile His Glu Leu Val
            2390                2395                2400
```

-continued

```
Glu Lys Gln Ala Leu Glu Arg Pro Gly Ala Pro Ala Val Val Gly
    2405                2410                2415
Trp Asp Arg Val Phe Thr Tyr Ala Glu Leu Asn Glu Ala Ala Asn
    2420                2425                2430
Arg Leu Ala His His Leu Thr Gln Thr Phe Ala Ile Lys Ala Asp
    2435                2440                2445
Glu Leu Ile His Val Cys Phe Glu Lys Ser Ala Trp His Phe Val
    2450                2455                2460
Ala Ile Leu Ala Ile Asn Lys Ala Gly Ala Gly Trp Val Pro Leu
    2465                2470                2475
Asp Pro Ser His Pro Glu Gln Arg Leu Arg Gln Ile Ala Ser Gln
    2480                2485                2490
Thr Arg Ala Arg Ile Ile Leu Thr Ser Pro Ala Asn Leu Asp Ile
    2495                2500                2505
Cys Ala Arg Leu Gly Leu Ser Val Ile Glu Ile Ser Pro Phe Phe
    2510                2515                2520
Asp Gln Lys Leu Ile Lys Ser Gly Met Asn Ser Ser Ala Gly Pro
    2525                2530                2535
Asp Val Lys Val Thr Pro Arg Asn Ile Ala Tyr Val Leu Phe Thr
    2540                2545                2550
Ser Gly Ser Thr Gly Thr Pro Lys Gly Leu Val Met Glu His Gly
    2555                2560                2565
Ser Val Cys Thr Ser Gln Thr Ala Ile Ser Arg Arg Leu Gly Leu
    2570                2575                2580
Thr Ala Asp Val Arg Met Leu Gln Phe Ala Ala Phe Val Phe Asp
    2585                2590                2595
Leu Ser Ile Gly Glu Ile Val Ala Pro Leu Ile Ser Gly Ala Ser
    2600                2605                2610
Leu His Ile Pro Asp Glu Asn Thr Arg Leu Asn Asp Leu Pro Asn
    2615                2620                2625
Phe Ile Gln Lys Lys Gln Ile Asn Trp Ala Phe Leu Thr Pro Ala
    2630                2635                2640
Phe Ala Arg Thr Leu Lys Pro Glu Asp Val Pro Ala Leu Asp Leu
    2645                2650                2655
Leu Leu Leu Ala Gly Glu Ala Val Ser Arg Asp Val Phe Glu Ser
    2660                2665                2670
Trp Phe Gly Lys Val Arg Leu Ile Asn Gly Trp Gly Pro Ala Glu
    2675                2680                2685
Thr Cys Val Phe Ser Thr Leu His Glu Trp Arg Ser Ile Asn Glu
    2690                2695                2700
Ser Pro Leu Thr Val Gly Arg Pro Val Gly Gly Phe Cys Trp Ile
    2705                2710                2715
Val Asp Pro Glu His Pro Asp Lys Leu Ala Pro Thr Gly Thr Val
    2720                2725                2730
Gly Glu Val Val Ile Gln Gly Pro Thr Leu Leu Arg Glu Tyr Leu
    2735                2740                2745
Ala Asp Ala Glu Arg Thr Lys Leu Ser Thr Val Tyr Asp Leu Pro
    2750                2755                2760
Ala Trp Ala Pro Arg Arg Glu Leu Gln His Trp Ser Arg Phe Tyr
    2765                2770                2775
Lys Ser Gly Asp Leu Cys Tyr Tyr Asn Pro Asp Gly Thr Ile Glu
    2780                2785                2790
```

```
Phe Ser Thr Arg Lys Asp Thr Gln Ile Lys Ile Arg Gly Leu Arg
2795                2800                2805

Val Glu Leu Gly Glu Ile Glu His His Leu Gln Leu Ala Leu Asp
2810                2815                2820

Asp Ile Arg Gln Val Ala Val Asp Val Phe Lys Gly Glu Ser Gly
2825                2830                2835

Ser Asn Leu Val Ala Tyr Phe Cys Phe Asn Glu Glu Ser Lys Thr
2840                2845                2850

Ala Asp Ala Arg Val Ala Gly Asp Asp Lys Gly Pro Phe Met Pro
2855                2860                2865

Ile Asp Glu Asp Leu Gln Ala Arg Leu Ile Ala Ala Ser Gly Glu
2870                2875                2880

Leu Arg Val Val Leu Pro Ser Tyr Met Val Pro Thr Phe Phe Ile
2885                2890                2895

Pro Cys Ser Tyr Met Pro Thr Ser Thr Ser Thr Lys Leu Asp Arg
2900                2905                2910

Lys Glu Leu Lys Arg Tyr Thr Ala Ala Leu Ser Val Glu Glu Leu
2915                2920                2925

Ser Lys Tyr Ser Leu Val Asp Gly Lys Lys Arg Ala Pro Glu Thr
2930                2935                2940

Pro Met Glu Ser Gln Leu Gln Gln Ile Trp Ala Glu Ile Leu Asn
2945                2950                2955

Ile Pro Met Glu Ser Val Gly Arg Asp Asp Ser Phe Leu Gly Leu
2960                2965                2970

Gly Gly Asp Ser Ile Thr Ala Ile His Leu Val Asn Val Met Arg
2975                2980                2985

Glu Glu Gly Ile Ser Leu Thr Val Lys Asp Ile Phe Asp Asp Pro
2990                2995                3000

Arg Leu Leu Ser Val Ala Ser Lys Ala Ile Thr Thr Glu Glu Val
3005                3010                3015

Leu Glu Leu Asp Glu Ile Glu Pro Phe Ser Leu Leu Glu Lys Glu
3020                3025                3030

Ile Arg Asp Ala Val Leu Ser Glu Asp Leu Arg Gln Glu Leu Lys
3035                3040                3045

Leu Ala Lys Cys Gln Leu Val Glu Asp Ala Tyr Pro Cys Ser Lys
3050                3055                3060

Leu Gln Glu Gly Leu Met Val Leu Ser Val Lys Gln Pro Gly Ser
3065                3070                3075

Tyr Val Ala Lys Tyr Thr Tyr Arg Leu Pro Ala His Val Asp Leu
3080                3085                3090

Gln Arg Phe Lys Glu Ala Trp Glu Tyr Thr Ser Ser Ala Val Glu
3095                3100                3105

Ala Leu Arg Thr Arg Leu Val Met Ile Asp Gly Ser Cys Val Gln
3110                3115                3120

Val Val Ile Asn Glu Glu Ile Pro Trp Glu Thr Thr Lys Thr Asp
3125                3130                3135

Asp Ile Arg Ser Ala Ile Ala Ser Ala Gln Ser Leu Arg Met Thr
3140                3145                3150

Tyr Gly Ser Ser Leu Ser Arg Tyr Thr Ile Leu Glu Asp Gln Asp
3155                3160                3165

Gly Ser Asn Tyr Phe Met Trp Ala Val His His Ser Val His Asp
3170                3175                3180

Gly Trp Ser Met Arg Ile Val Leu Glu Thr Leu Arg Arg Glu Tyr
```

```
            3185                3190                3195

Glu Gly Arg Ala Ser Ala Pro Val Met Pro Tyr Asn Gly Phe Ile
    3200                3205                3210

Arg Tyr Thr Leu Gly Leu Asp Leu Glu Ala Ala Ala Glu Tyr Trp
    3215                3220                3225

Ser Ser Gln Leu Asp Asn Ala Lys Arg Ala Ser Phe Pro Ala Ala
    3230                3235                3240

Ala Thr Thr Ser Ser Glu Thr Lys His Ile Thr Arg Met Met Thr
    3245                3250                3255

Lys Ser Ile Pro Phe Pro Ala Ser Met Asn Pro Ala Ile Thr Lys
    3260                3265                3270

Ala Thr Val Leu Arg Ala Ala Trp Ala Val Ile Leu Ala Arg Tyr
    3275                3280                3285

Cys Asp Thr Asp Asp Val Thr Phe Gly Ser Thr Ile Ser Gly Arg
    3290                3295                3300

Gln Ala Ala Val Pro Gly Leu Thr Glu Met Ala Gly Pro Ala Val
    3305                3310                3315

Ala Thr Val Pro Val Arg Ile Arg Leu Asp Lys Gln Gln Arg Val
    3320                3325                3330

Ser Lys Phe Leu Gln Gly Val Gln Ser Gln Ala Ser Glu Met Ile
    3335                3340                3345

Pro Phe Glu Gln Phe Gly Leu Gln Ser Ile Ser Arg Leu Gly Ala
    3350                3355                3360

Asp Ala Arg Asp Ala Cys Asp Phe Thr Ser Leu Met Leu Val Gln
    3365                3370                3375

Pro Met Gln His Leu Ala Gly Glu Asp Leu Asp Ser Val Met Val
    3380                3385                3390

Pro Ala Leu Glu Gln Glu Thr Gln Glu Asp Gln Leu Gln Asn Tyr
    3395                3400                3405

Phe Ser Tyr Pro Leu Val Leu Gln Gly His Ile His Asp Asp Arg
    3410                3415                3420

Val Glu Leu Val Leu Ile Tyr Asp Ser Val Val Leu Pro Glu Pro
    3425                3430                3435

Gln Leu Val Ala Leu Ser His Gln Phe Asn Gly Val Val Gln Gln
    3440                3445                3450

Leu Leu Ser Gly Lys Asp Cys Lys Leu Gly Glu Ile Ser Val Ala
    3455                3460                3465

Ser Pro Trp Asp Leu Asp Leu Ala Gln Ala Ser Asn Gly Asp Gly
    3470                3475                3480

Pro Glu Ile Val Asp Asp Cys Ala His Leu Ile Ile Glu Arg Gln
    3485                3490                3495

Thr Lys Gln Thr Pro His Ala His Ala Val His Ala Trp Asp Gly
    3500                3505                3510

Ser Leu Thr Tyr Ser Glu Leu Asp Leu Ala Ala Asn Arg Leu Ala
    3515                3520                3525

Asn Leu Leu Ile Gln Arg His Gly Val Lys Val Gly Asp Val Val
    3530                3535                3540

His Val Cys Phe Glu Lys Ser Leu Trp Tyr Val Val Ser Val Leu
    3545                3550                3555

Ala Ile Asn Lys Ala Gly Ala Ala Trp Val Pro Met Asp Pro Ala
    3560                3565                3570

His Pro Phe Gln Arg Leu Gln Gln Val Ala Ser Gln Thr Gly Ala
    3575                3580                3585
```

```
Lys Leu Ala Leu Ser Ser Ala Ile His Ser Pro Leu Cys Ser Lys
3590                3595                3600

Leu Leu Asp Thr Val Val Glu Val Ser Ser Asn Leu Asp Glu Gln
3605                3610                3615

Leu Lys Ser Asp Glu Thr Ile Ser His Val Lys Pro Thr Thr Lys
3620                3625                3630

Val Thr Pro Asn Asp Ala Val Tyr Leu Leu Phe Thr Ser Gly Ser
3635                3640                3645

Thr Gly Val Pro Lys Gly Ile Ile Met Glu His Ala Ser Leu Cys
3650                3655                3660

Thr Ser Gln Arg Asp Ile Ala Lys Arg Leu Gly Leu Thr Ser Ser
3665                3670                3675

Val Arg Met Leu Gln Phe Ser Ser Phe Val Phe Asp Val Ser Val
3680                3685                3690

Gly Glu Ile Met Leu Ser Leu Met His Gly Gly Cys Ile Cys Ile
3695                3700                3705

Pro Ser Asp His Asp Arg Leu Asn Asn Leu Asp Gly Phe Ile Arg
3710                3715                3720

Asp Ala Glu Val Thr Trp Ala Phe Leu Thr Pro Ser Phe Ala Arg
3725                3730                3735

Thr Leu Arg Pro Gln Asp Val Pro Ser Leu Glu Leu Ile Val Leu
3740                3745                3750

Ala Gly Glu Pro Val Ser Gln Asp Val Phe Asp Leu Trp Phe Gly
3755                3760                3765

Lys Ala Arg Leu Val Asn Gly Trp Gly Pro Ala Glu Thr Cys Val
3770                3775                3780

Leu Ser Ala Ile His Glu Trp Lys Ser Ala Asp Glu Ser Pro Leu
3785                3790                3795

Thr Ile Gly Arg Ser Val Gly Ser Phe Ala Trp Ile Val Asp Ala
3800                3805                3810

Glu Asn Ser Asn Arg Leu Ala Pro Val Gly Cys Ile Gly Glu Ile
3815                3820                3825

Val Met Gln Gly Pro Thr Leu Leu Arg Glu Tyr Leu Ala Asp Pro
3830                3835                3840

Ala Lys Thr Ala Ser Ser Thr Met Thr Ser Leu Pro Asn Trp Ala
3845                3850                3855

Pro Arg Ala Asn Asp Lys Lys Trp Gly Arg Phe Tyr Lys Thr Gly
3860                3865                3870

Asp Leu Gly Phe Tyr Asn Pro Asp Gly Thr Ile His Tyr Ser Gly
3875                3880                3885

Arg Lys Asp Thr Gln Val Lys Ile Arg Gly Leu Arg Val Glu Leu
3890                3895                3900

Gly Glu Val Glu His His Ile Arg Asn Ala Leu Glu Ser Ile Arg
3905                3910                3915

Gln Val Ala Val Asp Val Phe Arg Thr Glu Thr Gly Thr Asn Leu
3920                3925                3930

Val Ser Tyr Ile Cys Phe Ser Ser Glu Thr Lys Thr Pro Gly Pro
3935                3940                3945

Asn Thr Asp Pro Asn Gly Asp Asp Val Phe Leu Tyr Met Thr Arg
3950                3955                3960

Asn Val Gln Ser Asp Leu Asn Ile Ala Ile Asn Lys Leu Asn Ala
3965                3970                3975
```

```
Leu Leu Pro Ser Tyr Met Ile Pro Thr Tyr Trp Ile Pro Cys Asp
    3980            3985                3990
Tyr Met Pro Leu Ile Ser Ser Gly Lys Leu Asp Arg Val Lys Leu
    3995            4000                4005
Arg Lys Gln Met Ala Ala Leu Thr Gln Glu Glu Leu Glu Ala Tyr
    4010            4015                4020
Ser Leu Thr Asp Ala Asp Lys Arg Ala Pro Asp Thr Ala Met Glu
    4025            4030                4035
Val Arg Leu Gln Ser Met Trp Ala Glu Ile Leu Asn Ile Pro Ala
    4040            4045                4050
Gln Thr Ile Gly Lys Asp Asp Asn Phe Leu Arg Ile Gly Gly Asp
    4055            4060                4065
Ser Ile Ala Ala Ile Arg Leu Val Ser Met Ala Arg Glu Arg Gly
    4070            4075                4080
Ile Thr Leu Thr Val Asn Gly Ile Phe Glu Asp Pro Arg Leu Ser
    4085            4090                4095
Ser Met Ala Ala Thr Ala Gly Ala Ala Asp Gly Asp Asp Glu Leu
    4100            4105                4110
Leu Thr Pro Ile Pro Ala Phe Ser Leu Leu Asp Asp Ser Thr Arg
    4115            4120                4125
Asp Pro Ile Gln Ala Pro Ser Ile Tyr Gln Asp Leu Gly Leu Asn
    4130            4135                4140
Val Thr Gln Arg Ile Glu Asp Ala Tyr Pro Thr Thr Lys Leu Gln
    4145            4150                4155
Glu Gly Leu Met Ala Leu Ser Ala Lys Gln Pro Gly Ser Tyr Ile
    4160            4165                4170
Ala Lys Phe Leu Tyr Arg Ile Pro Lys His Ile Glu Val Ala Arg
    4175            4180                4185
Phe Lys Asp Ala Trp Arg Arg Thr Val Asp Ala Cys Pro Asn Leu
    4190            4195                4200
Arg Thr Arg Ile Leu Leu Thr Glu Gly Gly His Ser Thr Gln Leu
    4205            4210                4215
Val Ile Ser His Asp Phe Glu Trp Asp Leu Val Glu Asn Glu Asp
    4220            4225                4230
Leu His Ser Tyr Leu Gln Leu Thr Gln Asp Phe Glu Met Gly Tyr
    4235            4240                4245
Gly Ser Gln Leu Ser Arg Tyr Ala Leu Ile Lys His Thr Asp Gly
    4250            4255                4260
Glu Thr Tyr Phe Met Trp Ser Val His His Ala Val Phe Asp Gly
    4265            4270                4275
Leu Ser Thr Gln Asn Val Leu Asn Ile Leu Glu Lys Ala Tyr Gln
    4280            4285                4290
Gly Lys Asp Val Leu Glu Thr Pro Pro Tyr Ala Arg Phe Ile Lys
    4295            4300                4305
Tyr Thr Leu Gly Leu Asp Ala Glu Ala Ala Thr Tyr Trp Arg
    4310            4315                4320
Glu Gln Leu Gln Ser Ser Arg Lys Ala Thr Phe Pro Ala Ser Ser
    4325            4330                4335
Glu Val Ser Asn Lys Pro Gly Ala Thr Arg Val Leu Glu Arg Ser
    4340            4345                4350
Ile Glu Leu Pro Lys Met Ala Ser Ser Gly Ile Thr Leu Ala Thr
    4355            4360                4365
Val Val Arg Ser Ala Trp Ala Met Val Leu Ala Arg Tyr Ser Asp
```

```
            4370            4375              4380

Ser Glu Asp Val Thr Phe Gly Thr Ser Ile Ser Gly Arg Gln Ala
    4385            4390              4395

Pro Val Pro Glu Leu Met Asp Met Val Gly Pro Ile Ile Ala Thr
    4400            4405              4410

Val Pro Val Arg Val Arg Val Asp Gln Ala Gln Leu Ala Thr Asp
    4415            4420              4425

Phe Leu Gln Ala Val Gln Arg Gln Thr Leu Glu Met Val Pro Tyr
    4430            4435              4440

Glu Gln Phe Gly Leu Gln Ser Ile Ala Lys Val Ser Glu Asp Ala
    4445            4450              4455

Lys Glu Ala Cys Asp Phe Thr Ser Leu Leu Val Ile Gln Pro Met
    4460            4465              4470

Gln His Val Ser Asp Ser Glu Ser Ala Asp Ser Val Leu Val His
    4475            4480              4485

Ala Asp Gly Ala Leu Lys Glu Glu Ala Glu Ser Met Glu Asn Tyr
    4490            4495              4500

Phe Ser Tyr Pro Leu Ile Val Gln Ala His Leu Tyr Glu Asp Arg
    4505            4510              4515

Ile Asn Ile Val Leu Ile Tyr Asp Ser Thr Ile Leu Ala Lys Thr
    4520            4525              4530

Gln Leu Glu Ala Leu Ser Gln Gln Leu Gly His Val Met Cys Gln
    4535            4540              4545

Leu Ala Ala Ala Thr Asp Glu Lys Ser Leu Gly Ser Val Ser Ile
    4550            4555              4560

Thr Ser Asp Trp Asp Leu Glu Arg Ala Val Ser Phe Asn Ser Asp
    4565            4570              4575

Val Pro Glu Ile Val Asp Ala Cys Val His Asp Leu Val Ala Arg
    4580            4585              4590

Gln Ala Glu Leu Arg Pro Asp Ser Val Ala Ile Ser Ala Trp Asp
    4595            4600              4605

Ala Glu Leu Thr Tyr Ser Gln Leu Asn Leu Ala Ala Asn Arg Leu
    4610            4615              4620

Ala Asn His Ile Ile Thr Ala Tyr Gly Ile Lys Pro Asn Asp Phe
    4625            4630              4635

Ile His Val Cys Phe Glu Lys Ser Ala Trp His Phe Val Ala Ile
    4640            4645              4650

Leu Ala Ile Asn Lys Ala Gly Ala Ala Trp Val Pro Leu Asp Ser
    4655            4660              4665

Ser His Pro Glu Gln Arg Leu Arg Gln Val Val Ser Gln Thr Asn
    4670            4675              4680

Ala Arg Leu Val Leu Thr Ser Pro Ser Asn Ser Thr Leu Cys Ser
    4685            4690              4695

Gly Leu Leu Ala Asp Val Leu Glu Val Thr Pro Ala Leu Asp Gln
    4700            4705              4710

Lys Leu Ala Ala Thr Val Gly Ser Gln Ala Pro Lys Val Ala Val
    4715            4720              4725

Thr Pro Glu His Ala Val Tyr Ala Leu Phe Thr Ser Gly Ser Thr
    4730            4735              4740

Gly Thr Pro Lys Gly Leu Val Met Gln His Arg Ala Val Cys Thr
    4745            4750              4755

Ser Gln Thr Ala Ile Ala Lys Arg Leu Gly Leu Ser Ser Asp Ile
    4760            4765              4770
```

-continued

Arg Gln Leu Gln Phe Ala Ala Phe Val Phe Asp Leu Ser Ile Gly
4775             4780                4785

Glu Ile Ile Ala Pro Leu Ile Ser Gly Ala Cys Val Cys Val Pro
4790             4795                4800

Ser Glu Asp Val Arg Met Asn Ser Ile Thr Glu Tyr Ile Arg Asp
4805             4810                4815

Gln Arg Ile Asn Trp Ala Phe Leu Thr Pro Ser Tyr Val Arg Thr
4820             4825                4830

Leu Arg Pro Lys Asp Val Pro Gly Leu Glu Leu Leu Leu Leu Ala
4835             4840                4845

Gly Glu Ala Val Pro Lys Glu Ile Leu Asn Thr Trp Phe Gly Lys
4850             4855                4860

Leu Arg Leu Val Asn Gly Trp Gly Pro Ala Glu Thr Cys Val Phe
4865             4870                4875

Ser Thr Leu His Glu Trp Lys Ser Val Asp Glu Ser Pro Leu Thr
4880             4885                4890

Val Gly Lys Pro Val Gly Gly Phe Cys Trp Val Val Asp Pro Glu
4895             4900                4905

Asn Pro His Lys Leu Ala Pro Val Gly Thr Leu Gly Glu Val Val
4910             4915                4920

Ile Gln Gly Pro Thr Leu Leu Arg Glu Tyr Leu Ala Asp Pro Glu
4925             4930                4935

Arg Thr Ala Ala Ser Ser Ala Thr Ala Pro Asp Trp Ala Pro Gln
4940             4945                4950

Pro Asp Ser Lys His Trp Gly Arg Leu Tyr Lys Ser Gly Asp Leu
4955             4960                4965

Cys Ser Tyr Asn Pro Asp Gly Thr Leu Glu Phe Ser Ser Arg Lys
4970             4975                4980

Asp Thr Gln Ile Lys Ile Arg Gly Leu Arg Val Glu Leu Gly Glu
4985             4990                4995

Val Glu His His Ile Gln Thr Ala Met Arg Gly Leu Arg Gln Ile
5000             5005                5010

Ala Val Asp Val Tyr Lys Gly Glu Ser Gly Thr Asn Leu Val Ala
5015             5020                5025

Tyr Leu Cys Phe Thr Asp Glu Thr Arg Ala Ser Ser Ala Asp His
5030             5035                5040

Ser Pro Phe Met Ser Val Asp Lys Lys Leu Gln Asn Gln Leu Asn
5045             5050                5055

Ala Leu Val Gly Glu Leu Gly Val Thr Leu Pro Arg Tyr Met Ile
5060             5065                5070

Pro Thr Leu Tyr Ile Pro Cys Ser Phe Met Pro Ser Ile Thr Ser
5075             5080                5085

Thr Lys Leu Asp Arg Asn Glu Leu Arg Arg Arg Thr Ala Ser Leu
5090             5095                5100

Thr Arg Asp Glu Leu Ser Gln Tyr Ser Leu Leu Gly Gly Asn Lys
5105             5110                5115

Arg Ala Pro Glu Thr Asp Val Glu Arg Ala Leu Gln Arg Ile Trp
5120             5125                5130

Ser Gly Ile Leu Gly Leu Ser Pro Asp Ala Ile Gly Arg Asp Asp
5135             5140                5145

Ser Phe Leu Gly Leu Gly Gly Asp Ser Ile Thr Ala Ile Gln Leu
5150             5155                5160

```
Val Gly Val Cys Arg Asp Gln Gly Ile Ser Leu Ser Val Lys Asp
    5165                5170                5175
Ile Phe Asn Asp Pro Arg Leu Ile Ala Val Ala Lys Ala Ala Gln
    5180                5185                5190
Ser Leu Ser Ser Val Asp Val Ala Ile Glu Pro Phe Gly Leu
    5195                5200                5205
Leu Asp Asp Glu Leu Arg Arg Leu Ala Thr Ser Glu Thr Ala Arg
    5210                5215                5220
Ala Gln Cys His Leu Ala Thr Glu Ala Val Ile Glu Asp Ala Tyr
    5225                5230                5235
Pro Cys Thr Lys Phe Gln Glu Gly Leu Met Ala Leu Ser Ile Lys
    5240                5245                5250
Ser Pro Gly Ser Tyr Val Ala Lys Tyr Ala Tyr Arg Leu Ala Asp
    5255                5260                5265
Asp Val Asp Ile Glu Gln Phe Lys Ser Ser Trp Lys Lys Thr Val
    5270                5275                5280
Ser Leu Cys Pro Thr Leu Arg Thr Arg Ile Val Leu Leu Gly Asp
    5285                5290                5295
Arg Cys Val Gln Leu Val Val Lys Glu Asp Ala Glu Phe Val Ser
    5300                5305                5310
Ser Thr Ala Ser Ser Phe Glu Ser Ala Met Leu Glu Ala Arg Asn
    5315                5320                5325
Val Gln Met Thr Tyr Gly Thr Pro Leu Ser Gln Tyr Thr Leu Phe
    5330                5335                5340
Gln Gly Glu Asp Gly Phe Tyr Phe Ile Trp Val Val His His Thr
    5345                5350                5355
Val His Asp Gly Trp Thr Met Arg Leu Val Leu Glu Thr Leu Gln
    5360                5365                5370
Asn Leu His Gln Gly Ser Thr Thr Ser Ser Leu Lys Pro Tyr Ser
    5375                5380                5385
Asn Phe Ile Lys Tyr Ala Met Asp Val Val Gln Asp Pro Ala Val
    5390                5395                5400
Glu Lys Tyr Trp Ser Gln Gln Leu Asp Gly Ala Val Gln Ala Ser
    5405                5410                5415
Tyr Pro Pro Arg Pro Arg Ser Asp Lys Gln His Lys Ala Val Thr
    5420                5425                5430
Arg Met Met Thr Lys Thr Ile Gln Val Pro Asn Asn Thr Gln Ser
    5435                5440                5445
Ser Val Thr Met Ala Thr Leu Leu Arg Ala Thr Trp Ala Ile Ile
    5450                5455                5460
Leu Ala Arg Tyr Ser Asn Thr Asp Asp Ile Cys Phe Ala Thr Thr
    5465                5470                5475
Val Ser Gly Arg Gln Ala Ser Val Ser Asp Ile Leu Gln Ile Pro
    5480                5485                5490
Gly Pro Ile Val Ala Thr Ile Pro Val Arg Val Arg Leu Asn Gly
    5495                5500                5505
Gln Gln Thr Val Leu Glu Tyr Leu Glu Ser Val Gln His Gln Ala
    5510                5515                5520
Thr Gln Met Ile Pro His Glu Gln Tyr Gly Leu Gln Asn Ile Ser
    5525                5530                5535
Arg Ile Ser Glu Asn Ile Ser Asp Ala Ile Asp Phe Ser Ser Leu
    5540                5545                5550
Leu Val Ile Gln Pro Arg Ser His Leu Asp Ser Gly Asn Gly Asp
```

```
            5555                5560                5565
Gly Ser Asn Glu Asn Ile Leu Ile Pro Thr Val Glu Asp Asp Glu
            5570                5575                5580
Ala Val Ala Asp Leu Leu Gln Asp Tyr Phe Thr Tyr Pro Leu Val
            5585                5590                5595
Ile Gln Gly Asn Leu Leu Asp Asp His Ile Asp Leu Leu Leu Thr
            5600                5605                5610
Tyr Asp Ser Thr Val Leu Ser Glu Val Glu Leu Ser Arg Leu Ala
            5615                5620                5625
Val Gln Phe Glu His Val Ala Gln Gln Leu Leu Asp Ser Asp His
            5630                5635                5640
Val Lys Leu Gly Asp Leu Ser Leu Val Pro Pro Gln Asp Val Gln
            5645                5650                5655
Gln Ala Ile Ala Trp Asn Thr Glu Asp Pro Glu Ile Val Glu Asp
            5660                5665                5670
Cys Ile His Lys Leu Val Glu Arg Gln Ala Ile Ser Thr Pro Asp
            5675                5680                5685
Ala Ile Ala Ile Asp Ser Trp Asp Gly Lys Leu Thr Tyr Ala Gln
            5690                5695                5700
Leu Asp Glu Ala Ala Thr Arg Leu Ser His His Leu Ile Lys Thr
            5705                5710                5715
Tyr Asp Val Ala Pro Asp Asp Leu Val Leu Leu Phe Gly Lys
            5720                5725                5730
Ser Leu Trp Tyr Ile Ile Ser Thr Ile Ala Val Asn Lys Ala Gly
            5735                5740                5745
Ala Ala Trp Val Pro Leu Asp Pro Ala His Pro Met Gln Arg Leu
            5750                5755                5760
Gln Gln Val Thr Arg Gln Thr Lys Ala Gln Val Ile Leu Ala Ser
            5765                5770                5775
Ser Leu Gln Cys Glu Leu Ala Gln Glu Leu Leu Asn Thr Val Val
            5780                5785                5790
Glu Val Ser Gln Ala Leu Asp Asp Ala Leu Thr Thr Ala Gly Ser
            5795                5800                5805
Thr Leu Arg Thr Pro Asp Ala Met Val Ser Ser Arg Asp Lys Ala
            5810                5815                5820
Tyr Val Leu Phe Thr Ser Gly Ser Thr Gly Val Pro Lys Gly Ile
            5825                5830                5835
Val Ile Ser His Gly Ser Val Cys Thr Ser Gln Thr Ala Ile Ser
            5840                5845                5850
Ser Arg Leu Gly Leu His Ser Gly Val Arg Met Leu Gln Phe Ser
            5855                5860                5865
Ala Phe Val Phe Asp Val Ser Val Gly Glu Ile Tyr Gly Ser Leu
            5870                5875                5880
Ile Arg Gly Ala Cys Val Val Ile Pro Ser Asp Glu Ile Arg Met
            5885                5890                5895
Asn Asp Leu Thr Arg Phe Met Arg Glu Lys Glu Val Thr Trp Ala
            5900                5905                5910
Cys Phe Thr Pro Ser Phe Ile Glu Thr Leu His Pro Ala Asp Leu
            5915                5920                5925
Glu Asn Leu Glu Leu Val Ile Leu Glu Gly Glu Pro Ser Lys Arg
            5930                5935                5940
His Ile Leu Glu Glu Trp Phe Gly Lys Val Lys Leu Ile Asn Gly
            5945                5950                5955
```

-continued

```
Trp Gly Pro Ala Glu Thr Cys Val Phe Ser Ser Met His Glu Trp
    5960            5965            5970

Lys Ser Ala Thr Glu Ser Pro Val Thr Ile Gly Lys Pro Val Gly
    5975            5980            5985

Cys Phe Ala Trp Ile Ala Asp Pro Asp Asn His His Arg Leu Ala
    5990            5995            6000

Pro Ile Gly Thr Val Gly Glu Ile Val Leu Gln Gly Pro Thr Leu
    6005            6010            6015

Leu Cys Glu Tyr Leu Asp Asp Pro Met Gln Thr Gln Ala Ser Ile
    6020            6025            6030

Leu Lys Ser Ile Pro Ser Trp Ala Pro Arg Arg Glu Ser Gln His
    6035            6040            6045

Trp Asn Arg Phe Tyr Leu Thr Gly Asp Leu Gly Cys Tyr Asn Pro
    6050            6055            6060

Asp Gly Thr Leu Ala Tyr His Gly Arg Lys Asp Thr Gln Val Lys
    6065            6070            6075

Ile Arg Gly Leu Arg Val Glu Leu Asp Glu Val Glu His His Ile
    6080            6085            6090

Arg Ser Leu Leu Ser Asp Val Val His Val Thr Val Asp Val His
    6095            6100            6105

Lys Ser Glu Ala Gly Ser Ser Leu Val Ala Tyr Leu Ala Tyr Thr
    6110            6115            6120

Glu Glu Ser Val Asp Asp Glu Asp Ala Leu Phe Leu Pro Leu Thr
    6125            6130            6135

Asn Glu Leu Gln Lys Asp Leu Asp Ala Met Ser Ser Gln Leu Ser
    6140            6145            6150

Val Leu Leu Pro Arg Tyr Met Val Pro Thr Leu Tyr Ile Pro Cys
    6155            6160            6165

Ser His Met Pro Phe Leu Ser Ser Gly Lys Thr Asp Arg Ala Gln
    6170            6175            6180

Leu Arg Arg Leu Thr Ser Glu Leu Ser Gln Glu Gln Leu Glu Ala
    6185            6190            6195

Tyr Ala Leu Asp Asp Thr Lys Lys Glu Ala Ala Glu Thr Glu Ala
    6200            6205            6210

Glu Leu Arg Leu Arg Asp Val Trp Ala Lys Ile Leu Gly Leu Ser
    6215            6220            6225

Ala Gln Ser Ile Gly Arg His Asp Ser Phe Leu Arg Ile Gly Gly
    6230            6235            6240

Asp Ser Ile Ala Ala Ile Gln Leu Val Thr Ala Ala Arg Glu Ala
    6245            6250            6255

Gly Ile Ile Phe Ser Val Lys Asp Val Phe Asp Asp Ser Arg Leu
    6260            6265            6270

Trp Lys Leu Ala Glu Phe Ala Ser Ser Lys Thr Glu Ser Glu Lys
    6275            6280            6285

Val Val Glu Ala Ile Ala Pro Phe Ser Leu Leu Arg Thr Ser Leu
    6290            6295            6300

Asn Glu Thr Ala Val Thr Ala Ile Leu Gln Gln Gln Tyr Gly Leu
    6305            6310            6315

Thr Asp Ser Val Val Val Glu Asp Ala Tyr Pro Ser Thr Lys Leu
    6320            6325            6330

Gln Glu Gly Leu Met Ala Ile Ser Ala Lys Gln Pro Gly Thr Tyr
    6335            6340            6345
```

```
Val Ala Lys Gln Val Tyr Gly Leu Pro Glu His Val Asp Leu Asp
6350                    6355                6360

Thr Phe Lys Ala Ala Trp Glu Arg Thr Val Glu Leu Cys Val Asn
6365                    6370                6375

Leu Arg Thr Arg Leu Val Ile Ala Gly Asp Ala Ser Val Gln Val
6380                    6385                6390

Val Ile Arg Asn Glu Glu Ile Glu Trp Glu Thr Cys Asn Thr Thr
6395                    6400                6405

Val Gln Ala Tyr Leu Ser Gln Gln Phe Asn Met Gly Tyr Gly Ser
6410                    6415                6420

Arg Leu Phe Arg Asn Gly Ile Val His Glu Pro Ser Gly Gln Asn
6425                    6430                6435

Phe Phe Val Leu Ser Ile His His Ala Ile Phe Asp Gly Trp Thr
6440                    6445                6450

Leu Pro Met Leu Met Glu Thr Leu Asp Ser Ala Tyr Arg Gly Val
6455                    6460                6465

Glu Ala Ser Ala Leu Arg Pro Tyr Ala Glu Phe Val Lys Tyr Ile
6470                    6475                6480

Leu Asp Ile Asp Glu Ala Ala Ala Gly Asp Tyr Trp Arg Gly Gln
6485                    6490                6495

Leu Gln Asp Ala Lys Arg Ala Ser Phe Pro Pro Ser Ala Pro Val
6500                    6505                6510

Gln Ser Ser Gln Thr Ile Thr Arg Ile Leu Glu Lys Pro Leu Asn
6515                    6520                6525

Phe Ser His Ser Ile Lys Ser Gly Ile Thr Lys Ala Ser Val Leu
6530                    6535                6540

Arg Ala Ala Trp Ala Leu Val Leu Ser Arg Tyr Ser Asp Ser Asp
6545                    6550                6555

Asp Val Thr Phe Gly Val Asn Val Ser Gly Arg Asn Ala Ala Val
6560                    6565                6570

Ala Gly Ile Glu Ser Met Pro Gly Leu Val Val Ala Thr Val Pro
6575                    6580                6585

Val Arg Val Arg Leu Asp Pro Glu Gln Thr Val Ser Gln Phe Val
6590                    6595                6600

Glu Ser Ile Gln Ser Gln Ser Thr Asp Met Ile Pro Tyr Glu Gln
6605                    6610                6615

Phe Gly Leu Gln Asp Ile Ser Lys Leu Ser Pro Glu Ala Lys Asp
6620                    6625                6630

Ala Cys Asp Phe Ser Ser Leu Met Val Ile Gln Pro Met Ser Ser
6635                    6640                6645

Ile Ala Asn Asn Lys Ser Val Leu Glu Pro Pro Glu Asp Lys
6650                    6655                6660

Ala Ala Ala Glu Glu Ser Leu Gln Asn Tyr Phe Thr Tyr Pro Leu
6665                    6670                6675

Val Ile Gln Ala His Leu His Asp Asp Gly Ala Val Asn Leu Leu
6680                    6685                6690

Leu Ile Tyr Asp Ala Asn Val Leu Ser Glu Asp Gln Leu Gln Ala
6695                    6700                6705

Leu Ser Ile Gln Phe Asp His Val Val Gln Leu Leu Gly Gln
6710                    6715                6720

Asp Ser Gly Ala Lys Leu Arg Asp Val Thr Ile Ala Gly Pro Trp
6725                    6730                6735

Asp Leu Gln Gln Ala Met Ser Tyr Asn Val Lys Glu Pro Gly Ile
```

```
                6740                6745                6750
Val Asn Ala Cys Val His Glu Leu Ile Ala Gln Gln Ala Ala Arg
                6755                6760                6765

Asp Pro His His Glu Ala Ile Tyr Ser Ser Glu Gly Thr Val Thr
                6770                6775                6780

Tyr Ala Thr Leu Asp Arg Leu Ser Ser Leu Leu Ala His His Leu
                6785                6790                6795

His Ala His Gly Val Arg Pro Glu Ser Val Val Pro Phe Cys Phe
                6800                6805                6810

Asp Lys Ser Ala Trp Ala Ile Ile Ala Met Leu Ala Ile Leu Lys
                6815                6820                6825

Ala Gly Gly Val Phe Leu Pro Leu Asp Pro Ser His Pro Arg Asn
                6830                6835                6840

Arg Arg Glu Ala Leu Ile Glu Glu Val Gly Ala Glu Val Met Ile
                6845                6850                6855

Val Ser Pro Ser Ser Ser Val Thr Cys Glu Gly Leu Thr Pro Thr
                6860                6865                6870

Met Val Glu Leu Thr Thr Pro Leu Leu Glu Gln Leu Ser Ser Thr
                6875                6880                6885

Tyr Asp Ala Phe Gln Gln Ile His Pro Lys Pro Lys Pro Ser Asn
                6890                6895                6900

Ala Ala Tyr Val Leu Phe Thr Ser Gly Ser Thr Gly Lys Pro Lys
                6905                6910                6915

Gly Val Leu Met Glu His Ser Gly Phe Ala Thr Ser Thr Leu Gly
                6920                6925                6930

His Gly Arg Val Tyr Asn Leu Gly Pro Thr Ser Arg Val Phe Gln
                6935                6940                6945

Phe Ser Asn Tyr Val Phe Asp Gly Ser Leu Gly Glu Ile Phe Thr
                6950                6955                6960

Thr Leu Ser Phe Gly Gly Thr Val Cys Val Pro Ser Glu Thr Glu
                6965                6970                6975

Arg Leu Gln Glu Ala Pro Thr Phe Met Arg Lys Ser Arg Val Asn
                6980                6985                6990

Thr Ala Met Leu Thr Pro Ser Phe Val Arg Thr Phe Thr Pro Asp
                6995                7000                7005

Gln Val Pro Ser Leu Gln Leu Leu Val Leu Gly Gly Glu Ala Ser
                7010                7015                7020

Ser Lys Asp Leu Ile Glu Thr Trp Cys Asp Arg Leu Arg Leu Val
                7025                7030                7035

Asn Gly Tyr Gly Pro Ala Glu Ala Cys Asn Tyr Ala Thr Thr His
                7040                7045                7050

Asp Phe Lys Pro Thr Asp Ser Pro Arg Thr Ile Gly Arg Gly Phe
                7055                7060                7065

Asn Ser Ala Cys Trp Ile Val Glu Pro Thr Asp Tyr Asn Arg Leu
                7070                7075                7080

Thr Pro Ile Gly Cys Val Gly Glu Leu Ile Ile Gln Gly Asn Ala
                7085                7090                7095

Leu Ala Arg Gly Tyr Ile Asn Asp Pro Lys Arg Thr Ala Asp Ser
                7100                7105                7110

Phe Val Thr Ala Val Asp Cys Leu Pro Arg Asp Met Ile Ser Gly
                7115                7120                7125

Pro His Arg Phe Tyr Leu Thr Gly Asp Leu Val Arg Tyr Asn Ser
                7130                7135                7140
```

```
Thr Gly Glu Met Glu Tyr Leu Gly Arg Lys Asp Thr Gln Val Lys
    7145            7150                7155

Leu Arg Gly Gln Arg Leu Glu Leu Gly Glu Ile Glu Tyr Gln Val
    7160            7165                7170

Lys Gln Ser Leu Pro Glu Ile Glu His Val Ala Val Asp Val Val
    7175            7180                7185

His Arg Glu Thr Gly Asp Ala Leu Ile Ala Phe Val Ser Phe Lys
    7190            7195                7200

Asp Thr Ala Ser Ser Ala Ser Ser Asp Ile Leu Ser Leu Asp Asp
    7205            7210                7215

Glu Met His Ser Thr Leu Ala Thr Val Met Glu His Leu Lys Ser
    7220            7225                7230

Ser Leu Pro Gly Tyr Met Val Pro Ser Thr Ile Leu Pro Leu Lys
    7235            7240                7245

Lys Met Pro Phe Ile Thr Ser Met Lys Val Asp Arg Lys Arg Leu
    7250            7255                7260

Ile Ala Val Ala Ala Glu Leu Ser Leu Glu Glu Leu Thr Ser Phe
    7265            7270                7275

Ser Leu Val Lys Arg Asp Phe Ala Pro Pro Thr Thr Ala Met Glu
    7280            7285                7290

Lys Lys Leu Ala Asp Leu Trp Ala Gln Val Leu Lys Ile Asp Val
    7295            7300                7305

Gly Ser Ile Gly Lys Asn Asp Ser Phe Leu Gln Ile Gly Gly Asp
    7310            7315                7320

Ser Ile Thr Ser Ile His Leu Val Thr Leu Ala Gln Lys Ser Gly
    7325            7330                7335

Ile Asn Leu Thr Val Ala Gly Ile Phe Asp Asp Ser Lys Leu Ser
    7340            7345                7350

Ser Met Ala His Ser Ala Gly Glu Gly Asp Ile Glu Pro Val Tyr
    7355            7360                7365

Glu Val Val Pro Phe Asp Met Val Ala Thr His Asn Leu Ser Ser
    7370            7375                7380

Leu Met Glu Glu Val Arg Thr Lys Cys Gly Leu Pro Gly Ser Ala
    7385            7390                7395

Val Ile Glu Asp Ile Tyr Pro Ala Thr Ser Phe Gln Glu Gly Leu
    7400            7405                7410

Met Ala Leu Ala Val Lys Gln Pro Gly Ser Tyr Ile Ala Lys Gln
    7415            7420                7425

Val Tyr Gln Leu Pro Arg Gly Val Asp Val Ala Arg Phe Lys Ala
    7430            7435                7440

Ala Trp Glu Thr Thr Ala Arg Met Cys Ser Asn Leu Arg Thr Arg
    7445            7450                7455

Ile Val Leu Ala Gly Asp Ala Ser Val Gln Val Ile Leu Lys Asp
    7460            7465                7470

Ile Gly Ser Trp Glu Val Thr Ser Asn Met Thr Leu Lys Ser Tyr
    7475            7480                7485

Leu Gln Ala Thr Gln Lys Ile Asn Met Asp Tyr Gly Ser Ala Leu
    7490            7495                7500

Ser Arg His Ala Leu Ile Glu Gln Ala Asp Gly Lys Asn Tyr Phe
    7505            7510                7515

Val Trp Ser Ile His His Thr Val Phe Asp Gly Trp Thr Thr Arg
    7520            7525                7530
```

```
Leu Val Leu Asn Thr Leu Leu Ser Ala Tyr Met Gly Glu Gln Ile
    7535                7540                7545
Val Pro Leu Glu Pro Tyr Ala Arg Phe Ile Asn Tyr Ala Ile Asn
    7550                7555                7560
Leu Asn Ile Asp Ala Ala Lys Ser Tyr Trp Thr Glu Gln Leu Leu
    7565                7570                7575
Asp Ala Lys Arg Ala Leu Phe Pro Ala Val Ser Asn Glu Val Ser
    7580                7585                7590
Arg Asn Lys Thr Ser Asn Thr Arg Val Leu Glu Lys Ala Leu Asp
    7595                7600                7605
Leu Pro Gln Val Lys Gln Thr Ser Ile Thr Met Ala Ser Ile Leu
    7610                7615                7620
Arg Ala Thr Trp Ser Ile Val Leu Ala Gln Tyr Cys Asp Thr Asp
    7625                7630                7635
Asp Val Thr Phe Gly Thr Thr Val Ser Gly Arg Gln Ala Pro Val
    7640                7645                7650
Ser Gly Ile Thr Glu Met Ala Gly Pro Val Val Ala Thr Val Pro
    7655                7660                7665
Val Arg Val Arg Leu Asp Arg Asn Ala Ser Val Pro Glu Phe Leu
    7670                7675                7680
Lys Gly Ile Gln Thr Gln Ala Ser Gln Met Ile Pro Phe Glu Gln
    7685                7690                7695
Phe Gly Leu Gln Asn Ile Ala Lys Leu Asn Val Glu Ala Lys Glu
    7700                7705                7710
Ala Cys Asp Phe Arg Ser Leu Leu Val Ile Gln Pro Met Lys Lys
    7715                7720                7725
Leu Leu Asp Thr Gly Asp Arg Glu Ala Ile Met Glu Pro Val Ser
    7730                7735                7740
Ala Thr Thr Arg Asp Glu Glu Asp Phe Met Gln Asn Tyr Phe Ser
    7745                7750                7755
Tyr Pro Leu Val Ile Gln Gly His Val Tyr Glu Glu Ser Val Asn
    7760                7765                7770
Leu Val Leu Ile Tyr Asp Ala Asp Ile Leu Pro Glu Gln Gln Leu
    7775                7780                7785
Leu Ala Leu Ala His Gln Phe Glu His Val Ala Gln Gln Leu Val
    7790                7795                7800
Ala Lys Gly Asn Arg Thr Thr Lys Leu Gly Asp Val Ser Val Ser
    7805                7810                7815
Gly Ala Trp Asp Leu Asp Phe Ala Leu Arg Gln Asn Ser Glu Val
    7820                7825                7830
Pro Glu Leu Ile Asp Ser Cys Phe His Thr Leu Val Glu Gln Gln
    7835                7840                7845
Ala Val Val Arg Pro Glu Ala Pro Ala Ile Asn Gly Trp Asp Ala
    7850                7855                7860
Lys Phe Thr Tyr Ala Gln Leu Asn Glu Ala Ala Asn Arg Leu Ala
    7865                7870                7875
Asn His Leu Val Ala Glu Tyr Glu Ile Asn Asn Asp Glu Leu Ile
    7880                7885                7890
His Val Cys Phe Glu Lys Ser Ala Trp Phe Phe Val Ala Ile Leu
    7895                7900                7905
Ala Ile Asn Lys Ala Gly Ala Ala Trp Val Pro Leu Asp Pro Ser
    7910                7915                7920
His Pro Ser Gln Arg His Gln Gln Val Val Asn Gln Thr Lys Ala
```

```
                        7925                    7930                    7935
Arg  Leu  Ala  Leu  Val  Ser  Thr  Ser  His  Ile  Ser  Thr  Cys  Val  Asp
             7940                    7945                    7950

Leu  Val  Asp  Asp  Ile  Leu  Glu  Val  Ser  Ser  Thr  Thr  Asp  Glu  Leu
             7955                    7960                    7965

Leu  Arg  Lys  Ser  Gln  Ser  Ser  Arg  His  Gly  Pro  Thr  Arg  Lys  Val
             7970                    7975                    7980

Ser  Pro  Ser  Asn  Ala  Ala  Tyr  Val  Leu  Phe  Thr  Ser  Gly  Ser  Thr
             7985                    7990                    7995

Gly  Thr  Pro  Lys  Gly  Leu  Val  Met  Glu  His  Gly  Ser  Val  Cys  Thr
             8000                    8005                    8010

Ser  Gln  Thr  Ala  Ile  Val  Lys  Arg  Leu  Asn  Met  Thr  Pro  Ser  Val
             8015                    8020                    8025

Arg  Ile  Leu  Gln  Phe  Ala  Ala  Phe  Val  Phe  Asp  Leu  Ser  Ile  Gly
             8030                    8035                    8040

Glu  Ile  Val  Ala  Pro  Leu  Ile  Thr  Gly  Ala  Cys  Ile  Cys  Val  Pro
             8045                    8050                    8055

Ser  Glu  His  Ala  Arg  Met  Asn  Ala  Leu  Pro  Glu  Phe  Val  Arg  Gln
             8060                    8065                    8070

Asn  Asn  Val  Asn  Trp  Ala  Tyr  Leu  Thr  Pro  Ser  Tyr  Ile  Gln  Thr
             8075                    8080                    8085

Leu  Ser  Pro  Lys  Asp  Val  Pro  Gly  Leu  Glu  Leu  Val  Leu  Leu  Ala
             8090                    8095                    8100

Gly  Glu  Ala  Val  Ser  Arg  Asp  Ile  Leu  Asp  Ala  Trp  Phe  Gly  Lys
             8105                    8110                    8115

Val  Arg  Leu  Val  Asn  Gly  Trp  Gly  Pro  Ala  Glu  Thr  Cys  Val  Phe
             8120                    8125                    8130

Ser  Thr  Leu  His  Glu  Trp  Arg  Ser  Lys  Asp  Glu  Glu  Ser  Pro  Leu
             8135                    8140                    8145

Thr  Ile  Gly  Arg  Pro  Val  Gly  Gly  Phe  Thr  Trp  Ile  Val  Asp  Pro
             8150                    8155                    8160

Glu  Asn  Pro  Gln  Lys  Leu  Ala  Pro  Ile  Gly  Val  Pro  Gly  Glu  Val
             8165                    8170                    8175

Val  Ile  Gln  Gly  Pro  Thr  Ile  Leu  Arg  Glu  Tyr  Leu  Asp  Asp  Pro
             8180                    8185                    8190

Val  Arg  Thr  Ser  Asp  Ser  Thr  Val  Tyr  Ser  Leu  Pro  Pro  Trp  Ala
             8195                    8200                    8205

Pro  Asn  Arg  Gly  Thr  Lys  Trp  Asn  Arg  Phe  Tyr  Lys  Ser  Gly  Asp
             8210                    8215                    8220

Leu  Cys  Ser  Tyr  Asn  Ala  Asp  Gly  Thr  Ile  Glu  Phe  Ile  Ser  Arg
             8225                    8230                    8235

Lys  Asp  Thr  Gln  Ile  Lys  Ile  Arg  Gly  Leu  Arg  Val  Glu  Leu  Gly
             8240                    8245                    8250

Glu  Val  Glu  His  His  Val  Lys  Ser  Ala  Leu  Asp  Val  Arg  His  Val
             8255                    8260                    8265

Ala  Val  Asp  Val  Leu  Arg  Ser  Ser  Asn  Gly  Ser  Asn  Leu  Val  Ala
             8270                    8275                    8280

Tyr  Phe  Cys  Phe  Ser  Asp  Gln  Thr  Arg  Met  Asn  Gly  Thr  Arg  Gly
             8285                    8290                    8295

Thr  Ser  Asp  Gly  Ser  Gly  Leu  Phe  Ala  Glu  Met  Asp  Asp  Glu  Leu
             8300                    8305                    8310

Gln  Thr  Arg  Leu  Thr  Ala  Val  Ile  Gly  Gln  Leu  Asn  Ile  Ser  Leu
             8315                    8320                    8325
```

```
Pro  Arg  Tyr  Met  Val  Pro  Thr  Phe  Phe  Ile  Pro  Cys  Gln  Tyr  Met
     8330                8335                8340

Pro  Thr  Ile  Thr  Ser  Thr  Lys  Leu  Asp  Arg  Asn  Tyr  Leu  Lys  Arg
     8345                8350                8355

Gln  Thr  Ala  Ala  Leu  Ser  Gln  Glu  Glu  Leu  Thr  Met  Tyr  Ser  Leu
     8360                8365                8370

Leu  Gln  Gly  Gly  Lys  Lys  Arg  Ala  Pro  Glu  Lys  Asp  Met  Glu  Lys
     8375                8380                8385

Gln  Leu  Gln  Ser  Ile  Trp  Ser  Gln  Ile  Leu  Ser  Ile  Pro  Ser  Glu
     8390                8395                8400

Ser  Ile  Gly  Leu  Asp  Asp  Ser  Phe  Leu  Gly  Leu  Gly  Gly  Asp  Ser
     8405                8410                8415

Ile  Ser  Ala  Ile  Arg  Leu  Val  Ala  Leu  Cys  Arg  Glu  Glu  Ala  Val
     8420                8425                8430

Ser  Leu  Thr  Ala  Gln  Asp  Ile  Phe  Asp  Asp  Pro  Arg  Leu  Phe  Ala
     8435                8440                8445

Val  Ala  Ala  Arg  Ala  Gln  Lys  Met  Asn  Val  Val  Val  Glu  Glu  Ser
     8450                8455                8460

Leu  Asp  Ile  Ala  Pro  Phe  Ser  Leu  Leu  Ser  Glu  Lys  Ser  Gln  Glu
     8465                8470                8475

Leu  Val  Lys  Ala  Asp  Asp  Val  Arg  Ala  Gln  Cys  Asn  Leu  Ser  Trp
     8480                8485                8490

Glu  Thr  Val  Val  Asp  Ala  Tyr  Pro  Cys  Thr  Pro  Leu  Gln  Glu  Gly
     8495                8500                8505

Leu  Met  Ala  Leu  Ser  Val  Lys  Gln  Pro  Gly  Ser  Tyr  Met  Ala  Arg
     8510                8515                8520

Tyr  Val  Tyr  Arg  Met  Pro  Arg  Thr  Val  Asn  Ile  Ala  Arg  Phe  Lys
     8525                8530                8535

Trp  Ser  Trp  Glu  Arg  Thr  Val  Ser  Leu  Cys  Asp  Asn  Leu  Arg  Thr
     8540                8545                8550

Arg  Ile  Val  Leu  Val  Gly  Gly  Arg  Ala  Thr  Gln  Ile  Val  Val  Asp
     8555                8560                8565

Gly  Pro  Ile  Asp  Trp  Asp  Val  Ser  His  Asp  Leu  Glu  Ala  His  Leu
     8570                8575                8580

Ser  Ala  Met  Lys  Ser  Ile  Lys  Met  Thr  Tyr  Gly  Ser  Ala  Leu  Ser
     8585                8590                8595

Gln  Ile  Ala  Leu  Val  Lys  Gln  Asp  Asn  Gly  Asp  Met  Phe  Phe  Thr
     8600                8605                8610

Trp  Ala  Val  His  His  Ser  Val  Phe  Asp  Gly  Trp  Thr  Val  Pro  Ile
     8615                8620                8625

Leu  Phe  Asn  Thr  Leu  Gln  Ala  Val  Tyr  Gln  Gly  Val  Lys  Pro  Ile
     8630                8635                8640

Pro  Pro  Ala  Pro  Tyr  Ala  Arg  Phe  Ile  Lys  Phe  Thr  Met  Gly  Ile
     8645                8650                8655

Asp  Asn  Asp  Asn  Thr  Val  Gln  Tyr  Trp  Lys  Asp  Gln  Leu  His  Asn
     8660                8665                8670

Ala  Lys  Lys  Ala  Thr  Phe  Pro  Pro  Ala  Ala  Ala  Gln  Ser  Gly  Ser
     8675                8680                8685

Val  Gln  Val  Leu  Glu  Thr  Ser  Ile  Asn  Tyr  Thr  Gln  Ala  Pro  Gly
     8690                8695                8700

Ser  Ser  Ile  Thr  Arg  Ala  Thr  Ile  Leu  Arg  Ala  Ala  Trp  Ala  Leu
     8705                8710                8715
```

-continued

| | | | | | | | | | | | |
|---|---|---|---|---|---|---|---|---|---|---|---|
| Val | Leu | Ala | Arg | Tyr | Ser | Glu | Ser | Asn | Asp | Ile | Thr | Phe | Gly | Thr |
| 8720 | | | | | 8725 | | | | | 8730 | | | | |

Thr Ile Ser Gly Arg Gln Ala Pro Val Asp Glu Ile Thr Asn Met
8735 8740 8745

Ala Gly Pro Ala Val Ala Thr Val Pro Val Arg Val Arg Leu Glu
8750 8755 8760

Lys Gln Gln Thr Val Ser Ala Phe Leu Gln Gly Val Gln Ser Gln
8765 8770 8775

Ala Met Lys Met Ile Ser Tyr Glu Gln Tyr Gly Leu Gln Asn Ile
8780 8785 8790

Ser Lys Val Ser Leu Asp Ala Lys Glu Val Cys Asp Phe Thr Ser
8795 8800 8805

Leu Leu Val Ile Gln Pro Val Glu Asp Leu Ala Tyr Leu Asp Asp
8810 8815 8820

Asp Ala Leu Leu Val Asn Ala Gly Pro Glu Leu Thr Gly Glu Thr
8825 8830 8835

Glu Met Met Gln Asn Tyr Phe Ser Tyr Pro Leu Ile Ile Gln Gly
8840 8845 8850

His Leu Tyr Glu Asn Ser Ile Lys Leu Met Leu Val Tyr Asp Thr
8855 8860 8865

Gln Val Ile Ser Thr Gly Lys Met Asp Ala Leu Ser His His Phe
8870 8875 8880

Asn Ala Ala Val Gln Gln Leu Thr Arg Asn Gly Asn Ala Leu Leu
8885 8890 8895

Asp Asn Val Ser Leu Ala Ser Glu Trp Asp Met Glu Lys Ala Ile
8900 8905 8910

Ala Leu Asn Ser Gly Ser Pro Asp Ala Ile Glu Arg Cys Phe His
8915 8920 8925

Asp Met Val Asp Glu Val Ala Leu Val Arg Gly Asp Ala Pro Ala
8930 8935 8940

Leu Ser Gly Trp Asp Lys Ser Phe Thr Tyr Lys Glu Met Thr Glu
8945 8950 8955

Ala Thr Asn Arg Leu Ala His Tyr Leu Val Asn Asp Tyr Gly Val
8960 8965 8970

Lys Val Gly Asp Ile Ile His Val Cys Phe Glu Lys Ser Ala Trp
8975 8980 8985

Phe Ile Ile Ala Thr Leu Ala Ile Asn Lys Ala Gly Ala Ala Trp
8990 8995 9000

Ser Thr Leu Asp Thr Ser His Pro Ile Glu Arg Tyr Gln Lys Ile
9005 9010 9015

Val Ser Gln Thr Gly Ser Lys Leu Ala Leu Ala Ser Ala Ala Asn
9020 9025 9030

Ser Tyr Arg Cys Val Gly Val Leu Pro His Val Ile Glu Leu Thr
9035 9040 9045

Pro Glu Leu Asp Ala Arg Leu Ala Lys Asn Thr Ser Trp Ser Ala
9050 9055 9060

Cys Gly Pro Ala Val Ala Val Ile Pro Ser Asp Met Ala Tyr Ile
9065 9070 9075

Leu Phe Thr Ser Gly Ser Thr Gly Val Pro Lys Gly Val Val Ile
9080 9085 9090

Glu His Ala Thr Leu Cys Thr Ser Gln Thr Ser Leu Ser Gln Thr
9095 9100 9105

Leu Gly Phe His Glu Glu Tyr Lys Val Leu Gln Phe Ser Ser Tyr

-continued

```
                9110                9115                9120
Ser  Phe  Asp  Ala  Ala  Val  Phe  Glu  Ile  Asp  Ser  Thr  Leu  Leu  Thr
     9125                9130                9135

Gly  Ala  Cys  Leu  Tyr  Val  Pro  Ser  Trp  Asp  Glu  Gln  Met  Asn  Glu
     9140                9145                9150

Leu  Val  Gly  Tyr  Ile  Arg  Lys  His  Thr  Ile  Thr  Cys  Thr  Leu  Leu
     9155                9160                9165

Thr  Pro  Thr  Leu  Ala  Arg  Thr  Leu  Arg  Pro  Glu  Asp  Val  Pro  Ser
     9170                9175                9180

Leu  Asn  Met  Leu  Ile  Leu  Gly  Gly  Glu  Ala  Pro  Thr  Arg  Asp  Ile
     9185                9190                9195

Leu  Asp  Ile  Trp  Phe  Gly  Lys  Leu  Lys  Leu  Val  Asn  Gly  Trp  Gly
     9200                9205                9210

Pro  Thr  Glu  Ala  Cys  Val  Ile  Ala  Cys  Leu  His  Ser  Trp  Thr  Ser
     9215                9220                9225

Val  Asp  Glu  Ser  Pro  Ser  Val  Ile  Gly  Arg  Pro  Ile  Gly  Gly  Ser
     9230                9235                9240

Ile  Trp  Val  Val  Asp  Pro  Asp  Ala  Thr  Arg  Met  Ala  Pro  Val
     9245                9250                9255

Gly  Thr  Val  Gly  Glu  Ile  Ala  Val  Gln  Gly  Arg  Asn  Leu  Phe  Arg
     9260                9265                9270

Gly  Tyr  Leu  Ser  Asp  Pro  Val  Lys  Thr  Ala  Ala  Thr  Val  Thr
     9275                9280                9285

Gly  Leu  Pro  Glu  Trp  Val  Pro  Lys  Arg  Asp  Ser  Ser  Ala  His  Trp
     9290                9295                9300

Asp  Arg  Phe  Tyr  Leu  Thr  Gly  Asp  Leu  Gly  Phe  Ile  Asn  Glu  Ala
     9305                9310                9315

Gly  Asn  Val  Glu  Tyr  Cys  Thr  Arg  Lys  Asp  Thr  Gln  Val  Lys  Ile
     9320                9325                9330

Arg  Gly  Gln  Arg  Leu  Glu  Leu  Gly  Glu  Ile  Glu  His  His  Ile  Gln
     9335                9340                9345

Ala  Asn  Leu  Glu  Gly  Val  Arg  Gln  Val  Ala  Val  Asp  Val  Ile  Lys
     9350                9355                9360

Ser  Asp  Ala  Gly  Ser  Thr  Leu  Val  Ala  Phe  Val  Ser  Phe  Ser  Asp
     9365                9370                9375

Ala  Thr  Glu  Pro  Ile  Asp  Ser  Asp  Thr  Ser  Ala  Phe  Leu  Pro  Leu
     9380                9385                9390

Ser  Gly  Asp  Leu  Gln  Ala  Thr  Ile  Thr  Ser  Leu  Val  Gly  Thr  Leu
     9395                9400                9405

Gly  Thr  Leu  Met  Pro  Arg  Tyr  Met  Val  Pro  Ser  Ala  Phe  Ile  Pro
     9410                9415                9420

Cys  Ala  Tyr  Met  Pro  Leu  Ala  Thr  Ser  Thr  Lys  Leu  Asp  Arg  Lys
     9425                9430                9435

Lys  Leu  Lys  Glu  Leu  Ala  Ala  Ser  Leu  Ser  Gln  Asp  Glu  Leu  Ser
     9440                9445                9450

Ile  Tyr  Ser  Leu  Ala  Asn  Glu  Gln  Lys  Ala  Ala  Pro  Gln  Thr  Ala
     9455                9460                9465

Met  Glu  Ser  Arg  Ile  Gln  Ala  Ile  Trp  Ser  Gln  Val  Leu  Asn  Val
     9470                9475                9480

Ser  Ile  Asp  Ser  Ile  Gly  Arg  Asp  Asp  Ser  Phe  Leu  Gln  Ile  Gly
     9485                9490                9495

Gly  Asp  Ser  Ile  Leu  Ala  Ile  Gln  Leu  Val  Ser  Val  Ala  Arg  Asp
     9500                9505                9510
```

```
Ala Asn Val Lys Ile Thr Val Gly Asp Val Phe Asp Asp Pro Arg
9515                9520                9525

Leu Leu Ala Val Ala Ala Lys Ala Thr Glu Leu Asp Asp Asn Gly
9530                9535                9540

Glu Val Ile Ala Asn Ile Glu Pro Phe Gly Leu Leu Asp Glu Pro
9545                9550                9555

Leu Lys Asp Leu Val Leu Ser Gln Arg Ile Gln Glu Gln Tyr Ser
9560                9565                9570

Leu Pro Thr Asp Arg Glu Ile Glu Asp Ala Tyr Pro Cys Thr Lys
9575                9580                9585

Leu Gln Glu Gly Leu Met Ala Leu Ala Val Lys Gln Pro Gly Ser
9590                9595                9600

Tyr Ile Ala Lys Phe Leu Tyr Arg Leu Ser Ser Asn Val Asp Val
9605                9610                9615

Ser His Phe Lys Ala Ser Trp Glu Glu Thr Val Arg Leu Leu Pro
9620                9625                9630

Asn Leu Arg Thr Arg Ile Phe Thr Ala Gly Asn Met Ser Ile Gln
9635                9640                9645

Ala Ile Leu Lys Asp Asp Ile Ser Trp Gln Pro Thr Glu Gly Asp
9650                9655                9660

Ser Leu Arg Ser Tyr Met Gly Ser Ala Gln Asn Phe Glu Met Thr
9665                9670                9675

Tyr Gly Ser Pro Leu Ala Arg Tyr Ala Leu Ile Glu Asp Asn Gly
9680                9685                9690

Asp Thr Tyr Phe Val Leu Ser Met His His Ala Val Phe Asp Gly
9695                9700                9705

Trp Gly Ile Arg Val Leu Met Ser Val Phe His Ser Val Phe Arg
9710                9715                9720

Lys Gln Ala Pro Val Ile Glu Pro Tyr Val Arg Phe Val Gln Tyr
9725                9730                9735

Thr Met Asp Val Asn Asn Asp Glu Ala Ser Asp Tyr Trp Arg Ser
9740                9745                9750

Gln Phe Gln Gly Ala Arg Gln Thr Ile Phe Pro Pro Asn Ala Ser
9755                9760                9765

Ala Ser Glu Ser Arg Lys Asn Ser Thr Gln Thr Val Glu Lys Met
9770                9775                9780

Ile Glu Leu Pro Ser Met Asn Lys Ser Ser Ile Thr Lys Ala Thr
9785                9790                9795

Met Leu Arg Ala Ala Trp Ala Ile Val Leu Ser Arg Tyr Cys Asp
9800                9805                9810

Ser Asp Asp Val Thr Phe Gly Ile Thr Ile Ser Gly Arg Gln Ala
9815                9820                9825

Pro Val His Gly Leu Ile Asn Met Thr Gly Pro Ala Ile Ala Thr
9830                9835                9840

Val Pro Val Arg Val Ala Met Asp Arg Lys Thr Val Val Lys Asp
9845                9850                9855

Tyr Leu Gln Ala Ile Gln Ser Gln Ala Asn Gly Met Val Pro Phe
9860                9865                9870

Glu Gln Phe Gly Leu Gln Asn Ile Ser Arg Leu Ser Ala Glu Ala
9875                9880                9885

Lys Asp Ala Cys Asp Phe Gly Ser Leu Leu Val Ile Gln Pro Ile
9890                9895                9900
```

```
Gln Ser Leu Ala Tyr Val Asp Glu Ser Ala Asp Thr Val Phe Ile
9905                9910                9915

Pro Leu Asp Val Asp Lys Glu Val Thr Asp Thr Val Gln Asn Tyr
9920                9925                9930

Phe Ser Tyr Pro Leu Val Ile Gln Gly His Met His Glu Asp Phe
9935                9940                9945

Ile Asn Leu Val Leu Ile Tyr Asp Thr Gly Val Leu Ala Glu Ser
9950                9955                9960

Gln Met Val Ala Leu Ser His Gln Phe Glu Asn Val Leu Lys Gln
9965                9970                9975

Leu Ala Ser Lys Pro Asp Leu Glu Leu Gly Ser Val Ser Met Ala
9980                9985                9990

Gly Asp Trp Asp Leu Glu Phe Ser Lys Arg Gln Asn Ser Glu Val
9995                10000               10005

Pro Glu Ile Leu Asp Val Cys Val His Gln Leu Ile Glu Lys Gln
10010               10015               10020

Ala Ala Ala Gln Pro Asp Ala Pro Ala Val Leu Ser Trp Asp His
10025               10030               10035

Ser Phe Thr Tyr Lys Gln Leu Asn Glu Ala Ser Asn Arg Leu Ala
10040               10045               10050

His Leu Leu Val Asn Lys Tyr His Val Lys Pro Asn Asp Leu Val
10055               10060               10065

His Val Cys Phe Asp Lys Cys Ala Trp His Phe Val Ala Ile Thr
10070               10075               10080

Ala Ile Asn Lys Val Gly Ala Ala Trp Val Pro Leu Asp Pro Ser
10085               10090               10095

His Pro Glu Met Arg Leu Arg Gln Ile Val Ser Gln Thr Arg Ala
10100               10105               10110

Thr Leu Thr Leu Val Ser Ser Ser Asn Ala Ser Leu Cys Ser Ser
10115               10120               10125

Leu Thr Glu Arg Val Ile Glu Val Asn Ala Ser Leu Asp Asn Glu
10130               10135               10140

Leu Leu Ala Val Glu Ser Gly Glu Tyr Gly Pro Ser Val Asp Val
10145               10150               10155

Ser Ser His Ser Ala Ala Tyr Val Leu Phe Thr Ser Gly Ser Thr
10160               10165               10170

Gly Val Pro Lys Gly Phe Val Met Glu His Gly Ser Val Cys Thr
10175               10180               10185

Ser Gln Ile Ala Ile Ala Arg Arg Leu Gly Leu Gly Pro Asn Val
10190               10195               10200

Arg Met Leu Gln Phe Ala Ala Phe Val Phe Asp Leu Ser Ile Gly
10205               10210               10215

Glu Ile Val Gly Pro Leu Ile Ser Gly Ala Cys Ile Cys Val Pro
10220               10225               10230

Ser Glu Asp Thr Arg Ile Asn Gly Ile Val Ala Phe Ile Asn Glu
10235               10240               10245

Thr Lys Val Thr Trp Ala Tyr Ile Thr Pro Ser Phe Ala Arg Thr
10250               10255               10260

Ile Lys Pro Ser Glu Val Pro His Leu Glu Leu Leu Leu Leu Ala
10265               10270               10275

Gly Glu Ala Val Pro Arg Asp Val Phe Ala Thr Trp Phe Gly Ser
10280               10285               10290

Thr Val Arg Leu Ile Asn Gly Trp Gly Pro Ala Glu Thr Cys Val
```

-continued

```
            10295               10300               10305
    Phe Ser Thr Leu His Glu Trp Lys Ser Ala Asp Glu Ser Pro Leu
            10310               10315               10320
    Thr Val Gly Arg Pro Val Gly Gly Phe Cys Trp Ile Ala Asp Pro
            10325               10330               10335
    Glu Asp Pro Ser Arg Leu Ala Ala Thr Gly Thr Leu Gly Glu Ile
            10340               10345               10350
    Leu Ile Gln Gly Pro Thr Ile Leu Arg Glu Tyr Leu Ser Asp Val
            10355               10360               10365
    Ala Arg Thr Glu Ala Thr Val Ile Lys Ser Leu Pro Glu Trp Ala
            10370               10375               10380
    Pro Phe Arg Asn Glu Pro Gly Trp Asp Arg Met Tyr Lys Ser Gly
            10385               10390               10395
    Asp Leu Gly Phe Tyr Asn Pro Asp Gly Thr Ile Glu Phe Ser Ser
            10400               10405               10410
    Arg Lys Asp Thr Gln Val Lys Ile Arg Gly Leu Arg Val Glu Leu
            10415               10420               10425
    Gly Glu Val Glu His His Val Gln Val Ala Leu Pro Gly Val Lys
            10430               10435               10440
    Gln Ile Ala Val Asp Val Phe Gln Gly Glu Asn Gly Thr Asn Leu
            10445               10450               10455
    Val Ala Phe Phe Ser Phe Asn Asp Glu Thr Arg Gln Ile His Glu
            10460               10465               10470
    Ala Asp Ser Ser Gly Pro Phe Glu Pro Leu Asp Asp Asn Leu Gln
            10475               10480               10485
    Asp Arg Leu Thr Ala Val Val Gly Glu Leu Ser Val Ser Leu Pro
            10490               10495               10500
    Arg Tyr Met Ile Pro Thr Leu Phe Ile Pro Cys Lys Tyr Met Pro
            10505               10510               10515
    Ser Ile Thr Ser Thr Lys Leu Asp Arg Asn Glu Leu Lys Arg Arg
            10520               10525               10530
    Ser Thr Ala Leu Ser Gln Ser Glu Leu Ala Val Tyr Ser Leu Gln
            10535               10540               10545
    Gly Gly Lys Lys Arg Ala Pro Glu Thr Pro Met Glu Ser Leu Ile
            10550               10555               10560
    Gln Ala Leu Trp Ser Asp Ile Leu His Val Pro Ala Asp Ser Ile
            10565               10570               10575
    Gly Arg Asp Asp Ser Phe Leu Gly Leu Gly Gly Asp Ser Ile Thr
            10580               10585               10590
    Ala Ile His Leu Val Ser Ile Ala Arg Glu Lys Gly Ile Gln Leu
            10595               10600               10605
    Val Val Lys Asp Ile Phe Asp Asp Pro Arg Leu Leu Ala Val Ser
            10610               10615               10620
    Ser Lys Ala Lys Glu Met Asp Ile Glu Ala Arg Gln Glu Leu Leu
            10625               10630               10635
    Glu Val Ser Pro Phe Ser Leu Leu Asn Ala Glu Thr His Asp Leu
            10640               10645               10650
    Ala Ile Gly Pro Ser Val Arg Gln Gln Leu Asn Leu Leu Glu Gly
            10655               10660               10665
    Gln Thr Ile Asp Asp Ala Tyr Pro Cys Thr Lys Leu Gln Glu Gly
            10670               10675               10680
    Leu Met Ala Leu Ser Val Thr Gln Pro Gly Ser Tyr Ile Ala Arg
            10685               10690               10695
```

```
Tyr Val Tyr Arg Leu Ser Arg     Gln Val Asp Val Ala     Arg Phe Lys
    10700               10705                 10710

Ser Ala Trp Glu Thr Thr Val     Ala Leu Arg Asp Ile     Leu Arg Thr
    10715               10720                 10725

Arg Ile Val Met Ile Asn Gly     Thr Cys Ile Gln Leu     Val Val Lys
    10730               10735                 10740

Gly Gly Val Val Trp Asp Leu     Ile Asp Ser Glu Ser     Leu Glu Glu
    10745               10750                 10755

Ala Ala His Lys Thr His Ser     His Thr Met Thr Tyr     Gly Ser Gln
    10760               10765                 10770

Leu Ser Arg Thr Ser Ile Tyr     Glu Thr Lys Thr Gly     Asp Lys Tyr
    10775               10780                 10785

Phe Leu Trp Thr Val His His     Ala Ile His Asp Gly     Trp Ser Val
    10790               10795                 10800

Pro Val Ile Phe Ser Thr Leu     Tyr Gln Ala Tyr Glu     Gly Leu Glu
    10805               10810                 10815

Leu Gly Thr Pro Lys Ser Tyr     Ser Gly Phe Ile Arg     Tyr Thr Leu
    10820               10825                 10830

Glu Leu Asp Gln Glu Ala Ala     Ser Asn Tyr Trp Arg     Glu Gln Leu
    10835               10840                 10845

Gln Asp Ala Lys Arg Ala Ser     Phe Pro Lys Thr Gly     Leu Thr Thr
    10850               10855                 10860

Lys Ser Ala Asp Asn Glu Gln     Lys Ile Gln Val Met     Ser Thr Ser
    10865               10870                 10875

Leu Ser Phe Pro Ser Ser Ser     Asn Glu Ala Val Thr     Lys Ala Ser
    10880               10885                 10890

Val Met Arg Ala Ala Trp Ala     Val Val Leu Ala Arg     Tyr Cys Asp
    10895               10900                 10905

Ser Asp Asp Val Cys Phe Gly     Ala Thr Ile Ser Gly     Arg Gln Ala
    10910               10915                 10920

Pro Val His Gly Val Leu Glu     Met Ala Gly Pro Ala     Val Ala Thr
    10925               10930                 10935

Val Pro Val Arg Val Lys Leu     Asp Lys Gly Gln Ser     Ile Pro Gln
    10940               10945                 10950

Phe Leu Gln Val Ile Gln Asn     Gln Ala His Glu Met     Val Pro Tyr
    10955               10960                 10965

Glu Gln Tyr Gly Leu Gln Ser     Ile Ala Lys Leu Gly     Ala Asp Ala
    10970               10975                 10980

Arg Asp Ala Cys Asp Phe Thr     Ser Leu Leu Leu Ile     Gln Pro Val
    10985               10990                 10995

Gln Arg Leu Ser Ser Gly Val     Ala Asp Glu Glu Gly     Leu Leu Val
    11000               11005                 11010

Pro Ala Gln Ser Glu Ile Lys     Asp Met Val Gln Asn     Tyr Tyr Ser
    11015               11020                 11025

Tyr Pro Leu Val Ile Gln Gly     His Val Tyr Asp Asp     Arg Ala Asp
    11030               11035                 11040

Leu Val Leu Ile Tyr Asp Ser     Thr Val Val Pro Glu     Pro Gln Met
    11045               11050                 11055

Thr Ala Leu Ser His His Phe     Asp Asn Val Val Gln     Gln Leu Leu
    11060               11065                 11070

Ala Val Asp Gly Lys Leu Gly     Asp Ile Ser Val Ala     Gly Ser Trp
    11075               11080                 11085
```

| | | | | | | | | | | |
|---|---|---|---|---|---|---|---|---|---|---|
| Asp<br>11090 | Leu | Glu | Leu | Ala | Gln | Lys<br>11095 | Ser | Asn | Gly | Asp<br>11100 | Gly | Pro | Glu | Ile |
| Ile<br>11105 | Glu | Asp | Cys | Ile | His | Ser<br>11110 | Ile | Ile | Glu | Arg<br>11115 | Gln | Val | Gln | Gln |
| Arg<br>11120 | Pro | Asn | Ser | Pro | Ala | Val<br>11125 | Asp | Ala | Trp | Asp<br>11130 | Gly | Arg | Leu | Thr |
| Tyr<br>11135 | Ser | Gln | Leu | Asp | His | Ala<br>11140 | Ala | Asn | Arg | Leu<br>11145 | Ala | His | Leu | Leu |
| Val<br>11150 | Asp | Asp | Tyr | Ala | Val | Gln<br>11155 | Val | Gly | Asp | Ile<br>11160 | Val | His | Val | Cys |
| Phe<br>11165 | Glu | Lys | Ser | Met | Trp | Tyr<br>11170 | Ile | Val | Ala | Ile<br>11175 | Leu | Ala | Ile | Asn |
| Lys<br>11180 | Ala | Gly | Ala | Ala | Trp | Ala<br>11185 | Pro | Leu | Asp | Ser<br>11190 | Ala | His | Pro | Phe |
| Gln<br>11195 | Arg | Leu | Gln | Ala | Val | Ala<br>11200 | Lys | Gln | Thr | Gly<br>11205 | Ala | Lys | Leu | Ala |
| Leu<br>11210 | Ala | Ser | Thr | Ala | Asn | Ala<br>11215 | Gly | Leu | Cys | Lys<br>11220 | Gln | Leu | Val | Asp |
| Arg<br>11225 | Val | Ile | Glu | Val | Ser | Ala<br>11230 | Ala | Leu | Asp | Glu<br>11235 | Lys | Leu | Ser | Ser |
| Asn<br>11240 | Ala | Val | Ser | Ser | Gly | Lys<br>11245 | Gly | Pro | Gln | Val<br>11250 | Asn | Val | Ser | Pro |
| Leu<br>11255 | Asp | Ala | Ala | Tyr | Ile | Leu<br>11260 | Phe | Thr | Ser | Gly<br>11265 | Ser | Thr | Gly | Thr |
| Pro<br>11270 | Lys | Gly | Ile | Val | Met | Gln<br>11275 | His | Gly | Ala | Leu<br>11280 | Cys | Thr | Ser | Gln |
| Thr<br>11285 | Asp | Ile | Ser | Arg | Trp | Leu<br>11290 | Gly | Leu | Asp | His<br>11295 | Thr | Val | Arg | Met |
| Leu<br>11300 | Gln | Phe | Ser | Ser | Phe | Val<br>11305 | Phe | Asp | Val | Ser<br>11310 | Val | Gly | Glu | Ile |
| Met<br>11315 | Glu | Pro | Leu | Met | Asn | Gly<br>11320 | Ala | Cys | Val | Cys<br>11325 | Val | Pro | Ser | Asp |
| His<br>11330 | Met | Arg | Leu | Asn | Ser | Leu<br>11335 | Asp | Val | Phe | Val<br>11340 | Arg | Asp | Phe | Asn |
| Val<br>11345 | Thr | Trp | Ala | Tyr | Leu | Thr<br>11350 | Pro | Ser | Phe | Thr<br>11355 | Arg | Thr | Leu | Lys |
| Pro<br>11360 | Glu | Asp | Phe | Pro | Gly | Leu<br>11365 | Glu | Leu | Leu | Leu<br>11370 | Leu | Ile | Gly | Glu |
| Ala<br>11375 | Val | Thr | Gln | Asp | Val | Leu<br>11380 | Asp | Thr | Trp | Phe<br>11385 | Gly | Leu | Pro | Asn |
| Thr<br>11390 | Arg | Phe | Val | Asn | Ala | Trp<br>11395 | Gly | Pro | Ala | Glu<br>11400 | Thr | Cys | Val | Phe |
| Ser<br>11405 | Thr | Leu | Tyr | Asp | Trp | Gln<br>11410 | Ser | Asn | Thr | Glu<br>11415 | Ser | Pro | Leu | Thr |
| Ile<br>11420 | Gly | Arg | Ala | Val | Gly | Ala<br>11425 | Tyr | Val | Trp | Val<br>11430 | Val | Asp | Ala | Glu |
| Asn<br>11435 | Pro | Gln | Arg | Leu | Ala | Pro<br>11440 | Thr | Gly | Cys | Leu<br>11445 | Gly | Glu | Ile | Val |
| Val<br>11450 | Gln | Gly | Pro | Pro | Leu | Leu<br>11455 | Arg | Glu | Tyr | Leu<br>11460 | Ala | Asp | Pro | Ser |
| Lys<br>11465 | Thr | Ala | Ala | Ala | Thr | Val<br>11470 | Thr | Glu | Leu | Pro<br>11475 | Glu | Trp | Ala | Pro |
| Arg | Arg | Glu | Leu | Thr | Lys | Trp | Asn | Arg | Phe | Tyr | Arg | Thr | Gly | Asp |

-continued

```
            11480             11485             11490
Leu Gly Phe Tyr Ser His Asp Gly Leu Leu His Tyr Ala Ser Arg
            11495             11500             11505
Lys Asp Thr Gln Val Lys Ile Arg Gly Leu Arg Val Glu Leu Gly
            11510             11515             11520
Glu Val Glu His His Ile Arg Ser Ser Leu Asp Gly Val Arg Gln
            11525             11530             11535
Val Ala Val Asp Val Phe Lys Thr Glu Thr Gly Ala Asn Leu Val
            11540             11545             11550
Thr Tyr Phe Cys Phe Thr Asp Asp Thr Lys Thr Pro Gly Pro Asp
            11555             11560             11565
Thr Asp Pro Glu Gly Lys Asp Val Phe Met Ser Ile Asp Ala Ala
            11570             11575             11580
Leu Gln Glu Lys Leu Gly Asn Met Leu Ser Lys Leu Asn Ser Ser
            11585             11590             11595
Leu Pro Gly Tyr Met Ile Pro Thr Leu Phe Ile Pro Cys Asp Tyr
            11600             11605             11610
Met Pro Leu Ile Ser Ser Ala Lys Leu Asp Arg Val Lys Leu Arg
            11615             11620             11625
Arg Ile Thr Ala Glu Leu Ser Gln Asp Gln Leu Glu Ser Tyr Ser
            11630             11635             11640
Leu Leu Asp Thr Asp Lys Arg Ala Pro Glu Thr Glu Met Glu Ile
            11645             11650             11655
Arg Leu Gln Lys Leu Trp Ala Glu Ile Leu Asn Leu Pro Glu Ser
            11660             11665             11670
Ser Ile Gly Arg Asp Asp Asn Phe Leu Arg Ile Gly Gly Asp Ser
            11675             11680             11685
Ile Ala Ala Ile Arg Leu Val Ser Met Ala Arg Asp Val Gly Ile
            11690             11695             11700
Ser Leu Thr Val Asp Asp Ile Phe Asn Asp Ala Arg Leu Ile Ser
            11705             11710             11715
Ile Ala Ala Lys Ala Val Asp Gly Asp Val Tyr Ser Ser Ile Met
            11720             11725             11730
Ala Pro Ile Asp Ala Phe Ser Leu Leu Ser Pro Gly Thr Gly Asp
            11735             11740             11745
Leu Val Leu Pro Ser Ala Leu Pro Glu Gly Gln Val Ile Glu Asp
            11750             11755             11760
Ala Tyr Pro Cys Ser Lys Leu Gln Glu Gly Leu Met Ala Leu Ala
            11765             11770             11775
Val Lys Gln Pro Gly Ser Tyr Ile Ala Lys Tyr Val Tyr Lys Leu
            11780             11785             11790
Pro Glu His Val Asp Val Val Lys Phe Lys Ala Ala Trp Glu Arg
            11795             11800             11805
Thr Val Glu Leu Ser Ser Ile Leu Arg Thr Arg Ile Ile Gln Ile
            11810             11815             11820
Asn Gly Arg Ser Ile Gln Val Val Ile Asn Gly Asp Val Thr Trp
            11825             11830             11835
Asp Glu Thr Asp Gly Ser Leu Gln Pro Cys Leu Ala Arg Ala Gln
            11840             11845             11850
Ser Leu Glu Met Gly Tyr Gly Asp Arg Leu Cys Gln Tyr Ala Leu
            11855             11860             11865
Ile Arg Asp Gly Asn Ser Thr Tyr Phe Met Trp Asn Val His His
            11870             11875             11880
```

```
Ala Val Ile Asp Gly Leu Ser   Thr Gln Asn Ile Leu   Ala Thr Leu
        11885           11890               11895

Phe Arg Leu Tyr Ser Gly Ile   Asp Val Leu Ser Val   Pro Pro Phe
        11900           11905               11910

Ala Arg Phe Ile Lys Tyr Ile   Leu Gly Leu Asp Glu   Glu Val Thr
        11915           11920               11925

Ala Asn Tyr Trp Lys Thr Gln   Leu Ser Asn Ala Arg   Lys Ala Ile
        11930           11935               11940

Phe Pro Pro Ser Lys Asp Ala   Ser Asn Asp Lys Pro   Glu Ala Thr
        11945           11950               11955

Arg Thr Leu Glu Thr Ser Ile   Asp Leu Pro Ser Ser   Ile Lys Asn
        11960           11965               11970

Ser Thr Ile Thr Met Ala Thr   Val Val Arg Ser Ala   Trp Ala Ile
        11975           11980               11985

Val Leu Ala Arg Tyr Cys Glu   Thr Asp Asp Val Thr   Phe Gly Thr
        11990           11995               12000

Thr Ile Ser Gly Arg Gln Ala   Pro Ile Pro Glu Val   Met Glu Met
        12005           12010               12015

Val Gly Pro Ile Ile Ala Thr   Val Pro Val Arg Val   Arg Ile Asp
        12020           12025               12030

Arg Arg Gln Leu Val Ser Glu   Phe Leu Glu Gly Val   Gln Lys Gln
        12035           12040               12045

Ala Val Glu Met Thr Ala Phe   Glu Gln Tyr Gly Leu   Gln Asn Ile
        12050           12055               12060

Ala Arg Leu Ser Glu Asp Ala   Arg Asp Ala Cys Asp   Phe Gly Ser
        12065           12070               12075

Leu Leu Val Val Gln Pro Met   Gln His Leu Gly Gly   Ala Gly Asn
        12080           12085               12090

Asp Asp Ala Ile Leu Val Asp   Ala Ala Ile Pro Asp   Asn Ser Ser
        12095           12100               12105

Ala Glu Ser Leu Arg Asn Tyr   Phe Ser Tyr Pro Leu   Val Ile Gln
        12110           12115               12120

Ala His Leu Tyr Asp Asp His   Val Asn Leu Val Leu   Val Tyr Asp
        12125           12130               12135

Ser Asn Val Ile Pro Glu Ala   Arg Leu Val Ala Leu   Ser His His
        12140           12145               12150

Leu Ser His Val Met Thr Gln   Leu Thr Thr Thr Glu   Pro Ala Ala
        12155           12160               12165

Leu Asp Thr Val Ser Val Ser   Ser Pro Tyr Asp Val   Gln Lys Ala
        12170           12175               12180

Leu Ser Phe Asn Thr Glu Val   Pro Glu Val Ile Asp   Ala Cys Ile
        12185           12190               12195

His Glu Leu Phe Glu Gln Gln   Ala Ser Leu Arg Pro   Gln Ala Pro
        12200           12205               12210

Ala Ile Ala Ala Trp Asp Gly   Asn Leu Thr Tyr Asp   Glu Leu Asn
        12215           12220               12225

Lys Ala Ala Asn Lys Leu Ala   His His Leu Val Asn   Val Tyr Gly
        12230           12235               12240

Val Lys Pro Asn Asp Phe Val   His Val Cys Phe Glu   Lys Ser Ala
        12245           12250               12255

Trp Tyr Ile Val Ser Ile Leu   Ala Ile Asn Lys Ala   Gly Ala Thr
        12260           12265               12270
```

| | | | | | | | | | | | |
|---|---|---|---|---|---|---|---|---|---|---|---|
|Trp|Val|Pro|Leu|Asp|Pro|Ser|His|Pro|Glu|Gln|Arg|Trp|Gln|Ser|

Trp Val Pro Leu Asp Pro Ser His Pro Glu Gln Arg Trp Gln Ser
    12275                12280                12285

Ile Ile Ser Gln Thr Lys Ala Thr Leu Ala Leu Val Ser Pro Gly
    12290                12295                12300

Ser Val Gly Pro Leu Ser Arg Leu Ile Asp Asn Val Val Ala Val
    12305                12310                12315

Asp Ser Asn Leu Asp Ser Leu Leu Pro Glu His Asp Ala Ala Arg
    12320                12325                12330

Gly Leu Ser Val Ser Ile Ser Pro Ser Thr Ala Ala Tyr Val Leu
    12335                12340                12345

Phe Thr Ser Gly Ser Thr Gly Thr Pro Lys Gly Phe Ile Ile Glu
    12350                12355                12360

His Arg Ser Ile Cys Thr Ser Gln Lys Ala Phe Asn Lys Arg Leu
    12365                12370                12375

Arg Tyr His Glu Asn Val Arg Val Leu His Phe Ala Ala Thr Val
    12380                12385                12390

Phe Asp Leu Ser Ile Gly Glu Ile Ile Met Ser Leu Leu Lys Gly
    12395                12400                12405

Ala Cys Leu Cys Val Pro Ser Glu His Thr Arg Leu Asn Gly Ile
    12410                12415                12420

Val Asp Phe Ile Arg Asp Met Lys Ile Asn Trp Leu Tyr Leu Thr
    12425                12430                12435

Pro Ser Phe Leu Arg Thr Ile Asp Pro Ser Gln Val Pro Asn Val
    12440                12445                12450

Glu Leu Ile Leu Leu Ala Gly Glu Ala Val Pro Arg Glu Val Phe
    12455                12460                12465

Glu Thr Trp Tyr Gly Arg Val Arg Leu Leu Asn Gly Trp Gly Pro
    12470                12475                12480

Ala Glu Thr Cys Val Thr Ser Ala Ile His Glu Phe Glu Ser Ala
    12485                12490                12495

Asp Asp Ser Pro Leu Thr Val Gly Arg Pro Val Gly Gly Phe Cys
    12500                12505                12510

Trp Ile Val Asp Pro Glu Asn Pro Gln Leu Leu Ala Pro Thr Gly
    12515                12520                12525

Thr Val Gly Glu Val Val Ile Gln Gly Pro Thr Leu Leu Arg Glu
    12530                12535                12540

Tyr Leu Asp Asn Pro Glu Lys Thr Gln Glu Thr Thr Val Tyr Glu
    12545                12550                12555

Leu Pro Asp Trp Ala Pro Arg Pro Asp Glu Lys Asn Trp Ser Arg
    12560                12565                12570

Phe Tyr Lys Thr Gly Asp Leu Cys Phe Tyr Asn Pro Asp Gly Thr
    12575                12580                12585

Ile Glu Phe Ser Ser Arg Lys Asp Thr Gln Val Lys Ile Arg Gly
    12590                12595                12600

Leu Arg Val Glu Leu Gly Glu Ile Glu Tyr His Val Gln Ala Ser
    12605                12610                12615

Leu Glu Gly Ile Arg Gln Ile Ala Val Asp Val Val Lys Thr Asp
    12620                12625                12630

Asn Gly Ser His Leu Val Ala Tyr Leu Cys Phe Asn Asp Gln Met
    12635                12640                12645

Arg Gln Pro Asp Glu Ala Glu Val Asn Gly Pro Phe Thr Pro Ile
    12650                12655                12660

Asp Ala Glu Leu Gln Asp Lys Leu Ile Gly Ala Val Ser Met Leu

```
            12665               12670               12675

Asn Val Thr Leu Pro Arg Tyr  Met Ile Pro Thr Phe  Tyr Ile Pro
            12680               12685               12690

Cys Ser Tyr Met Pro Tyr Asn  Thr Ser Gly Lys Leu  Asp Arg Arg
            12695               12700               12705

Glu Leu Lys Thr Gln Thr Ala  Ala Leu Gly Gln Ser  Gly Leu Ser
            12710               12715               12720

Asn Phe Ser Leu His Gly Val  Asp Lys Arg Ala Pro  Glu Thr Pro
            12725               12730               12735

Met Glu Ile Glu Leu Gln Lys  Val Trp Ser Thr Val  Leu Ser Leu
            12740               12745               12750

Pro Thr Asp Ser Ile Gly Arg  Asp Asp Ser Phe Leu  Gly Leu Gly
            12755               12760               12765

Gly Asp Ser Ile Met Ala Ile  His Leu Val Ser Ala  Cys Arg Glu
            12770               12775               12780

Ala Gly Ile Ser Leu Thr Val  Lys Asp Val Phe Asp  Asp Pro Arg
            12785               12790               12795

Leu Ser Ala Val Ala Ser Lys  Ala Ser Arg Leu Asp  Ser Thr Asp
            12800               12805               12810

Gln Glu Thr Ser Val Ala Pro  Phe Ser Leu Leu Pro  Asp Arg Ile
            12815               12820               12825

Arg Glu Met Ala Leu Ser Asn  Asp Val Arg Ser Gln  Val Ser Leu
            12830               12835               12840

Ser Ala Ser Asp Ser Val Glu  Asp Ala Tyr Pro Cys  Ser Lys Leu
            12845               12850               12855

Gln Asp Gly Leu Met Ala Leu  Ser Val Lys Gln Arg  Gly Ser Tyr
            12860               12865               12870

Val Ala Gln Tyr Val Tyr Lys  Leu Ser Thr Ser Val  Asp Leu Glu
            12875               12880               12885

Arg Phe Lys Ala Ala Trp Glu  Lys Thr Leu Gln Leu  Cys Ala Asn
            12890               12895               12900

Leu Arg Thr Arg Ile Val Met  Leu Asp Gly Ile Cys  Val Gln Leu
            12905               12910               12915

Leu Ile Asp Gly Pro Ala Glu  Trp Asp Asp Gln Ser  Pro Thr Asp
            12920               12925               12930

Leu Lys Ala Thr Val Asp Ala  Thr Arg Thr Asp Met  Thr Tyr Gly
            12935               12940               12945

Ser Arg Leu Asn Arg Phe Ala  Leu Val Gln Asp Pro  Glu Phe Gly
            12950               12955               12960

Asn His Phe Val Trp Ser Ser  His His Ala Val His  Asp Gly Trp
            12965               12970               12975

Thr Leu Arg Ile Val Met Asn  Thr Leu Tyr Gly Val  Tyr Leu Asn
            12980               12985               12990

Gln Thr Ala Pro Arg Leu Leu  Pro Tyr Ser Ala Phe  Ile Arg Tyr
            12995               13000               13005

Thr Val Asn Ile Asn Ala Asp  Asp Ala Asn Ala Phe  Trp Ser Glu
            13010               13015               13020

Gln Leu Arg Asn Ala Lys Arg  Ala Thr Phe Pro Pro  Met Pro Arg
            13025               13030               13035

Ile Glu Ser His Ala Ser Ile  Thr Arg Met Met Asn  Lys Thr Ile
            13040               13045               13050

Ser Phe Pro Pro Ser Val Lys  Thr Thr Thr Thr Lys  Ala Thr Ile
            13055               13060               13065
```

| | | | | | | | | | | | |
|---|---|---|---|---|---|---|---|---|---|---|---|
| Leu | Arg | Ala | Ala | Trp | Ala | Ile | Leu | Leu | Ala | Arg | Tyr | Cys | Asp | Ser |
| | 13070 | | | | 13075 | | | | | 13080 | | | | |
| Asp | Asp | Ile | Thr | Phe | Gly | Thr | Thr | Ile | Ser | Gly | Arg | Gln | Ala | Pro |
| | 13085 | | | | 13090 | | | | | 13095 | | | | |
| Val | Pro | Gly | Leu | Thr | Glu | Met | Pro | Gly | Pro | Val | Val | Ala | Thr | Val |
| | 13100 | | | | 13105 | | | | | 13110 | | | | |
| Pro | Ile | Arg | Val | Arg | Ile | Asp | Ala | Ser | Gln | Pro | Val | Ser | Arg | Phe |
| | 13115 | | | | 13120 | | | | | 13125 | | | | |
| Leu | Ser | Lys | Ile | Gln | Ser | Gln | Ala | Thr | Asp | Met | Ile | Ala | Tyr | Glu |
| | 13130 | | | | 13135 | | | | | 13140 | | | | |
| Gln | Phe | Gly | Leu | Gln | Asn | Ile | Ile | Lys | Leu | Gly | Ala | Asp | Ala | Lys |
| | 13145 | | | | 13150 | | | | | 13155 | | | | |
| Asp | Ala | Cys | Glu | Phe | Ser | Ser | Leu | Leu | Val | Ile | Gln | Pro | Arg | Thr |
| | 13160 | | | | 13165 | | | | | 13170 | | | | |
| His | Leu | Asp | Ala | Ile | Glu | Ser | Lys | Glu | Ala | Ser | Asp | Pro | Leu | Met |
| | 13175 | | | | 13180 | | | | | 13185 | | | | |
| Thr | Thr | Ser | Val | Ala | Ala | Lys | Gly | Ala | Glu | Gln | Leu | Met | Gln | Gly |
| | 13190 | | | | 13195 | | | | | 13200 | | | | |
| Tyr | Phe | Thr | Tyr | Pro | Leu | Val | Ile | Gln | Gly | His | Val | Phe | Asp | Asp |
| | 13205 | | | | 13210 | | | | | 13215 | | | | |
| Ser | Ile | Glu | Leu | Leu | Thr | Tyr | Asp | Ser | Thr | Ile | Leu | Ser | Glu | |
| | 13220 | | | | 13225 | | | | | 13230 | | | | |
| Val | Ala | Met | Glu | Ala | Leu | Cys | His | Gln | Phe | Asp | Val | Val | Ser | Asn |
| | 13235 | | | | 13240 | | | | | 13245 | | | | |
| Gln | Leu | Val | Lys | Glu | Ser | Asn | Asp | Pro | Leu | Gly | Ser | Val | Ala | Val |
| | 13250 | | | | 13255 | | | | | 13260 | | | | |
| Ser | Gly | Glu | Trp | Asp | Leu | Glu | Gln | Ala | Lys | Lys | Trp | Asn | Val | Glu |
| | 13265 | | | | 13270 | | | | | 13275 | | | | |
| Asn | Pro | Asp | Ile | Leu | Asp | Thr | Cys | Ile | His | Asn | Leu | Ile | Glu | Glu |
| | 13280 | | | | 13285 | | | | | 13290 | | | | |
| Gln | Ala | Arg | Ile | Arg | Pro | Asp | Ala | Pro | Ala | Ile | Cys | Ala | Trp | Asn |
| | 13295 | | | | 13300 | | | | | 13305 | | | | |
| Gly | Glu | Met | Ser | Tyr | Ser | Gln | Leu | Asn | Phe | Ala | Ala | Asn | Lys | Leu |
| | 13310 | | | | 13315 | | | | | 13320 | | | | |
| Ala | His | His | Leu | Leu | Asn | Ala | Gly | Val | Lys | Ser | Glu | Asp | Leu | Val |
| | 13325 | | | | 13330 | | | | | 13335 | | | | |
| His | Val | Cys | Phe | Glu | Lys | Ser | Leu | Trp | Phe | Phe | Ile | Ser | Ile | Val |
| | 13340 | | | | 13345 | | | | | 13350 | | | | |
| Ala | Ile | Asn | Lys | Val | Gly | Ala | Ala | Trp | Val | Pro | Leu | Asp | Ser | Ser |
| | 13355 | | | | 13360 | | | | | 13365 | | | | |
| His | Pro | Glu | Gln | Arg | Leu | Arg | Gln | Val | Val | Ser | Gln | Thr | Arg | Ala |
| | 13370 | | | | 13375 | | | | | 13380 | | | | |
| Gln | Phe | Ala | Leu | Ser | Ser | Pro | Thr | Asn | Ala | Ala | Leu | Cys | Gly | Ser |
| | 13385 | | | | 13390 | | | | | 13395 | | | | |
| Leu | Val | Asp | Lys | Val | Ile | Glu | Val | Ser | Gln | Gly | Leu | Ile | Asp | Ser |
| | 13400 | | | | 13405 | | | | | 13410 | | | | |
| Phe | Pro | Tyr | Asp | Gly | Ala | Asn | Gly | Pro | Ala | Ile | Lys | Val | Pro | Ser |
| | 13415 | | | | 13420 | | | | | 13425 | | | | |
| Ser | Asn | Ala | Ala | Tyr | Val | Leu | Phe | Thr | Ser | Gly | Ser | Thr | Gly | Thr |
| | 13430 | | | | 13435 | | | | | 13440 | | | | |
| Pro | Lys | Gly | Leu | Val | Met | Gln | His | Gln | Ala | Val | Cys | Thr | Ser | Gln |
| | 13445 | | | | 13450 | | | | | 13455 | | | | |

| | | | | | | | | | | | | |
|---|---|---|---|---|---|---|---|---|---|---|---|---|
| Ala | Ala | Ile | Ala | Lys | Arg | Leu | Arg | Leu | Thr | Pro | Asp | Val | Arg | Ile |
| | 13460 | | | | 13465 | | | | | 13470 | | | | |
| Leu | Gln | Phe | Ala | Ala | Tyr | Val | Phe | Asp | Leu | Ser | Ile | Gly | Glu | Ile |
| | 13475 | | | | 13480 | | | | | 13485 | | | | |
| Val | Ala | Pro | Leu | Ile | His | Gly | Ala | Cys | Val | Cys | Val | Pro | Ser | Glu |
| | 13490 | | | | 13495 | | | | | 13500 | | | | |
| Glu | Met | Arg | Met | Asn | Gly | Leu | Lys | Glu | Phe | Ile | Arg | Asp | Ala | Ser |
| | 13505 | | | | 13510 | | | | | 13515 | | | | |
| Ile | Asn | Trp | Val | Phe | Leu | Thr | Pro | Ser | Phe | Val | Arg | Thr | Leu | Arg |
| | 13520 | | | | 13525 | | | | | 13530 | | | | |
| Pro | Glu | Asp | Val | Pro | Asn | Leu | Asp | Leu | Leu | Leu | Leu | Ala | Gly | Glu |
| | 13535 | | | | 13540 | | | | | 13545 | | | | |
| Ala | Val | Gly | Arg | Asp | Ile | Leu | Asp | Thr | Trp | Phe | Gly | Lys | Val | Arg |
| | 13550 | | | | 13555 | | | | | 13560 | | | | |
| Leu | Val | Asn | Gly | Trp | Gly | Pro | Ala | Glu | Thr | Cys | Val | Phe | Ser | Thr |
| | 13565 | | | | 13570 | | | | | 13575 | | | | |
| Leu | His | Glu | Trp | Ala | Ser | Ile | Asp | Glu | Ser | Pro | Leu | Thr | Val | Gly |
| | 13580 | | | | 13585 | | | | | 13590 | | | | |
| Thr | Pro | Val | Gly | Gly | His | Cys | Trp | Ile | Val | Asp | Ala | Glu | Asp | Ser |
| | 13595 | | | | 13600 | | | | | 13605 | | | | |
| Ser | Lys | Leu | Ala | Pro | Ile | Gly | Cys | Leu | Gly | Glu | Val | Val | Leu | Gln |
| | 13610 | | | | 13615 | | | | | 13620 | | | | |
| Gly | Pro | Thr | Leu | Leu | Arg | Glu | Tyr | Leu | Ala | Asp | Pro | Gln | Arg | Ser |
| | 13625 | | | | 13630 | | | | | 13635 | | | | |
| Lys | Glu | Ala | Ile | Ile | Thr | Ser | Leu | Pro | Ser | Trp | Ala | Pro | Lys | Gln |
| | 13640 | | | | 13645 | | | | | 13650 | | | | |
| Asp | Ser | Gln | Pro | Trp | Ser | Arg | Phe | Tyr | Lys | Ser | Gly | Asp | Leu | Cys |
| | 13655 | | | | 13660 | | | | | 13665 | | | | |
| Tyr | Tyr | Asn | Pro | Asp | Gly | Thr | Leu | Glu | Phe | Tyr | Ser | Arg | Lys | Asp |
| | 13670 | | | | 13675 | | | | | 13680 | | | | |
| Thr | Gln | Val | Lys | Ile | Arg | Gly | Leu | Arg | Val | Glu | Leu | Gly | Glu | Val |
| | 13685 | | | | 13690 | | | | | 13695 | | | | |
| Glu | His | His | Ile | Arg | Glu | Ser | Leu | Glu | Gly | Val | Arg | Gln | Val | Ala |
| | 13700 | | | | 13705 | | | | | 13710 | | | | |
| Val | Asp | Val | Leu | Lys | Ser | Glu | Thr | Gly | Thr | Asn | Leu | Val | Ser | Tyr |
| | 13715 | | | | 13720 | | | | | 13725 | | | | |
| Leu | Cys | Phe | Asn | Asp | Asp | Ser | Gln | Pro | Val | Ser | Ser | Glu | Leu | Gln |
| | 13730 | | | | 13735 | | | | | 13740 | | | | |
| Ala | Ser | Asp | Val | Tyr | Leu | Pro | Leu | Asp | Ala | Asp | Ile | Gln | Thr | Arg |
| | 13745 | | | | 13750 | | | | | 13755 | | | | |
| Ile | Thr | Ala | Met | Val | Gly | Glu | Leu | Ser | Val | Thr | Leu | Pro | Arg | Tyr |
| | 13760 | | | | 13765 | | | | | 13770 | | | | |
| Met | Ile | Pro | Thr | Leu | Phe | Ile | Pro | Cys | Lys | Phe | Met | Pro | Val | Ile |
| | 13775 | | | | 13780 | | | | | 13785 | | | | |
| Thr | Ser | Thr | Lys | Leu | Asp | Arg | Lys | Thr | Leu | Lys | Ala | Met | Thr | Ala |
| | 13790 | | | | 13795 | | | | | 13800 | | | | |
| Ser | Leu | Asp | Arg | Asp | Gln | Leu | Ala | His | Tyr | Ser | Leu | Ile | Asp | Ser |
| | 13805 | | | | 13810 | | | | | 13815 | | | | |
| Lys | Lys | Arg | Ala | Pro | Glu | Thr | Glu | Met | Glu | Thr | Arg | Leu | Gln | Val |
| | 13820 | | | | 13825 | | | | | 13830 | | | | |
| Ile | Trp | Ala | Asp | Ile | Leu | Gly | Leu | Pro | Val | Asp | Ser | Ile | Gly | Arg |
| | 13835 | | | | 13840 | | | | | 13845 | | | | |
| Asp | Asp | Ser | Phe | Leu | Gln | Ile | Gly | Gly | Asp | Ser | Ile | Thr | Ala | Ile |

```
         13850              13855              13860
Tyr Leu  Val Ser Lys Ala Arg  Glu Ala Gly Ile Ser  Leu Val Val
         13865              13870              13875
Lys Asp  Val Phe Glu Asp Ser  Arg Leu Leu Ala Val  Ala Ser Lys
         13880              13885              13890
Ala Val  Phe Ser Glu Tyr Ala  Gln Glu Asp Gln Glu  Pro Val Val
         13895              13900              13905
Pro Phe  Ser Leu Leu Asn Glu  Gln Thr Arg Ala Leu  Val Leu Gly
         13910              13915              13920
Gly Glu  Val Arg Lys Leu Cys  Gly Leu Ala Glu Asp  Gln Ile Ile
         13925              13930              13935
Glu Asp  Ala Tyr Pro Cys Thr  Ser Leu Gln Glu Gly  Leu Met Ala
         13940              13945              13950
Leu Thr  Val Lys Gln Pro Gly  Ser Tyr Val Ala Lys  Tyr Val Tyr
         13955              13960              13965
Lys Leu  Ala Pro Phe Val Asp  Val Asp Arg Leu Lys  Ala Ala Trp
         13970              13975              13980
Ser Arg  Thr Val Glu Leu Cys  Gly Asn Met Arg Thr  Arg Ile Val
         13985              13990              13995
Leu Leu  Asn Gly Ser Pro Val  Gln Leu Leu Leu Lys  Glu Asp Ser
         14000              14005              14010
Gln Trp  Gln Ser Leu Glu Ala  Glu Thr Leu Ala Ser  Val Ala Thr
         14015              14020              14025
Ser Ser  Arg Asp Leu Met Met  Gly Tyr Gly Ser Pro  Leu Cys Trp
         14030              14035              14040
Tyr Gly  Ile Leu Glu Glu Asn  Asp Ala Arg Tyr Leu  Val Trp Ser
         14045              14050              14055
Ala His  His Ser Ile Tyr Asp  Gly Trp Val Met Arg  Ile Leu Val
         14060              14065              14070
Thr Thr  Leu Tyr Thr Val Tyr  His Gly Ala Glu Val  Thr Pro Leu
         14075              14080              14085
Gln Pro  Tyr Ser Gly Phe Ile  Lys Tyr Asn Met Glu  Leu Asp Ser
         14090              14095              14100
Ala Ser  Ser Ala Glu Phe Trp  Arg Glu Gln Leu Ser  Gly Ser Lys
         14105              14110              14115
Arg Ala  Ala Phe Pro Ala Arg  Gln Pro Ala Ala Thr  Ser Ser Ser
         14120              14125              14130
Ser Thr  Gln Ile Phe Lys Ser  Ser Ile Ser Ile Gly  Gln Ala Lys
         14135              14140              14145
Gln Ser  Ser Ile Thr Lys Ala  Ser Ile Leu Arg Ala  Ala Trp Ala
         14150              14155              14160
Ile Val  Leu Ala Arg Tyr Cys  Asp Thr Asn Asp Val  Ser Phe Gly
         14165              14170              14175
Ala Thr  Val Ser Gly Arg His  Ala Pro Val Ala Gly  Leu Glu Thr
         14180              14185              14190
Met Pro  Gly Pro Met Ile Ala  Thr Val Pro Val Arg  Val His Leu
         14195              14200              14205
Asp Arg  Ala Ser Thr Lys Ser  Gln Phe Leu Ala Ser  Ile Gln Ser
         14210              14215              14220
Gln Ala  His Glu Met Val Pro  Tyr Glu Gln Phe Gly  Leu Gln Asn
         14225              14230              14235
Ile Ser  Lys Val Ser Gln Asp  Ala Arg Asp Thr Cys  Asp Phe Ser
         14240              14245              14250
```

-continued

```
Ser Leu Leu Val Ile Gln Pro Pro Ala Thr Thr Ile Ser Glu Glu
    14255               14260              14265

Asp Ser Lys Thr Asn Ile Leu Val Tyr Gly Asp Ala Glu Gln Ser
    14270               14275              14280

Arg Thr Asp Asp Ala Met Gln Asn Tyr Phe Asn Tyr Pro Leu Val
    14285               14290              14295

Ile Ile Met Asn Thr Phe Glu Asp His Ile Leu Gln Arg Phe Phe
    14300               14305              14310

Tyr Asn Pro Asp Val Leu Asp Glu Ala Arg Val Ser Ala Leu Ser
    14315               14320              14325

Gln His Ile Gly His Val Val Glu Gln Leu Leu Ala Ser Ser Asp
    14330               14335              14340

Glu Ala Leu Asp Ser Ile Asp Leu Val Ser Asp Trp Asp Val Gln
    14345               14350              14355

His Ala Val Glu Ser Thr Arg Leu Lys Pro Ser Thr Glu Ser Cys
    14360               14365              14370

Thr His Trp Leu Ile Arg Asp Arg Ile Glu Lys Gln Pro Ser Asp
    14375               14380              14385

Pro Ala Ile Ala Ser Trp Asp Gly Asp Leu Thr Tyr Glu Glu Leu
    14390               14395              14400

Gly Val Leu Ala Ser Arg Leu Ala Trp Lys Leu Gln Gly Leu Gly
    14405               14410              14415

Val Gly Pro Glu Ser Leu Ile Pro Leu Cys Phe Pro Lys Ser Thr
    14420               14425              14430

Trp Ala Val Val Ala Met Val Ala Ile Glu Met Ala Gly Gly Ala
    14435               14440              14445

Phe Val Pro Leu Asp Pro Lys Ala Pro Val Ala Arg Leu Arg Gly
    14450               14455              14460

Ile Ile Glu Asp Thr Lys Ser Thr Leu Ala Val Ala Ser Pro Ser
    14465               14470              14475

Cys Gln Asp Ala Leu His Glu Ile Gly Ile Asp Val Leu Ala Val
    14480               14485              14490

Asp Glu Ala Leu Leu Leu Glu Leu Ser Asp Pro Val Glu Gly Ile
    14495               14500              14505

Gln Ser Lys Ala Gly Pro Lys Asp Ala Ser Val Val Leu Phe Thr
    14510               14515              14520

Ser Gly Ser Thr Gly Lys Pro Lys Gly Met Val Ile Gln His Asn
    14525               14530              14535

Ser Leu Cys Ser Ser Gly Asn Ala Tyr Gly Gln Asp Leu Asn Ile
    14540               14545              14550

Gly Pro Gly Thr Arg Val Phe Gln Phe Ser Ala Tyr Thr Phe Asp
    14555               14560              14565

Val Gly Val Leu Asp Cys Leu Val Ser Leu Met Arg Gly Ala Thr
    14570               14575              14580

Ile Cys Ile Pro Ser Asp His Ala Arg Leu Asn Asp Leu Ala Gly
    14585               14590              14595

Ala Met Thr Ala Thr Lys Ala Asn Trp Val Phe Leu Thr Pro Thr
    14600               14605              14610

Val Ala Asp Leu Leu Ser Pro Ala Asp Val Pro Tyr Leu Lys Val
    14615               14620              14625

Leu Cys Leu Gly Gly Glu Ala Ile Ser Lys Lys Cys Ala Asp Arg
    14630               14635              14640
```

-continued

```
Trp Ile Asn Tyr Thr Glu Leu His Gly Leu Tyr Gly Pro Ala Glu
    14645               14650               14655

Ala Ser Ile Cys Ala Trp Asn Pro Ser Val Gly Lys Ser Gly Arg
    14660               14665               14670

Ser Thr Asn Leu Gly Arg Pro Ile Ser Ser Ala Phe Trp Val Val
    14675               14680               14685

Glu Pro Asn Asn His Lys Gln Leu Val Pro Val Gly Cys Ile Gly
    14690               14695               14700

Glu Leu Leu Ile Glu Gly Pro Met Leu Ala Arg Gly Tyr Leu Asn
    14705               14710               14715

Val Ser Ala Asp Val Ala Ser Asn Trp Met Asp Asn Val Asp Trp
    14720               14725               14730

Leu Pro Gly Ser Asp Lys Lys Arg Val Tyr Arg Thr Gly Asp Leu
    14735               14740               14745

Val Arg Arg Asn Ala Asp Gly Thr Phe Glu Phe Met Gly Arg Lys
    14750               14755               14760

Asp Thr Gln Val Lys Leu His Gly Gln Arg Val Glu Leu Gly Glu
    14765               14770               14775

Ile Glu Ala Arg Ile His Glu Phe Leu Pro Ser Asp Met Ala Ala
    14780               14785               14790

Ile Val Ala Val Val Lys Asp Glu His Gly His Asp Ser Leu Leu
    14795               14800               14805

Ala Phe Met Trp Tyr Thr Glu Gly Val Val Ala Ser Arg Ser Thr
    14810               14815               14820

Ala His Leu Met Glu Val Val Ser Asp Glu Ala Arg Ala Thr Ile
    14825               14830               14835

Ser His Val Asp Ser Ser Leu Glu Met Val Leu Pro Ser Tyr Met
    14840               14845               14850

Ile Pro Ser Ser Tyr Leu Val Phe Glu Gly Lys Pro Glu Gln Thr
    14855               14860               14865

Val Asn Gly Lys Val Asp Arg Lys Ala Leu Leu Ala His Ala Gln
    14870               14875               14880

Asn Leu Ser Thr Gln Asp Arg Leu Arg Phe Ala Pro Val Val Gly
    14885               14890               14895

Lys Ser Glu Pro Pro Ser Thr Pro Met Glu Phe Arg Leu Arg Asp
    14900               14905               14910

Leu Trp Ala Gln Val Leu Gln Ile Asp Ala Glu Ser Ile Ser Lys
    14915               14920               14925

Asn Asp Ser Phe Leu Arg Ile Gly Gly Asp Ser Ile Ser Ala Ile
    14930               14935               14940

Gln Leu Val Ser Leu Ala Gln Gln Asn Asn Ile Gly Leu Thr Val
    14945               14950               14955

Ala Ala Ile Phe Asn Asp Pro Arg Leu Ser His Met Ala Glu Ala
    14960               14965               14970

Ala Asn Val Asp Asp Ile Met Pro Val Tyr Glu Thr Lys Pro Phe
    14975               14980               14985

Ser Ile Ile Pro Ala Ser Ala Met Asp Glu Val Leu Ala Gln Val
    14990               14995               15000

Arg Ser Gln Cys Asp Asn Leu Ser Glu Thr Ala Ile Ile Glu Asp
    15005               15010               15015

Ala Tyr Pro Cys Thr Arg Leu Gln Glu Gly Leu Met Ile Leu Ala
    15020               15025               15030

Val Lys Gln Pro Gly Ser Tyr Val Ala Lys His Val Tyr Arg Leu
```

|   |   |   |   |   |   |   |   |   |   |
|---|---|---|---|---|---|---|---|---|---|
|  |  |  |  | 15035 |  |  | 15040 |  | 15045 |
| Ser | Asp | Asn | Ile | Asn | Val | Ala | Arg | Phe | Lys | Arg | Ala | Trp | Asp | Gln |

Ser Asp Asn Ile Asn Val Ala Arg Phe Lys Arg Ala Trp Asp Gln
            15050              15055              15060

Thr Val Glu Ala Cys Ala Ala Leu Arg Thr Arg Ile Val Leu Val
            15065              15070              15075

Asp Gly Ser Ala Tyr Gln Ala Val Ile Lys Asp Ser Val Lys Trp
            15080              15085              15090

Gln Thr Ala Ser Asp Ile Arg Ser Phe Ser Met Ser Pro Asp Asn
            15095              15100              15105

Thr Gln Met Gly Tyr Gly Ser Pro Leu Cys Arg Tyr Ala Leu Ile
            15110              15115              15120

Glu Gln Asn Gly Glu Arg Tyr Phe Val Trp Asn Thr His His Thr
            15125              15130              15135

Val Tyr Asp Gly Trp Thr Leu Pro Leu Ile Met Gly Thr Leu His
            15140              15145              15150

Ala Phe Tyr Ser Gly Thr Asp Ala Pro Pro Leu Leu Pro Tyr Ser
            15155              15160              15165

Gly Phe Val Lys Tyr Val Thr Glu Met Asp Ser Ala Ala Ala Ser
            15170              15175              15180

Glu Tyr Trp Thr Gln Gln Leu Glu Gly Ala Arg Lys Thr Thr Phe
            15185              15190              15195

Pro Pro Gly Ala Glu Ala Val Lys Thr Lys Lys Ser Gln Met Ser
            15200              15205              15210

Thr Arg Val Met Arg Asn Thr Val Gln Phe Pro Arg Ser Thr Asn
            15215              15220              15225

Thr Ser Ile Thr Lys Ala Ser Val Leu Arg Ala Ala Trp Ala Ile
            15230              15235              15240

Val Leu Ala Arg Tyr Asn Asp Thr Asp Asp Val Cys Phe Gly Ser
            15245              15250              15255

Thr Val Ser Gly Arg His Ala Pro Val Pro Gly Ile Glu Arg Met
            15260              15265              15270

Pro Gly Leu Ala Val Ala Thr Val Pro Val Arg Val Lys Leu Asp
            15275              15280              15285

Gln Lys Gln Ser Leu Asp Ala Phe Met Glu Gly Ile Gln Ser Gln
            15290              15295              15300

Ala Ser Glu Met Val Ala Tyr Glu Gln Phe Gly Ile Gln Asn Ile
            15305              15310              15315

Ser Lys Leu Asn Ala Lys Ala Lys Glu Ala Cys Asp Phe Thr Ser
            15320              15325              15330

Leu Leu Val Val Gln Pro Thr Gln His Ile Thr Ser Thr Gly Asn
            15335              15340              15345

Ala Ser Glu Glu Ala Leu Leu Thr Ala Ala Ala Thr Asp Asp Ile
            15350              15355              15360

Ala Ala Asp Glu Met Leu Asp Asn Tyr Phe Asn Tyr Pro Leu Val
            15365              15370              15375

Leu Gln Cys Tyr Val Leu Asp Asn Gln Val Glu Leu Val Leu Val
            15380              15385              15390

Tyr Asp Cys Asp Val Ile Ala Glu His Gln Leu Val Gly Leu Ser
            15395              15400              15405

His Gln Phe Gln His Val Val Thr Gln Leu Leu Ser Gln Asp Gly
            15410              15415              15420

Pro Leu Ser Ala Val Ser Val Ala Ser Glu Trp Asp Leu Glu Phe
            15425              15430              15435

-continued

| | | | | | | | | | |
|---|---|---|---|---|---|---|---|---|---|
| Ala | Gln 15440 | Ala | Ser | Asn | His 15445 | Asp | Glu | Pro | Ala | Val 15450 | Val | Asp | Asp | Cys |
| Ile | His 15455 | Asn | Met | Ile | Glu 15460 | Gln | Arg | Ala | Leu | Met 15465 | Asn | Pro | Asn | Ala |
| Glu | Ala 15470 | Val | Ser | Ala | Trp 15475 | Asp | Ala | Arg | Phe | Thr 15480 | Tyr | Ala | Glu | Leu |
| Asp | Arg 15485 | Ser | Ala | Asn | Ile 15490 | Leu | Ala | Asn | His | Leu 15495 | Ile | Gln | Ser | Arg |
| Gly | Val 15500 | Gln | Val | Gly | Asp 15505 | Leu | Val | His | Val | Cys 15510 | Phe | Glu | Lys | Ser |
| Ala | Trp 15515 | Tyr | Val | Val | Ser 15520 | Ile | Leu | Ala | Ile | Asn 15525 | Lys | Ala | Gly | Ala |
| Ala | Trp 15530 | Ile | Pro | Leu | Asp 15535 | Pro | Ser | His | Pro | Ala 15540 | Glu | Arg | His | Gln |
| Gln | Val 15545 | Val | Gly | Gln | Thr 15550 | Arg | Ser | Arg | Leu | Ala 15555 | Leu | Thr | Ser | Pro |
| Ala | Asn 15560 | Ala | Ala | Lys | Cys 15565 | Ala | Asn | Leu | Val | Ala 15570 | Asn | Val | Leu | Glu |
| Val | Thr 15575 | Arg | Gly | Leu | Leu 15580 | Asp | Asp | Leu | Glu | Thr 15585 | Gln | Val | Asn | His |
| Ala | Arg 15590 | Pro | Val | Thr | Ser 15595 | Val | Gly | Pro | Gln | Asp 15600 | Val | Ala | Tyr | Ile |
| Leu | Phe 15605 | Thr | Ser | Gly | Ser 15610 | Thr | Gly | Val | Pro | Lys 15615 | Gly | Val | Val | Met |
| Glu | His 15620 | Gly | Ala | Leu | Cys 15625 | Ser | Ser | Gln | Thr | Ser 15630 | Ile | Ser | Lys | Arg |
| Leu | Gly 15635 | Tyr | Ala | Pro | Gly 15640 | Val | Arg | Met | Leu | Gln 15645 | Phe | Ala | Ser | Phe |
| Val | Phe 15650 | Asp | Ala | Cys | Ile 15655 | Gly | Glu | Ile | Ile | Ala 15660 | Pro | Leu | Ile | Ser |
| Gly | Ser 15665 | Cys | Val | Cys | Ile 15670 | Pro | Ser | Trp | Glu | Thr 15675 | Gln | Met | Asn | Ser |
| Leu | Thr 15680 | Ser | Tyr | Ile | Arg 15685 | Glu | Glu | Asn | Val | Thr 15690 | Trp | Ala | Met | Leu |
| Thr | Pro 15695 | Ser | Phe | Ala | Arg 15700 | Thr | Met | Asp | Pro | Ser 15705 | Glu | Val | Pro | Cys |
| Leu | Glu 15710 | Leu | Leu | Ile | Leu 15715 | Ile | Gly | Glu | Ala | Val 15720 | Ser | Arg | Asp | Val |
| Phe | Glu 15725 | Leu | Trp | Phe | Gly 15730 | Lys | Leu | Arg | Leu | Leu 15735 | Asn | Gly | Trp | Gly |
| Pro | Thr 15740 | Glu | Thr | Cys | Val 15745 | Phe | Gly | Ala | Leu | His 15750 | Glu | Trp | Gln | Ser |
| Ile | Asp 15755 | Glu | Ser | Gln | Met 15760 | Thr | Ile | Gly | Gln | Pro 15765 | Val | Gly | Gly | Tyr |
| Cys | Trp 15770 | Ile | Val | Asp | Pro 15775 | Glu | Asp | Pro | Gln | Arg 15780 | Leu | Ala | Pro | Thr |
| Gly | Thr 15785 | Phe | Gly | Glu | Val 15790 | Val | Ile | Gln | Gly | Pro 15795 | Asn | Leu | Leu | Arg |
| Glu | Tyr 15800 | Leu | Ala | Asp | Glu 15805 | Val | Lys | Thr | Ala | Ser 15810 | Ser | Thr | Val | Pro |
| Val | Leu 15815 | Pro | Glu | Trp | Ala 15820 | Pro | Asn | Arg | His | Leu 15825 | Arg | His | Trp | Asn |

```
Arg Phe Tyr Lys Thr Gly Asp   Leu Ala Met Tyr   Asn Pro Asp Gly
    15830               15835               15840

Thr Ile Gln Tyr Tyr Ser Arg   Lys Asp Thr Gln   Val Lys Ile Arg
    15845               15850               15855

Gly Leu Arg Val Glu Leu Gly   Glu Val Glu His   His Val Arg Gln
    15860               15865               15870

Asn Leu Asp Ala Val Gln Gln   Val Ala Val Asp   Val Phe Lys Thr
    15875               15880               15885

Asp Ser Gly Val Asn Leu Val   Ser Phe Val Cys   Phe Asn Asn Asp
    15890               15895               15900

Thr Leu Pro Ala Ser Met Thr   Gly Asp Ile Thr   Ser Lys Asp Ile
    15905               15910               15915

Ile Thr Pro Leu Thr Gly Glu   Leu Lys Glu Ser   Ile Asn Ser Leu
    15920               15925               15930

Leu Gly Arg Leu Asn Val Leu   Leu Pro Gly Tyr   Met Ile Pro Thr
    15935               15940               15945

Leu Phe Ile Pro Phe Lys Ala   Met Pro Leu Val   Thr Ser Gly Lys
    15950               15955               15960

Leu Asp Arg Lys Leu Leu Leu   Lys Leu Thr Ala   Ser Leu Glu Lys
    15965               15970               15975

Glu Gln Leu Glu Glu Tyr Ala   Leu Thr Gly Gly   Asp Lys Arg Glu
    15980               15985               15990

Pro Glu Thr Glu Leu Glu Tyr   Arg Leu Gln Glu   Leu Trp Ala Thr
    15995               16000               16005

Leu Leu Asn Met Pro Ala Ser   Ala Ile Gly Arg   Asp Asp Ser Phe
    16010               16015               16020

Leu Arg Ile Gly Gly Asp Ser   Ile Ala Ala Ile   Arg Leu Val Ser
    16025               16030               16035

Lys Ala Arg Glu Ser Gly Ile   Ser Leu Ser Val   Asp Asp Ile Phe
    16040               16045               16050

Ser Asp Pro Arg Leu Leu Ala   Val Ala Ala Lys   Ala Thr Asp Ser
    16055               16060               16065

Ala Ala Glu Ile Glu Asp Ile   Val Pro Ile Glu   Pro Phe Ser Leu
    16070               16075               16080

Ile Asn Glu Ala Gln His Ser   Met Val Leu Ser   Ser Ser Ser Asp
    16085               16090               16095

Leu His Leu Ser Ala Asp Met   Glu Ile Glu Asp   Ala Tyr Pro Cys
    16100               16105               16110

Ser Lys Leu Gln Glu Gly Leu   Met Ala Leu Ala   Val Lys Gln Pro
    16115               16120               16125

Gly Ser Tyr Ile Ala Lys Tyr   His Tyr Arg Leu   Pro Ser His Ile
    16130               16135               16140

Asp Val Ala Arg Phe Lys Arg   Ala Trp Glu Met   Thr Val Glu Thr
    16145               16150               16155

Cys Ala Asn Met Arg Thr Arg   Ile Ile Thr Val   Gly Gly Met Thr
    16160               16165               16170

Ile Gln Thr Val Ile Lys Asn   Asp Ile Ala Trp   Glu Asp Thr Thr
    16175               16180               16185

Gly Met Thr Leu Met Ser Tyr   Val Arg Ala Thr   Gln Lys Thr Glu
    16190               16195               16200

Met Gly Tyr Gly Ser Arg Leu   Cys Arg Tyr Ala   Leu Val Glu Glu
    16205               16210               16215

Glu Gly Gln Asp Val Gln Phe   Val Trp Ser Ile   His His Ala Val
```

```
                16220              16225              16230
Phe Asp Gly Trp Thr Thr Pro Ile Ile Met Ser Ala Leu His Ser
                16235              16240              16245
Ala Tyr Arg Gly Leu Glu Met Pro Lys Ile Glu Asn Tyr Ala Arg
                16250              16255              16260
Phe Ile Lys Tyr Thr Met Asp Ile Asn Tyr Gln Asp Ala Ser Glu
                16265              16270              16275
Tyr Trp Met Arg Glu Leu His Asp Val Lys Lys Ala Thr Phe Pro
                16280              16285              16290
Ser Ser Val Ser Val Glu Ala Ser Asp Lys Gly Asp Val Thr Lys
                16295              16300              16305
Phe Met Glu Thr Arg Ile Asp Leu Pro Arg Asn Asp Val Gly Val
                16310              16315              16320
Thr Lys Ala Thr Ile Leu Arg Ala Ala Trp Ala Val Val Leu Ala
                16325              16330              16335
Arg Tyr Cys Asp Thr Asp Asp Val Cys Phe Gly Thr Thr Ile Ser
                16340              16345              16350
Gly Arg Gln Ala Pro Ile Ala Gly Leu Met Glu Met Pro Gly Pro
                16355              16360              16365
Val Ile Ala Thr Val Pro Ile Arg Val Arg Leu Asp Arg Gln Lys
                16370              16375              16380
Thr Val Asp Asp Phe Leu Gln Gly Val Gln Asp Gln Ala Thr Lys
                16385              16390              16395
Met Val Ala Tyr Glu Gln Phe Gly Leu Gln Ser Ile Gly Lys Leu
                16400              16405              16410
Ser Ala Asp Ala Lys Asp Ala Cys Asp Phe Ser Ser Leu Leu Val
                16415              16420              16425
Ile Gln Pro Leu Gln Thr Leu Ile Tyr Asn Asp Asp Asp Glu Gln
                16430              16435              16440
Ala Leu Leu Ala Ala Ser Ala Ala Ala Ala Asp Thr Lys Asp Gln
                16445              16450              16455
Val Met Gln Asn Tyr Phe Ser Tyr Pro Leu Val Ile Gln Ala His
                16460              16465              16470
Leu His Asp Asp His Ile Ser Leu Val Leu Ile Tyr Asn Ser Met
                16475              16480              16485
Ala Leu Pro Glu Ala Gln Leu Phe Ala Leu Ser Gln Gln Phe Lys
                16490              16495              16500
His Val Val Glu Gln Leu Val Leu Glu Pro Gln Leu Ser Leu Gly
                16505              16510              16515
Ser Leu Ser Ile Ala Ser Gly Trp Asp Val Ala Gln Ser Leu Lys
                16520              16525              16530
Phe Asn Ala Glu Ile Pro Glu Ile Val Asp Ser Cys Val His Gln
                16535              16540              16545
Leu Ile Glu Arg Gln Ala Glu Ile Arg Pro Asp Ala Met Ala Ile
                16550              16555              16560
Arg Ala Trp Asp Ala Glu Leu Thr Tyr Arg Glu Phe Asn Arg Ala
                16565              16570              16575
Ala Asn Arg Leu Ala Asn Tyr Leu Thr Ala Ser Tyr Asp Ile Lys
                16580              16585              16590
Pro Asp Glu Leu Ile His Val Cys Phe Glu Lys Ser Ala Trp Phe
                16595              16600              16605
Phe Val Ser Ile Leu Ala Ile Asn Lys Ser Gly Ala Ala Trp Val
                16610              16615              16620
```

```
Pro Leu Asp Pro Ser His Pro Glu Gln Arg Leu Arg Gln Val Val
16625               16630               16635

Ser Gln Thr Arg Ala Arg Ile Ala Leu Thr Ser Pro Ser Asn Arg
16640               16645               16650

Asp Leu Val Thr Gly Leu Val Asp Ser Val Val Thr Val Asp Ser
16655               16660               16665

Gln Leu Asp Val Gln Leu Ser Lys Val Asp Glu His Ser Gln Lys
16670               16675               16680

Gly Pro Glu Thr Ala Val Ser Ser Asp Asn Ala Val Tyr Val Leu
16685               16690               16695

Phe Thr Ser Gly Ser Thr Gly Thr Pro Lys Gly Leu Val Met Gln
16700               16705               16710

His Gly Ser Val Cys Thr Ser Gln Thr Ala Ile Val Lys Arg Leu
16715               16720               16725

Gly Leu Thr Pro Asp Val Arg Met Leu Gln Phe Ala Ala Phe Val
16730               16735               16740

Phe Asp Leu Ser Ile Gly Glu Ile Ile Ala Pro Leu Ile Thr Gly
16745               16750               16755

Ala Cys Leu Cys Ile Pro Ser Asp His Thr Arg Met Asn Gly Leu
16760               16765               16770

Thr Gln Tyr Ile Arg Asp Thr Gly Ile Asn Trp Ala Phe Leu Thr
16775               16780               16785

Pro Ser Phe Ile Arg Thr Ile Asn Pro Ala Glu Val Pro Gly Leu
16790               16795               16800

Glu Leu Val Leu Leu Ala Gly Glu Ala Val Pro Arg Asp Val Leu
16805               16810               16815

Thr Thr Trp Phe Gly Lys Val Arg Leu Val Asn Gly Trp Gly Pro
16820               16825               16830

Ala Glu Thr Cys Val Phe Ser Thr Leu His Glu Trp Gln Ser Val
16835               16840               16845

Asn Glu Ser Pro Leu Thr Val Gly Arg Pro Val Gly Gly Phe Cys
16850               16855               16860

Trp Val Val Asp Pro Glu Asp Pro His Arg Leu Ala Pro Thr Gly
16865               16870               16875

Thr Leu Gly Glu Val Val Ile Gln Gly Pro Thr Leu Leu Arg Glu
16880               16885               16890

Tyr Leu Ser Asp Pro Glu Arg Thr Gln Ala Ser Thr Val Tyr Asp
16895               16900               16905

Leu Pro Lys Trp Ala Pro Arg Pro Asp Ser Arg His Trp Asn Lys
16910               16915               16920

Phe Tyr Lys Ser Gly Asp Leu Cys Tyr Tyr Asn Gln Asp Gly Thr
16925               16930               16935

Ile Glu Phe Ser Thr Arg Lys Asp Thr Gln Ile Lys Ile Arg Gly
16940               16945               16950

Leu Arg Val Glu Leu Gly Glu Val Gln His His Ile Gln Gln Ala
16955               16960               16965

Leu Pro Ser Ala Arg Gln Val Ala Val Asp Val Tyr Arg Gly Glu
16970               16975               16980

Asn Gly Thr Asn Leu Val Ala Tyr Leu Cys Phe Ser Asp Asp Thr
16985               16990               16995

Arg Thr Ala Gly Ile Ser Gly Gly Ala Ser Asp Gly Pro Phe Leu
17000               17005               17010
```

```
Pro Leu Ser Glu Asp Leu Gln     Ser Thr Leu Ala     Val Val Gly
    17015           17020               17025

Gln Leu Ser Ile Ser Leu Pro     Arg Tyr Met Ile     Thr Met Phe
    17030           17035               17040

Ile Pro Cys Ser Tyr Met Pro     Phe Ile Thr Ser     Thr Lys Leu Asp
    17045           17050               17055

Arg Asn Glu Leu Lys Lys Leu     Thr Ser Ser Leu     Asp Lys Ala Gln
    17060           17065               17070

Ile Ala Gln Tyr Ser Leu Leu     Gly Gly Lys Lys     Arg Ser Pro Glu
    17075           17080               17085

Thr Pro Met Glu Val Phe Leu     Gln Lys Leu Trp     Ser Glu Leu Leu
    17090           17095               17100

Gly Val Pro Val Glu Ser Ile     Gly Arg Asp Asp     Ser Phe Leu Gly
    17105           17110               17115

Leu Gly Gly Asp Ser Ile Thr     Ala Ile His Met     Val Ser Ala Ala
    17120           17125               17130

Arg Glu Ser Gly Val Ser Leu     Ala Val Lys Glu     Ile Phe Asp Asp
    17135           17140               17145

Pro Arg Leu Ser Ala Val Ala     Ser Lys Ala Arg     Glu Ile Glu Gln
    17150           17155               17160

Asp Glu Gln Thr Ser Leu Val     Asp Ala Thr Pro     Phe Tyr Leu Val
    17165           17170               17175

Asp Glu Ser Ile Arg Gln Leu     Ala Ile Gly Asp     Glu Val Arg Gln
    17180           17185               17190

Leu Cys Asp Leu Thr Asn Asn     Glu Glu Val Glu     Asp Ala Tyr Pro
    17195           17200               17205

Val Thr Met Phe Gln Glu Gly     Leu Met Ala Leu     Ser Ala Lys Gln
    17210           17215               17220

Pro Gly Ser Tyr Ile Ala Lys     Tyr Ala Tyr Arg     Leu Ser Glu His
    17225           17230               17235

Val Asp Val Ala Arg Phe Lys     Ala Ala Trp Glu     Thr Thr Val Ser
    17240           17245               17250

Leu Cys Pro Thr Leu Arg Thr     Arg Leu Val Leu     Leu Asn Gly Lys
    17255           17260               17265

Cys Thr Gln Val Val Val Lys     Gly Glu Thr Gly     Trp Gln Ser Gln
    17270           17275               17280

Glu His Thr Asp Val His Ala     Ala Ile Gln Asp     Ala Gln Thr Ala
    17285           17290               17295

Glu Met Thr Tyr Gly Ser His     Leu Ser Gln Ala     Ile Met Val Asn
    17300           17305               17310

Asp Ala Ser Asn Gly Asn Asn     Tyr Phe Ile Trp     Thr Val His His
    17315           17320               17325

Ala Val His Asp Gly Trp Thr     Val Arg Leu Ile     Met Thr Thr Leu
    17330           17335               17340

Gln Asn Ala Tyr Asn Asn Leu     Glu Val Pro Asp     Leu Lys Pro Tyr
    17345           17350               17355

Ser Gly Phe Ile Gln Tyr Leu     Gly Ser Ile Lys     Ala Asp Asp Thr
    17360           17365               17370

Ile Asn Phe Trp Thr Gln Gln     Leu Gln Gly Ala     Ser Lys Ala Ser
    17375           17380               17385

Tyr Pro Pro Ser Lys Pro Ala     Ser Ala Pro Glu     Ser Val Thr Arg
    17390           17395               17400

Leu Ile Thr Lys Thr Ile Gln     Ala Ser Ser Ser Ala     Asn Ala Ala
```

-continued

```
            17405              17410              17415
Ile Thr Lys Ala Thr Ile Met Arg Ala Thr Trp Ala Ile Leu Leu
    17420              17425              17430
Ala Arg Tyr Cys Asp Thr Asp Asp Val Thr Leu Gly Thr Ser Ile
    17435              17440              17445
Ser Gly Arg Gln Ala Pro Val Ser Gly Leu Met Asp Met Pro Gly
    17450              17455              17460
Pro Val Val Ala Thr Val Pro Val Arg Val Arg Leu Asp Arg Ser
    17465              17470              17475
Gln Thr Ile Ser Lys Tyr Leu Gln Ala Ile Gln Ser Gln Ala His
    17480              17485              17490
Glu Met Val Pro Tyr Glu Gln Tyr Gly Leu Thr Asn Ile Gly Lys
    17495              17500              17505
Ile Asn Ser Asp Phe Arg Asp Val Cys Asp Phe Thr Ser Leu Leu
    17510              17515              17520
Val Val Gln Pro Arg Thr His Leu Asp Ser Arg Ser Lys Gly Thr
    17525              17530              17535
Ser Thr Glu Ser Asp Ala Ser Ser Ala Ala Leu Leu Leu Pro Ala
    17540              17545              17550
Asn Val Glu Gly Gly Ser Val Glu Asp Leu Met Gln Gly Tyr Phe
    17555              17560              17565
Ser Tyr Pro Leu Val Ile Gln Gly His Leu Met Ser Asp Ser Ile
    17570              17575              17580
Glu Leu Val Ile Thr Tyr Asp Ser Ser Val Leu Ser Glu Ala Ser
    17585              17590              17595
Met Glu Ala Met Cys His Gln Phe Glu His Val Ala Ser Gln Leu
    17600              17605              17610
Phe Ala Asp Glu Gly Arg Thr Leu Gly Asp Leu Thr Val Ala Ser
    17615              17620              17625
Ser Trp Asp Leu Glu Arg Ala Arg Ala Phe Asn Ser Glu Ala Pro
    17630              17635              17640
Met Val Met Asp Thr Cys Ile His His Leu Ile Glu Ala Gln Val
    17645              17650              17655
Arg Lys Thr Pro Asp Leu Pro Ala Val Trp Ala Trp Asp Gly Gln
    17660              17665              17670
Leu Thr Tyr Arg Gln Leu Asn Glu Ala Ala Asn Arg Leu Ala His
    17675              17680              17685
Tyr Leu Ile Asn Glu His Asn Val Gln Val Glu Asp Leu Val His
    17690              17695              17700
Val Cys Phe Glu Lys Ser Val Trp His Trp Val Ser Val Leu Ala
    17705              17710              17715
Ile Asn Lys Ala Gly Ala Val Trp Val Pro Leu Asp Pro Ser His
    17720              17725              17730
Pro Glu Gln Arg Leu Arg Gln Val Ala Ser Gln Thr Gln Ser Thr
    17735              17740              17745
Leu Ala Leu Thr Ser Asp Thr Thr Lys Ser Leu Leu Ser His Ile
    17750              17755              17760
Ile Asp Arg Val Val Glu Val Ser Pro Ala Leu Phe Glu Gln Ile
    17765              17770              17775
Asp Val Arg Leu Gly Glu Lys Glu Pro Gln Val Ser Val Ser Ala
    17780              17785              17790
Ser Asn Ala Ala Tyr Ile Leu Phe Thr Ser Gly Ser Thr Gly Thr
    17795              17800              17805
```

```
Pro Lys Gly Leu Val Met Thr His Gly Ala Leu Thr Thr Ser Gln
    17810             17815                 17820

Thr Ala Ile Lys Lys Arg Met Gly Thr Gly Thr His Thr Arg Ala
    17825             17830                 17835

Leu Gln Phe Ala Ser Tyr Val Phe Asp Met Ser Val Gly Glu Gly
    17840             17845                 17850

Phe Val Gln Leu Ile Ser Gly Ala Cys Ile Phe Ile Pro Ser Glu
    17855             17860                 17865

His Thr Arg Met Asn Gly Leu Lys Gln Phe Ile Thr Glu His Arg
    17870             17875                 17880

Ile Asn Ser Leu Trp Leu Thr Pro Ser Phe Ile Arg Thr Leu Ser
    17885             17890                 17895

Pro Glu Gln Val Pro Thr Val Asp Phe Val Phe Leu Ala Gly Glu
    17900             17905                 17910

Ala Ile Pro Arg Asp Val Phe Thr Thr Trp Cys Thr Lys Val Arg
    17915             17920                 17925

Leu Trp Asn Gly Trp Gly Pro Ala Glu Thr Cys Val Val Ser Ser
    17930             17935                 17940

Leu His Glu Phe Thr Ser Leu Asp Glu Ser Pro Leu Thr Ile Gly
    17945             17950                 17955

Arg Pro Ile Gly Gly Tyr Cys Trp Ile Val Asp Pro Thr Asp His
    17960             17965                 17970

Thr Lys Leu Ala Pro Ile Gly Thr Met Gly Glu Val Val Ile Gln
    17975             17980                 17985

Ser Pro Thr Ile Leu Arg Glu Tyr Leu Ala Asp Val Glu Arg Thr
    17990             17995                 18000

Lys Ala Ser Thr Val Tyr Glu Leu Pro Glu Trp Ala Pro Tyr Arg
    18005             18010                 18015

Asp Gln Ala Pro Trp Ser Arg Phe Phe Lys Ser Gly Asp Leu Ala
    18020             18025                 18030

Ser Tyr Asn Pro Asp Gly Thr Leu Glu Phe Ala Ser Arg Lys Asp
    18035             18040                 18045

Thr Gln Val Lys Ile Arg Gly Leu Arg Val Glu Leu Gly Glu Ile
    18050             18055                 18060

Glu His His Val Arg Ser Ser Leu Thr Asp Ala Arg Gln Val Ala
    18065             18070                 18075

Val Asp Val Phe Arg Thr Asp Ala Gly Thr Arg Leu Ile Ala Tyr
    18080             18085                 18090

Phe Cys Tyr Ser Asp Val Thr Arg Thr Ala Gly Asn Ser Gln Pro
    18095             18100                 18105

Asp Asn Asp Asp Ile Phe Leu Pro Val Thr Glu Asp Leu Gln Arg
    18110             18115                 18120

Gln Leu Thr Ser Met Val Ser Gln Leu His Val Thr Leu Pro Arg
    18125             18130                 18135

Tyr Met Val Pro Ser Leu Phe Ile Pro Cys Arg Tyr Met Pro Phe
    18140             18145                 18150

Ile Thr Ser Thr Lys Leu Asp Arg Asn Arg Leu Lys Lys Leu Val
    18155             18160                 18165

Ser Glu Leu Ser Gln Glu Asp His Ala Ala Tyr Ser Leu Ser Asn
    18170             18175                 18180

Gly Val Lys Arg Met Pro Asp Thr Glu Met Glu Ala Arg Met Gln
    18185             18190                 18195
```

```
Glu Leu Trp Ser Val Val Leu His Met Pro Lys Glu Ile Gly
18200               18205               18210

Cys Asp Glu Ser Phe Leu Gln Ile Gly Gly Asp Ser Ile Thr Ala
18215               18220               18225

Ile Gln Leu Val Thr Asn Ala Arg Glu Ala Gly Ile Ser Ile Ala
18230               18235               18240

Val Lys Asp Ile Phe Asp Asp Pro Arg Leu Ser Lys Leu Ala Leu
18245               18250               18255

Val Ala Ala Ala Asn Ser Asp Gln Ser Asn Ala Ser Thr Ile Val
18260               18265               18270

Glu Pro Phe Ser Leu Leu Gly Asp Ser Leu Thr Lys Glu Leu Val
18275               18280               18285

Thr Glu Ala Ala Lys Glu Gln Cys Asn Leu Ala Gly Asp Asp Leu
18290               18295               18300

Leu Asp Asp Ala Tyr Pro Cys Thr Lys Leu Gln Glu Gly Leu Met
18305               18310               18315

Ala Leu Ala Ile Lys Gln Pro Gly Ser Tyr Ile Ala Lys Tyr Val
18320               18325               18330

Tyr Gln Ile Pro Asp His Val Asp Val Ser Arg Phe Arg Lys Ala
18335               18340               18345

Trp Glu Arg Thr Val Gln Ser Cys Ala Asn Leu Arg Thr Arg Met
18350               18355               18360

Val Leu Val Asn Gly Ile Thr Val Gln Val Leu Leu Lys Asp Asp
18365               18370               18375

Ile Glu Trp Asp Asn Thr Asp Asp Thr Ser Leu Glu Thr Tyr Ala
18380               18385               18390

Arg Ser Thr Leu His Ile Glu Met Gly Phe Ala Gln Arg Leu Cys
18395               18400               18405

Arg Tyr Ala Leu Ile Glu Glu Glu Thr Gly Asn Tyr Phe Ala Phe
18410               18415               18420

Ser Ile His His Thr Ile Phe Asp Gly Trp Ser Leu Pro Leu Val
18425               18430               18435

Met Gly Thr Leu Ser Ala Ala Tyr Tyr Asp Leu Glu Leu Pro Ser
18440               18445               18450

Leu Gln Ser Tyr Ala Ala Phe Val Lys Tyr Thr Met Glu Leu Asp
18455               18460               18465

His Gly Val Ala Ser Asp Tyr Trp Glu Lys Gln Leu Lys Gly Ala
18470               18475               18480

Lys Arg Ala Ser Phe Pro Ala Pro Ser Asp Lys Ser Gly Ser Ser
18485               18490               18495

Gln Thr Arg Val Ala Asn Lys Thr Ile Gly Phe Pro Lys Ser Lys
18500               18505               18510

Thr Ser Ile Thr Lys Ala Ser Ile Leu Arg Ala Ala Trp Ala Ile
18515               18520               18525

Val Leu Ala Arg Tyr Ser Asp Ser Asp Asp Val Cys Phe Gly Thr
18530               18535               18540

Thr Val Ser Gly Arg Asn Ala Asn Val Ala Gly Leu Glu Ala Met
18545               18550               18555

Pro Gly Leu Val Val Ala Thr Val Pro Val Arg Ile His Val Asp
18560               18565               18570

Lys Gln Lys Pro Leu Ser Gly Phe Leu Gln Asp Val Gln Lys Gln
18575               18580               18585

Ala Asn Asp Met Val Asp Phe Glu Gln Phe Gly Ile Gln Asn Ile
```

-continued

|  |  |  |  |  |  |  |  |  |  |
|---|---|---|---|---|---|---|---|---|---|
|  | 18590 |  |  | 18595 |  |  | 18600 |  |  |
| Ser | Arg 18605 | Leu | Gly | Ser 18610 | Asp | Ala | Lys 18615 | Asp | Ala | Cys | Asp | Phe | Thr | Ser |
| Leu | Leu 18620 | Ala | Ile | Gln 18625 | Pro | Val | Gln 18630 | His | Met | Ser | Ala | Asp | Ser | Gly |
| Asn | Pro 18635 | Ala | Asp | Gln 18640 | Gly | Ala | Ile 18645 | Val | Ile | Pro | Ala | Ala | Ser | Pro |
| His | Val 18650 | Asn | Ala | Glu 18655 | Asp | Met | Leu 18660 | Gln | Asn | Tyr | Phe | Ser | Tyr | Pro |
| Leu | Val 18665 | Ile | Gln | Cys 18670 | His | Leu | Met 18675 | Asp | Asp | His | Val | Asn | Leu | Val |
| Leu | Val 18680 | Tyr | Asp | Thr 18685 | Asp | Val | Leu 18690 | Glu | Glu | Thr | Gln | Leu | Asn | Ala |
| Leu | Met 18695 | Gln | Gln | Phe 18700 | Asp | His | Val 18705 | Val | Gln | Leu | Ser | Ala | Gln |
| Gly | Asn 18710 | Glu | Pro | Leu 18715 | Gly | Asp | Val 18720 | Ser | Ile | Ser | Gly | Pro | Trp | Asp |
| Leu | Glu 18725 | Gln | Ala | Leu 18730 | Gln | Leu | Asn 18735 | Ser | Arg | Lys | Pro | Asp | Phe | Val |
| His | Thr 18740 | Cys | Leu | His 18745 | Asp | Ile | Phe 18750 | Ser | Lys | His | Ala | Leu | Ser | Ser |
| Pro | His 18755 | His | Glu | Ala 18760 | Ile | Tyr | Ser 18765 | Ser | Glu | Gly | Ser | Leu | Thr | Tyr |
| Gly | Glu 18770 | Leu | Asp | His 18775 | Leu | Thr | Asp 18780 | Ile | Leu | Ala | Thr | His | Leu | Ser |
| Ser | Leu 18785 | Gly | Ala | Gly 18790 | Pro | Glu | Thr 18795 | Val | Val | Pro | Phe | Cys | Phe | Glu |
| Lys | Ser 18800 | Met | Trp | Ala 18805 | Val | Val | Ala 18810 | Ile | Leu | Ala | Ile | Leu | Lys | Ala |
| Gly | Ala 18815 | Ala | Phe | Val 18820 | Pro | Leu | Asp 18825 | Pro | Ser | His | Pro | Thr | Ser | Arg |
| Arg | Glu 18830 | Ala | Leu | Val 18835 | Lys | Glu | Val 18840 | Ser | Ala | Arg | Val | Leu | Val | Ala |
| Ser | Ser 18845 | Ser | Ala | Ile 18850 | Ala | Ser | Cys 18855 | Lys | Gly | Met | Phe | Glu | His | Val |
| Val | Glu 18860 | Leu | Ser | Pro 18865 | Ser | Val | Met 18870 | Ala | Lys | Leu | Ala | Ala | Ser | Val |
| Thr | Pro 18875 | Arg | Ile | Leu 18880 | Pro | Lys | Val 18885 | Gly | Pro | Arg | Asn | Thr | Ala | Tyr |
| Val | Leu 18890 | Phe | Thr | Ser 18895 | Gly | Ser | Thr 18900 | Gly | Lys | Pro | Lys | Gly | Val | Val |
| Met | Gln 18905 | His | Gly | Ser 18910 | Phe | Ser | Ser 18915 | Thr | Thr | Ile | Gly | Tyr | Gly | Lys |
| Val | Tyr 18920 | Asn | Leu | Ser 18925 | Pro | Leu | Ser 18930 | Arg | Val | Phe | Gln | Phe | Ser | Asn |
| Tyr | Ile 18935 | Phe | Asp | Gly 18940 | Ser | Leu | Gly 18945 | Glu | Ile | Phe | Gly | Pro | Leu | Ala |
| Phe | Gly 18950 | Gly | Thr | Ile 18955 | Cys | Ile | Pro 18960 | Ser | Glu | Asp | Glu | Arg | Leu | Gly |
| Ser | Ala 18965 | Pro | Ala | Phe 18970 | Met | Ser | Thr 18975 | Ser | Lys | Val | Asn | Thr | Ala | Met |
| Leu | Thr 18980 | Pro | Ser | Phe 18985 | Val | Arg | Thr 18990 | Phe | Thr | Pro | Asp | Gln | Val | Pro |

-continued

| | | | | | | | | | | | |
|---|---|---|---|---|---|---|---|---|---|---|---|
| His | Leu | Thr | Thr | Leu | Val | Leu | Gly | Gly | Glu | Ala | Ala | Ser | Lys | Ser |
| | 18995 | | | | 19000 | | | | | 19005 | |

His Leu Thr Thr Leu Val Leu Gly Gly Glu Ala Ala Ser Lys Ser
    18995                19000                    19005

Thr Leu Glu Met Trp Val Asn Arg Val Thr Leu Tyr Asn Gly Tyr
    19010                19015                    19020

Gly Pro Ala Glu Ala Cys Asn Tyr Ala Thr Thr His Val Phe Lys
    19025                19030                    19035

Ser Ser Ser Glu Ser Pro Arg Ile Ile Gly Ser Gly Phe Asn Gly
    19040                19045                    19050

Ala Cys Trp Val Val Glu Pro Asp Asn His Asn Ile Leu Ala Pro
    19055                19060                    19065

Ile Gly Cys Thr Gly Glu Leu Val Leu Gln Gly His Ala Leu Ala
    19070                19075                    19080

Arg Gly Tyr Leu Asn Asp Lys Ala Lys Thr Glu Gln Ser Phe Val
    19085                19090                    19095

Ser Asp Ile Ser Ser Leu Pro Ser Ser Ser Leu His Glu Pro Lys
    19100                19105                    19110

Arg Phe Tyr Leu Thr Gly Asp Leu Val Arg Tyr Asn Ser Asn Gly
    19115                19120                    19125

Lys Leu Glu Tyr Leu Gly Arg Lys Asp Ser Gln Val Lys Leu Arg
    19130                19135                    19140

Gly Gln Arg Leu Glu Leu Gly Glu Ile Glu Tyr Asn Ile Thr Gln
    19145                19150                    19155

Ser Leu Lys Ser Val Arg Asp Val Ala Val Asp Val Ile His Lys
    19160                19165                    19170

Asp Thr Gly Asp Leu Leu Val Ala Phe Ile Ser Phe Ser Gly Asn
    19175                19180                    19185

Ala Asp Ala Gln Trp Asp Ser Asp Asn Leu Leu Leu Asn Leu Leu
    19190                19195                    19200

Ala Ala Asp Glu Ser Met Arg Ser Leu Leu Asp Gly Leu Arg Glu
    19205                19210                    19215

Gly Leu Lys Ala Ser Leu Pro Gly Tyr Met Ala Val Leu Pro Ala
    19220                19225                    19230

Phe Met Met Pro Ser Leu Val Leu Pro Val Arg Asn Met Pro Phe
    19235                19240                    19245

Ile Thr Ser Met Lys Leu Asp Arg Lys Gln Leu Arg Thr Leu Ala
    19250                19255                    19260

Ser Ser Leu Ser Pro Glu Glu Leu Ala Thr Phe Ala Pro Ser Lys
    19265                19270                    19275

Ala Asp Lys Val Glu Pro Thr Thr Asp Met Glu Leu Lys Leu Arg
    19280                19285                    19290

Asp Leu Trp Ala Gln Ile Leu Gly Ile Pro Ala Glu Glu Ile Gly
    19295                19300                    19305

Lys Asn Asp Ser Phe Leu Gln Ile Gly Gly Asp Ser Ile Ser Ala
    19310                19315                    19320

Ile His Leu Val Thr Leu Ala Gln Glu Thr Gly Ile Ser Leu Thr
    19325                19330                    19335

Val Ala Thr Ile Phe Ala Asp Pro Arg Leu Ser Ser Val Ala Ala
    19340                19345                    19350

Ser Ala His Leu Gly Gly Ile Ser Asp Ala Tyr Glu Ala Glu Pro
    19355                19360                    19365

Phe Ser Leu Ile Gln His Ser Glu Ser Asp Ala Ile Thr Arg Glu
    19370                19375                    19380

```
Ile Glu Gln Gln Cys Lys Leu     Ser Ala Gly Gln Ser     Ile Glu Asp
    19385               19390                   19395

Ala Tyr Pro Thr Thr Lys Leu     Gln Glu Gly Leu Met     Ala Leu Ser
    19400               19405                   19410

Val Lys Gln Pro Gly Ser Tyr     Thr Ala Arg Tyr Val     Tyr Arg Leu
    19415               19420                   19425

Pro Asp His Val Asp Val Glu     Arg Phe Lys Ala Ala     Trp Asp Lys
    19430               19435                   19440

Thr Val Glu Val Cys His Asn     Leu Arg Thr Ser Ile     Val Leu Val
    19445               19450                   19455

Gly Tyr Thr Ala Ile Gln Ala     Val Ile Lys Asp Thr     Ser Arg Ser
    19460               19465                   19470

Leu Trp Glu Pro Ala Thr Gly     Val Ser Leu Gln Ser     Tyr Met Lys
    19475               19480                   19485

Lys Ala Ile Gly Ser Phe Asn     Met Gly Tyr Gly Ser     Arg Leu Cys
    19490               19495                   19500

Arg Tyr Ala Leu Ile Glu Asp     Gly Gly Ser Thr Tyr     Phe Ala Trp
    19505               19510                   19515

His Ile His His Ser Val Tyr     Asp Gly Trp Thr His     Pro Leu Ile
    19520               19525                   19530

Met Gly Ser Leu Tyr Ala Ala     Tyr Phe Gly Thr Glu     Met Pro Pro
    19535               19540                   19545

Leu Arg Pro Phe Ala Arg Phe     Val Lys Tyr Thr Thr     Ser Ile Asp
    19550               19555                   19560

Gln His Glu Ala Ala Glu Tyr     Trp Arg Arg Gln Leu     His Asp Ala
    19565               19570                   19575

Arg Pro Ala Ser Phe Pro Ala     Val Asp Gln Gln Leu     Thr Ala Ser
    19580               19585                   19590

Lys Ser Lys Ala Asp Val Thr     Arg Ile Leu Arg Lys     Ala Val Asp
    19595               19600                   19605

Phe Pro Arg Leu Thr Asn Ser     Ser Ile Thr Lys Ala     Thr Ile Met
    19610               19615                   19620

Arg Ala Ala Trp Ser Ile Val     Leu Ala Gln Tyr Cys     Gly Val Asp
    19625               19630                   19635

Asp Val Cys Phe Gly Thr Thr     Leu Ser Gly Arg His     Ala Pro Val
    19640               19645                   19650

Pro Gly Leu Asp Ser Met Pro     Gly Pro Met Leu Ala     Thr Val Pro
    19655               19660                   19665

Val Arg Ile Arg Leu Ala Gln     Asp Gln Pro Ala Ser     Arg Phe Leu
    19670               19675                   19680

Gln Asp Val Gln Ile Gln Ala     Ala Glu Met Val Ala     Tyr Glu Gln
    19685               19690                   19695

Phe Gly Leu Gln Asn Ile Ala     Ala Leu Ser Pro Asp     Ala Lys Gln
    19700               19705                   19710

Ala Cys Asp Phe Ser Ser Leu     Leu Val Ile Gln Pro     Ala Gln Gln
    19715               19720                   19725

Gln Ile Ser Asp Asp Lys Ala     Val Ser Glu Thr Asp     Met Ile Leu
    19730               19735                   19740

Leu Pro Gly Asp Ser Glu Asn     Ser Ala Glu Glu Ser     Met Gln Asn
    19745               19750                   19755

Phe Ala Asn Tyr Pro Leu Val     Leu Gln Ile Ala Ile     Met Asp Ser
    19760               19765                   19770

His Val Glu Leu Leu Leu Ile     Tyr Asp Thr Asn Ala     Leu Thr Glu
```

```
        19775               19780              19785
Phe Gln Ala Thr Ala Ile Ser Glu Gln Phe Gly Asn Val Ala Arg
        19790               19795              19800
Gln Leu Val Ala Gln Asp Glu Thr Leu Ile Gly Asp Val Lys Val
        19805               19810              19815
Ala Gly Ser Trp Asp Leu Gln Lys Gln Leu Glu Trp Asn His Glu
        19820               19825              19830
Ile Tyr Gly Pro Ser Glu Thr Thr Leu His Asp Leu Phe Ser Lys
        19835               19840              19845
Gln Val Ala Arg Arg Pro Ala His Gln Ala Leu Tyr Ser Ser Glu
        19850               19855              19860
Gly Ser Met Thr Tyr Ser Lys Leu Asp Arg Leu Thr Thr Gln Leu
        19865               19870              19875
Ala Val Tyr Leu Ser Ser Leu Gly Val Arg Pro Glu Thr Ile Val
        19880               19885              19890
Pro Phe Cys Phe Asp Lys Ser Ile Trp Ala Ile Val Ala Met Ile
        19895               19900              19905
Gly Ile Leu Lys Ala Gly Gly Val Phe Met Pro Leu Asp Pro Ser
        19910               19915              19920
Tyr Pro Ala Ser Arg Arg Gln Ala Leu Ile Asp Glu Val Asn Ala
        19925               19930              19935
Gln Phe Met Ile Val Ser Pro Thr Thr Ala Pro Asp Ser Gln Gly
        19940               19945              19950
Met Val Gln Asn Met Ile Glu Leu Ser Pro Ser Leu Ile Ala Phe
        19955               19960              19965
Phe Ser Thr Ile Asp Thr Gly Asp Gln Ser Phe Ile Lys Ser Gly
        19970               19975              19980
Pro Asn Asn Ala Ala Tyr Val Leu Phe Thr Ser Gly Ser Thr Gly
        19985               19990              19995
Lys Pro Lys Gly Val Val Ile Asp His Lys Ala Ile Ser Ala Ala
        20000               20005              20010
Leu Leu Arg Gln Arg Glu Ala Phe Ser Phe Asn Asp Asp Thr Arg
        20015               20020              20025
Thr Leu Gln Phe Ala Asn Phe Val Phe Asp Ala Cys Ile Ala Glu
        20030               20035              20040
Ile Phe Ser Ala Leu Val Ala Gly Ala Thr Val Cys Val Pro Thr
        20045               20050              20055
Glu His Glu Arg Val His Asn Thr Ala Ala Phe Ile Arg Glu Ala
        20060               20065              20070
Arg Ile Asn His Ala Phe Leu Thr Pro Thr Phe Ile Lys Thr Leu
        20075               20080              20085
Ser Pro Glu Gln Ile Pro Gly Met Lys Thr Val Ile Leu Met Gly
        20090               20095              20100
Glu Ala Pro Ser Gln Glu Ile Ile Asp Thr Trp Ala Asp Glu Ile
        20105               20110              20115
Asp Leu His Asn Gly Tyr Gly Pro Ala Glu Gly Cys Val Gly Ser
        20120               20125              20130
Thr Asn Asn Thr Tyr Ser Ser Ser Ile Lys Val Ser Val Thr Asn
        20135               20140              20145
Val Gly Arg Ser Phe Thr His Gly Leu Trp Ile Val Asp Pro Asp
        20150               20155              20160
Asn His Asn Arg Leu Met Pro Ile Gly Cys Val Gly Glu Leu Leu
        20165               20170              20175
```

```
Leu Gln Gly Ser Ser Leu Ala Arg Gly Tyr Ile Asn Asp Glu Glu
    20180               20185                   20190

Lys Ser Arg Gln Ser Phe Ile Asp Gln Val Glu Trp Leu Pro Ala
    20195               20200                   20205

Asn Val Asn Val Gly Glu Arg Arg Phe Tyr Lys Thr Gly Asp Leu
    20210               20215                   20220

Val Arg Tyr Thr Pro Asp Gly Ser Ile Glu Tyr Val Ser Arg Lys
    20225               20230                   20235

Asp Thr Gln Val Lys Ile Arg Gly Gln Arg Ile Glu Leu Gly Glu
    20240               20245                   20250

Ile Glu Tyr His Val Lys Arg Ser Asn Ala Ser Ile Glu His Val
    20255               20260                   20265

Val Val Asp Ile Thr Arg Gln Ala Gly Arg Glu Ser Leu Leu Ala
    20270               20275                   20280

Phe Val Cys Phe Ser Ser His Gln Glu Thr Glu Ser Ala Ser Lys
    20285               20290                   20295

Glu Thr Arg Leu Thr Glu Leu Thr Ser Glu Leu Arg Glu Thr Leu
    20300               20305                   20310

Ser Asp Ile Ala Thr Thr Ile Ala Ser Thr Leu Pro Ser His Met
    20315               20320                   20325

Val Pro Lys Tyr Leu Ile Pro Val Asp His Met Pro His Asn Ala
    20330               20335                   20340

Ala Gly Lys Leu Asp Arg Lys Met Leu Leu Ala Ser Ile Ala Asn
    20345               20350                   20355

Leu Thr Pro Asp Asp Leu Ser Lys Tyr Leu Ala Gly Gln Arg Leu
    20360               20365                   20370

Pro Phe Arg Asp Cys Ser Thr Asp Val Glu Phe Trp Leu Arg Asn
    20375               20380                   20385

Gln Trp Ala Ser Thr Leu Asp Leu Pro Ala Glu Thr Ile Gly Met
    20390               20395                   20400

Asp Asp Asn Phe Tyr Ser Leu Gly Gly Asp Ser Ile Arg Ile Val
    20405               20410                   20415

Thr Ile Ser Lys Ala Ile Leu Ser Gln Tyr Asp Val Ser Leu Gly
    20420               20425                   20430

Met Ser Leu Leu Asn Ser Lys His Thr Thr Ile Ala Asn Met Ala
    20435               20440                   20445

Lys His Ile Asp Ser Glu Arg Ser Gly Gln Asp Gly Ala Glu Leu
    20450               20455                   20460

Gly Val Val Asp Ile Asn Gly Glu Ile Ser Ser Leu Ser Arg Ser
    20465               20470                   20475

Ile Leu Ala Ser Gly Asp Leu Asn Val Val Ser His Ser Lys Thr
    20480               20485                   20490

Glu Leu Pro Glu Gln Ala Thr Val Phe Leu Thr Gly Ala Thr Gly
    20495               20500                   20505

Phe Leu Gly Gln Glu Leu Leu Arg Gln Leu Leu Cys Asn Asp Ser
    20510               20515                   20520

Ile Ala Ser Ile Ile Ala Leu Val Arg Ser Lys Ser Ala Asn His
    20525               20530                   20535

Gly Met Asp Arg Leu Arg Asp Thr Ala Lys Ile Ala Gly Trp Trp
    20540               20545                   20550

Arg Glu Glu Tyr Thr Ser Lys Ile Glu Ile Trp Cys Gly Asp Leu
    20555               20560                   20565
```

| | | | | | | | | | | |
|---|---|---|---|---|---|---|---|---|---|---|
| Ser | Lys | Arg | Met | Gly | Leu | Ser | Ser | Ser | Gln | Trp | Ala | Arg | Leu |
| | 20570 | | | | 20575 | | | | 20580 | | | | |
| Ala | Gly | Gln | Ser | Ser | Asn | Asn | Val | Asp | Ala | Ile | Ile | His | Asn |
| 20585 | | | | | 20590 | | | | 20595 | | | | |
| Gly | Ala | Ile | Val | Asn | Trp | Asn | Ala | Asp | Tyr | Asp | Lys | Met | Arg | Ala |
| 20600 | | | | | 20605 | | | | 20610 | | | | |
| Ala | Asn | Val | Asp | Ser | Thr | Val | Asp | Leu | Leu | Lys | Ala | Thr | Val | Thr |
| 20615 | | | | | 20620 | | | | 20625 | | | | |
| Ser | Pro | Ala | Ser | Pro | Lys | Phe | Val | Phe | Val | Ser | Gly | Gly | Ile | Lys |
| 20630 | | | | | 20635 | | | | 20640 | | | | |
| Ser | Asp | Pro | Thr | Thr | Asp | Arg | Thr | Ala | Leu | Gly | Gln | Tyr | Leu | Asn |
| 20645 | | | | | 20650 | | | | 20655 | | | | |
| Asn | Ser | Thr | Gly | Tyr | Ile | Gln | Thr | Lys | Phe | Val | Ser | Glu | Gly | Ile |
| 20660 | | | | | 20665 | | | | 20670 | | | | |
| Ile | Gln | Glu | Val | Ile | Lys | Thr | Leu | Pro | Ala | Asp | Gln | Asn | Arg | Ile |
| 20675 | | | | | 20680 | | | | 20685 | | | | |
| Ser | Thr | Leu | Lys | Pro | Gly | Arg | Ile | Ile | Gly | Ser | Pro | Glu | Thr | Gly |
| 20690 | | | | | 20695 | | | | 20700 | | | | |
| Val | Ala | Asn | Val | Asp | Asp | Val | Leu | Trp | Arg | Ile | Val | Ser | Ala | Ala |
| 20705 | | | | | 20710 | | | | 20715 | | | | |
| Ala | Ser | Leu | Gly | Val | Tyr | Pro | Ala | Glu | Pro | Glu | Asp | His | Trp | Val |
| 20720 | | | | | 20725 | | | | 20730 | | | | |
| Tyr | Ile | Ser | Asp | Val | Asp | Thr | Val | Ala | Ser | Ser | Val | Leu | Ser | Gln |
| 20735 | | | | | 20740 | | | | 20745 | | | | |
| Leu | Tyr | Ser | Lys | Gln | Gly | Ile | Ala | Pro | Tyr | Val | Ser | Ala | Thr | Gly |
| 20750 | | | | | 20755 | | | | 20760 | | | | |
| Gly | Met | Pro | Ala | Thr | Val | Phe | Trp | Asp | Leu | Ile | Asn | Lys | Glu | Leu |
| 20765 | | | | | 20770 | | | | 20775 | | | | |
| Asp | Val | Pro | Cys | Glu | Pro | Leu | Ser | Gln | Asp | Glu | Trp | Thr | His | Arg |
| 20780 | | | | | 20785 | | | | 20790 | | | | |
| Ala | Leu | Glu | Ser | Met | Asn | Gln | Val | Gly | Asp | Lys | His | Pro | Leu | Trp |
| 20795 | | | | | 20800 | | | | 20805 | | | | |
| Pro | Val | Gln | His | Phe | Leu | Gly | Asn | Leu | Gly | Thr | Pro | Arg | Ser | Ala |
| 20810 | | | | | 20815 | | | | 20820 | | | | |
| Gln | Asp | Ile | Glu | Ile | Glu | Gly | Ser | Glu | His | Lys | Gln | Trp | His | Met |
| 20825 | | | | | 20830 | | | | 20835 | | | | |
| Ala | Val | Lys | Met | Ser | Met | Arg | Tyr | Leu | Met | Lys | Val | Gly | Phe | Ile |
| 20840 | | | | | 20845 | | | | 20850 | | | | |
| Gln | Thr | Ser | Thr | Asp | Gly | Phe | Ala | Gln | Pro | Arg | Arg | Ala | Asp | Thr |
| 20855 | | | | | 20860 | | | | 20865 | | | | |
| Phe | Gln | Arg | His | Gly |
| | 20870 | | | |

<210> SEQ ID NO 5
<211> LENGTH: 1014
<212> TYPE: DNA
<213> ORGANISM: Trichoderma reesei

<400> SEQUENCE: 5

```
atgtctactc taacagttct ggagcctacc ttgcggctag acgcacctac agtcaagtta      60
caatcaccaa agcaagcaga caggcaactc caggtcgtga ttccggattt gttctcctcg     120
atcatggctg ttgagcccac catcaatcct cattacaaag atgtcaaggc cgaagcagat     180
gcgtggttca aaagtttgtt gcagttgaaa gggaaagcag aggcgacttt caacaagacc     240
```

```
gactttggat tcgcagctgc tgtatgggcc ccttcagcag acaaggacag gttccgcaca    300
gctgtcgact gggcaaattg gatattctat tttgatgatc aattcgatga aggacatcta    360
gcaaacgatc cagctgcggc gcaggcagag attgattcca tactcgccat cctggatgac    420
aagccaactc ttgctcagac cgacaagcca ctcatatatg cttttcagtc tatttgggac    480
agaataaagg cggtatgtag acctctgcta cgcgaacgtt ggaaagatgc ccataagaaa    540
tacgtcgagg ggttgatcta tcaaactcag cgaacaaagc ttggttctgc tgcctccgca    600
agcgtggatg aatacatgag ttaccgaagg gaaacgatcg gtgttatatt ggctattcga    660
ctggttgaat atgcagagaa catcaagctt tcccaagctc agatggatca cccggcactg    720
cagttgtgca ctcgaacgat tgtagatctc gtgattctct caaatgacat cttatcatac    780
aagaaagaag agctcaatga tgcagggaac aatctagtca caatactcaa ggcacagaac    840
ctctccgatc aggaggcaat ggacaaaata ggcagaatgc tcgacgcttg ctatgagagt    900
tggtacaacg caatggatga gctaccagtt tgggggcag gaatcgacca agaggtgcgc    960
agatatctgg ttgtttgtcg taacgtgggt cttggcaatc ttcactggag gtaa         1014
```

<210> SEQ ID NO 6
<211> LENGTH: 337
<212> TYPE: PRT
<213> ORGANISM: Trichoderma reesei

<400> SEQUENCE: 6

```
Met Ser Thr Leu Thr Val Leu Glu Pro Thr Leu Arg Leu Asp Ala Pro
1               5                   10                  15

Thr Val Lys Leu Gln Ser Pro Lys Gln Ala Asp Arg Gln Leu Gln Val
            20                  25                  30

Val Ile Pro Asp Leu Phe Ser Ser Ile Met Ala Val Glu Pro Thr Ile
        35                  40                  45

Asn Pro His Tyr Lys Asp Val Lys Ala Glu Ala Asp Ala Trp Phe Lys
    50                  55                  60

Ser Leu Leu Gln Leu Lys Gly Lys Ala Glu Ala Thr Phe Asn Lys Thr
65                  70                  75                  80

Asp Phe Gly Phe Ala Ala Ala Val Trp Ala Pro Ser Ala Asp Lys Asp
                85                  90                  95

Arg Phe Arg Thr Ala Val Asp Trp Ala Asn Trp Ile Phe Tyr Phe Asp
            100                 105                 110

Asp Gln Phe Asp Glu Gly His Leu Ala Asn Asp Pro Ala Ala Ala Gln
        115                 120                 125

Ala Glu Ile Asp Ser Ile Leu Ala Ile Leu Asp Asp Lys Pro Thr Leu
    130                 135                 140

Ala Gln Thr Asp Lys Pro Leu Ile Tyr Ala Phe Gln Ser Ile Trp Asp
145                 150                 155                 160

Arg Ile Lys Ala Val Cys Arg Pro Leu Leu Arg Glu Arg Trp Lys Asp
                165                 170                 175

Ala His Lys Lys Tyr Val Glu Gly Leu Ile Tyr Gln Thr Gln Arg Thr
            180                 185                 190

Lys Leu Gly Ser Ala Ala Ser Ala Ser Val Asp Glu Tyr Met Ser Tyr
        195                 200                 205

Arg Arg Glu Thr Ile Gly Val Ile Leu Ala Ile Arg Leu Val Glu Tyr
    210                 215                 220

Ala Glu Asn Ile Lys Leu Ser Gln Ala Gln Met Asp His Pro Ala Leu
225                 230                 235                 240
```

```
Gln Leu Cys Thr Arg Thr Ile Val Asp Leu Val Ile Leu Ser Asn Asp
                245                 250                 255

Ile Leu Ser Tyr Lys Lys Glu Glu Leu Asn Asp Ala Gly Asn Asn Leu
            260                 265                 270

Val Thr Ile Leu Lys Ala Gln Asn Leu Ser Asp Gln Glu Ala Met Asp
        275                 280                 285

Lys Ile Gly Arg Met Leu Asp Ala Cys Tyr Glu Ser Trp Tyr Asn Ala
    290                 295                 300

Met Asp Glu Leu Pro Val Trp Gly Ala Gly Ile Asp Gln Glu Val Arg
305                 310                 315                 320

Arg Tyr Leu Val Val Cys Arg Asn Val Gly Leu Gly Asn Leu His Trp
                325                 330                 335

Arg

<210> SEQ ID NO 7
<211> LENGTH: 684
<212> TYPE: DNA
<213> ORGANISM: Trichoderma reesei

<400> SEQUENCE: 7
atgcagcgta ttctcgctct cactgctgct gcggcaggcc tctttgtgac agccttgggc     60
accaaagttc caagtgtcaa tgtcccatca tgcccgcgca tcggttccgt ttcctacacc    120
acgtcggtgc ccgaccggac tccatttccg cgtacgcagg tcgacctgtg ctataccgac    180
gatagcctcg agctcacatt tatcgcctat gacgaggtga attacttctt caacgcgtcc    240
caggaaccaa cgacgacat ctgggagtac gaagtcatgg aggccttcat ctacaagggc    300
actgaagacc ctcagacata cgtcgagctc gaggtcaatc ccaacaatgt gacataccaa    360
gcatttgttt acaatccttc caagaaccgg acagcgggcg caccgttcga ccacttcttc    420
atttcggatc ccgcaaccga cggcttcaag gccaagacga tcctcaacaa gccagcaaag    480
acttggagaa gcacccttac cgtccctcta ggtatcttca atgttgatgt cggcaaggca    540
aagggtacct cttggaggat gaattttttc aggactgtag ttagcccgga gatttatcca    600
aatcagattc tgggcggctg gggtgtcccg gatcaggcga gcttccatat caccaagtat    660
tttggcaagg tgaagtttat ctga                                          684

<210> SEQ ID NO 8
<211> LENGTH: 227
<212> TYPE: PRT
<213> ORGANISM: Trichoderma reesei

<400> SEQUENCE: 8

Met Gln Arg Ile Leu Ala Leu Thr Ala Ala Ala Gly Leu Phe Val
1               5                   10                  15

Thr Ala Leu Gly Thr Lys Val Pro Ser Val Asn Val Pro Ser Cys Pro
            20                  25                  30

Arg Ile Gly Ser Val Ser Tyr Thr Thr Ser Val Pro Asp Arg Thr Pro
        35                  40                  45

Phe Pro Arg Thr Gln Val Asp Leu Cys Tyr Thr Asp Ser Leu Glu
    50                  55                  60

Leu Thr Phe Ile Ala Tyr Asp Glu Val Asn Tyr Phe Phe Asn Ala Ser
65                  70                  75                  80

Gln Gly Thr Asn Asp Asp Ile Trp Glu Tyr Glu Val Met Glu Ala Phe
                85                  90                  95

Ile Tyr Lys Gly Thr Glu Asp Pro Gln Thr Tyr Val Glu Leu Glu Val
```

```
                100                 105                 110
Asn Pro Asn Val Thr Tyr Gln Ala Phe Val Tyr Asn Pro Ser Lys
            115                 120                 125
Asn Arg Thr Ala Gly Ala Pro Phe Asp His Phe Phe Ile Ser Asp Pro
        130                 135                 140
Ala Thr Asp Gly Phe Lys Ala Lys Thr Ile Leu Asn Lys Pro Ala Lys
145                 150                 155                 160
Thr Trp Arg Ser Thr Leu Thr Val Pro Leu Gly Ile Phe Asn Val Asp
                165                 170                 175
Val Gly Lys Ala Lys Gly Thr Ser Trp Arg Met Asn Phe Phe Arg Thr
            180                 185                 190
Val Val Ser Pro Glu Ile Tyr Pro Asn Gln Ile Leu Gly Gly Trp Gly
                195                 200                 205
Val Pro Asp Gln Ala Ser Phe His Ile Thr Lys Tyr Phe Gly Lys Val
            210                 215                 220
Lys Phe Ile
225
```

<210> SEQ ID NO 9
<211> LENGTH: 993
<212> TYPE: DNA
<213> ORGANISM: Trichoderma reesei

<400> SEQUENCE: 9

```
atggaaccgg agcagatcac ggtgctcctt cctgacatgt tccagacgtt cctcaagcag    60
ccgcctcgca tcaatcctca ctaccaatcg gttaagttgg agtctgaaga agggcttgcg   120
aggttctgct ctttcgagcc gagcatgagg aagagagtga acaaatgcga cttttcatac   180
ttttgtgcca ttgccgctcc ctttgcctct cgagcgagat tcgtaccat ctgcgattgg    240
gggaactggg tatttccata cgatgacatg tttgataatg gcatcttcg caacgagccg    300
gaagaatctc aacgcgtcat ggagagcctc atgatgccca tgttgggcaa tacggcgaat   360
ttgaactctc aagaccggct tcgcatcgtg cagtttcacg acacggtcgt tgagagaatg   420
gctctaagaa caccaaaagg cgtgcagaga agatttgccc ttgccatgca gggatactgc   480
cgaggcgctc tcacccaaat cgatcatcaa ttctctggaa agatcccgac actggaggaa   540
attgccatga ttcgccgaga gtctgctgga tgcaggcctc tatactacct tgttgaatac   600
gcacatcgcc tccgagtgcc ggatgaggtg tttgagcatc ccattatcca ggagctggag   660
aatcttggcc aggatatggc agagggcgta ccgcacaaca tggtcacagt ctgtcgacgg   720
aacggcatgt cggcacaaaa ggcattcaac acagtcggca ggctcctcga gcgccgctat   780
gagcgatggg acaaagccga ggcaagcctt ccgagctggg gcagggaggc tgatgttgag   840
gtccgaaagt acattgaggg catcaaatgt gttgtcaagg ccaatctcaa ttggagtttc   900
aaatcggagc gctacctcgg cgcaaatcct gaagtggttc gagccactcg gaaagttcac   960
attctggcag attcgcctcc cattggcgtt tga                                 993
```

<210> SEQ ID NO 10
<211> LENGTH: 330
<212> TYPE: PRT
<213> ORGANISM: Trichoderma reesei

<400> SEQUENCE: 10

```
Met Glu Pro Glu Gln Ile Thr Val Leu Leu Pro Asp Met Phe Gln Thr
1               5                   10                  15
```

Phe Leu Lys Gln Pro Pro Arg Ile Asn Pro His Tyr Gln Ser Val Lys
                        20                  25                  30

Leu Glu Ser Glu Glu Gly Leu Ala Arg Phe Cys Ser Phe Glu Pro Ser
                    35                  40                  45

Met Arg Lys Arg Val Asn Lys Cys Asp Phe Ser Tyr Phe Cys Ala Ile
            50                  55                  60

Ala Ala Pro Phe Ala Ser Arg Ala Arg Phe Arg Thr Ile Cys Asp Trp
            65                  70                  75                  80

Gly Asn Trp Val Phe Pro Tyr Asp Asp Met Phe Asp Asn Gly His Leu
                            85                  90                  95

Arg Asn Glu Pro Glu Glu Ser Gln Arg Val Met Glu Ser Leu Met Met
                        100                 105                 110

Pro Met Leu Gly Asn Thr Ala Asn Leu Asn Ser Gln Asp Arg Leu Arg
                    115                 120                 125

Ile Val Gln Phe His Asp Thr Val Val Glu Arg Met Ala Leu Arg Thr
            130                 135                 140

Pro Lys Gly Val Gln Arg Arg Phe Ala Leu Ala Met Gln Gly Tyr Cys
            145                 150                 155                 160

Arg Gly Ala Leu Thr Gln Ile Asp His Gln Phe Ser Gly Lys Ile Pro
                            165                 170                 175

Thr Leu Glu Glu Ile Ala Met Ile Arg Arg Glu Ser Ala Gly Cys Arg
                        180                 185                 190

Pro Leu Tyr Tyr Leu Val Glu Tyr Ala His Arg Leu Arg Val Pro Asp
                    195                 200                 205

Glu Val Phe Glu His Pro Ile Ile Gln Glu Leu Glu Asn Leu Gly Gln
            210                 215                 220

Asp Met Ala Glu Gly Val Pro His Asn Met Val Thr Val Cys Arg Arg
            225                 230                 235                 240

Asn Gly Met Ser Ala Gln Lys Ala Phe Asn Thr Val Gly Arg Leu Leu
                            245                 250                 255

Glu Arg Arg Tyr Glu Arg Trp Asp Lys Ala Glu Ala Ser Leu Pro Ser
                        260                 265                 270

Trp Gly Arg Glu Ala Asp Val Glu Val Arg Lys Tyr Ile Glu Gly Ile
                    275                 280                 285

Lys Cys Val Val Lys Ala Asn Leu Asn Trp Ser Phe Lys Ser Glu Arg
            290                 295                 300

Tyr Leu Gly Ala Asn Pro Glu Val Val Arg Ala Thr Arg Lys Val His
            305                 310                 315                 320

Ile Leu Ala Asp Ser Pro Pro Ile Gly Val
                            325                 330

<210> SEQ ID NO 11
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 11
tcacatggtt taaacggcgc gccgacccga aagaacgcaa aagtccat                48

<210> SEQ ID NO 12
<211> LENGTH: 41
<212> TYPE: DNA
<213> ORGANISM: Artificial Sequence
<220> FEATURE:
<223> OTHER INFORMATION: Artificial DNA Primer

<400> SEQUENCE: 12
agccttgttt tgtcgtgtca agaacttgga tctcctagga g                41

<210> SEQ ID NO 13
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 13
cctagttgga gtattcctgc aggtcctcat ctgtggctca tattaggt          48

<210> SEQ ID NO 14
<211> LENGTH: 55
<212> TYPE: DNA
<213> ORGANISM: Artificial Sequence
<220> FEATURE:
<223> OTHER INFORMATION: Artificial DNA Primer

<400> SEQUENCE: 14
tggccatatt taaatcctgc agggtttaaa ccaaggcggg atagtgtcgg ttctt   55

<210> SEQ ID NO 15
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 15
tgccccacga tatctctcct tctcc                                   25

<210> SEQ ID NO 16
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 16
ctacatcgaa gctgaaagca cgaga                                   25

<210> SEQ ID NO 17
<211> LENGTH: 30
<212> TYPE: DNA
<213> ORGANISM: Artificial Sequence
<220> FEATURE:
<223> OTHER INFORMATION: Artificial DNA Primer

<400> SEQUENCE: 17
tagctagctg tcttggatga atcgaggttg                              30

<210> SEQ ID NO 18
<211> LENGTH: 25
<212> TYPE: DNA
<213> ORGANISM: Artificial Sequence
<220> FEATURE:
<223> OTHER INFORMATION: Artificial DNA Primer

<400> SEQUENCE: 18
tcgtcttcat gagcatgttg ttggg                                   25

<210> SEQ ID NO 19

```
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 19
tcacatggtt taaacggcgc gcctactacc tagtacagtg cttattta           48

<210> SEQ ID NO 20
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 20
agccttgttt tgtcgttttt tctccaaatt tgtacagaat tatct              45

<210> SEQ ID NO 21
<211> LENGTH: 48
<212> TYPE: DNA
<213> ORGANISM: Artificial Sequence
<220> FEATURE:
<223> OTHER INFORMATION: Artificial DNA Primer

<400> SEQUENCE: 21
cctagttgga gtattcctgc aggaggaatt gtgcctggct gttgagtt           48

<210> SEQ ID NO 22
<211> LENGTH: 56
<212> TYPE: DNA
<213> ORGANISM: Artificial Sequence
<220> FEATURE:
<223> OTHER INFORMATION: Artificial DNA Primer

<400> SEQUENCE: 22
tggccatatt taaatcctgc agggtttaaa cgcttatcga tccggcatat cgctct  56

<210> SEQ ID NO 23
<211> LENGTH: 25
<212> TYPE: DNA
<213> ORGANISM: Artificial Sequence
<220> FEATURE:
<223> OTHER INFORMATION: ARTIFICIAL DNA PRIMER

<400> SEQUENCE: 23
taccttacag gccctccgcg agcta                                    25

<210> SEQ ID NO 24
<211> LENGTH: 25
<212> TYPE: DNA
<213> ORGANISM: Artificial Sequence
<220> FEATURE:
<223> OTHER INFORMATION: ARTIFICIAL DNA PRIMER

<400> SEQUENCE: 24
ctacatcgaa gctgaaagca cgaga                                    25

<210> SEQ ID NO 25
<211> LENGTH: 30
<212> TYPE: DNA
<213> ORGANISM: Artificial Sequence
<220> FEATURE:
<223> OTHER INFORMATION: ARTIFICIAL DNA PRIMER

<400> SEQUENCE: 25
```

```
atgttggagc cttgcctcca gagtcctcac                                30

<210> SEQ ID NO 26
<211> LENGTH: 30
<212> TYPE: DNA
<213> ORGANISM: Artificial Sequence
<220> FEATURE:
<223> OTHER INFORMATION: ARTIFICIAL DNA PRIMER

<400> SEQUENCE: 26
gggttcagtc cagaagcaga accaggatca                                30

<210> SEQ ID NO 27
<211> LENGTH: 25
<212> TYPE: DNA
<213> ORGANISM: Artificial Sequence
<220> FEATURE:
<223> OTHER INFORMATION: ARTIFICIAL DNA PRIMER

<400> SEQUENCE: 27
cagatgagcc ctacatgacg ccagc                                     25

<210> SEQ ID NO 28
<211> LENGTH: 21
<212> TYPE: DNA
<213> ORGANISM: Artificial Sequence
<220> FEATURE:
<223> OTHER INFORMATION: ARTIFICIAL DNA PRIMER

<400> SEQUENCE: 28
ggctccatac cgacgatatg c                                         21
```